US011377491B2

(12) United States Patent
Liao et al.

(10) Patent No.: US 11,377,491 B2
(45) Date of Patent: Jul. 5, 2022

(54) ANTI-LEUKOCYTE-ASSOCIATED IMMUNOGLOBULIN-LIKE RECEPTOR 1 (LAIR1) MONOCLONAL ANTIBODIES AND METHOD OF USE THEREOF TO TREAT CANCER

(71) Applicant: THE BOARD OF REGENTS OF THE UNIVERSITY OF TEXAS SYSTEM, Austin, TX (US)

(72) Inventors: X. Charlene Liao, Palo Alto, CA (US); Qiang Liu, Palo Alto, CA (US); Zhiqiang An, Houston, TX (US); Ningyan Zhang, Houston, TX (US); Xun Gui, Houston, TX (US); Chengcheng Zhang, Dallas, TX (US); Mi Deng, Plano, TX (US); Jingjing Xie, Plano, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 184 days.

(21) Appl. No.: 16/475,223

(22) PCT Filed: Jan. 2, 2018

(86) PCT No.: PCT/US2018/012040
§ 371 (c)(1),
(2) Date: Jul. 1, 2019

(87) PCT Pub. No.: WO2018/126259
PCT Pub. Date: Jul. 5, 2018

(65) Prior Publication Data
US 2019/0338026 A1  Nov. 7, 2019

Related U.S. Application Data

(60) Provisional application No. 62/445,673, filed on Jan. 12, 2017, provisional application No. 62/441,551, filed on Jan. 2, 2017.

(51) Int. Cl.
C07K 16/28 (2006.01)
C12N 5/12 (2006.01)
C12N 15/85 (2006.01)

(52) U.S. Cl.
CPC ............ *C07K 16/2803* (2013.01); *C12N 5/12* (2013.01); *C12N 15/85* (2013.01); *C07K 2317/34* (2013.01); *C07K 2317/75* (2013.01); *C07K 2317/76* (2013.01); *C07K 2317/92* (2013.01); *C12N 2015/8518* (2013.01)

(58) Field of Classification Search
CPC ............ C07K 16/2803; C07K 2317/34; C07K 2317/75; C07K 2317/76; C12N 5/12; C12N 5/85
See application file for complete search history.

(56) References Cited

U.S. PATENT DOCUMENTS

| 2009/0304686 A1 | 12/2009 | Meyaard et al. |
| 2011/0268741 A1 | 11/2011 | Tamada |

FOREIGN PATENT DOCUMENTS

| WO | WO 2010/078580 | 7/2010 |
| WO | WO 2016/172583 | 10/2016 |

OTHER PUBLICATIONS

Abnova.pdf. Accessed online on Sep. 24, 2021.*
Antibodypedia.pdf. Accessed online on Sep. 24, 2021.*
Thermofisher.pdf. Accessed online on Sep. 24, 2021.*
Poggi A, et al. (Feb. 1995) Eur J Immunol. 25(2):369-376. (doi: 10.1002/eji.1830250210).*
Kinosada H, et al. (Jan. 3, 2017). PLoS Pathog. 13(1):e1006120. (doi: 10.1371/journal.ppat.1006120).*
Acris, "Monoclonal antibody to CD305/LAIR1-Purified", dated Aug. 12, 2015, retrieved from https://m1.acris-antibodies.com/pdf/SM6003.pdf.
EPO, Extended search report issued in European Application No. 18734005.4, dated Mar. 4, 2021.
EPO, Partial supplementary search report issued in European Application No. 18734005.4, dated Nov. 20, 2020.
International Preliminary Report on Patentability issued in International Application No. PCT/US2018/012040, dated Jul. 11, 2019.
International Search Report and Written Opinion issued in International Application No. PCT/US2018/012040, dated May 11, 2018.
Invitation to pay additional fees issued in International Application No. PCT/US2018/012040, dated Mar. 12, 2018.
Kang, Xunlei, et al. "The ITIM-containing receptor LAIR1 is essential for acute myeloid leukaemia development." *Nature Cell Biology* 17.5 (2015): 665-677.
Meyaard, Linde, et al. "LAIR-1, a novel inhibitory receptor expressed on human mononuclear leukocytes." *Immunity* 7.2 (1997): 283-290.
Zhang, Yuan, et al. "Expression of leukocyte-associated immunoglobulin-like receptor-1 (LAIR-1) on osteoclasts and its potential role in rheumatoid arthritis." *Clinics* 68.4 (2013): 475-481.

* cited by examiner

*Primary Examiner* — Robert S Landsman
(74) *Attorney, Agent, or Firm* — Parker Highlander, PLLC

(57) ABSTRACT

The present disclosure is directed to antibodies binding to LAIR 1 and their treating cancer, inflammation, immune-related diseases or transplantation.

10 Claims, 41 Drawing Sheets

Specification includes a Sequence Listing.

D25, (not included: aa26-29), <u>S30, I31, S32, A33, E34</u>, P35, G36, <u>T37, V38, I39, P40, L41</u>, G42, S43, H44, <u>V45, T46, F47</u>, (not included: aa48-52), V53, G54, V55, Q56, <u>T57, F58, R59, E61</u>, R62, E63, S64, R65, <u>S66, T67, Y68</u>, N69, D70, T71, E72, D73, V74, S75, Q76, A77, S78, P79, S80, E81, (not included: aa82-87), <u>I88</u>, D89, S90, V91, S92, E93, G94, N95, A96, <u>G97, P98, Y99, R100</u>, (not include C101), <u>I102, Y103, Y104, K105</u>, P106, P107, <u>K108, W109, S110</u>, E111, Q112, S113, D114, Y115, <u>L116, E117, L118, L119</u>.

| | Epitope bins | | | | | | | | | | | | | |
|---|---|---|---|---|---|---|---|---|---|---|---|---|---|---|
| | bin 1 | | | Bin 2 | bin 3 | | | | | bin 4 | bin 5 | | | |
| Pair-Wise | LA-56 | LA-89 | LA-141 | LA-235 | LA-192 | LA-199 | LA-61 | LA-111 | LA-245 | LA-94 | LA-6 | LA-171 | LA-145 | LA-29 |
| LA-56 | | | | - | - | - | - | - | - | - | - | - | - | - |
| LA-89 | | | | - | - | - | - | - | - | - | - | - | - | - |
| LA-141 | | | | - | - | - | - | - | - | - | - | - | - | - |
| LA-235 | - | - | - | | - | - | + | - | - | - | - | - | - | - |
| LA-192 | - | - | - | - | | | | | | - | - | - | - | - |
| LA-199 | - | - | - | - | | | | | | - | - | - | - | - |
| LA-61 | - | - | - | - | | | | | | + | - | - | - | - |
| LA-111 | - | - | - | - | | | | | | + | - | - | - | - |
| LA-245 | - | - | - | - | | | | | | + | - | - | - | - |
| LA-94 | - | - | - | - | - | - | - | + | + | | - | + | + | + |
| LA-6 | - | - | - | - | - | - | - | - | - | - | | | | |
| LA-171 | - | - | - | - | - | - | - | - | - | + | | | | |
| LA-145 | - | - | - | - | - | - | - | - | - | + | | | | |
| LA-29 | - | - | - | - | - | - | - | - | - | + | | | | |

FIG 45

| Pair-Wise | Epitope bins | | | | | | |
|---|---|---|---|---|---|---|---|
| | bin 1 | | | | | bin 2 | |
| | LA-121 | LA-142-1 | LA-142-2 | LA-259-1 | LA-259-2 | LA-258-2 | LA-258-3 |
| LA-121 | ▨ | ▨ | ▨ | ▨ | ▨ | - | - |
| LA-142-1 | ▨ | ▨ | ▨ | ▨ | ▨ | - | - |
| LA-142-2 | ▨ | ▨ | ▨ | ▨ | ▨ | - | - |
| LA-259-1 | ▨ | ▨ | ▨ | ▨ | ▨ | - | - |
| LA-259-2 | ▨ | ▨ | ▨ | ▨ | ▨ | - | - |
| LA-258-2 | - | - | - | - | - | ▨ | ▨ |
| LA-258-3 | - | - | - | - | - | ▨ | ▨ |

FIG 46

|  | Epitope bins | | | | | | |
| --- | --- | --- | --- | --- | --- | --- | --- |
|  | bin 1 | | | | | bin 2 | |
| Pair-Wise | LA-30 | LA-64 | LA-82 | LA-117 | LA-219 | LA-60 | LA-252 |
| LA-30 |  |  |  |  |  | - | - |
| LA-64 |  |  |  |  |  | - | - |
| LA-82 |  |  |  |  |  | - | - |
| LA-117 |  |  |  |  |  | - | - |
| LA-219 |  |  |  |  |  | - | - |
| LA-60 | - | - | - | - | - |  |  |
| LA-252 | - | - | - | - | - |  |  |

FIG 47

| Pair-Wise | Epitope bins | | | | | | |
|---|---|---|---|---|---|---|---|
| | bin 1 | | | | | | bin2 |
| | LA-35 | LA-37 | LA-87 | LA-95 | LA-155 | LA-222 | LA-151 |
| LA-35 | | | | | | | - |
| LA-37 | | | | | | | - |
| LA-87 | | | | | | | - |
| LA-95 | | | | | | | - |
| LA-155 | | | | | | | - |
| LA-222 | | | | | | | - |
| LA-151 | - | - | - | - | - | - | |

FIG 48

Collagen I coated

| Ab | GFP+% | Ab | GFP+% | Ab | GFP+% | Ab | GFP+% |
|---|---|---|---|---|---|---|---|
| LA-21 | 0.943 | LA-94 | 50.4 | LA-143 | 1.79 | LA-197 | 1.44 |
| LA-23 | 1.43 | LA-95 | 0.711 | LA-144 | 1.78 | LA-203 | 0.383 |
| LA-27 | 1.76 | LA-100 | 1.21 | LA-151 | 0.678 | LA-212 | 1.87 |
| LA-30 | 1.51 | LA-101 | 2.92 | LA-153 | 1.3 | LA-214 | 0.918 |
| LA-31 | 3.59 | LA-103 | 1.06 | LA-154 | 1.03 | LA-219 | 0.924 |
| LA-35 | 1.1 | LA-105 | 4.26 | LA-155 | 0.746 | LA-220 | 0.678 |
| LA-37 | 0.86 | LA-106 | 2.57 | LA-157 | 3.16 | LA-222 | 0.905 |
| LA-38 | 6.04 | LA-107 | 1.15 | LA-158 | 0.788 | LA-228 | 0.711 |
| LA-41 | 1.36 | LA-108 | 1.5 | LA-161 | 5.03 | LA-229 | 0.748 |
| LA-47 | 2.35 | LA-109 | 1.4 | LA-165 | 0.944 | LA-231 | 1.29 |
| LA-52 | 0.876 | LA-110 | 0.74 | LA-166 | 0.872 | LA-233 | 5.26 |
| LA-53 | 0.956 | LA-113 | 0.992 | LA-167 | 2.01 | LA-235 | 5.76 |
| LA-57 | 7.92 | LA-117 | 3.19 | LA-172 | 5.09 | LA-239 | 0.666 |
| LA-58 | 0.991 | LA-119 | 1.2 | LA-173 | 0.967 | LA-241 | 6.13 |
| LA-60 | 6.5 | LA-121 | 1.11 | LA-178 | 2.37 | LA-242 | 1.01 |
| LA-63 | 2.42 | LA-122 | 8.16 | LA-179 | 0.687 | LA-243 | 0.664 |
| LA-64 | 1.5 | LA-124 | 3.44 | LA-182 | 2.44 | LA-244 | 5.67 |
| LA-65 | 1.04 | LA-125 | 1.4 | LA-183 | 0.813 | LA-246 | 0.793 |
| LA-72 | 2.09 | LA-126 | 1.19 | LA-184 | 9.06 | LA-247 | 1 |
| LA-73 | 2.29 | LA-127 | 1.36 | LA-186 | 0.685 | LA-252 | 0.679 |
| LA-76 | 1.39 | LA-128 | 1.01 | LA-187 | 0.83 | LA-253 | 1.08 |
| LA-78 | 1.55 | LA-129 | 1.72 | LA-188 | 0.767 | LA-255 | 0.61 |
| LA-80 | 2.4 | LA-130 | 2.24 | LA-189 | 0.762 | LA-257 | 0.962 |
| LA-81 | 1.58 | LA-132 | 1.24 | LA-191 | 0.751 | LA-258 | 1.2 |
| LA-82 | 1.1 | LA-134 | 1.2 | LA-192 | 63.2 | LA-259 | 0.757 |
| LA-85 | 2.16 | LA-135 | 1.71 | LA-194 | 0.718 | collagen I-ctrl | 31.3 |
| LA-87 | 1.45 | LA-142 | 0.607 | LA-196 | 6.62 | negative-ctrl | 2.37 |

FIG 53B

K562 coculture

| Ab | GFP+% | Ab | GFP+% | Ab | GFP+% | Ab | GFP+% |
|---|---|---|---|---|---|---|---|
| LA-21 | 0.874 | LA-81 | 1.28 | LA-143 | 2.75 | LA-219 | 2.11 |
| LA-23 | 1.86 | LA-87 | 0.844 | LA-144 | 4.03 | LA-220 | 4.27 |
| LA-27 | 9.75 | LA-94 | 24.6 | LA-151 | 1.95 | LA-222 | 0.792 |
| LA-30 | 1.94 | LA-95 | 0.595 | LA-154 | 0.696 | LA-228 | 3.59 |
| LA-35 | 1.13 | LA-107 | 9.63 | LA-155 | 0.867 | LA-229 | 1.4 |
| LA-37 | 1.08 | LA-108 | 2.36 | LA-165 | 4.92 | LA-231 | 1.05 |
| LA-38 | 8.8 | LA-110 | 0.518 | LA-166 | 2.28 | LA-235 | 19.0 |
| LA-41 | 5.48 | LA-113 | 0.495 | LA-179 | 1.83 | LA-239 | 1.39 |
| LA-47 | 18.2 | LA-119 | 1.98 | LA-183 | 1.05 | LA-241 | 5.03 |
| LA-52 | 1.16 | LA-121 | 0.891 | LA-184 | 7.06 | LA-242 | 1.88 |
| LA-53 | 1.86 | LA-125 | 1.8 | LA-186 | 7.91 | LA-246 | 2.96 |
| LA-58 | 1.14 | LA-126 | 1.29 | LA-187 | 0.891 | LA-247 | 1.33 |
| LA-63 | 1.31 | LA-127 | 1.2 | LA-189 | 1.31 | LA-252 | 0.698 |
| LA-64 | 2.29 | LA-128 | 2.3 | LA-192 | 18.7 | LA-255 | 3.9 |
| LA-72 | 3.39 | LA-129 | 1.32 | LA-194 | 0.466 | LA-258 | 3.19 |
| LA-73 | 3.1 | LA-132 | 0.976 | LA-197 | 2.55 | LA-259 | 0.569 |
| LA-76 | 1.66 | LA-134 | 0.867 | LA-203 | 1.65 | Collagen I-ctrl | 42.5 |
| LA-78 | 0.693 | LA-142 | 0.632 | LA-214 | 1.31 | negative-ctrl | 2.37 |

FIG 53C ized monoclonal antibody or an antigen-binding fragment thereof that binds specifically to LAIR1. In certain embodiments, the antibody or antigen-binding fragment, when bound to LAIR1, modulates the activity of LAIR1. In certain embodiments, the antibody or antigen-binding fragment, when bound to LAIR1, activates LAIR1. In certain embodiments, the antibody or antigen-binding fragment, when bound to LAIR1, suppresses activation of LAIR1. In certain embodiments, the antibody or antigen-binding fragment, when bound to LAIR1, specifically blocks binding of collagen Ito LAIR1.

SEQUENCE LISTING

```
<160> NUMBER OF SEQ ID NOS: 535

<210> SEQ ID NO 1
<211> LENGTH: 113
<212> TYPE: PRT
<213> ORGANISM: Artificial sequence
<220> FEATURE:
<223> OTHER INFORMATION: Synthetic peptide

<400> SEQUENCE: 1

Ser Ser Ser Val Glu Glu Ser Gly Gly Arg Leu Val Thr Pro Gly Thr
1               5                   10                  15

Pro Leu Thr Leu Thr Cys Thr Val Ser Gly Phe Ser Leu Ser Ala Tyr
            20                  25                  30

Trp Val Gly Trp Val Arg Gln Ala Pro Gly Lys Gly Leu Glu Tyr Ile
        35                  40                  45

Gly Phe Val Asp Val Asp Ile Tyr Tyr Ala Ser Trp Ala Arg Gly Arg
    50                  55                  60

Phe Thr Ile Ser Lys Thr Ser Ser Thr Val Asp Leu Ile Leu Thr
65                  70                  75                  80

Ser Pro Thr Met Glu Asp Thr Ala Thr Tyr Phe Cys Val Arg Met Ser
                85                  90                  95
```

```
Tyr Asn Ala Met Asp Leu Trp Gly Pro Gly Thr Leu Val Thr Ile Ser
            100                 105                 110

Ser

<210> SEQ ID NO 2
<211> LENGTH: 111
<212> TYPE: PRT
<213> ORGANISM: Artificial sequence
<220> FEATURE:
<223> OTHER INFORMATION: Synthetic peptide

<400> SEQUENCE: 2

Glu Leu Asp Leu Thr Gln Thr Ala Ser Ser Val Ser Ala Ala Val Gly
1               5                   10                  15

Asp Thr Val Thr Ile Asn Cys Gln Ser Ser Glu Ser Val Tyr Lys Asp
            20                  25                  30

Asn Phe Leu Ser Trp Tyr Gln Gln Lys Pro Gly Gln Pro Pro Lys Leu
        35                  40                  45

Leu Ile Tyr Arg Ala Ser Thr Leu Ala Ser Gly Val Pro Ser Arg Phe
    50                  55                  60

Lys Gly Ser Gly Ser Gly Ser Gln Phe Thr Leu Thr Ile Ser Asp Val
65                  70                  75                  80

Val Cys Asp Asp Ala Ala Thr Tyr Tyr Cys Ser Gly Tyr Arg Asn Ser
                85                  90                  95

His Asp Gly Leu Pro Phe Gly Gly Gly Thr Glu Val Glu Ile Lys
            100                 105                 110

<210> SEQ ID NO 3
<211> LENGTH: 8
<212> TYPE: PRT
<213> ORGANISM: Artificial sequence
<220> FEATURE:
<223> OTHER INFORMATION: Synthetic peptide

<400> SEQUENCE: 3

Gly Phe Ser Leu Ser Ala Tyr Trp
1               5

<210> SEQ ID NO 4
<211> LENGTH: 7
<212> TYPE: PRT
<213> ORGANISM: Artificial sequence
<220> FEATURE:
<223> OTHER INFORMATION: Synthetic peptide

<400> SEQUENCE: 4

Val Asp Val Asp Ile Tyr Tyr
1               5

<210> SEQ ID NO 5
<211> LENGTH: 9
<212> TYPE: PRT
<213> ORGANISM: Artificial sequence
<220> FEATURE:
<223> OTHER INFORMATION: Synthetic peptide

<400> SEQUENCE: 5

Arg Met Ser Tyr Asn Ala Met Asp Leu
1               5

<210> SEQ ID NO 6
<211> LENGTH: 8
<212> TYPE: PRT
```

```
<213> ORGANISM: Artificial sequence
<220> FEATURE:
<223> OTHER INFORMATION: Synthetic peptide

<400> SEQUENCE: 6

Gln Ser Val Tyr Asn Lys Asn Gln
1               5

<210> SEQ ID NO 7
<211> LENGTH: 10
<212> TYPE: PRT
<213> ORGANISM: Artificial sequence
<220> FEATURE:
<223> OTHER INFORMATION: Synthetic peptide

<400> SEQUENCE: 7

Leu Gly Glu Tyr Thr Gly Asn Ile Tyr Thr
1               5                   10

<210> SEQ ID NO 8
<211> LENGTH: 339
<212> TYPE: DNA
<213> ORGANISM: Artificial sequence
<220> FEATURE:
<223> OTHER INFORMATION: Synthetic oligonucleotide

<400> SEQUENCE: 8
agcagttcgg tggaggagtc cggggggtcgc ctggtcacgc ctgggacacc cctgacactc      60
acctgcacag tctctggatt ctccctcagt gcctactggg tgggctgggt ccgccaggct     120
ccagggaagg gactgaaata catcggattc gttgatgtcg atatatacta cgcgagttgg     180
gcgagaggcc gattcaccat ctccaaaacc tcgtcgacca cggtggatct gatattgacc     240
agtccgacaa tggaggacac ggccacctat ttctgtgtta gaatgtctta caatgcaatg     300
gacctctggg gcccagggac cctcgtcacc atctcctca                            339

<210> SEQ ID NO 9
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 9
gagctcgatc tgacccagac tgcatcgtcc gtgtctgcag ctgtgggaga cacagtcacc      60
atcaattgcc agtccagtga gagtgtttat aaggacaact tcttatcctg gtatcagcag     120
aaaccagggc agcctcccaa gctcctgatc tacagggcat ccactctggc atctggggtc     180
ccttcgcggt tcaaaggcag tggatctggg tcacagttca ctctcaccat cagtgatgtg     240
gtgtgtgacg atgctgccac ttattactgt tcagggtaca gaaatagtca tgatggtctt     300
cctttcggcg agggaccga ggtggaaatc aaa                                   333

<210> SEQ ID NO 10
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 10
ggattctccc tcagtgccta ctgg                                             24
```

<210> SEQ ID NO 11
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 11
gttgatgtcg atatatacta c                                              21

<210> SEQ ID NO 12
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 12
agaatgtctt acaatgcaat ggacctc                                        27

<210> SEQ ID NO 13
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 13
caaagtgttt ataataagaa ccaa                                           24

<210> SEQ ID NO 14
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 14
ctaggagaat atactggtaa tatatatact                                     30

<210> SEQ ID NO 15
<211> LENGTH: 109
<212> TYPE: PRT
<213> ORGANISM: Artificial sequence
<220> FEATURE:
<223> OTHER INFORMATION: Synthetic peptide

<400> SEQUENCE: 15

Gln Ser Val Lys Glu Ser Gly Gly Arg Leu Val Thr Pro Gly Thr Pro
1               5                   10                  15

Leu Thr Leu Thr Cys Thr Val Ser Gly Phe Ser Leu Ser Ser Asn Ala
            20                  25                  30

Ile Ser Trp Val Arg Gln Ala Pro Gly Lys Gly Leu Glu Trp Ile Gly
        35                  40                  45

Tyr Ile Tyr Gly Asp Gly Arg Thr Phe Tyr Ala Ser Trp Ala Lys Gly
    50                  55                  60

Arg Phe Thr Ile Ser Lys Thr Ser Thr Val Asp Leu Lys Met Thr
65                  70                  75                  80

Ser Leu Thr Ser Glu Asp Thr Ala Thr Tyr Phe Cys Ile Lys Ser Leu
                85                  90                  95

His Leu Trp Gly Pro Gly Thr Leu Val Thr Ile Ser Ser
            100                 105

<210> SEQ ID NO 16
<211> LENGTH: 110
<212> TYPE: PRT
<213> ORGANISM: Artificial sequence
<220> FEATURE:
<223> OTHER INFORMATION: Synthetic peptide

<400> SEQUENCE: 16

```
Glu Leu Asp Met Thr Gln Thr Ala Ser Pro Val Ser Ala Ala Val Gly
1               5                   10                  15

Gly Thr Val Thr Ile Asn Cys Gln Ser Ser Gln Ser Val Tyr Asn Lys
            20                  25                  30

Asn Gln Leu Phe Trp Tyr Gln Gln Lys Pro Gly Gln Pro Pro Lys Leu
        35                  40                  45

Leu Ile Tyr Asp Ala Ser Thr Leu Ala Ser Gly Val Pro Ser Arg Tyr
    50                  55                  60

Lys Gly Ser Gly Ser Gly Thr Gln Phe Thr Leu Thr Ile Ser Gly Val
65                  70                  75                  80

Gln Cys Asp Asp Ala Ala Thr Tyr Tyr Cys Leu Gly Glu Tyr Thr Gly
                85                  90                  95

Asn Ile Tyr Thr Phe Gly Glu Gly Thr Glu Val Val Val Lys
            100                 105                 110
```

<210> SEQ ID NO 17
<211> LENGTH: 8
<212> TYPE: PRT
<213> ORGANISM: Artificial sequence
<220> FEATURE:
<223> OTHER INFORMATION: Synthetic peptide

<400> SEQUENCE: 17

```
Gly Phe Ser Leu Ser Ser Asn Ala
1               5
```

<210> SEQ ID NO 18
<211> LENGTH: 7
<212> TYPE: PRT
<213> ORGANISM: Artificial sequence
<220> FEATURE:
<223> OTHER INFORMATION: Synthetic peptide

<400> SEQUENCE: 18

```
Ile Tyr Gly Asp Gly Arg Thr
1               5
```

<210> SEQ ID NO 19
<211> LENGTH: 6
<212> TYPE: PRT
<213> ORGANISM: Artificial sequence
<220> FEATURE:
<223> OTHER INFORMATION: Synthetic peptide

<400> SEQUENCE: 19

```
Ile Lys Ser Leu His Leu
1               5
```

<210> SEQ ID NO 20
<211> LENGTH: 6
<212> TYPE: PRT
<213> ORGANISM: Artificial sequence
<220> FEATURE:
<223> OTHER INFORMATION: Synthetic peptide

<400> SEQUENCE: 20

Gln Ser Ile Tyr Ser Asn
1               5

<210> SEQ ID NO 21
<211> LENGTH: 13
<212> TYPE: PRT
<213> ORGANISM: Artificial sequence
<220> FEATURE:
<223> OTHER INFORMATION: Synthetic peptide

<400> SEQUENCE: 21

Gln Cys Thr Tyr Asp Gly Ile Ser Tyr Val Pro Ser Ser
1               5                   10

<210> SEQ ID NO 22
<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 22
cagtcggtga aggagtccgg gggtcgcctg gtcacgcctg ggacacccct gacactcacc      60
tgcaccgtct ctggattctc cctcagtagc aatgcaataa gctgggtccg ccaggctcca     120
gggaaggggc tggagtggat cggatatatt tatggtgatg gtcgtacatt ctacgcgagc     180
tgggcgaaag gccgattcac catctccaaa acctcgacca cggtggatct gaaaatgacc     240
agtctgacgt ccgaggacac ggccacctat ttctgtatca aatcactgca cttgtggggc     300
ccaggcaccc tggtcaccat ctcttca                                        327

<210> SEQ ID NO 23
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 23
gagctcgata tgacccagac tgcatccccc gtgtctgcgg ctgtgggagg cacagtcacc      60
atcaattgcc agtccagtca agtgtttat aataagaacc aattattctg gtatcagcag     120
aaaccagggc agcctcctaa gctcctgatc tacgatgcat ccactctggc atctggggtc     180
ccatcgcggt acaaaggcag tggatctggg acacagttca ctctcaccat cagcggcgtg     240
cagtgtgacg atgctgccac ttactattgt ctaggagaat atactggtaa tatatatact     300
ttcggcgaag ggaccgaggt ggtggtcaaa                                     330

<210> SEQ ID NO 24
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 24
ggattctccc tcagtagcaa tgca                                            24

<210> SEQ ID NO 25
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 25
atttatggtg atggtcgtac a                                    21

<210> SEQ ID NO 26
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 26
atcaaatcac tgcacttg                                        18

<210> SEQ ID NO 27
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 27
cagagcattt acagcaat                                        18

<210> SEQ ID NO 28
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 28
caatgtactt atgatggtat tagttatgtc cccagttct                 39

<210> SEQ ID NO 29
<211> LENGTH: 123
<212> TYPE: PRT
<213> ORGANISM: Artificial sequence
<220> FEATURE:
<223> OTHER INFORMATION: Synthetic peptide

<400> SEQUENCE: 29

Ser Ser Ser Val Glu Glu Ser Gly Gly Gly Leu Val Gln Pro Glu Gly
1               5                   10                  15

Ser Leu Thr Leu Thr Cys Thr Ala Ser Gly Phe Ser Phe Ser Ser Arg
            20                  25                  30

Tyr Tyr Met Cys Trp Val Arg Gln Ala Pro Gly Lys Gly Leu Glu Trp
        35                  40                  45

Ile Ala Cys Ile Tyr Asn Gly Asp Gly Ser Arg Tyr Tyr Ala Ser Trp
    50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Val Arg Asp Arg His Thr Ala Phe Val Asp Tyr Gly Asp Asp Asn Leu
            100                 105                 110

Trp Gly Pro Gly Thr Leu Val Thr Val Ser Ser
        115                 120

<210> SEQ ID NO 30
<211> LENGTH: 111
<212> TYPE: PRT

```
<213> ORGANISM: Artificial sequence
<220> FEATURE:
<223> OTHER INFORMATION: Synthetic peptide

<400> SEQUENCE: 30

Glu Leu Asp Leu Thr Gln Thr Pro Ala Ser Val Ser Glu Pro Val Gly
1               5                   10                  15

Gly Thr Val Thr Ile Lys Cys Gln Ala Ser Gln Ser Ile Tyr Ser Asn
            20                  25                  30

Leu Ala Trp Tyr Gln Gln Lys Pro Gly Gln Pro Pro Lys Leu Leu Ile
        35                  40                  45

Tyr Arg Ala Ser Thr Leu Ala Ser Gly Val Pro Ser Arg Phe Lys Gly
    50                  55                  60

Ser Gly Ala Gly Thr Glu Phe Thr Leu Thr Ile Ser Asp Leu Glu Cys
65                  70                  75                  80

Ala Asp Ala Ala Thr Tyr Tyr Cys Gln Cys Thr Tyr Asp Gly Ile Ser
                85                  90                  95

Tyr Val Pro Ser Ser Phe Gly Gly Thr Glu Val Val Val Lys
            100                 105                 110

<210> SEQ ID NO 31
<211> LENGTH: 9
<212> TYPE: PRT
<213> ORGANISM: Artificial sequence
<220> FEATURE:
<223> OTHER INFORMATION: Synthetic peptide

<400> SEQUENCE: 31

Gly Phe Ser Phe Ser Ser Arg Tyr Tyr
1               5

<210> SEQ ID NO 32
<211> LENGTH: 7
<212> TYPE: PRT
<213> ORGANISM: Artificial sequence
<220> FEATURE:
<223> OTHER INFORMATION: Synthetic peptide

<400> SEQUENCE: 32

Ile Tyr Asn Gly Asp Gly Ser
1               5

<210> SEQ ID NO 33
<211> LENGTH: 16
<212> TYPE: PRT
<213> ORGANISM: Artificial sequence
<220> FEATURE:
<223> OTHER INFORMATION: Synthetic peptide

<400> SEQUENCE: 33

Val Arg Asp Arg His Thr Ala Phe Val Asp Tyr Gly Asp Asp Asn Leu
1               5                   10                  15

<210> SEQ ID NO 34
<211> LENGTH: 8
<212> TYPE: PRT
<213> ORGANISM: Artificial sequence
<220> FEATURE:
<223> OTHER INFORMATION: Synthetic peptide

<400> SEQUENCE: 34

His Ser Val Tyr Asn Ala Asn Gln
1               5
```

```
<210> SEQ ID NO 35
<211> LENGTH: 10
<212> TYPE: PRT
<213> ORGANISM: Artificial sequence
<220> FEATURE:
<223> OTHER INFORMATION: Synthetic peptide

<400> SEQUENCE: 35

Leu Gly Glu Tyr Ser Gly Asn Ile Tyr Val
1               5                   10

<210> SEQ ID NO 36
<211> LENGTH: 369
<212> TYPE: DNA
<213> ORGANISM: Artificial sequence
<220> FEATURE:
<223> OTHER INFORMATION: Synthetic oligonucleotide

<400> SEQUENCE: 36
agcagttcgg tggaggagtc cgggggaggc ctggtccagc ctgagggatc cctgacactc     60
acctgcacag cttctggatt ctccttcagt agcagatact acatgtgctg ggtccgccag    120
gctccaggga aggggctgga gtggatcgca tgcatttata atggtgatgg cagcagatac    180
tacgcgagct gggcgaaagg ccgattcacc atctccaaaa cctcgtcgac cacggtgact    240
ctgcaaatga ccagtctgac agccgcggac acggccacct atttctgtgt gagagatcgc    300
catactgctt ttgttgatta tggtgatgat aacttgtggg gcccaggcac cctggtcacc    360
gtctcttca                                                            369

<210> SEQ ID NO 37
<211> LENGTH: 369
<212> TYPE: DNA
<213> ORGANISM: Artificial sequence
<220> FEATURE:
<223> OTHER INFORMATION: Synthetic oligonucleotide

<400> SEQUENCE: 37
agcagttcgg tggaggagtc cgggggaggc ctggtccagc ctgagggatc cctgacactc     60
acctgcacag cttctggatt ctccttcagt agcagatact acatgtgctg ggtccgccag    120
gctccaggga aggggctgga gtggatcgca tgcatttata atggtgatgg cagcagatac    180
tacgcgagct gggcgaaagg ccgattcacc atctccaaaa cctcgtcgac cacggtgact    240
ctgcaaatga ccagtctgac agccgcggac acggccacct atttctgtgt gagagatcgc    300
catactgctt ttgttgatta tggtgatgat aacttgtggg gcccaggcac cctggtcacc    360
gtctcttca                                                            369

<210> SEQ ID NO 38
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 38
ggattctcct tcagtagcag atactac                                         27

<210> SEQ ID NO 39
<211> LENGTH: 21
<212> TYPE: DNA
<213> ORGANISM: Artificial sequence
<220> FEATURE:
```

-continued

<223> OTHER INFORMATION: Synthetic oligonucleotide

<400> SEQUENCE: 39
atttataatg gtgatggcag c                                              21

<210> SEQ ID NO 40
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 40
gtgagagatc gccatactgc ttttgttgat tatggtgatg ataacttg                 48

<210> SEQ ID NO 41
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 41
cacagtgttt ataatgccaa ccaa                                           24

<210> SEQ ID NO 42
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 42
ctaggagaat atagtggtaa tatctatgtt                                     30

<210> SEQ ID NO 43
<211> LENGTH: 109
<212> TYPE: PRT
<213> ORGANISM: Artificial sequence
<220> FEATURE:
<223> OTHER INFORMATION: Synthetic peptide

<400> SEQUENCE: 43

Gln Ser Leu Glu Glu Ser Gly Gly Arg Leu Val Lys Pro Asp Glu Ser
1               5                   10                  15

Leu Thr Leu Thr Cys Thr Val Ser Gly Phe Ser Leu Ser Ser Asn Ala
            20                  25                  30

Met Ser Trp Val Arg Gln Ala Pro Gly Lys Gly Leu Glu Trp Ile Gly
        35                  40                  45

Tyr Ile Tyr Gly Asp Gly Arg Thr Phe Tyr Ala Asn Trp Ala Lys Gly
    50                  55                  60

Arg Ile Thr Ile Ser Arg Thr Ser Thr Val Asp Leu Lys Met Thr
65                  70                  75                  80

Ser Leu Arg Thr Glu Asp Thr Ala Thr Tyr Phe Cys Val Lys Ser Leu
            85                  90                  95

Ile Leu Trp Gly Pro Gly Thr Leu Val Thr Ile Ser Ser
            100                 105

<210> SEQ ID NO 44
<211> LENGTH: 110
<212> TYPE: PRT
<213> ORGANISM: Artificial sequence
<220> FEATURE:

<223> OTHER INFORMATION: Synthetic peptide

<400> SEQUENCE: 44

Glu Leu Asp Met Thr Gln Thr Pro Ser Pro Val Ser Ala Ala Val Gly
1               5                   10                  15

Gly Thr Val Thr Ile Asn Cys Gln Ser Ser His Ser Val Tyr Asn Ala
            20                  25                  30

Asn Gln Leu Tyr Trp Tyr Gln Gln Lys Pro Gly Gln Pro Pro Lys Leu
        35                  40                  45

Leu Ile Tyr Asp Ala Ser Thr Leu Ala Ser Gly Val Pro Ser Arg Phe
    50                  55                  60

Lys Gly Ser Gly Ser Gly Thr Gln Phe Thr Leu Thr Ile Ser Gly Val
65                  70                  75                  80

Gln Cys Asp Asp Ala Ala Thr Tyr Tyr Cys Leu Gly Glu Tyr Ser Gly
                85                  90                  95

Asn Ile Tyr Val Phe Gly Glu Gly Thr Glu Val Glu Ile Asn
            100                 105                 110

<210> SEQ ID NO 45
<211> LENGTH: 8
<212> TYPE: PRT
<213> ORGANISM: Artificial sequence
<220> FEATURE:
<223> OTHER INFORMATION: Synthetic peptide

<400> SEQUENCE: 45

Gly Phe Ser Leu Ser Ser Asn Ala
1               5

<210> SEQ ID NO 46
<211> LENGTH: 7
<212> TYPE: PRT
<213> ORGANISM: Artificial sequence
<220> FEATURE:
<223> OTHER INFORMATION: Synthetic peptide

<400> SEQUENCE: 46

Ile Tyr Gly Asp Gly Arg Thr
1               5

<210> SEQ ID NO 47
<211> LENGTH: 6
<212> TYPE: PRT
<213> ORGANISM: Artificial sequence
<220> FEATURE:
<223> OTHER INFORMATION: Synthetic peptide

<400> SEQUENCE: 47

Val Lys Ser Leu Ile Leu
1               5

<210> SEQ ID NO 48
<211> LENGTH: 6
<212> TYPE: PRT
<213> ORGANISM: Artificial sequence
<220> FEATURE:
<223> OTHER INFORMATION: Synthetic peptide

<400> SEQUENCE: 48

Gln Ser Ile Gly Ser Asn
1               5

<210> SEQ ID NO 49

```
<211> LENGTH: 15
<212> TYPE: PRT
<213> ORGANISM: Artificial sequence
<220> FEATURE:
<223> OTHER INFORMATION: Synthetic peptide

<400> SEQUENCE: 49

Gln Cys Thr Tyr Gly Ser Ser Asn Asn Asn Asn Tyr Gly Asp Pro
1               5                   10                  15

<210> SEQ ID NO 50
<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 50
cagtcgctgg aggagtccgg gggtcgcctg gtaaagcctg acgaatccct gacactcacc      60
tgcaccgtct ctggattctc cctcagtagc aatgcaatga gctgggtccg ccaggctcca     120
gggaaggggc tggagtggat cggatacatt tatggtgatg gtcgcacatt ctacgcgaac     180
tgggcaaaag gccgaatcac catctccaga acctcaacca cggtggatct gaaaatgacc     240
agtctgagaa ccgaggacac ggccacctat ttctgtgtca atcacttat cttgtggggc      300 ccaggcaccc tggtcaccat ctcttca                                         327

<210> SEQ ID NO 51
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 51
gagctcgata tgacccagac tccatccccc gtgtctgcgg ctgtgggagg cacagtcacc      60
atcaattgcc agtccagtca cagtgtttat aatgccaacc aattatactg gtatcagcag     120
aaaccagggc agcctcccaa gctcctgatc tatgatgcat ccactctggc atctggggtc     180
ccatcgcggt tcaaaggcag tggatctggg acacagttca ctctcaccat cagtggcgtg     240
cagtgtgacg atgctgccac ttactactgt ctaggagaat atagtggtaa tatctatgtt     300
ttcggcgaag ggaccgaggt ggaaatcaac                                      330

<210> SEQ ID NO 52
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 52
ggattctccc tcagtagcaa tgca                                             24

<210> SEQ ID NO 53
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 53
atttatggtg atggtcgcac a                                                21
```

<210> SEQ ID NO 54
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 54
gtcaaatcac ttatcttg                                                 18

<210> SEQ ID NO 55
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 55
cagagcattg gtagtaat                                                 18

<210> SEQ ID NO 56
<211> LENGTH: 45
<212> TYPE: DNA
<213> ORGANISM: Artificial sequence
<220> FEATURE:
<223> OTHER INFORMATION: Synthetic oligonucleotide

<400> SEQUENCE: 56
caatgcactt atggtagtag taataataat aattatggtg atcct                   45

<210> SEQ ID NO 57
<211> LENGTH: 114
<212> TYPE: PRT
<213> ORGANISM: Artificial sequence
<220> FEATURE:
<223> OTHER INFORMATION: Synthetic peptide

<400> SEQUENCE: 57

Ser Ser Ser Val Glu Glu Ser Glu Gly Arg Leu Val Thr Pro Gly Thr
1               5                   10                  15

Pro Leu Thr Leu Thr Cys Thr Val Ser Gly Phe Ser Leu Ser Ser Tyr
            20                  25                  30

Thr Met Gly Trp Val Arg Gln Ala Pro Gly Glu Gly Leu Glu Trp Ile
        35                  40                  45

Gly Thr Thr Ser Asn Asp Gly Ser Thr Tyr Tyr Ala Ser Trp Ala Lys
    50                  55                  60

Gly Arg Phe Thr Ile Ser Lys Thr Ser Ser Thr Thr Val Asp Leu Met
65                  70                  75                  80

Met Thr Ser Leu Thr Thr Glu Asp Thr Ala Thr Tyr Phe Cys Val Arg
                85                  90                  95

Gly Thr Asn Ile Arg Ser Leu Trp Gly Pro Gly Thr Leu Val Thr Ile
            100                 105                 110

Ser Ser

<210> SEQ ID NO 58
<211> LENGTH: 113
<212> TYPE: PRT
<213> ORGANISM: Artificial sequence
<220> FEATURE:
<223> OTHER INFORMATION: Synthetic peptide

<400> SEQUENCE: 58

```
Glu Leu Val Met Thr Gln Thr Pro Ala Ser Val Glu Ala Ala Val Gly
1               5                   10                  15

Gly Thr Val Thr Ile Lys Cys Gln Ala Ser Gln Ser Ile Gly Ser Asn
            20                  25                  30

Leu Ala Trp Tyr Gln Gln Lys Pro Gly Gln Pro Pro Lys Leu Leu Ile
            35                  40                  45

Tyr Leu Ala Ser Ala Leu Ala Ser Gly Val Ser Ser Arg Phe Lys Gly
    50                  55                  60

Ser Gly Ser Gly Ser Asp Phe Thr Leu Thr Ile Ser Asp Leu Glu Cys
65              70                  75                  80

Ala Asp Ala Ala Thr Tyr Tyr Cys Gln Cys Thr Tyr Gly Ser Ser Asn
                85                  90                  95

Asn Asn Asn Tyr Gly Asp Pro Phe Gly Gly Gly Thr Glu Val Glu Ile
                100                 105                 110

Lys
```

<210> SEQ ID NO 59
<211> LENGTH: 8
<212> TYPE: PRT
<213> ORGANISM: Artificial sequence
<220> FEATURE:
<223> OTHER INFORMATION: Synthetic peptide

<400> SEQUENCE: 59

```
Gly Phe Ser Leu Ser Ser Tyr Thr
1               5
```

<210> SEQ ID NO 60
<211> LENGTH: 7
<212> TYPE: PRT
<213> ORGANISM: Artificial sequence
<220> FEATURE:
<223> OTHER INFORMATION: Synthetic peptide

<400> SEQUENCE: 60

```
Thr Ser Asn Asp Gly Ser Thr
1               5
```

<210> SEQ ID NO 61
<211> LENGTH: 9
<212> TYPE: PRT
<213> ORGANISM: Artificial sequence
<220> FEATURE:
<223> OTHER INFORMATION: Synthetic peptide

<400> SEQUENCE: 61

```
Val Arg Gly Thr Asn Ile Arg Ser Leu
1               5
```

<210> SEQ ID NO 62
<211> LENGTH: 7
<212> TYPE: PRT
<213> ORGANISM: Artificial sequence
<220> FEATURE:
<223> OTHER INFORMATION: Synthetic peptide

<400> SEQUENCE: 62

```
Pro Ser Val Tyr Thr Asn Asn
1               5
```

<210> SEQ ID NO 63
<211> LENGTH: 11
<212> TYPE: PRT

<213> ORGANISM: Artificial sequence
<220> FEATURE:
<223> OTHER INFORMATION: Synthetic peptide

<400> SEQUENCE: 63

Ala Gly Ala Tyr Leu Ser Asp Ser Asp Thr Thr
1               5                   10

<210> SEQ ID NO 64
<211> LENGTH: 342
<212> TYPE: DNA
<213> ORGANISM: Artificial sequence
<220> FEATURE:
<223> OTHER INFORMATION: Synthetic oligonucleotide

<400> SEQUENCE: 64
agcagttcgg tggaggagtc cgagggtcgc ctggtcacgc ctgggacacc cctgacactc      60
acctgcacag tctctggatt ctccctcagt agctacacca tgggctgggt ccgccaggct     120
ccaggggagg ggctggaatg gatcggaacc actagtaatg atggtagtac atactacgcg     180
agctgggcga aaggccgatt caccatctcc aaaacctcgt cgaccacggt ggatctgatg     240
atgaccagtc tgacaaccga ggacacggcc acctatttct gtgtcagagg tacgaatatt     300
agaagcttgt ggggcccagg caccctggtc accatctcct ca                        342

<210> SEQ ID NO 65
<211> LENGTH: 339
<212> TYPE: DNA
<213> ORGANISM: Artificial sequence
<220> FEATURE:
<223> OTHER INFORMATION: Synthetic oligonucleotide

<400> SEQUENCE: 65
gagctcgtga tgacccagac accagcctcc gtggaggcag ctgtgggagg cacagtcacc      60
atcaagtgcc aggccagtca gagcattggt agtaatttag cctggtatca gcagaaacca     120
gggcagcctc ccaagctcct gatctatctg catctgctc tggcatctgg ggtctcatcg      180
cggttcaaag gcagtggatc tgggtcagat ttcactctca ccatcagcga cctggagtgt     240
gccgatgctg ccacttacta ctgtcaatgc acttatggta gtagtaataa taataattat     300
ggtgatcctt tcggcggagg gaccgaggtg gaaatcaaa                             339

<210> SEQ ID NO 66
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 66
ggattctccc tcagtagcta cacc                                             24

<210> SEQ ID NO 67
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 67
actagtaatg atggtagtac a                                                21

<210> SEQ ID NO 68

```
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 68
gtcagaggta cgaatattag aagcttg                                           27

<210> SEQ ID NO 69
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 69
ccgagtgttt atactaacaa c                                                 21

<210> SEQ ID NO 70
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 70
gcaggcgctt acctcagtga tagtgatact act                                    33

<210> SEQ ID NO 71
<211> LENGTH: 119
<212> TYPE: PRT
<213> ORGANISM: Artificial sequence
<220> FEATURE:
<223> OTHER INFORMATION: Synthetic peptide

<400> SEQUENCE: 71
```

Glu Gln Ser Leu Glu Glu Ser Gly Gly Arg Leu Val Thr Pro Gly Thr
1               5                   10                  15

Pro Leu Thr Leu Thr Cys Thr Ala Ser Gly Phe Ser Leu Ser Ser Tyr
                20                  25                  30

Tyr Met Thr Trp Val Arg Gln Ala Pro Gly Lys Gly Leu Glu Trp Ile
            35                  40                  45

Gly Tyr Met His Thr Gly Gly Val Val Tyr Ala Ser Trp Ala Thr
        50                  55                  60

Gly Arg Phe Thr Ile Ser Arg Thr Ser Thr Thr Val Asp Leu Lys Ile
65                  70                  75                  80

Thr Ser Pro Thr Thr Glu Asp Thr Ala Thr Tyr Phe Cys Ala Arg Ser
                85                  90                  95

His Ala Gly Tyr Ser Thr Ile Asn Arg Leu Asp Leu Trp Gly Val Gly
            100                 105                 110

Thr Leu Val Thr Ile Ser Ser
        115

```
<210> SEQ ID NO 72
<211> LENGTH: 110
<212> TYPE: PRT
<213> ORGANISM: Artificial sequence
<220> FEATURE:
<223> OTHER INFORMATION: Synthetic peptide

<400> SEQUENCE: 72
```

Glu Leu Asp Leu Thr Gln Thr Pro Ser Ser Val Ser Ala Ala Val Gly

```
1               5                   10                  15
Gly Thr Val Thr Ile Ser Cys Gln Ser Ser Pro Ser Val Tyr Thr Asn
                20                  25                  30

Asn Leu Ser Trp Phe Gln Gln Lys Pro Gly Gln Pro Pro Lys Leu Leu
            35                  40                  45

Ile Tyr Asp Ala Ser Lys Leu Glu Ser Gly Val Pro Ser Arg Phe Arg
        50                  55                  60

Gly Ser Gly Ser Gly Thr Gln Phe Thr Leu Thr Ile Ser Asp Val Gln
65                  70                  75                  80

Cys Asp Asp Ala Ala Thr Tyr Tyr Cys Ala Gly Ala Tyr Leu Ser Asp
                85                  90                  95

Ser Asp Thr Thr Phe Gly Gly Gly Thr Glu Leu Glu Ile Lys
                100                 105                 110
```

<210> SEQ ID NO 73
<211> LENGTH: 8
<212> TYPE: PRT
<213> ORGANISM: Artificial sequence
<220> FEATURE:
<223> OTHER INFORMATION: Synthetic peptide

<400> SEQUENCE: 73

```
Gly Phe Ser Leu Ser Ser Tyr Tyr
1               5
```

<210> SEQ ID NO 74
<211> LENGTH: 7
<212> TYPE: PRT
<213> ORGANISM: Artificial sequence
<220> FEATURE:
<223> OTHER INFORMATION: Synthetic peptide

<400> SEQUENCE: 74

```
Met His Thr Gly Gly Gly Val
1               5
```

<210> SEQ ID NO 75
<211> LENGTH: 15
<212> TYPE: PRT
<213> ORGANISM: Artificial sequence
<220> FEATURE:
<223> OTHER INFORMATION: Synthetic peptide

<400> SEQUENCE: 75

```
Ala Arg Ser His Ala Gly Tyr Ser Thr Ile Asn Arg Leu Asp Leu
1               5                   10                  15
```

<210> SEQ ID NO 76
<211> LENGTH: 6
<212> TYPE: PRT
<213> ORGANISM: Artificial sequence
<220> FEATURE:
<223> OTHER INFORMATION: Synthetic peptide

<400> SEQUENCE: 76

```
Gln Ser Ile Ser Val Tyr
1               5
```

<210> SEQ ID NO 77
<211> LENGTH: 10
<212> TYPE: PRT
<213> ORGANISM: Artificial sequence
<220> FEATURE:
<223> OTHER INFORMATION: Synthetic peptide

<400> SEQUENCE: 77

Gln Ser Tyr Asp Gly Thr Pro Thr Ala Ala
1               5                   10

<210> SEQ ID NO 78
<211> LENGTH: 357
<212> TYPE: DNA
<213> ORGANISM: Artificial sequence
<220> FEATURE:
<223> OTHER INFORMATION: Synthetic oligonucleotide

<400> SEQUENCE: 78

```
gagcagtcgt tggaggagtc cgggggtcgc ctggtcacgc ctgggacacc cctgacactc    60
acctgcacag cctctggatt ctccctcagt agctactaca tgacctgggt ccgccaggct   120
ccagggaagg gactggagtg gatcggatac atgcatacgg gtggtggcgt agtctacgcg   180
agttgggcga caggccggtt caccatctcc agaacctcga ccacggtgga tctgaaaatc   240
accagtccga caactgagga cacggccact tatttctgtg ccagaagtca tgctggttat   300
agtactataa atcggttgga tctctggggc gtgggcaccc tggtcaccat ctcctca      357
```

<210> SEQ ID NO 79
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 79

```
gagctcgatc tgacccagac tccatcctcc gtgtctgccg ctgtgggagg cacagtcacc    60
atcagttgcc agtccagtcc gagtgtttat actaacaact tatcctggtt tcagcagaaa   120
ccagggcagc ctcccaagct cctgatctat gatgcatcca aactggaatc aggggtccca   180
tcgcggttca gaggcagtgg atctgggaca cagttcactc tcaccatcag cgacgtgcag   240
tgtgacgatg ctgccactta ttattgtgca ggcgcttacc tcagtgatag tgatactact   300
ttcggcggag ggaccgagct ggaaatcaaa                                    330
```

<210> SEQ ID NO 80
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 80

```
ggattctccc tcagtagcta ctac                                           24
```

<210> SEQ ID NO 81
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 81

```
atgcatacgg gtggtggcgt a                                              21
```

<210> SEQ ID NO 82
<211> LENGTH: 45
<212> TYPE: DNA
<213> ORGANISM: Artificial sequence -continued
<220> FEATURE:
<223> OTHER INFORMATION: Synthetic oligonucleotide

<400> SEQUENCE: 82
gccagaagtc atgctggtta tagtactata aatcggttgg atctc          45

<210> SEQ ID NO 83
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 83
cagagtatta gtgtctac          18

<210> SEQ ID NO 84
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 84
caaagttatg atggtactcc tactgcggct          30

<210> SEQ ID NO 85
<211> LENGTH: 119
<212> TYPE: PRT
<213> ORGANISM: Artificial sequence
<220> FEATURE:
<223> OTHER INFORMATION: Synthetic peptide

<400> SEQUENCE: 85

Gly Glu Gln Leu Met Glu Ser Gly Gly Arg Leu Val Thr Pro Gly
1               5                   10                  15

Thr Pro Leu Thr Leu Thr Cys Thr Ala Ser Gly Phe Asp Val Asn Ala
            20                  25                  30

Tyr His Met Gly Trp Val Arg Gln Ala Pro Gly Lys Gly Leu Glu Trp
        35                  40                  45

Ile Gly Tyr Ile Tyr Ser Gly Gly Thr Ile Phe Tyr Ala Asn Trp Ala
    50                  55                  60

Lys Gly Arg Phe Thr Leu Ser Arg Thr Ser Thr Thr Val Asp Leu Lys
65                  70                  75                  80

Ile Thr Ser Pro Thr Thr Glu Asp Thr Ala Thr Tyr Phe Cys Ala Arg
                85                  90                  95

Gly Gly Tyr Asp Asn Tyr Asn Ile Leu Tyr Asp Leu Trp Gly Pro Gly
            100                 105                 110

Thr Leu Val Thr Ile Ser Ser
        115

<210> SEQ ID NO 86
<211> LENGTH: 108
<212> TYPE: PRT
<213> ORGANISM: Artificial sequence
<220> FEATURE:
<223> OTHER INFORMATION: Synthetic peptide

<400> SEQUENCE: 86

Glu Leu Asp Met Thr Gln Thr Pro Ala Ser Val Ser Glu Pro Val Gly
1               5                   10                  15

Gly Thr Val Thr Ile Lys Cys Gln Ala Ser Gln Ser Ile Ser Val Tyr

```
                    20                  25                  30
Leu Ala Trp Tyr Gln Gln Lys Pro Gly Gln Pro Pro Lys Leu Leu Ile
                35                  40                  45

Tyr Asp Ala Ser Thr Leu Thr Ser Gly Val Pro Ser Arg Phe Lys Gly
            50                  55                  60

Ser Gly Ser Gly Thr Glu Phe Thr Leu Thr Ile Ser Asp Leu Glu Cys
65                  70                  75                  80

Ala Asp Ala Ala Ala Tyr Tyr Cys Gln Ser Tyr Asp Gly Thr Pro Thr
                85                  90                  95

Ala Ala Phe Gly Gly Gly Thr Glu Val Val Val Lys
                100                 105
```

<210> SEQ ID NO 87
<211> LENGTH: 8
<212> TYPE: PRT
<213> ORGANISM: Artificial sequence
<220> FEATURE:
<223> OTHER INFORMATION: Synthetic peptide

<400> SEQUENCE: 87

```
Gly Phe Asp Val Asn Ala Tyr His
1               5
```

<210> SEQ ID NO 88
<211> LENGTH: 7
<212> TYPE: PRT
<213> ORGANISM: Artificial sequence
<220> FEATURE:
<223> OTHER INFORMATION: Synthetic peptide

<400> SEQUENCE: 88

```
Ile Tyr Ser Gly Gly Thr Ile
1               5
```

<210> SEQ ID NO 89
<211> LENGTH: 14
<212> TYPE: PRT
<213> ORGANISM: Artificial sequence
<220> FEATURE:
<223> OTHER INFORMATION: Synthetic peptide

<400> SEQUENCE: 89

```
Ala Arg Gly Gly Tyr Asp Asn Tyr Asn Ile Leu Tyr Asp Leu
1               5                   10
```

<210> SEQ ID NO 90
<211> LENGTH: 8
<212> TYPE: PRT
<213> ORGANISM: Artificial sequence
<220> FEATURE:
<223> OTHER INFORMATION: Synthetic peptide

<400> SEQUENCE: 90

```
Gln Ser Val Tyr Asn Asn Asn Tyr
1               5
```

<210> SEQ ID NO 91
<211> LENGTH: 12
<212> TYPE: PRT
<213> ORGANISM: Artificial sequence
<220> FEATURE:
<223> OTHER INFORMATION: Synthetic peptide

<400> SEQUENCE: 91

Ala Gly Phe Val Ser Arg Ser Thr Asp Gly Ala Ala
1               5                   10

<210> SEQ ID NO 92
<211> LENGTH: 355
<212> TYPE: DNA
<213> ORGANISM: Artificial sequence
<220> FEATURE:
<223> OTHER INFORMATION: Synthetic oligonucleotide

<400> SEQUENCE: 92
gagcagctga tggaggagtc cggggtcgc ctggtcacgc ctgggacacc cctgacactc      60
acctgcacag cctctggatt cgacgtcaat gcctaccaca tgggctgggt ccgccaggct    120
ccagggaagg ggctggaatg gatcggatac atttatagcg gtggtaccat attctacgcg    180
aactgggcaa aggccgatt caccctctcc agaacctcga ccacggtgga tctgaagatc     240
accagtccga caaccgagga cacggccacc tatttctgtg ccagagggg ttatgataat    300 tacaacattc tatatgactt gtggggccca ggcaccctgg tcaccatctc ttcag         355

<210> SEQ ID NO 93
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 93
gagctcgata tgacccagac tccagcctcc gtgtctgaac ctgtgggagg cacagtcacc     60
atcaagtgcc aggccagtca gagtattagt gtctacttag cctggtatca gcagaaacca    120
gggcagcctc ccaagctcct aatctatgat gcatccactc tgacatctgg ggtcccatcg    180
cggttcaaag gcagtggatc tgggacagag ttcactctca ccatcagcga cctggagtgt    240
gccgatgctg ccgcttacta ctgtcaaagt tatgatggta ctcctactgc ggctttcggc    300
ggagggaccg aggtggtggt caaa                                            324

<210> SEQ ID NO 94
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 94
ggattcgacg tcaatgccta ccac                                            24

<210> SEQ ID NO 95
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 95
atttatagcg gtggtaccat a                                               21

<210> SEQ ID NO 96
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 96
gccagagggg gttatgataa ttacaacatt ctatatgact tg                             42

<210> SEQ ID NO 97
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 97
cagagtgttt ataataacaa ctac                                                24

<210> SEQ ID NO 98
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 98
gcaggatttg tgagtagaag tactgatggt gctgct                                   36

<210> SEQ ID NO 99
<211> LENGTH: 120
<212> TYPE: PRT
<213> ORGANISM: Artificial sequence
<220> FEATURE:
<223> OTHER INFORMATION: Synthetic peptide

<400> SEQUENCE: 99

Ser Ser Ser Val Glu Glu Ser Gly Gly Arg Leu Val Thr Pro Gly Thr
1               5                   10                  15

Pro Leu Thr Leu Thr Cys Thr Val Ser Gly Phe Ser Leu Ser Ser Tyr
            20                  25                  30

Val Met Gly Trp Val Arg Gln Ala Pro Gly Lys Gly Leu Glu Trp Ile
        35                  40                  45

Gly Thr Ile Ser Ile Arg Ser Asn Thr Tyr Tyr Ala Ser Trp Ala Lys
    50                  55                  60

Gly Arg Phe Thr Ile Ser Lys Thr Ser Thr Thr Val Asp Leu Lys Ile
65                  70                  75                  80

Thr Ser Pro Ile Thr Glu Asp Thr Ala Thr Tyr Phe Cys Ala Arg Gly
                85                  90                  95

Ala Gly Asn Val Tyr Tyr Ser Asp Tyr Tyr Phe Ser Leu Trp Gly Pro
            100                 105                 110

Gly Thr Leu Val Thr Ile Ser Ser
        115                 120

<210> SEQ ID NO 100
<211> LENGTH: 110
<212> TYPE: PRT
<213> ORGANISM: Artificial sequence
<220> FEATURE:
<223> OTHER INFORMATION: Synthetic peptide

<400> SEQUENCE: 100

Glu Leu Val Met Thr Gln Pro Pro Ala Ser Val Ser Ala Ala Val Gly
1               5                   10                  15

Gly Thr Val Thr Ile Asn Cys Gln Ala Ser Gln Asn Ile Tyr Ser Asn
            20                  25                  30

Leu Ala Trp Tyr Gln Gln Arg Pro Gly Gln Pro Pro Lys Leu Leu Ile

```
                35                  40                  45
Tyr Lys Ala Ser Thr Leu Ala Ser Gly Val Pro Ser Arg Phe Lys Gly
     50                  55                  60

Ser Gly Ser Gly Thr Asp Tyr Thr Leu Thr Ile Thr Asp Leu Glu Cys
 65                  70                  75                  80

Ala Asp Ala Ala Thr Tyr Tyr Cys Gln Thr Tyr Tyr Asn Met Met Asp
                 85                  90                  95

Asp Gly Ala Ala Phe Gly Gly Gly Thr Glu Val Glu Ile Lys
            100                 105                 110
```

<210> SEQ ID NO 101
<211> LENGTH: 8
<212> TYPE: PRT
<213> ORGANISM: Artificial sequence
<220> FEATURE:
<223> OTHER INFORMATION: Synthetic peptide

<400> SEQUENCE: 101

```
Gly Phe Ser Leu Ser Ser Tyr Val
 1               5
```

<210> SEQ ID NO 102
<211> LENGTH: 7
<212> TYPE: PRT
<213> ORGANISM: Artificial sequence
<220> FEATURE:
<223> OTHER INFORMATION: Synthetic peptide

<400> SEQUENCE: 102

```
Ile Ser Ile Arg Ser Asn Thr
 1               5
```

<210> SEQ ID NO 103
<211> LENGTH: 16
<212> TYPE: PRT
<213> ORGANISM: Artificial sequence
<220> FEATURE:
<223> OTHER INFORMATION: Synthetic peptide

<400> SEQUENCE: 103

```
Ala Arg Gly Ala Gly Asn Val Tyr Tyr Ser Asp Tyr Tyr Phe Ser Leu
 1               5                  10                  15
```

<210> SEQ ID NO 104
<211> LENGTH: 6
<212> TYPE: PRT
<213> ORGANISM: Artificial sequence
<220> FEATURE:
<223> OTHER INFORMATION: Synthetic peptide

<400> SEQUENCE: 104

```
Gln Asn Ile Tyr Ser Asn
 1               5
```

<210> SEQ ID NO 105
<211> LENGTH: 12
<212> TYPE: PRT
<213> ORGANISM: Artificial sequence
<220> FEATURE:
<223> OTHER INFORMATION: Synthetic peptide

<400> SEQUENCE: 105

```
Gln Thr Tyr Tyr Asn Met Met Asp Asp Gly Ala Ala
 1               5                  10
```

<210> SEQ ID NO 106
<211> LENGTH: 360
<212> TYPE: DNA
<213> ORGANISM: Artificial sequence
<220> FEATURE:
<223> OTHER INFORMATION: Synthetic oligonucleotide

<400> SEQUENCE: 106

```
agcagttcgg tggaggagtc cggggggtcgc ctggtcacgc ctgggacacc cctgacactc    60
acctgcacag tctctggatt ctccctcagt agctatgtaa tgggctgggt ccgccaggct   120
ccagggaagg gactagagtg gatcgggact attagtattc gaagtaatac atactacgcg   180
agctgggcga aaggccgatt caccatctcc aaaacctcga ccacggtgga tctcaaaatc   240
accagtccga taaccgagga cacggccacc tatttctgtg ccagaggtgc tggtaatgtt   300
tattatagcg actactactt ttccttgtgg ggcccaggca ccctggtcac catctcttca   360
```

<210> SEQ ID NO 107
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 107

```
gagctcgtga tgacccagcc tccagcctcc gtgtctgcag ctgtgggagg cacagtcacc    60
atcaattgcc aggccagtca gaacatttac agtaatttag cctggtatca gcagagacca   120
gggcagcctc ccaagctcct gatttataag gcatcgactc tggcatctgg ggtcccatcg   180
cggttcaaag gcagtggatc tgggacagac tacactctca ccatcaccga cctggagtgt   240
gccgatgctg ccacttacta ttgtcaaacc tattataata tgatggatga tggtgctgct   300
ttcggcggag ggaccgaggt ggaaatcaaa                                    330
```

<210> SEQ ID NO 108
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 108

```
ggattctccc tcagtagcta tgta                                           24
```

<210> SEQ ID NO 109
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 109

```
attagtattc gaagtaatac a                                              21
```

<210> SEQ ID NO 110
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 110

```
gccagaggtg ctggtaatgt tattatagc gactactact tttccttg                  48
```

<210> SEQ ID NO 111
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 111
cagaacattt acagtaat                                                 18

<210> SEQ ID NO 112
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 112
caaacctatt ataatatgat ggatgatggt gctgct                             36

<210> SEQ ID NO 113
<211> LENGTH: 118
<212> TYPE: PRT
<213> ORGANISM: Artificial sequence
<220> FEATURE:
<223> OTHER INFORMATION: Synthetic peptide

<400> SEQUENCE: 113

Glu Gln Ser Val Glu Glu Ser Gly Gly Gly Leu Val Ala Pro Gly Gly
1               5                   10                  15

Ser Leu Thr Leu Thr Cys Thr Val Ser Gly Phe Ser Leu Ser Asn Tyr
            20                  25                  30

His Met Gly Trp Val Arg Gln Ala Pro Gly Lys Gly Leu Glu Trp Ile
        35                  40                  45

Gly Tyr Ile Tyr Thr His Gly Thr Thr Phe Tyr Ala Ser Trp Ala Lys
    50                  55                  60

Gly Arg Phe Thr Ile Ser Lys Thr Ser Thr Thr Val Asp Leu Lys Met
65                  70                  75                  80

Thr Arg Leu Thr Thr Gly Asp Thr Ala Thr Tyr Phe Cys Ala Arg Gly
                85                  90                  95

Gly Tyr Ala Asp Tyr Asn Ile Leu Tyr Asn Leu Trp Gly Pro Gly Thr
            100                 105                 110

Leu Val Thr Ile Ser Ser
        115

<210> SEQ ID NO 114
<211> LENGTH: 108
<212> TYPE: PRT
<213> ORGANISM: Artificial sequence
<220> FEATURE:
<223> OTHER INFORMATION: Synthetic peptide

<400> SEQUENCE: 114

Glu Leu Val Leu Thr Gln Thr Pro Ala Ser Val Glu Ala Ala Val Gly
1               5                   10                  15

Gly Thr Val Thr Ile Asn Cys Gln Ala Ser Gln Ser Ile Ser Ser Tyr
            20                  25                  30

Leu Ala Trp Tyr Gln Gln Lys Pro Gly Gln Pro Pro Lys Leu Leu Ile
        35                  40                  45

Tyr Asp Ala Ser Asp Leu Ala Ser Gly Val Pro Ser Arg Phe Lys Gly

```
                    50                  55                  60
Ser Arg Ser Gly Thr Glu Phe Thr Phe Thr Ile Ser Asp Leu Glu Cys
 65                  70                  75                  80

Ala Asp Ala Ala Thr Tyr Tyr Cys Gln Thr Tyr Asp Ser Ser Thr Thr
                 85                  90                  95

Ala Ala Phe Gly Gly Gly Thr Glu Val Glu Ile Lys
            100                 105

<210> SEQ ID NO 115
<211> LENGTH: 8
<212> TYPE: PRT
<213> ORGANISM: Artificial sequence
<220> FEATURE:
<223> OTHER INFORMATION: Synthetic peptide

<400> SEQUENCE: 115

Gly Phe Ser Leu Ser Asn Tyr His
 1               5

<210> SEQ ID NO 116
<211> LENGTH: 7
<212> TYPE: PRT
<213> ORGANISM: Artificial sequence
<220> FEATURE:
<223> OTHER INFORMATION: Synthetic peptide

<400> SEQUENCE: 116

Ile Tyr Thr His Gly Thr Thr
 1               5

<210> SEQ ID NO 117
<211> LENGTH: 14
<212> TYPE: PRT
<213> ORGANISM: Artificial sequence
<220> FEATURE:
<223> OTHER INFORMATION: Synthetic peptide

<400> SEQUENCE: 117

Ala Arg Gly Gly Tyr Ala Asp Tyr Asn Ile Leu Tyr Asn Leu
 1               5                   10

<210> SEQ ID NO 118
<211> LENGTH: 6
<212> TYPE: PRT
<213> ORGANISM: Artificial sequence
<220> FEATURE:
<223> OTHER INFORMATION: Synthetic peptide

<400> SEQUENCE: 118

Gln Ser Ile Ser Ser Tyr
 1               5

<210> SEQ ID NO 119
<211> LENGTH: 10
<212> TYPE: PRT
<213> ORGANISM: Artificial sequence
<220> FEATURE:
<223> OTHER INFORMATION: Synthetic peptide

<400> SEQUENCE: 119

Gln Thr Tyr Asp Ser Ser Thr Thr Ala Ala
 1               5                   10

<210> SEQ ID NO 120
<211> LENGTH: 354
```

```
<212> TYPE: DNA
<213> ORGANISM: Artificial sequence
<220> FEATURE:
<223> OTHER INFORMATION: Synthetic oligonucleotide

<400> SEQUENCE: 120
gagcagtcgg tggaggagtc cggaggaggc ctggtagcgc ctggaggatc cctgacactc      60
acctgcacag tctctggatt ctccctcagt aactaccaca tgggctgggt ccgccaggct     120
ccagggaagg ggctggagtg gatcggatac atttatactc atggtaccac attctacgct     180
agctgggcga aaggccgatt caccatctcc aaaacctcga ccacggtgga tctgaaaatg     240
accaggctga caaccgggga cacggccacc tatttctgtg ccagagggg ttatgctgat      300 tataatattt tatataattt gtggggccca ggcaccctgg tcaccatctc ttca           354

<210> SEQ ID NO 121
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 121
gagctcgtgc tgacccagac accagcctcc gtggaggcag ctgtgggagg cacagtcacc      60
atcaattgcc aggccagtca gagtattagt agttacctag cctggtatca gcagaaacca     120
gggcagcctc ccaagctcct gatctatgat gcatccgatc tggcatctgg ggtcccatcg     180
cggttcaaag gcagtagatc tgggacagag ttcactttca ccatcagcga cctggagtgt     240
gccgatgctg ccacttacta ctgtcagact tatgatagta gtactacagc ggctttcggc     300
ggagggaccg aggtggaaat caaa                                            324

<210> SEQ ID NO 122
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 122
ggattctccc tcagtaacta ccac                                             24

<210> SEQ ID NO 123
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 123
atttatactc atggtaccac a                                                21

<210> SEQ ID NO 124
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 124
gccagagggg gttatgctga ttataatatt ttatataatt tg                         42

<210> SEQ ID NO 125
```

<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 125
cagagtatta gtagttac                                                18

<210> SEQ ID NO 126
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 126
cagacttatg atagtagtac tacagcggct                                   30

<210> SEQ ID NO 127
<211> LENGTH: 118
<212> TYPE: PRT
<213> ORGANISM: Artificial sequence
<220> FEATURE:
<223> OTHER INFORMATION: Synthetic peptide

<400> SEQUENCE: 127

Gln Ser Leu Gln Glu Ser Arg Gly Arg Leu Val Thr Pro Gly Thr Pro
1               5                   10                  15

Leu Thr Leu Thr Cys Thr Ala Ser Gly Phe Ser Leu Ser Ser Tyr His
            20                  25                  30

Met Gly Trp Val Arg Gln Ala Pro Gly Lys Gly Leu Glu Trp Ile Gly
        35                  40                  45

Tyr Ile His Thr Asn Arg Asn Thr Trp Tyr Ala Asn Trp Ala Lys Gly
    50                  55                  60

Arg Phe Thr Ile Ser Lys Thr Ser Ser Thr Thr Val Asn Leu Arg Met
65                  70                  75                  80

Thr Ser Pro Thr Thr Glu Asp Thr Ala Thr Tyr Phe Cys Ala Arg Gly
                85                  90                  95

Ser Tyr Gly Asp Tyr Asn Phe Leu Phe Asp Val Trp Gly Pro Gly Thr
            100                 105                 110

Leu Val Thr Val Ser Ser
        115

<210> SEQ ID NO 128
<211> LENGTH: 109
<212> TYPE: PRT
<213> ORGANISM: Artificial sequence
<220> FEATURE:
<223> OTHER INFORMATION: Synthetic peptide

<400> SEQUENCE: 128

Glu Leu Val Met Thr Gln Thr Pro Ala Ser Val Ser Glu Pro Val Gly
1               5                   10                  15

Gly Thr Val Thr Ile Asn Cys Gln Ala Ser Glu Asp Ile Ser Ile Tyr
            20                  25                  30

Leu Ala Trp Tyr Gln Gln Lys Pro Gly Gln Pro Pro Lys Leu Leu Ile
        35                  40                  45

Tyr Asp Ala Ser Thr Leu Glu Ser Gly Val Pro Ser Arg Phe Ser Gly
    50                  55                  60

Ser Gly Ser Arg Thr Gln Phe Thr Leu Thr Ile Ser Asp Leu Glu Cys

```
                65                  70                  75                  80
Ala Asp Ala Ala Thr Tyr Tyr Cys Gln Gln Tyr Ser Thr Thr Asp Thr
                    85                  90                  95

Asn Asn Leu Phe Gly Gly Gly Thr Glu Val Glu Ile Lys
            100                 105
```

<210> SEQ ID NO 129
<211> LENGTH: 8
<212> TYPE: PRT
<213> ORGANISM: Artificial sequence
<220> FEATURE:
<223> OTHER INFORMATION: Synthetic peptide

<400> SEQUENCE: 129

```
Gly Phe Ser Leu Ser Ser Tyr His
1               5
```

<210> SEQ ID NO 130
<211> LENGTH: 7
<212> TYPE: PRT
<213> ORGANISM: Artificial sequence
<220> FEATURE:
<223> OTHER INFORMATION: Synthetic peptide

<400> SEQUENCE: 130

```
Ile His Thr Asn Arg Asn Thr
1               5
```

<210> SEQ ID NO 131
<211> LENGTH: 14
<212> TYPE: PRT
<213> ORGANISM: Artificial sequence
<220> FEATURE:
<223> OTHER INFORMATION: Synthetic peptide

<400> SEQUENCE: 131

```
Ala Arg Gly Ser Tyr Gly Asp Tyr Asn Phe Leu Phe Asp Val
1               5                   10
```

<210> SEQ ID NO 132
<211> LENGTH: 6
<212> TYPE: PRT
<213> ORGANISM: Artificial sequence
<220> FEATURE:
<223> OTHER INFORMATION: Synthetic peptide

<400> SEQUENCE: 132

```
Glu Asp Ile Ser Ile Tyr
1               5
```

<210> SEQ ID NO 133
<211> LENGTH: 11
<212> TYPE: PRT
<213> ORGANISM: Artificial sequence
<220> FEATURE:
<223> OTHER INFORMATION: Synthetic peptide

<400> SEQUENCE: 133

```
Gln Gln Tyr Ser Thr Thr Asp Thr Asn Asn Leu
1               5                   10
```

<210> SEQ ID NO 134
<211> LENGTH: 354
<212> TYPE: DNA
<213> ORGANISM: Artificial sequence
<220> FEATURE:

<223> OTHER INFORMATION: Synthetic oligonucleotide

<400> SEQUENCE: 134

| | | |
|---|---|---|
| cagtcgttgc aggagtccag gggtcgcctg gtcacgcctg ggacacccct gacactcacc | 60 | |
| tgcacagcct ctggattctc cctcagtagc taccacatgg gctgggtccg ccaggctcca | 120 | |
| gggaagggc tggaatggat cggatacatt catactaatc gtaatacatg gtacgcgaac | 180 | |
| tgggcgaaag gccgattcac catctccaaa acctcgtcga ccacggtgaa tctgaggatg | 240 | |
| accagtccga caaccgagga cacggccacc tatttctgtg ctagaggctc ttatggtgat | 300 | |
| tataatttc ttttgacgt gtggggccca ggcaccctgg tcaccgtctc ctca | 354 | |

<210> SEQ ID NO 135
<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 135

| | | |
|---|---|---|
| gagctcgtga tgacccagac tccagcctcc gtgtctgaac ctgtgggagg cacagtcacc | 60 | |
| atcaattgcc aggccagtga ggatattagt atctacttag cctggtatca gcagaaacca | 120 | |
| gggcagcctc ccaagctcct gatctatgat gcatccactc tggaatctgg ggtcccatcg | 180 | |
| cggttcagcg gcagtggatc taggacacaa ttcactctca ccatcagcga cctggagtgt | 240 | |
| gccgatgctg ccacttacta ctgtcaacaa tatagtacta cagatactaa taatcttttc | 300 | |
| ggcggaggga ccgaggtgga aatcaaa | 327 | |

<210> SEQ ID NO 136
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 136
ggattctccc tcagtagcta ccac                                        24

<210> SEQ ID NO 137
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 137
attcatacta atcgtaatac a                                           21

<210> SEQ ID NO 138
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 138
gctagaggct cttatggtga ttataatttt cttttgacg tg                     42

<210> SEQ ID NO 139
<211> LENGTH: 18
<212> TYPE: DNA
<213> ORGANISM: Artificial sequence

```
<220> FEATURE:
<223> OTHER INFORMATION: Synthetic oligonucleotide

<400> SEQUENCE: 139
gaggatatta gtatctac                                                 18

<210> SEQ ID NO 140
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 140
caacaatata gtactacaga tactaataat ctt                                33

<210> SEQ ID NO 141
<211> LENGTH: 120
<212> TYPE: PRT
<213> ORGANISM: Artificial sequence
<220> FEATURE:
<223> OTHER INFORMATION: Synthetic peptide

<400> SEQUENCE: 141
```

Glu Gln Ser Val Glu Glu Ser Gly Gly Arg Leu Val Thr Pro Gly Gly
1               5                   10                  15

Ser Leu Thr Leu Thr Cys Thr Val Ser Gly Phe Ser Leu Ser Ser Tyr
            20                  25                  30

Asn Met Gly Trp Val Arg Gln Ala Pro Gly Lys Gly Leu Glu Tyr Ile
        35                  40                  45

Gly Trp Ile Ser Leu Gly Gly Asn Thr Tyr Tyr Ala Ser Trp Val Asn
    50                  55                  60

Gly Arg Phe Thr Ile Ser Lys Thr Ser Thr Thr Val Glu Leu Lys Ile
65                  70                  75                  80

Ser Ser Pro Thr Thr Glu Asp Thr Ala Thr Tyr Phe Cys Ala Arg Gly
                85                  90                  95

Ala Gly Ser Leu Tyr Tyr Gly Asp Tyr Tyr Phe Thr Leu Trp Gly Pro
            100                 105                 110

Gly Thr Leu Val Thr Ile Ser Ser
        115                 120

```
<210> SEQ ID NO 142
<211> LENGTH: 110
<212> TYPE: PRT
<213> ORGANISM: Artificial sequence
<220> FEATURE:
<223> OTHER INFORMATION: Synthetic peptide

<400> SEQUENCE: 142
```

Glu Leu Val Leu Thr Gln Thr Pro Ser Ser Val Ser Ala Ala Val Gly
1               5                   10                  15

Gly Thr Val Thr Ile Lys Cys Gln Ala Ser Gln Ser Ile Tyr Ser Asn
            20                  25                  30

Leu Ala Trp Tyr Gln Gln Lys Pro Gly Gln Pro Pro Lys Leu Leu Ile
        35                  40                  45

Tyr Lys Ala Ser Asn Leu Ala Ser Gly Val Pro Ser Arg Phe Lys Gly
    50                  55                  60

Ser Gly Ser Gly Thr Glu Tyr Thr Leu Thr Ile Ser Asp Leu Glu Cys
65                  70                  75                  80

Ala Asp Ala Ala Thr Tyr Tyr Cys Gln Asn Tyr Tyr Gly Ile Asn Asp

```
                    85                  90                  95

Tyr Gly Ala Ala Phe Gly Gly Gly Thr Glu Val Val Val Lys
                100                 105                 110

<210> SEQ ID NO 143
<211> LENGTH: 8
<212> TYPE: PRT
<213> ORGANISM: Artificial sequence
<220> FEATURE:
<223> OTHER INFORMATION: Synthetic peptide

<400> SEQUENCE: 143

Gly Phe Ser Leu Ser Ser Tyr Asn
1               5

<210> SEQ ID NO 144
<211> LENGTH: 7
<212> TYPE: PRT
<213> ORGANISM: Artificial sequence
<220> FEATURE:
<223> OTHER INFORMATION: Synthetic peptide

<400> SEQUENCE: 144

Ile Ser Leu Gly Gly Asn Thr
1               5

<210> SEQ ID NO 145
<211> LENGTH: 16
<212> TYPE: PRT
<213> ORGANISM: Artificial sequence
<220> FEATURE:
<223> OTHER INFORMATION: Synthetic peptide

<400> SEQUENCE: 145

Ala Arg Gly Ala Gly Ser Leu Tyr Tyr Gly Asp Tyr Tyr Phe Thr Leu
1               5                   10                  15

<210> SEQ ID NO 146
<211> LENGTH: 6
<212> TYPE: PRT
<213> ORGANISM: Artificial sequence
<220> FEATURE:
<223> OTHER INFORMATION: Synthetic peptide

<400> SEQUENCE: 146

Gln Ser Ile Tyr Ser Asn
1               5

<210> SEQ ID NO 147
<211> LENGTH: 12
<212> TYPE: PRT
<213> ORGANISM: Artificial sequence
<220> FEATURE:
<223> OTHER INFORMATION: Synthetic peptide

<400> SEQUENCE: 147

Gln Asn Tyr Tyr Gly Ile Asn Asp Tyr Gly Ala Ala
1               5                   10

<210> SEQ ID NO 148
<211> LENGTH: 360
<212> TYPE: DNA
<213> ORGANISM: Artificial sequence
<220> FEATURE:
<223> OTHER INFORMATION: Synthetic oligonucleotide

<400> SEQUENCE: 148
```

```
gagcagtcgg tggaggagtc cggggtcgc ctggtcacgc ctggaggatc cctgacactc    60
acctgcacag tctctggatt ctccctcagt agctacaaca tgggctgggt ccgccaggct   120
ccagggaagg ggctggaata catcggatgg attagtcttg gtggtaacac atattacgcg   180
agctgggtga atggtcgatt caccatctcc aaaacctcga ccacggtgga gctgaaaatc   240
agcagcccga caaccgagga cacggccacc tatttctgtg ccagaggggc tggtagtctt   300
tattatgggg attactactt taccttgtgg ggcccaggca ccctggtcac catctcctca   360

<210> SEQ ID NO 149
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 149
gagctcgtgc tgacccagac tccatcctcc gtgtctgcag ctgtgggagg cacagtcacc    60
atcaagtgcc aggccagtca gagcatttac agcaatttag cctggtatca gcagaaacca   120 ggcagcctc ccaagctcct gatctacaag gcatccaatc tggcatctgg ggtcccatcg   180
cggttcaaag gcagtggatc tgggacagag tacactctca ccatcagcga cctggagtgt   240
gccgatgctg ccacttacta ctgtcaaaac tactatggta ttaatgatta tggtgctgct   300
ttcggcggag ggaccgaggt ggtggtcaaa                                    330

<210> SEQ ID NO 150
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 150
ggattctccc tcagtagcta caac                                           24

<210> SEQ ID NO 151
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 151
attagtcttg gtggtaacac a                                              21

<210> SEQ ID NO 152
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 152
gccagagggg ctggtagtct ttattatggg gattactact ttaccttg                 48

<210> SEQ ID NO 153
<211> LENGTH: 18
<212> TYPE: DNA
<213> ORGANISM: Artificial sequence
<220> FEATURE:
<223> OTHER INFORMATION: Synthetic oligonucleotide
```

```
<400> SEQUENCE: 153
cagagcattt acagcaat                                                   18

<210> SEQ ID NO 154
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 154
caaaactact atggtattaa tgattatggt gctgct                               36

<210> SEQ ID NO 155
<211> LENGTH: 115
<212> TYPE: PRT
<213> ORGANISM: Artificial sequence
<220> FEATURE:
<223> OTHER INFORMATION: Synthetic peptide

<400> SEQUENCE: 155
```

Glu Gln Ser Val Glu Glu Ser Gly Gly Arg Leu Val Thr Pro Gly Thr
1               5                   10                  15

Pro Leu Thr Leu Thr Cys Thr Ala Ser Gly Phe Ser Leu Ser Ser Tyr
            20                  25                  30

Ala Met Ile Trp Val Arg Gln Ala Pro Gly Glu Gly Leu Glu Trp Ile
        35                  40                  45

Gly Asp Ile Tyr Ala Gly Gly Ala Thr Tyr Tyr Ala Ser Trp Ala
    50                  55                  60

Lys Gly Arg Phe Thr Ile Ser Lys Thr Ser Thr Thr Val Asp Leu Lys
65                  70                  75                  80

Ile Thr Ser Pro Thr Thr Glu Asp Thr Ala Thr Tyr Phe Cys Ala Arg
                85                  90                  95

Ala Tyr Gly Ser Gly Tyr Asp Leu Trp Gly Pro Gly Thr Leu Val Thr
            100                 105                 110

Val Ser Ser
        115

```
<210> SEQ ID NO 156
<211> LENGTH: 110
<212> TYPE: PRT
<213> ORGANISM: Artificial sequence
<220> FEATURE:
<223> OTHER INFORMATION: Synthetic peptide

<400> SEQUENCE: 156
```

Glu Leu Asp Leu Thr Gln Thr Pro Ala Ser Val Glu Val Ala Val Gly
1               5                   10                  15

Gly Thr Val Thr Ile Lys Cys Gln Ala Ser Gln Ser Ile Ser Ser Tyr
            20                  25                  30

Leu Ser Trp Tyr Gln Gln Lys Pro Gly Gln Pro Pro Lys Leu Leu Ile
        35                  40                  45

Tyr Tyr Ala Ser Thr Met Ala Ser Gly Val Pro Ser Arg Phe Ser Gly
    50                  55                  60

Ser Gly Ser Gly Thr Gln Phe Thr Leu Thr Ile Ser Asp Leu Glu Cys
65                  70                  75                  80

Ala Asp Ala Ala Thr Tyr Tyr Cys Gln Gln Gly Asp Ser Arg Ser Asn
                85                  90                  95

Val Asp Asn Ile Phe Gly Gly Gly Thr Glu Val Val Val Lys

<210> SEQ ID NO 157
<211> LENGTH: 8
<212> TYPE: PRT
<213> ORGANISM: Artificial sequence
<220> FEATURE:
<223> OTHER INFORMATION: Synthetic peptide

<400> SEQUENCE: 157

Gly Phe Ser Leu Ser Ser Tyr Ala
1               5

<210> SEQ ID NO 158
<211> LENGTH: 8
<212> TYPE: PRT
<213> ORGANISM: Artificial sequence
<220> FEATURE:
<223> OTHER INFORMATION: Synthetic peptide

<400> SEQUENCE: 158

Ile Tyr Ala Gly Gly Gly Ala Thr
1               5

<210> SEQ ID NO 159
<211> LENGTH: 10
<212> TYPE: PRT
<213> ORGANISM: Artificial sequence
<220> FEATURE:
<223> OTHER INFORMATION: Synthetic peptide

<400> SEQUENCE: 159

Ala Arg Ala Tyr Gly Ser Gly Tyr Asp Leu
1               5                   10

<210> SEQ ID NO 160
<211> LENGTH: 6
<212> TYPE: PRT
<213> ORGANISM: Artificial sequence
<220> FEATURE:
<223> OTHER INFORMATION: Synthetic peptide

<400> SEQUENCE: 160

Gln Ser Ile Ser Ser Tyr
1               5

<210> SEQ ID NO 161
<211> LENGTH: 12
<212> TYPE: PRT
<213> ORGANISM: Artificial sequence
<220> FEATURE:
<223> OTHER INFORMATION: Synthetic peptide

<400> SEQUENCE: 161

Gln Gln Gly Asp Ser Arg Ser Asn Val Asp Asn Ile
1               5                   10

<210> SEQ ID NO 162
<211> LENGTH: 345
<212> TYPE: DNA
<213> ORGANISM: Artificial sequence
<220> FEATURE:
<223> OTHER INFORMATION: Synthetic oligonucleotide

<400> SEQUENCE: 162
gagcagtcgg tggaggagtc cggggggtcgc ctggtcacgc ctgggacacc cctgacactc    60

| | |
|---|---|
| acctgcacag cctctggatt ctccctcagt agctatgcaa tgatctgggt ccgccaggct | 120 |
| ccaggggagg ggctggagtg gatcggagac atttatgctg gtggtggtgc cacatactac | 180 |
| gcgagctggg cgaaaggccg attcaccatc tccaaaacct cgaccacggt ggatctgaaa | 240 |
| atcaccagtc cgacaaccga ggacacggcc acctatttct gtgccagagc atatggtagt | 300 |
| ggttatgact tgtggggccc aggcaccctg gtcaccgtct cttca | 345 |

<210> SEQ ID NO 163
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 163

| | |
|---|---|
| gagctcgatc tgacccagac tccagcctct gtggaggtag ctgtgggagg cacagtcacc | 60 |
| atcaagtgcc aggccagtca gagcattagt agttatttat cctggtatca gcagaaacca | 120 |
| gggcagcctc ccaaactcct gatctattat gcatccacta tggcatctgg ggtcccatcg | 180 |
| cggttcagcg gcagtggatc tgggacacag ttcactctca ccatcagcga cctggagtgt | 240 |
| gccgatgctg ccacttacta ctgtcaacag ggtgatagta ggagtaatgt tgataatatt | 300 |
| ttcggcggag ggaccgaggt ggtggtcaaa | 330 |

<210> SEQ ID NO 164
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 164

| | |
|---|---|
| ggattctccc tcagtagcta tgca | 24 |

<210> SEQ ID NO 165
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 165

| | |
|---|---|
| atttatgctg gtggtggtgc caca | 24 |

<210> SEQ ID NO 166
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 166

| | |
|---|---|
| gccagagcat atggtagtgg ttatgacttg | 30 |

<210> SEQ ID NO 167
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 167

| | |
|---|---|
| cagagcatta gtagttat | 18 |

<210> SEQ ID NO 168
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 168
caacagggtg atagtaggag taatgttgat aatatt                              36

<210> SEQ ID NO 169
<211> LENGTH: 117
<212> TYPE: PRT
<213> ORGANISM: Artificial sequence
<220> FEATURE:
<223> OTHER INFORMATION: Synthetic peptide

<400> SEQUENCE: 169

Glu Gln Ser Leu Glu Glu Ser Glu Gly Arg Leu Val Thr Pro Gly Thr
1               5                   10                  15

Pro Leu Thr Leu Thr Cys Thr Ala Ser Gly Phe Ser Leu Ser Gly Tyr
                20                  25                  30

His Met Ser Trp Val Arg Gln Ala Pro Gly Lys Gly Leu Glu Tyr Ile
            35                  40                  45

Gly Tyr Ile Ser Glu Arg Gly Thr Ser Tyr Tyr Ala Asn Trp Ala Lys
        50                  55                  60

Gly Arg Phe Thr Val Ser Lys Ser Ser Ser Thr Val Val Leu Ser
65                  70                  75                  80

Ile Ile Ser Pro Thr Ala Glu Asp Thr Ala Thr Tyr Phe Cys Ala Arg
                85                  90                  95

Tyr Gly Gly Gly Asp Ser Ala Phe Ile Leu Trp Gly Pro Gly Thr Leu
            100                 105                 110

Val Thr Ile Ser Ser
        115

<210> SEQ ID NO 170
<211> LENGTH: 109
<212> TYPE: PRT
<213> ORGANISM: Artificial sequence
<220> FEATURE:
<223> OTHER INFORMATION: Synthetic peptide

<400> SEQUENCE: 170

Glu Leu Val Met Thr Gln Thr Pro Ala Ser Val Ser Gly Pro Val Gly
1               5                   10                  15

Gly Thr Val Thr Ile Lys Cys Gln Ala Ser His Asn Ile Asp Asn Ser
                20                  25                  30

Leu Ala Trp Tyr Gln Gln Lys Pro Gly Gln Pro Pro Lys Leu Leu Ile
            35                  40                  45

Tyr Lys Ala Ser Thr Leu Ala Ser Gly Val Ser Arg Phe Lys Gly
        50                  55                  60

Ser Gly Ser Gly Thr Glu Tyr Thr Leu Thr Ile Ser Asp Leu Glu Cys
65                  70                  75                  80

Ala Asp Ala Ala Thr Tyr Phe Cys Gln Gly Thr Ile Gly Leu Asn Ser
                85                  90                  95

Gly Cys Ala Phe Gly Gly Gly Thr Glu Val Glu Ile Lys
            100                 105

<210> SEQ ID NO 171
<211> LENGTH: 8
<212> TYPE: PRT
<213> ORGANISM: Artificial sequence
<220> FEATURE:
<223> OTHER INFORMATION: Synthetic peptide

<400> SEQUENCE: 171

Gly Phe Ser Leu Ser Gly Tyr His
1               5

<210> SEQ ID NO 172
<211> LENGTH: 7
<212> TYPE: PRT
<213> ORGANISM: Artificial sequence
<220> FEATURE:
<223> OTHER INFORMATION: Synthetic peptide

<400> SEQUENCE: 172

Ile Ser Glu Arg Gly Thr Ser
1               5

<210> SEQ ID NO 173
<211> LENGTH: 12
<212> TYPE: PRT
<213> ORGANISM: Artificial sequence
<220> FEATURE:
<223> OTHER INFORMATION: Synthetic peptide

<400> SEQUENCE: 173

Ala Arg Tyr Gly Gly Gly Asp Ser Ala Phe Ile Leu
1               5                   10

<210> SEQ ID NO 174
<211> LENGTH: 6
<212> TYPE: PRT
<213> ORGANISM: Artificial sequence
<220> FEATURE:
<223> OTHER INFORMATION: Synthetic peptide

<400> SEQUENCE: 174

His Asn Ile Asp Asn Ser
1               5

<210> SEQ ID NO 175
<211> LENGTH: 11
<212> TYPE: PRT
<213> ORGANISM: Artificial sequence
<220> FEATURE:
<223> OTHER INFORMATION: Synthetic peptide

<400> SEQUENCE: 175

Gln Gly Thr Ile Gly Leu Asn Ser Gly Cys Ala
1               5                   10

<210> SEQ ID NO 176
<211> LENGTH: 351
<212> TYPE: DNA
<213> ORGANISM: Artificial sequence
<220> FEATURE:
<223> OTHER INFORMATION: Synthetic oligonucleotide

<400> SEQUENCE: 176
gagcagtcgt tggaggagtc cgagggtcgc ctggtcacgc ctgggacacc cctgacactc      60
acctgcacag cctctggatt ctccctcagt ggctatcata tgtcttgggt ccgccaggct     120
ccagggaagg ggctggaata catcggctat attagtgagc gtggtacctc atattacgcg     180

```
aactgggcga aaggccgatt caccgtctcc aaatcctcgt cgtccacggt ggttctatca    240
atcatcagtc cgacagccga ggacacggcc acctatttct gtgccagata tggtggtggt    300
gattcggctt ttatcttgtg gggcccaggc accctggtca ccatctcttc a             351
```

<210> SEQ ID NO 177
<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 177

```
gagctcgtga tgacccagac tccagcctcc gtgtctggac ctgtgggagg cacagtcacc     60
atcaagtgcc aggccagtca caacattgat aatagtttgg cctggtatca gcagaaacca    120
gggcagcctc ccaagctcct catctacaag gcatccactc tggcatctgg ggtctcatcg    180
cggttcaaag gcagtggatc tgggacagag tacactctca ccatcagcga ccttgagtgt    240
gccgatgctg ccacttactt ctgtcaaggc actattggtc ttaatagtgg gtgtgctttc    300
ggcggaggga ccgaggtgga aatcaaa                                         327
```

<210> SEQ ID NO 178
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 178

```
ggattctccc tcagtggcta tcat                                             24
```

<210> SEQ ID NO 179
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 179

```
attagtgagc gtggtacctc a                                                21
```

<210> SEQ ID NO 180
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 180

```
gccagatatg gtggtggtga ttcggctttt atcttg                                36
```

<210> SEQ ID NO 181
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 181

```
cacaacattg ataatagt                                                    18
```

<210> SEQ ID NO 182

```
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 182
caaggcacta ttggtcttaa tagtgggtgt gct                                    33

<210> SEQ ID NO 183
<211> LENGTH: 122
<212> TYPE: PRT
<213> ORGANISM: Artificial sequence
<220> FEATURE:
<223> OTHER INFORMATION: Synthetic peptide

<400> SEQUENCE: 183
```

Gly Glu Gln Ser Val Glu Glu Ser Gly Gly Asp Leu Val Lys Pro Glu
1               5                   10                  15

Gly Ser Leu Thr Leu Thr Cys Thr Ala Ser Gly Phe Ser Phe Ser Ser
            20                  25                  30

Gly Tyr Tyr Met Cys Trp Val Arg Gln Ala Pro Gly Lys Gly Leu Glu
        35                  40                  45

Trp Ile Gly Cys Ile His Ser Ser Gly Asn Ile Tyr Tyr Ala Ser
    50                  55                  60

Trp Ala Lys Gly Arg Phe Thr Ile Ser Lys Thr Ser Ser Thr Thr Val
65                  70                  75                  80

Asp Leu Gln Leu Thr Ser Leu Thr Ala Ala Asp Thr Ala Thr Tyr Phe
                85                  90                  95

Cys Ala Arg Asp Ser Glu Val Tyr Gly Trp Asn Pro Asn Asp Leu Trp
            100                 105                 110

Gly Pro Gly Thr Leu Val Thr Val Ser Ser
        115                 120

```
<210> SEQ ID NO 184
<211> LENGTH: 111
<212> TYPE: PRT
<213> ORGANISM: Artificial sequence
<220> FEATURE:
<223> OTHER INFORMATION: Synthetic peptide

<400> SEQUENCE: 184
```

Glu Leu Asp Met Thr Gln Thr Pro Ala Ser Val Ser Glu Pro Val Gly
1               5                   10                  15

Gly Thr Val Thr Ile Lys Cys Gln Ala Ser Gln Ser Ile Ser Ser Tyr
            20                  25                  30

Leu Ala Trp Tyr Gln Gln Lys Pro Gly Gln Arg Pro Lys Leu Leu Ile
        35                  40                  45

Tyr Gly Ala Ser Asn Leu Ala Ser Gly Val Ser Ser Arg Phe Lys Gly
    50                  55                  60

Ser Arg Ser Gly Thr Gln Phe Thr Leu Thr Ile Thr Asp Leu Glu Cys
65                  70                  75                  80

Asp Asp Ala Ala Thr Tyr Tyr Cys Gln Cys Ser Tyr Tyr Gly Asn Ser
                85                  90                  95

Tyr Val Gly Gly Ala Phe Gly Gly Gly Thr Glu Val Val Val Lys
            100                 105                 110

```
<210> SEQ ID NO 185
<211> LENGTH: 9
<212> TYPE: PRT
```

```
<213> ORGANISM: Artificial sequence
<220> FEATURE:
<223> OTHER INFORMATION: Synthetic peptide

<400> SEQUENCE: 185

Gly Phe Ser Phe Ser Ser Gly Tyr Tyr
1               5

<210> SEQ ID NO 186
<211> LENGTH: 7
<212> TYPE: PRT
<213> ORGANISM: Artificial sequence
<220> FEATURE:
<223> OTHER INFORMATION: Synthetic peptide

<400> SEQUENCE: 186

Ile His Ser Ser Ser Gly Asn
1               5

<210> SEQ ID NO 187
<211> LENGTH: 14
<212> TYPE: PRT
<213> ORGANISM: Artificial sequence
<220> FEATURE:
<223> OTHER INFORMATION: Synthetic peptide

<400> SEQUENCE: 187

Ala Arg Asp Ser Glu Val Tyr Gly Trp Asn Pro Asn Asp Leu
1               5                   10

<210> SEQ ID NO 188
<211> LENGTH: 6
<212> TYPE: PRT
<213> ORGANISM: Artificial sequence
<220> FEATURE:
<223> OTHER INFORMATION: Synthetic peptide

<400> SEQUENCE: 188

Gln Ser Ile Ser Ser Tyr
1               5

<210> SEQ ID NO 189
<211> LENGTH: 13
<212> TYPE: PRT
<213> ORGANISM: Artificial sequence
<220> FEATURE:
<223> OTHER INFORMATION: Synthetic peptide

<400> SEQUENCE: 189

Gln Cys Ser Tyr Tyr Gly Asn Ser Tyr Val Gly Gly Ala
1               5                   10

<210> SEQ ID NO 190
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 190
gagcagtcgg tggaggagtc cgggggagac ctggtcaagc ctgagggatc cctgacactc      60
acctgcacag cttctggatt ctccttcagt agcggctact acatgtgctg ggtccgccag     120
gctccaggga aggggctgga gtggatcgga tgcatccata gtagtagtgg taatatttac     180
tacgcgagct gggcaaaagg ccgattcacc atctccaaaa cctcgtcgac cacggtggat     240
```

```
ctgcaattga ccagtctgac agccgcggac acggccacct atttctgtgc gagggattcg    300
gaagtttatg gttggaatcc taacgacttg tggggcccag gcaccctggt caccgtctcc    360
tca                                                                  363
```

```
<210> SEQ ID NO 191
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 191
gagctcgata tgacccagac tccagcctcc gtgtctgaac ctgtgggagg cacagtcacc     60
atcaagtgcc aggccagtca gagcattagt agctacttag cctggtatca gcagaaacca    120
gggcagcgtc ccaagctcct gatctatggt gcatccaatc tggcatctgg ggtctcatcg    180
cggttcaaag gcagtagatc tgggacacag ttcactctca ccatcaccga cctggagtgt    240
gacgatgctg ccacttacta ctgtcaatgt agttattatg gtaatagtta tgttgggggg    300
gctttcggcg agggaccga ggtggtggtc aaa                                  333
```

```
<210> SEQ ID NO 192
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 192
ggattctcct tcagtagcgg ctactac                                         27
```

```
<210> SEQ ID NO 193
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 193
atccatagta gtagtggtaa t                                               21
```

```
<210> SEQ ID NO 194
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 194
gcgagggatt cggaagttta tggttggaat cctaacgact tg                        42
```

```
<210> SEQ ID NO 195
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 195
cagagcatta gtagctac                                                   18
```

```
<210> SEQ ID NO 196
<211> LENGTH: 39
```

<212> TYPE: DNA
<213> ORGANISM: Artificial sequence
<220> FEATURE:
<223> OTHER INFORMATION: Synthetic oligonucleotide

<400> SEQUENCE: 196
caatgtagtt attatggtaa tagttatgtt gggggggct         39

<210> SEQ ID NO 197
<211> LENGTH: 117
<212> TYPE: PRT
<213> ORGANISM: Artificial sequence
<220> FEATURE:
<223> OTHER INFORMATION: Synthetic peptide

<400> SEQUENCE: 197

Glu Gln Ser Val Glu Glu Ser Gly Gly Arg Leu Val Thr Pro Gly Thr
1               5                   10                  15

Pro Leu Thr Leu Thr Cys Thr Ala Ser Gly Phe Ser Leu Tyr Lys Tyr
                20                  25                  30

Asn Ile Gln Trp Val Arg Gln Ala Pro Gly Lys Gly Leu Glu Tyr Ile
            35                  40                  45

Gly Ala Ser Thr Tyr Ala Gly Tyr Thr Tyr Tyr Ala Ser Trp Ala Ile
        50                  55                  60

Gly Arg Val Thr Ile Ser Arg Thr Ser Thr Thr Val Asp Leu Lys Met
65                  70                  75                  80

Thr Ser Pro Thr Thr Glu Asp Thr Ala Thr Tyr Phe Cys Ala Arg His
                85                  90                  95

Ile Asp Gly Asp Tyr Ser Gly Tyr Ala Leu Trp Gly Pro Gly Thr Leu
            100                 105                 110

Val Thr Ile Ser Ser
        115

<210> SEQ ID NO 198
<211> LENGTH: 111
<212> TYPE: PRT
<213> ORGANISM: Artificial sequence
<220> FEATURE:
<223> OTHER INFORMATION: Synthetic peptide

<400> SEQUENCE: 198

Glu Leu Asp Leu Thr Gln Thr Pro Ala Ser Val Ser Ala Ala Val Gly
1               5                   10                  15

Gly Thr Val Thr Ile Lys Cys Gln Ala Ser Gln Ser Ile Asp Thr Trp
                20                  25                  30

Phe Gly Trp Tyr Gln Gln Lys Pro Gly Gln Ser Pro Lys Leu Leu Ile
            35                  40                  45

Tyr Gly Ala Ser Lys Leu Ala Ser Gly Val Pro Pro Arg Phe Lys Gly
        50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Asn Thr Tyr Tyr Gly Val Arg
                85                  90                  95

Tyr Leu Gly Gly Ala Phe Gly Gly Gly Thr Glu Val Glu Ile Lys
            100                 105                 110

<210> SEQ ID NO 199
<211> LENGTH: 8
<212> TYPE: PRT
<213> ORGANISM: Artificial sequence

```
<220> FEATURE:
<223> OTHER INFORMATION: Synthetic peptide

<400> SEQUENCE: 199

Gly Phe Ser Leu Tyr Lys Tyr Asn
1               5

<210> SEQ ID NO 200
<211> LENGTH: 7
<212> TYPE: PRT
<213> ORGANISM: Artificial sequence
<220> FEATURE:
<223> OTHER INFORMATION: Synthetic peptide

<400> SEQUENCE: 200

Ser Thr Tyr Ala Gly Tyr Thr
1               5

<210> SEQ ID NO 201
<211> LENGTH: 13
<212> TYPE: PRT
<213> ORGANISM: Artificial sequence
<220> FEATURE:
<223> OTHER INFORMATION: Synthetic peptide

<400> SEQUENCE: 201

Ala Arg His Ile Asp Gly Asp Tyr Ser Gly Tyr Ala Leu
1               5                   10

<210> SEQ ID NO 202
<211> LENGTH: 6
<212> TYPE: PRT
<213> ORGANISM: Artificial sequence
<220> FEATURE:
<223> OTHER INFORMATION: Synthetic peptide

<400> SEQUENCE: 202

Gln Ser Ile Asp Thr Trp
1               5

<210> SEQ ID NO 203
<211> LENGTH: 13
<212> TYPE: PRT
<213> ORGANISM: Artificial sequence
<220> FEATURE:
<223> OTHER INFORMATION: Synthetic peptide

<400> SEQUENCE: 203

Gln Asn Thr Tyr Tyr Gly Val Arg Tyr Leu Gly Gly Ala
1               5                   10

<210> SEQ ID NO 204
<211> LENGTH: 351
<212> TYPE: DNA
<213> ORGANISM: Artificial sequence
<220> FEATURE:
<223> OTHER INFORMATION: Synthetic oligonucleotide

<400> SEQUENCE: 204
gagcagtcgg tggaggagtc cggggggtcgc ctggtcacgc ctgggacacc cctgacactc      60
acctgcacag cctctggatt ctccctctat aagtacaaca ttcaatgggt ccgccaggct     120
ccagggaagg ggctggaata catcggagcc agtacttatg ctggttacac atactacgcg     180
agctgggcga taggccgagt caccatctcc agaacctcga ccacggtgga tctgaaaatg     240
accagtccga caaccgagga cacggccacc tatttctgtg ccagacatat tgatggtgat     300
```

```
tatagtggat acgccttgtg gggcccaggc accctggtca ccatctcttc a        351
```

<210> SEQ ID NO 205
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 205

```
gagctcgatc tgacccagac accagcctcc gtgtctgcag ctgtgggagg cacagtcacc   60
atcaagtgcc aggccagtca gagcattgat acttggttcg gctggtatca gcagaaacca  120
gggcagtctc ccaagctcct gatctatggt gcatccaaac tggcatctgg ggtcccaccg  180
cggttcaaag gcagtggatc tgggacagag ttcactctca ccatcagcga cctggagtgt  240
gccgatgctg ccacttacta ctgtcaaaac acttattatg gtgttcgtta tcttggaggt  300
gctttcggcg agggaccga ggtggaaatc aaa                                333
```

<210> SEQ ID NO 206
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 206

```
ggattctccc tctataagta caac                                          24
```

<210> SEQ ID NO 207
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 207

```
agtacttatg ctggttacac a                                             21
```

<210> SEQ ID NO 208
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 208

```
gccagacata ttgatggtga ttatagtgga tacgccttg                          39
```

<210> SEQ ID NO 209
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 209

```
cagagcattg atacttgg                                                 18
```

<210> SEQ ID NO 210
<211> LENGTH: 39
<212> TYPE: DNA
<213> ORGANISM: Artificial sequence
<220> FEATURE:

<223> OTHER INFORMATION: Synthetic oligonucleotide

<400> SEQUENCE: 210
caaaacactt attatggtgt tcgttatctt ggaggtgct                    39

<210> SEQ ID NO 211
<211> LENGTH: 116
<212> TYPE: PRT
<213> ORGANISM: Artificial sequence
<220> FEATURE:
<223> OTHER INFORMATION: Synthetic peptide

<400> SEQUENCE: 211

Ala Ala Val Lys Glu Ser Gly Gly Arg Leu Val Thr Pro Gly Thr Pro
1               5                   10                  15

Leu Thr Leu Thr Cys Thr Ala Ser Gly Phe Ser Leu Tyr Lys Tyr Asn
                20                  25                  30

Ile Gln Trp Val Arg Gln Ala Pro Gly Lys Gly Leu Glu Tyr Ile Gly
            35                  40                  45

Ala Ser Thr Tyr Ala Gly Tyr Thr Tyr Tyr Ala Ser Trp Ala Lys Gly
        50                  55                  60

Arg Val Thr Ile Ser Arg Thr Ser Thr Thr Val Asp Leu Lys Met Thr
65                  70                  75                  80

Ser Pro Thr Thr Glu Asp Thr Ala Thr Tyr Phe Cys Ala Arg His Ile
                85                  90                  95

Asp Gly Asp Tyr Ser Gly Tyr Ala Leu Trp Gly Pro Gly Thr Leu Val
            100                 105                 110

Thr Val Ser Ser
            115

<210> SEQ ID NO 212
<211> LENGTH: 111
<212> TYPE: PRT
<213> ORGANISM: Artificial sequence
<220> FEATURE:
<223> OTHER INFORMATION: Synthetic peptide

<400> SEQUENCE: 212

Glu Leu Val Leu Thr Gln Thr Pro Ala Ser Val Ser Ala Ala Val Gly
1               5                   10                  15

Gly Thr Val Thr Ile Lys Cys Gln Ala Ser Gln Ser Ile Gly Thr Trp
                20                  25                  30

Phe Ala Trp Tyr Gln Gln Lys Pro Gly Gln Ser Pro Lys Leu Leu Ile
            35                  40                  45

Tyr Gly Pro Ser Lys Leu Ala Ser Gly Val Pro Pro Arg Phe Lys Gly
        50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Ser Thr Tyr Phe Gly Val Asp
                85                  90                  95

Tyr Leu Gly Gly Thr Phe Gly Gly Gly Thr Glu Val Glu Ile Lys
            100                 105                 110

<210> SEQ ID NO 213
<211> LENGTH: 8
<212> TYPE: PRT
<213> ORGANISM: Artificial sequence
<220> FEATURE:
<223> OTHER INFORMATION: Synthetic peptide

<400> SEQUENCE: 213

Gly Phe Ser Leu Tyr Lys Tyr Asn
1               5

<210> SEQ ID NO 214
<211> LENGTH: 7
<212> TYPE: PRT
<213> ORGANISM: Artificial sequence
<220> FEATURE:
<223> OTHER INFORMATION: Synthetic peptide

<400> SEQUENCE: 214

Ser Thr Tyr Ala Gly Tyr Thr
1               5

<210> SEQ ID NO 215
<211> LENGTH: 13
<212> TYPE: PRT
<213> ORGANISM: Artificial sequence
<220> FEATURE:
<223> OTHER INFORMATION: Synthetic peptide

<400> SEQUENCE: 215

Ala Arg His Ile Asp Gly Asp Tyr Ser Gly Tyr Ala Leu
1               5                   10

<210> SEQ ID NO 216
<211> LENGTH: 6
<212> TYPE: PRT
<213> ORGANISM: Artificial sequence
<220> FEATURE:
<223> OTHER INFORMATION: Synthetic peptide

<400> SEQUENCE: 216

Gln Ser Ile Gly Thr Trp
1               5

<210> SEQ ID NO 217
<211> LENGTH: 13
<212> TYPE: PRT
<213> ORGANISM: Artificial sequence
<220> FEATURE:
<223> OTHER INFORMATION: Synthetic peptide

<400> SEQUENCE: 217

Gln Ser Thr Tyr Phe Gly Val Asp Tyr Leu Gly Gly Thr
1               5                   10

<210> SEQ ID NO 218
<211> LENGTH: 348
<212> TYPE: DNA
<213> ORGANISM: Artificial sequence
<220> FEATURE:
<223> OTHER INFORMATION: Synthetic oligonucleotide

<400> SEQUENCE: 218
gcagcggtga aggagtccgg gggtcgcctg gtcacgcctg gacacccct gacactcacc      60 tgcacagcct ctggattctc cctctataag tacaatatac aatgggtccg ccaggctcca    120
gggaaggggc tggaatacat cggagccagt acttatgctg ttacacata ctacgcgagc    180 tgggcaaaag gccgagtcac catctccaga acctcgacca cggtggatct gaaaatgacc    240
agtccgacaa ccgaggacac ggccacctat ttctgtgcca gacatattga tggtgattat    300
agtggatacg ccttgtgggg cccaggcacc ctggtcaccg tctcctca                348

<210> SEQ ID NO 219
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 219

```
gagctcgtgc tgacccagac accagcctcc gtgtctgcag ctgtgggagg cacagtcacc    60
atcaagtgcc aggccagtca gagcattggt acttggttcg cctggtatca gcagaaacca   120
gggcagtctc ccaagctcct gatctatggt ccatccaaac tggcatctgg ggtcccaccg   180
cggttcaaag gcagtggatc tgggacagag ttcactctca ccatcagcga cctggagtgt   240
gccgatgctg ccacttacta ctgtcaaagc acttatttcg gtgttgatta tcttggaggt   300
actttcggcg gagggaccga ggtggaaatc aaa                                333
```

<210> SEQ ID NO 220
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 220

```
ggattctccc tctataagta caat                                           24
```

<210> SEQ ID NO 221
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 221

```
agtacttatg ctggttacac a                                              21
```

<210> SEQ ID NO 222
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 222

```
gccagacata ttgatggtga ttatagtgga tacgccttg                           39
```

<210> SEQ ID NO 223
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 223

```
cagagcattg gtacttgg                                                  18
```

<210> SEQ ID NO 224
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 224
caaagcactt atttcggtgt tgattatctt ggaggtact                          39

<210> SEQ ID NO 225
<211> LENGTH: 116
<212> TYPE: PRT
<213> ORGANISM: Artificial sequence
<220> FEATURE:
<223> OTHER INFORMATION: Synthetic peptide

<400> SEQUENCE: 225

Ala Ala Val Lys Glu Ser Gly Gly Arg Leu Val Thr Pro Gly Thr Pro
1               5                   10                  15

Leu Thr Leu Thr Cys Thr Ala Ser Gly Phe Ser Leu Tyr Lys Tyr Asn
            20                  25                  30

Ile Gln Trp Val Arg Gln Ala Pro Gly Lys Gly Leu Glu Tyr Ile Gly
        35                  40                  45

Ala Ser Thr Tyr Ala Gly Tyr Thr Tyr Tyr Ala Ser Trp Ala Lys Gly
    50                  55                  60

Arg Val Thr Ile Ser Arg Thr Ser Thr Thr Val Asp Leu Lys Met Thr
65                  70                  75                  80

Ser Pro Thr Thr Glu Asp Thr Ala Thr Tyr Phe Cys Ala Arg His Ile
                85                  90                  95

Asp Gly Asp Tyr Ser Gly Tyr Ala Leu Trp Gly Pro Gly Thr Leu Val
            100                 105                 110

Thr Val Ser Ser
        115

<210> SEQ ID NO 226
<211> LENGTH: 110
<212> TYPE: PRT
<213> ORGANISM: Artificial sequence
<220> FEATURE:
<223> OTHER INFORMATION: Synthetic peptide

<400> SEQUENCE: 226

Glu Leu Val Leu Thr Gln Thr Pro Ala Ser Val Ser Ala Ala Val Gly
1               5                   10                  15

Gly Thr Val Thr Ile Lys Cys Gln Ala Ser Gln Ser Ile Gly Thr Trp
            20                  25                  30

Phe Ala Trp Tyr Gln Gln Lys Pro Gly Gln Ser Pro Lys Leu Leu Ile
        35                  40                  45

Tyr Gly Ala Ser Asn Leu Ala Ser Gly Val Ser Ser Arg Phe Lys Gly
    50                  55                  60

Ile Arg Ser Gly Thr Glu Tyr Thr Leu Thr Ile Ser Asp Leu Glu Cys
65                  70                  75                  80

Ala Asp Ala Ala Thr Tyr Tyr Cys Gln Cys Ser Asp Val Gly Asn Thr
                85                  90                  95

Tyr Gly Ala Ala Phe Gly Gly Gly Thr Glu Val Glu Ile Asn
            100                 105                 110

<210> SEQ ID NO 227
<211> LENGTH: 8
<212> TYPE: PRT
<213> ORGANISM: Artificial sequence
<220> FEATURE:
<223> OTHER INFORMATION: Synthetic peptide

<400> SEQUENCE: 227

Gly Phe Ser Leu Tyr Lys Tyr Asn

<210> SEQ ID NO 228
<211> LENGTH: 7
<212> TYPE: PRT
<213> ORGANISM: Artificial sequence
<220> FEATURE:
<223> OTHER INFORMATION: Synthetic peptide

<400> SEQUENCE: 228

Ser Thr Tyr Ala Gly Tyr Thr
1               5

<210> SEQ ID NO 229
<211> LENGTH: 13
<212> TYPE: PRT
<213> ORGANISM: Artificial sequence
<220> FEATURE:
<223> OTHER INFORMATION: Synthetic peptide

<400> SEQUENCE: 229

Ala Arg His Ile Asp Gly Asp Tyr Ser Gly Tyr Ala Leu
1               5                   10

<210> SEQ ID NO 230
<211> LENGTH: 6
<212> TYPE: PRT
<213> ORGANISM: Artificial sequence
<220> FEATURE:
<223> OTHER INFORMATION: Synthetic peptide

<400> SEQUENCE: 230

Gln Ser Ile Gly Thr Trp
1               5

<210> SEQ ID NO 231
<211> LENGTH: 12
<212> TYPE: PRT
<213> ORGANISM: Artificial sequence
<220> FEATURE:
<223> OTHER INFORMATION: Synthetic peptide

<400> SEQUENCE: 231

Gln Cys Ser Asp Val Gly Asn Thr Tyr Gly Ala Ala
1               5                   10

<210> SEQ ID NO 232
<211> LENGTH: 348
<212> TYPE: DNA
<213> ORGANISM: Artificial sequence
<220> FEATURE:
<223> OTHER INFORMATION: Synthetic oligonucleotide

<400> SEQUENCE: 232
gcagcggtga aggagtccgg gggtcgcctg gtcacgcctg ggacacccct gacactcacc      60
tgcacagcct ctggattctc cctctataag tacaatatac aatgggtccg ccaggctcca     120 gggaagggc tggaatacat cggagccagt acttatgctg gttacacata ctacgcgagc     180
tgggcaaaag gccgagtcac catctccaga acctcgacca cggtggatct gaaaatgacc     240
agtccgacaa ccgaggacac ggccacctat ttctgtgcca gacatattga tggtgattat     300
agtggatacg ccttgtgggg cccaggcacc ctggtcaccg tctcctca                  348

<210> SEQ ID NO 233
<211> LENGTH: 330

```
<212> TYPE: DNA
<213> ORGANISM: Artificial sequence
<220> FEATURE:
<223> OTHER INFORMATION: Synthetic oligonucleotide

<400> SEQUENCE: 233
gagctcgtgc tgacccagac accagcctcc gtgtctgcag ctgtgggagg cacagtcacc    60
atcaagtgcc aggccagtca gagcattggt acttggttcg cctggtatca gcagaaacca   120
gggcagtctc ccaagctcct gatctatggt gcatccaatc tggcatctgg ggtctcatcg   180
cggttcaaag gcattagatc tgggacagaa tacactctca ccatcagcga cctggagtgt   240
gccgatgctg ccacttacta ttgtcaatgt tctgatgttg gtaatactta tggcgctgct   300
ttcggcggag ggaccgaggt ggaaatcaac                                    330

<210> SEQ ID NO 234
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 234
ggattctccc tctataagta caat                                           24

<210> SEQ ID NO 235
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 235
agtacttatg ctggttacac a                                              21

<210> SEQ ID NO 236
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 236
gccagacata ttgatggtga ttatagtgga tacgccttg                           39

<210> SEQ ID NO 237
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 237
cagagcattg gtacttgg                                                  18

<210> SEQ ID NO 238
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 238
caatgttctg atgttggtaa tacttatggc gctgct                              36
```

```
<210> SEQ ID NO 239
<211> LENGTH: 116
<212> TYPE: PRT
<213> ORGANISM: Artificial sequence
<220> FEATURE:
<223> OTHER INFORMATION: Synthetic peptide

<400> SEQUENCE: 239

Gln Ser Val Lys Glu Ser Gly Gly Arg Leu Val Thr Pro Gly Thr Pro
1               5                   10                  15

Leu Thr Leu Thr Cys Thr Ala Ser Gly Phe Ser Leu Tyr Lys Tyr Asn
                20                  25                  30

Ile Gln Trp Val Arg Gln Ala Pro Gly Lys Gly Leu Glu Tyr Ile Gly
            35                  40                  45

Ala Ser Thr Tyr Ala Gly Tyr Thr Tyr Tyr Ala Ser Trp Ala Lys Gly
        50                  55                  60

Arg Val Thr Ile Ser Arg Thr Ser Thr Val Asp Leu Lys Met Thr
65                  70                  75                  80

Ser Pro Thr Thr Glu Asp Thr Ala Thr Tyr Phe Cys Ala Arg His Ile
                85                  90                  95

Asp Gly Asp Tyr Ser Gly Tyr Ala Leu Trp Gly Pro Gly Thr Leu Val
                100                 105                 110

Thr Ile Ser Ser
        115

<210> SEQ ID NO 240
<211> LENGTH: 111
<212> TYPE: PRT
<213> ORGANISM: Artificial sequence
<220> FEATURE:
<223> OTHER INFORMATION: Synthetic peptide

<400> SEQUENCE: 240

Glu Leu Val Leu Thr Gln Thr Pro Ala Ser Val Ser Ala Ala Val Gly
1               5                   10                  15

Gly Thr Val Thr Ile Lys Cys Gln Ala Ser Gln Ser Ile Gly Thr Trp
                20                  25                  30

Phe Ala Trp Tyr Gln Gln Lys Pro Gly Gln Ser Pro Lys Leu Leu Ile
            35                  40                  45

Tyr Gly Pro Ser Lys Leu Ala Ser Gly Val Pro Pro Arg Phe Lys Gly
        50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Ser Thr Tyr Phe Gly Val Asp
                85                  90                  95

Tyr Leu Gly Gly Thr Phe Gly Gly Thr Glu Val Val Val Lys
                100                 105                 110

<210> SEQ ID NO 241
<211> LENGTH: 8
<212> TYPE: PRT
<213> ORGANISM: Artificial sequence
<220> FEATURE:
<223> OTHER INFORMATION: Synthetic peptide

<400> SEQUENCE: 241

Gly Phe Ser Leu Tyr Lys Tyr Asn
1               5
```

<210> SEQ ID NO 242
<211> LENGTH: 7
<212> TYPE: PRT
<213> ORGANISM: Artificial sequence
<220> FEATURE:
<223> OTHER INFORMATION: Synthetic peptide

<400> SEQUENCE: 242

Ser Thr Tyr Ala Gly Tyr Thr
1               5

<210> SEQ ID NO 243
<211> LENGTH: 13
<212> TYPE: PRT
<213> ORGANISM: Artificial sequence
<220> FEATURE:
<223> OTHER INFORMATION: Synthetic peptide

<400> SEQUENCE: 243

Ala Arg His Ile Asp Gly Asp Tyr Ser Gly Tyr Ala Leu
1               5                   10

<210> SEQ ID NO 244
<211> LENGTH: 6
<212> TYPE: PRT
<213> ORGANISM: Artificial sequence
<220> FEATURE:
<223> OTHER INFORMATION: Synthetic peptide

<400> SEQUENCE: 244

Gln Ser Ile Gly Thr Trp
1               5

<210> SEQ ID NO 245
<211> LENGTH: 13
<212> TYPE: PRT
<213> ORGANISM: Artificial sequence
<220> FEATURE:
<223> OTHER INFORMATION: Synthetic peptide

<400> SEQUENCE: 245

Gln Ser Thr Tyr Phe Gly Val Asp Tyr Leu Gly Gly Thr
1               5                   10

<210> SEQ ID NO 246
<211> LENGTH: 348
<212> TYPE: DNA
<213> ORGANISM: Artificial sequence
<220> FEATURE:
<223> OTHER INFORMATION: Synthetic oligonucleotide

<400> SEQUENCE: 246
cagtcggtga aggagtccgg gggtcgcctg gtcacgcctg ggacacccct gacactcacc      60
tgcacagcct ctggattctc cctctataag tacaatatac aatgggtccg ccaggctcca     120
gggaaggggc tggaatacat cggagccagt acttatgctg gttacacata ctacgcgagc     180
tgggcaaaag gccgagtcac catctccaga acctcgacca cggtggatct gaaaatgacc     240
agtccgacaa ccgaggacac ggccacctat ttctgtgcca gacatattga tggtgattat     300
agtggatacg ccttgtgggg cccaggcacc ctggtcacca tctcctca                  348

<210> SEQ ID NO 247
<211> LENGTH: 333
<212> TYPE: DNA
<213> ORGANISM: Artificial sequence
<220> FEATURE:

<223> OTHER INFORMATION: Synthetic oligonucleotide

<400> SEQUENCE: 247

```
gagctcgtgc tgacccagac accagcctcc gtgtctgcag ctgtgggagg cacagtcacc      60
atcaagtgcc aggccagtca gagcattggt acttggttcg cctggtatca gcagaaacca     120
gggcagtctc ccaagctcct gatctatggt ccatccaaac tggcatctgg ggtcccaccg     180
cggttcaaag gcagtggatc tgggacagag ttcactctca ccatcagcga cctggagtgt     240
gccgatgctg ccacttacta ctgtcaaagc acttatttcg gtgttgatta tcttggaggt     300
actttcggcg gagggaccga ggtggtggtc aaa                                  333
```

<210> SEQ ID NO 248
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 248

```
ggattctccc tctataagta caat                                             24
```

<210> SEQ ID NO 249
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 249

```
agtacttatg ctggttacac a                                                21
```

<210> SEQ ID NO 250
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 250

```
gccagacata ttgatggtga ttatagtgga tacgccttg                             39
```

<210> SEQ ID NO 251
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 251

```
cagagcattg gtacttgg                                                    18
```

<210> SEQ ID NO 252
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 252

```
caaagcactt atttcggtgt tgattatctt ggaggtact                             39
```

<210> SEQ ID NO 253
<211> LENGTH: 116

```
<212> TYPE: PRT
<213> ORGANISM: Artificial sequence
<220> FEATURE:
<223> OTHER INFORMATION: Synthetic peptide

<400> SEQUENCE: 253

Gln Ser Val Lys Glu Ser Gly Gly Arg Leu Val Thr Pro Gly Thr Pro
1               5                   10                  15
Leu Thr Leu Thr Cys Thr Ala Ser Gly Phe Ser Leu Tyr Lys Tyr Asn
                20                  25                  30
Ile Gln Trp Val Arg Gln Ala Pro Gly Lys Gly Leu Glu Tyr Ile Gly
            35                  40                  45
Ala Ser Thr Tyr Ala Gly Tyr Thr Tyr Tyr Ala Ser Trp Ala Lys Gly
        50                  55                  60
Arg Val Thr Ile Ser Arg Thr Ser Thr Val Asp Leu Lys Met Thr
65                  70                  75                  80
Ser Pro Thr Thr Glu Asp Thr Ala Thr Tyr Phe Cys Ala Arg His Ile
                85                  90                  95
Asp Gly Asp Tyr Ser Gly Tyr Ala Leu Trp Gly Pro Gly Thr Leu Val
                100                 105                 110
Thr Ile Ser Ser
            115

<210> SEQ ID NO 254
<211> LENGTH: 111
<212> TYPE: PRT
<213> ORGANISM: Artificial sequence
<220> FEATURE:
<223> OTHER INFORMATION: Synthetic peptide

<400> SEQUENCE: 254

Glu Leu Val Met Thr Gln Thr Pro Ala Ser Val Ser Ala Ala Val Gly
1               5                   10                  15
Gly Thr Val Thr Ile Lys Cys Gln Ala Ser Gln Ser Ile Gly Thr Trp
                20                  25                  30
Phe Ala Trp Tyr Gln Gln Lys Pro Gly Gln Ser Pro Lys Leu Leu Ile
            35                  40                  45
Tyr Gly Pro Ser Lys Leu Ala Ser Gly Val Pro Pro Arg Phe Lys Gly
        50                  55                  60
Ser Gly Ser Gly Thr Glu Phe Thr Leu Thr Ile Ser Asp Leu Glu Cys
65                  70                  75                  80
Asp Asp Ala Ala Thr Tyr Tyr Cys Gln Ser Asn Gly Gly Ser Ile Ser
                85                  90                  95
Asn Gly Trp Gly Ser Phe Gly Gly Gly Thr Glu Val Val Val Lys
                100                 105                 110

<210> SEQ ID NO 255
<211> LENGTH: 8
<212> TYPE: PRT
<213> ORGANISM: Artificial sequence
<220> FEATURE:
<223> OTHER INFORMATION: Synthetic peptide

<400> SEQUENCE: 255

Gly Phe Ser Leu Tyr Lys Tyr Asn
1               5

<210> SEQ ID NO 256
<211> LENGTH: 7
<212> TYPE: PRT
```

<213> ORGANISM: Artificial sequence
<220> FEATURE:
<223> OTHER INFORMATION: Synthetic peptide

<400> SEQUENCE: 256

Ser Thr Tyr Ala Gly Tyr Thr
1               5

<210> SEQ ID NO 257
<211> LENGTH: 13
<212> TYPE: PRT
<213> ORGANISM: Artificial sequence
<220> FEATURE:
<223> OTHER INFORMATION: Synthetic peptide

<400> SEQUENCE: 257

Ala Arg His Ile Asp Gly Asp Tyr Ser Gly Tyr Ala Leu
1               5                   10

<210> SEQ ID NO 258
<211> LENGTH: 6
<212> TYPE: PRT
<213> ORGANISM: Artificial sequence
<220> FEATURE:
<223> OTHER INFORMATION: Synthetic peptide

<400> SEQUENCE: 258

Gln Ser Ile Gly Thr Trp
1               5

<210> SEQ ID NO 259
<211> LENGTH: 13
<212> TYPE: PRT
<213> ORGANISM: Artificial sequence
<220> FEATURE:
<223> OTHER INFORMATION: Synthetic peptide

<400> SEQUENCE: 259

Gln Ser Asn Gly Gly Ser Ile Ser Asn Gly Trp Gly Ser
1               5                   10

<210> SEQ ID NO 260
<211> LENGTH: 348
<212> TYPE: DNA
<213> ORGANISM: Artificial sequence
<220> FEATURE:
<223> OTHER INFORMATION: Synthetic oligonucleotide

<400> SEQUENCE: 260
cagtcggtga aggagtccgg gggtcgcctg gtcacgcctg ggacacccct gacactcacc      60
tgcacagcct ctggattctc cctctataag tacaatatac aatgggtccg ccaggctcca     120
gggaaggggc tggaatacat cggagccagt acttatgctg ttacacata ctacgcgagc      180 tgggcaaaag gccgagtcac catctccaga acctcgacca cggtggatct gaaaatgacc     240
agtccgacaa ccgaggacac ggccacctat ttctgtgcca gacatattga tggtgattat     300
agtggatacg ccttgtgggg cccaggcacc ctggtcacca tctcctca                  348

<210> SEQ ID NO 261
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 261

```
gagctcgtga tgacccagac accagcctcc gtgtctgcag ctgtgggagg cacagtcacc    60
atcaagtgcc aggccagtca gagcattggt acttggttcg cctggtatca gcagaaacca   120
gggcagtctc ccaagctcct gatctatggt ccatccaaac tggcatctgg ggtcccaccg   180
cggttcaaag gcagtggatc tgggacagag ttcactctca ccatcagcga cctggagtgt   240
gacgatgctg ccacttacta ctgtcaaagc aatggtggta gtattagtaa tggttggggt   300
agtttcggcg agggaccga ggtggtggtc aaa                                 333
```

<210> SEQ ID NO 262
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 262

```
ggattctccc tctataagta caat                                          24
```

<210> SEQ ID NO 263
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 263

```
agtacttatg ctggttacac a                                             21
```

<210> SEQ ID NO 264
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 264

```
gccagacata ttgatggtga ttatagtgga tacgccttg                          39
```

<210> SEQ ID NO 265
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 265

```
cagagcattg gtacttgg                                                 18
```

<210> SEQ ID NO 266
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 266

```
caaagcaatg gtggtagtat tagtaatggt tggggtagt                          39
```

<210> SEQ ID NO 267
<211> LENGTH: 121
<212> TYPE: PRT
<213> ORGANISM: Artificial sequence
<220> FEATURE:

<223> OTHER INFORMATION: Synthetic peptide

<400> SEQUENCE: 267

Gln Ser Val Lys Glu Ser Gly Gly Asp Leu Val Lys Pro Glu Gly Ser
1               5                   10                  15
Leu Thr Leu Thr Cys Lys Ala Ser Gly Phe Ser Phe Ser Asn Ser Tyr
            20                  25                  30
Tyr Met Cys Trp Val Arg Gln Ala Pro Gly Lys Gly Leu Glu Trp Ile
        35                  40                  45
Ala Cys Ile Tyr Thr Gly Ser Thr Gly Thr Tyr Tyr Ala Ser Trp
    50                  55                  60
Val Asn Gly Arg Phe Thr Ile Ser Lys Thr Pro Ser Thr Thr Val Thr
65                  70                  75                  80
Leu Gln Met Thr Ser Leu Thr Val Ala Asp Thr Ala Thr Tyr Phe Cys
                85                  90                  95
Ser Arg Lys Leu Thr Asn Phe Asn Gly Ala Tyr Leu Asp Leu Trp Gly
            100                 105                 110
Pro Gly Thr Leu Val Thr Ile Ser Ser
            115                 120

<210> SEQ ID NO 268
<211> LENGTH: 110
<212> TYPE: PRT
<213> ORGANISM: Artificial sequence
<220> FEATURE:
<223> OTHER INFORMATION: Synthetic peptide

<400> SEQUENCE: 268

Glu Leu Val Leu Thr Gln Thr Pro Ala Ser Val Glu Ala Ala Val Gly
1               5                   10                  15
Gly Thr Val Thr Ile Asn Cys Gln Ala Ser Gln Ser Ile Ser Asn Leu
            20                  25                  30
Leu Ala Trp Tyr Gln Gln Lys Pro Gly Gln Arg Pro Lys Leu Leu Ile
        35                  40                  45
Tyr Arg Ala Ser Thr Leu Ala Ser Gly Val Ser Ser Arg Phe Lys Gly
    50                  55                  60
Ser Gly Ser Gly Thr Glu Tyr Thr Leu Thr Ile Ser Gly Val Gln Cys
65                  70                  75                  80
Asp Asp Ala Ala Thr Tyr Tyr Cys Gln Gln Gly Tyr Thr Ser Asn Asn
                85                  90                  95
Val Asp Asn Ala Phe Gly Gly Gly Thr Glu Val Glu Ile Lys
            100                 105                 110

<210> SEQ ID NO 269
<211> LENGTH: 9
<212> TYPE: PRT
<213> ORGANISM: Artificial sequence
<220> FEATURE:
<223> OTHER INFORMATION: Synthetic peptide

<400> SEQUENCE: 269

Gly Phe Ser Phe Ser Asn Ser Tyr Tyr
1               5

<210> SEQ ID NO 270
<211> LENGTH: 9
<212> TYPE: PRT
<213> ORGANISM: Artificial sequence
<220> FEATURE:
<223> OTHER INFORMATION: Synthetic peptide

<400> SEQUENCE: 270

Ile Tyr Thr Gly Ser Thr Ser Gly Thr
1               5

<210> SEQ ID NO 271
<211> LENGTH: 14
<212> TYPE: PRT
<213> ORGANISM: Artificial sequence
<220> FEATURE:
<223> OTHER INFORMATION: Synthetic peptide

<400> SEQUENCE: 271

Ser Arg Lys Leu Thr Asn Phe Asn Gly Ala Tyr Leu Asp Leu
1               5                   10

<210> SEQ ID NO 272
<211> LENGTH: 6
<212> TYPE: PRT
<213> ORGANISM: Artificial sequence
<220> FEATURE:
<223> OTHER INFORMATION: Synthetic peptide

<400> SEQUENCE: 272

Gln Ser Ile Ser Asn Leu
1               5

<210> SEQ ID NO 273
<211> LENGTH: 12
<212> TYPE: PRT
<213> ORGANISM: Artificial sequence
<220> FEATURE:
<223> OTHER INFORMATION: Synthetic peptide

<400> SEQUENCE: 273

Gln Gln Gly Tyr Thr Ser Asn Asn Val Asp Asn Ala
1               5                   10

<210> SEQ ID NO 274
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 274

```
cagtcggtga aggagtccgg gggagacctg gtcaagcctg agggatccct gacactcacc        60
tgcaaagcct ctggattctc cttcagtaat agtattacta tgtgctgggt ccgccaggct       120
ccagggaagg ggctggagtg gatcgcatgc atttatactg gtagtactag tggcacttac       180
tacgcgagct gggtgaatgg ccgattcacc atctccaaaa ccccgtcgac cacggtgact       240
ctgcaaatga ccagtctgac agtcgcggac acggccacct atttctgttc gagaaagctt       300
accaatttca atggtgctta tttagatttg tggggccag gcaccctggt caccatctcc        360
tca                                                                     363
```

<210> SEQ ID NO 275
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 275
gagctcgtgc tgacccagac accagcctcc gtggaggcag ctgtgggagg cacagtcacc    60
atcaattgcc aggccagtca gagcattagc aacctcttag cctggtatca gcagaaacca   120
gggcagcgtc ccaagctcct gatctacagg gcatccactc tggcatctgg ggtctcatcg   180
cggttcaaag gcagtggatc tgggacagag tacactctca ccatcagcgg cgtgcagtgt   240
gacgatgctg ccacttacta ctgtcaacag gttatacta gtaataatgt cgataatgct   300
ttcggcggag ggaccgaggt ggaaatcaaa                                     330

<210> SEQ ID NO 276
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 276
ggattctcct tcagtaatag ttattac                                         27

<210> SEQ ID NO 277
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 277
atttatactg gtagtactag tggcact                                         27

<210> SEQ ID NO 278
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 278
tcgagaaagc ttaccaattt caatggtgct tatttagatt tg                        42

<210> SEQ ID NO 279
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 279
cagagcatta gcaacctc                                                   18

<210> SEQ ID NO 280
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 280
caacagggtt atactagtaa taatgtcgat aatgct                               36

<210> SEQ ID NO 281
<211> LENGTH: 121
<212> TYPE: PRT
<213> ORGANISM: Artificial sequence
<220> FEATURE:
<223> OTHER INFORMATION: Synthetic peptide

<400> SEQUENCE: 281

Gln Ser Val Lys Glu Ser Gly Gly Asp Leu Val Lys Pro Gly Ser
1               5                   10                  15

Leu Thr Leu Thr Cys Lys Ala Ser Gly Phe Ser Phe Ser Asn Ser Tyr
                20                  25                  30

Tyr Met Cys Trp Val Arg Gln Ala Pro Gly Lys Gly Leu Glu Trp Ile
            35                  40                  45

Ala Cys Ile Tyr Thr Gly Ser Thr Ser Gly Thr Tyr Tyr Ala Ser Trp
        50                  55                  60

Val Asn Gly Arg Phe Thr Ile Ser Lys Thr Pro Ser Thr Thr Val Thr
65                  70                  75                  80

Leu Gln Met Thr Ser Leu Thr Val Ala Asp Thr Ala Thr Tyr Phe Cys
                85                  90                  95

Ser Arg Lys Leu Thr Asn Phe Asn Gly Ala Tyr Leu Asp Leu Trp Gly
            100                 105                 110

Pro Gly Thr Leu Val Thr Ile Ser Ser
        115                 120

<210> SEQ ID NO 282
<211> LENGTH: 108
<212> TYPE: PRT
<213> ORGANISM: Artificial sequence
<220> FEATURE:
<223> OTHER INFORMATION: Synthetic peptide

<400> SEQUENCE: 282

Glu Leu Val Met Thr Gln Thr Pro Ser Ser Val Glu Ala Ala Val Gly
1               5                   10                  15

Gly Thr Val Thr Ile Lys Cys Gln Ala Ser Gln Ser Ile Tyr Ser Tyr
                20                  25                  30

Leu Ala Trp Tyr Gln Gln Lys Pro Gly Gln Pro Pro Lys Val Leu Ile
            35                  40                  45

Tyr Lys Ala Ser Thr Leu Ala Ser Gly Val Pro Ser Arg Phe Lys Gly
        50                  55                  60

Ser Gly Ser Gly Thr Asp Phe Thr Leu Thr Ile Ser Asp Leu Glu Cys
65                  70                  75                  80

Ala Asp Ala Ala Thr Tyr Tyr Cys Gln Ala Asn Asn Gly Gly Ser Asp
                85                  90                  95

Asn Asn Phe Gly Gly Gly Thr Glu Val Glu Ile Lys
            100                 105

<210> SEQ ID NO 283
<211> LENGTH: 9
<212> TYPE: PRT
<213> ORGANISM: Artificial sequence
<220> FEATURE:
<223> OTHER INFORMATION: Synthetic peptide

<400> SEQUENCE: 283

Gly Phe Ser Phe Ser Asn Ser Tyr Tyr
1               5

<210> SEQ ID NO 284
<211> LENGTH: 9
<212> TYPE: PRT
<213> ORGANISM: Artificial sequence
<220> FEATURE:
<223> OTHER INFORMATION: Synthetic peptide

<400> SEQUENCE: 284

Ile Tyr Thr Gly Ser Thr Ser Gly Thr
1               5

<210> SEQ ID NO 285
<211> LENGTH: 14
<212> TYPE: PRT
<213> ORGANISM: Artificial sequence
<220> FEATURE:
<223> OTHER INFORMATION: Synthetic peptide

<400> SEQUENCE: 285

Ser Arg Lys Leu Thr Asn Phe Asn Gly Ala Tyr Leu Asp Leu
1               5                   10

<210> SEQ ID NO 286
<211> LENGTH: 6
<212> TYPE: PRT
<213> ORGANISM: Artificial sequence
<220> FEATURE:
<223> OTHER INFORMATION: Synthetic peptide

<400> SEQUENCE: 286

Gln Ser Ile Tyr Ser Tyr
1               5

<210> SEQ ID NO 287
<211> LENGTH: 10
<212> TYPE: PRT
<213> ORGANISM: Artificial sequence
<220> FEATURE:
<223> OTHER INFORMATION: Synthetic peptide

<400> SEQUENCE: 287

Gln Ala Asn Asn Gly Gly Ser Asp Asn Asn
1               5                   10

<210> SEQ ID NO 288
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 288
cagtcggtga aggagtccgg gggagacctg gtcaagcctg agggatccct gacactcacc      60
tgcaaagcct ctggattctc cttcagtaat agttattaca tgtgctgggt ccgccaggct     120
ccagggaagg ggctggagtg gatcgcatgc atttatactg gtagtactag tggcacttac     180
tacgcgagct gggtgaatgg ccgattcacc atctccaaaa ccccgtcgac cacggtgact     240
ctgcaaatga ccagtctgac agtcgcggac acggccacct atttctgttc gagaaagctt     300
accaatttca atggtgctta tttagatttg tggggcccag gcaccctggt caccatctcc     360
tca                                                                    363

<210> SEQ ID NO 289
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 289
gagctcgtga tgacccagac tccatcctcc gtggaggcag ctgtgggagg cacagtcacc      60

| | |
|---|---|
| atcaagtgcc aggccagtca gagcatttac agctacttag cctggtatca gcagaaacca | 120 |
| gggcagcctc ccaaggtcct gatctacaag gcttccactc tggcatctgg ggtcccatcg | 180 |
| cggttcaaag gcagtggatc tgggacagac ttcactctca ccattagcga cctggagtgt | 240 |
| gccgatgctg ccacttacta ctgtcaagct aataatggtg gtagtgataa taatttcggc | 300 |
| ggagggaccg aggtggaaat caaa | 324 |

<210> SEQ ID NO 290
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 290

| | |
|---|---|
| ggattctcct tcagtaatag ttattac | 27 |

<210> SEQ ID NO 291
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 291

| | |
|---|---|
| atttatactg gtagtactag tggcact | 27 |

<210> SEQ ID NO 292
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 292

| | |
|---|---|
| tcgagaaagc ttaccaattt caatggtgct tatttagatt tg | 42 |

<210> SEQ ID NO 293
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 293

| | |
|---|---|
| cagagcattt acagctac | 18 |

<210> SEQ ID NO 294
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 294

| | |
|---|---|
| caagctaata atggtggtag tgataataat | 30 |

<210> SEQ ID NO 295
<211> LENGTH: 121
<212> TYPE: PRT
<213> ORGANISM: Artificial sequence
<220> FEATURE:
<223> OTHER INFORMATION: Synthetic peptide

<400> SEQUENCE: 295

Gln Ser Val Lys Glu Ser Gly Gly Asp Leu Val Lys Pro Glu Gly Ser
1               5                   10                  15

Leu Thr Leu Thr Cys Lys Ala Ser Gly Phe Ser Phe Ser Asn Ser Tyr
            20                  25                  30

Tyr Met Cys Trp Val Arg Gln Ala Pro Gly Lys Gly Leu Glu Trp Ile
        35                  40                  45

Ala Cys Ile Tyr Thr Gly Ser Thr Ser Gly Thr Tyr Tyr Ala Ser Trp
    50                  55                  60

Val Asn Gly Arg Phe Thr Ile Ser Lys Thr Pro Ser Thr Thr Val Thr
65                  70                  75                  80

Leu Gln Met Thr Ser Leu Thr Val Ala Asp Thr Ala Thr Tyr Phe Cys
                85                  90                  95

Ser Arg Lys Leu Thr Asn Phe Asn Gly Ala Tyr Leu Asp Leu Trp Gly
            100                 105                 110

Pro Gly Thr Leu Val Thr Ile Ser Ser
        115                 120

<210> SEQ ID NO 296
<211> LENGTH: 109
<212> TYPE: PRT
<213> ORGANISM: Artificial sequence
<220> FEATURE:
<223> OTHER INFORMATION: Synthetic peptide

<400> SEQUENCE: 296

Glu Leu Val Leu Thr Gln Thr Pro Ala Ser Val Glu Ala Ala Val Gly
1               5                   10                  15

Gly Thr Val Thr Ile Asn Cys Gln Ala Ser Gln Ser Ile Ser Asn Leu
            20                  25                  30

Leu Ala Trp Tyr Gln Gln Lys Pro Gly Gln Pro Pro Lys Val Leu Ile
        35                  40                  45

Tyr Lys Ala Ser Thr Leu Ala Ser Gly Val Pro Ser Arg Phe Lys Gly
    50                  55                  60

Ser Gly Ser Gly Thr Asp Phe Thr Leu Thr Ile Ser Asp Leu Glu Cys
65                  70                  75                  80

Ala Asp Ala Ala Thr Tyr Tyr Cys Gln Ala Asn Asn Gly Gly Ser Asp
                85                  90                  95

Asn Asn Phe Gly Gly Gly Thr Glu Val Val Val Lys Ala
            100                 105

<210> SEQ ID NO 297
<211> LENGTH: 9
<212> TYPE: PRT
<213> ORGANISM: Artificial sequence
<220> FEATURE:
<223> OTHER INFORMATION: Synthetic peptide

<400> SEQUENCE: 297

Gly Phe Ser Phe Ser Asn Ser Tyr Tyr
1               5

<210> SEQ ID NO 298
<211> LENGTH: 9
<212> TYPE: PRT
<213> ORGANISM: Artificial sequence
<220> FEATURE:
<223> OTHER INFORMATION: Synthetic peptide

<400> SEQUENCE: 298

Ile Tyr Thr Gly Ser Thr Ser Gly Thr
1               5

<210> SEQ ID NO 299
<211> LENGTH: 14
<212> TYPE: PRT
<213> ORGANISM: Artificial sequence
<220> FEATURE:
<223> OTHER INFORMATION: Synthetic peptide

<400> SEQUENCE: 299

Ser Arg Lys Leu Thr Asn Phe Asn Gly Ala Tyr Leu Asp Leu
1               5                   10

<210> SEQ ID NO 300
<211> LENGTH: 6
<212> TYPE: PRT
<213> ORGANISM: Artificial sequence
<220> FEATURE:
<223> OTHER INFORMATION: Synthetic peptide

<400> SEQUENCE: 300

Gln Ser Ile Ser Asn Leu
1               5

<210> SEQ ID NO 301
<211> LENGTH: 10
<212> TYPE: PRT
<213> ORGANISM: Artificial sequence
<220> FEATURE:
<223> OTHER INFORMATION: Synthetic peptide

<400> SEQUENCE: 301

Gln Ala Asn Asn Gly Gly Ser Asp Asn Asn
1               5                   10

<210> SEQ ID NO 302
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 302
cagtcggtga aggagtccgg gggagacctg gtcaagcctg agggatccct gacactcacc      60
tgcaaagcct ctggattctc cttcagtaat agttattaca tgtgctgggt ccgccaggct     120
ccagggaagg ggctggagtg gatcgcatgc atttatactg gtagtactag tggcacttac     180
tacgcgagct gggtgaatgg ccgattcacc atctccaaaa ccccgtcgac cacggtgact     240
ctgcaaatga ccagtctgac agtcgcggac acggccacct atttctgttc gagaaagctt     300
accaatttca atggtgctta tttagatttg tggggccag gcaccctggt caccatctcc      360
tca                                                                  363

<210> SEQ ID NO 303
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 303
gagctcgtgc tgacccagac accagcctcc gtggaggcag ctgtgggagg cacagtcacc      60
atcaattgcc aggccagtca gagcattagc aacctcttag cctggtatca gcagaaacca    120
gggcagcctc ccaaggtcct gatctacaag gcttccactc tggcatctgg ggtcccatcg    180
cggttcaaag gcagtggatc tgggacagac ttcactctca ccattagcga cctggagtgt    240
gccgatgctg ccacttacta ctgtcaagct aataatggtg gtagtgataa taatttcggc    300
ggagggaccg aggtggtggt caaa                                          324

<210> SEQ ID NO 304
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 304
ggattctcct tcagtaatag ttattac                                        27

<210> SEQ ID NO 305
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 305
atttatactg gtagtactag tggcact                                        27

<210> SEQ ID NO 306
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 306
tcgagaaagc ttaccaattt caatggtgct tatttagatt tg                       42

<210> SEQ ID NO 307
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 307
cagagcatta gcaacctc                                                  18

<210> SEQ ID NO 308
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 308
caagctaata atggtggtag tgataataat                                     30

<210> SEQ ID NO 309
<211> LENGTH: 119
<212> TYPE: PRT
<213> ORGANISM: Artificial sequence
<220> FEATURE:
<223> OTHER INFORMATION: Synthetic peptide

<400> SEQUENCE: 309

Glu Gln Ser Val Glu Ser Gly Gly Gly Leu Val Gln Pro Glu Gly Ser
1               5                   10                  15

Leu Thr Leu Thr Cys Lys Ala Ser Gly Phe Asp Phe Ser Arg Asn Ala
                20                  25                  30

Ile Cys Trp Val Arg Gln Ala Pro Gly Lys Gly Pro Glu Trp Ile Ala
            35                  40                  45

Cys Tyr Ser Phe Ser Ser Ser Ala Thr Tyr Tyr Ala Ser Trp Ala Lys
        50                  55                  60

Ser Arg Phe Thr Ile Ser Lys Thr Ser Ser Thr Val Thr Leu Gln
65                  70                  75                  80

Met Thr Ser Leu Thr Ala Ala Asp Thr Ala Thr Tyr Phe Cys Ala Arg
                85                  90                  95

Val Asp Ile Tyr Gly Gly Ser Arg Tyr Trp Gly Met Trp Gly Pro Gly
            100                 105                 110

Thr Leu Val Thr Ile Ser Ser
        115

<210> SEQ ID NO 310
<211> LENGTH: 107
<212> TYPE: PRT
<213> ORGANISM: Artificial sequence
<220> FEATURE:
<223> OTHER INFORMATION: Synthetic peptide

<400> SEQUENCE: 310

Glu Leu Val Met Thr Gln Thr Pro Ala Ser Val Glu Ala Ala Val Gly
1               5                   10                  15

Gly Thr Val Thr Ile Lys Cys Gln Ala Ser Gln Asn Ile Gly Gly Asp
                20                  25                  30

Leu Ala Trp Tyr Gln Gln Lys Pro Gly Gln Pro Pro Lys Leu Leu Ile
            35                  40                  45

Tyr Arg Ala Ser Thr Leu Glu Ser Gly Val Pro Ser Arg Phe Ser Gly
        50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Asp Thr Asp Ile Gly Ser Gly
                85                  90                  95

Ala Phe Gly Gly Gly Thr Glu Leu Glu Ile Lys
            100                 105

<210> SEQ ID NO 311
<211> LENGTH: 8
<212> TYPE: PRT
<213> ORGANISM: Artificial sequence
<220> FEATURE:
<223> OTHER INFORMATION: Synthetic peptide

<400> SEQUENCE: 311

Gly Phe Asp Phe Ser Arg Asn Ala
1               5

<210> SEQ ID NO 312
<211> LENGTH: 7
<212> TYPE: PRT
<213> ORGANISM: Artificial sequence
<220> FEATURE:
<223> OTHER INFORMATION: Synthetic peptide

<400> SEQUENCE: 312

```
<210> SEQ ID NO 313
<211> LENGTH: 14
<212> TYPE: PRT
<213> ORGANISM: Artificial sequence
<220> FEATURE:
<223> OTHER INFORMATION: Synthetic peptide

<400> SEQUENCE: 313

Ala Arg Val Asp Ile Tyr Gly Gly Ser Arg Tyr Trp Gly Met
1               5                   10

<210> SEQ ID NO 314
<211> LENGTH: 6
<212> TYPE: PRT
<213> ORGANISM: Artificial sequence
<220> FEATURE:
<223> OTHER INFORMATION: Synthetic peptide

<400> SEQUENCE: 314

Gln Asn Ile Gly Gly Asp
1               5

<210> SEQ ID NO 315
<211> LENGTH: 9
<212> TYPE: PRT
<213> ORGANISM: Artificial sequence
<220> FEATURE:
<223> OTHER INFORMATION: Synthetic peptide

<400> SEQUENCE: 315

Gln Asp Thr Asp Ile Gly Ser Gly Ala
1               5

<210> SEQ ID NO 316
<211> LENGTH: 357
<212> TYPE: DNA
<213> ORGANISM: Artificial sequence
<220> FEATURE:
<223> OTHER INFORMATION: Synthetic oligonucleotide

<400> SEQUENCE: 316
gagcagtcgg tggagtccgg gggaggcctg gtccagcctg agggatccct gacactcacc    60
tgcaaagcct ctggattcga cttcagtaga aatgcaatct gctgggtccg ccaggctcca   120
gggaaggggc tgagtggat cgcatgctat agtttagta gtagtgccac atactacgcg     180
agctgggcga agagccgatt caccatctcc aaaacctcgt cgaccacggt gactctgcaa   240
atgaccagtc tgacagccgc ggacacggcc acctatttct gtgcgagagt tgatatttat   300
ggtggtagcc gttattgggg catgtggggc ccaggcaccc tggtcaccat ctcctca      357

<210> SEQ ID NO 317
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 317
gagctcgtga tgacccagac accagcctcc gtggaggcag ctgtgggagg cacagtcacc    60
atcaagtgcc aggccagtca gaacattggt ggcgacttgg cctggtatca gcagaaacca   120
gggcagcctc ccaagctcct gatctacagg gcatccactc tggaatctgg ggtcccatcg   180
```
cggttcagcg gcagtggatc tgggacagag ttcactctca ccatcagcga cctggagtgt    240
gccgatgctg ccacttatta ctgtcaagat actgatattg gtagtggtgc tttcggcgga    300
gggaccgagc tggaaatcaa a                                              321

<210> SEQ ID NO 318
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 318
ggattcgact tcagtagaaa tgca                                            24

<210> SEQ ID NO 319
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 319
tatagtttta gtagtagtgc c                                               21

<210> SEQ ID NO 320
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 320
gcgagagttg atatttatgg tggtagccgt tattggggca tg                        42

<210> SEQ ID NO 321
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 321
cagaacattg gtggcgac                                                   18

<210> SEQ ID NO 322
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 322
caagatactg atattggtag tggtgct                                         27

<210> SEQ ID NO 323
<211> LENGTH: 117
<212> TYPE: PRT
<213> ORGANISM: Artificial sequence
<220> FEATURE:
<223> OTHER INFORMATION: Synthetic peptide

<400> SEQUENCE: 323

Glu Gln Ser Val Lys Glu Ser Gly Gly Arg Leu Val Thr Pro Gly Thr
1               5                   10                  15

Pro Leu Thr Leu Thr Cys Thr Val Ser Gly Ile Asp Leu Ser Tyr Tyr
            20                  25                  30

Ser Met Gly Trp Phe Arg Gln Ala Pro Gly Lys Gly Leu Glu Trp Ile
        35                  40                  45

Gly Val Ile Ser Ser Asp Ser Thr Tyr Tyr Ala Asn Trp Ala Lys
 50                  55                  60

Gly Arg Phe Thr Ile Ser Lys Thr Ser Thr Thr Val Asp Leu Lys Ile
 65                  70                  75                  80

Ala Gly Pro Thr Thr Glu Asp Thr Ala Thr Tyr Phe Cys Ala Arg Val
                85                  90                  95

Leu Ala Asn Ser Tyr Asn Ala Phe Asn Leu Trp Gly Pro Gly Ser Leu
               100                 105                 110

Val Thr Ile Ser Ser
            115

<210> SEQ ID NO 324
<211> LENGTH: 110
<212> TYPE: PRT
<213> ORGANISM: Artificial sequence
<220> FEATURE:
<223> OTHER INFORMATION: Synthetic peptide

<400> SEQUENCE: 324

Glu Leu Asp Leu Thr Gln Thr Pro Ala Ser Val Ser Glu Pro Val Gly
1               5                   10                  15

Gly Thr Val Thr Ile Lys Cys Gln Ala Ser Gln Ser Val Gly Ser Arg
            20                  25                  30

Leu Ala Trp Tyr Gln Gln Lys Pro Gly Gln Pro Pro Lys Leu Leu Ile
        35                  40                  45

Tyr Lys Ala Ser Thr Leu Ala Ser Gly Val Pro Ser Arg Phe Lys Gly
 50                  55                  60

Ser Gly Ser Gly Thr Gln Phe Thr Leu Thr Met Ser Asp Leu Glu Cys
65                  70                  75                  80

Ala Asp Ala Ala Thr Tyr Tyr Cys Gln Cys Thr Asn Ile Ser Ser Ala
                85                  90                  95

Tyr Leu Gly Ala Phe Gly Gly Gly Thr Glu Val Glu Ile Lys
               100                 105                 110

<210> SEQ ID NO 325
<211> LENGTH: 8
<212> TYPE: PRT
<213> ORGANISM: Artificial sequence
<220> FEATURE:
<223> OTHER INFORMATION: Synthetic peptide

<400> SEQUENCE: 325

Gly Ile Asp Leu Ser Tyr Tyr Ser
1               5

<210> SEQ ID NO 326
<211> LENGTH: 7
<212> TYPE: PRT
<213> ORGANISM: Artificial sequence
<220> FEATURE:
<223> OTHER INFORMATION: Synthetic peptide

<400> SEQUENCE: 326

Ile Ser Ser Ser Asp Ser Thr
1               5

<210> SEQ ID NO 327
<211> LENGTH: 13
<212> TYPE: PRT
<213> ORGANISM: Artificial sequence
<220> FEATURE:
<223> OTHER INFORMATION: Synthetic peptide

<400> SEQUENCE: 327

Ala Arg Val Leu Ala Asn Ser Tyr Asn Ala Phe Asn Leu
1               5                   10

<210> SEQ ID NO 328
<211> LENGTH: 6
<212> TYPE: PRT
<213> ORGANISM: Artificial sequence
<220> FEATURE:
<223> OTHER INFORMATION: Synthetic peptide

<400> SEQUENCE: 328

Gln Ser Val Gly Ser Arg
1               5

<210> SEQ ID NO 329
<211> LENGTH: 12
<212> TYPE: PRT
<213> ORGANISM: Artificial sequence
<220> FEATURE:
<223> OTHER INFORMATION: Synthetic peptide

<400> SEQUENCE: 329

Gln Cys Thr Asn Ile Ser Ser Ala Tyr Leu Gly Ala
1               5                   10

<210> SEQ ID NO 330
<211> LENGTH: 351
<212> TYPE: DNA
<213> ORGANISM: Artificial sequence
<220> FEATURE:
<223> OTHER INFORMATION: Synthetic oligonucleotide

<400> SEQUENCE: 330

```
gagcagtcgg tgaaggagtc cggggggtcgc ctggtcacgc ctgggacacc cctgacactc      60
acctgcacag tctctggaat cgacctcagt tactattcaa tgggctggtt ccgccaggct     120
ccagggaagg ggctggaatg gatcggagtc attagtagta gtgatagcac atactacgcg     180
aactgggcaa aggccggtt caccatctcc aaaacctcga ccacagtgga tctgaaaatc     240
gccggtccga caaccgagga cacggccacc tatttctgtg ccagggtatt ggctaatagt     300
tataatgcct ttaacttgtg gggcccaggc tccctggtca ccatctcttc a              351
```

<210> SEQ ID NO 331
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 331

```
gagctcgatc tgacccagac accagcctcc gtgtctgaac tgtgggagg cacagtcacc       60 atcaagtgcc aggccagtca gagcgttggt agtaggttag cctggtatca gcagaaacca    120
gggcagcctc ccaagctcct gatctacaag gcatccactc tggcatctgg gtcccatcg     180 cggttcaaag gcagtggatc tgggacacag ttcactctca ccatgagcga cctggagtgt    240
```

```
gccgatgctg ccacttacta ctgtcaatgt actaatatta gtagtgctta tctaggggct    300
ttcggcggag ggaccgaggt ggaaatcaaa                                     330
```

<210> SEQ ID NO 332
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 332

```
ggaatcgacc tcagttacta ttca                                            24
```

<210> SEQ ID NO 333
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 333

```
attagtagta gtgatagcac a                                               21
```

<210> SEQ ID NO 334
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 334

```
gccagggtat tggctaatag ttataatgcc tttaacttg                            39
```

<210> SEQ ID NO 335
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 335

```
cagagcgttg gtagtagg                                                   18
```

<210> SEQ ID NO 336
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 336

```
caatgtacta atattagtag tgcttatcta ggggct                               36
```

<210> SEQ ID NO 337
<211> LENGTH: 121
<212> TYPE: PRT
<213> ORGANISM: Artificial sequence
<220> FEATURE:
<223> OTHER INFORMATION: Synthetic peptide

<400> SEQUENCE: 337

```
Glu Gln Ser Leu Glu Glu Ser Gly Gly Asp Leu Val Lys Pro Gly Ala
1               5                   10                  15

Ser Leu Thr Leu Thr Cys Lys Ala Ser Gly Phe Ser Phe Ser Ser Ser
            20                  25                  30
```

Glu Phe Met Cys Trp Val Arg Gln Ala Pro Gly Lys Gly Leu Glu Trp
            35                  40                  45

Ile Ala Cys Ile Tyr Gly Gly Leu Ser Asp Asp Thr Tyr Phe Ala Ser
        50                  55                  60

Trp Ala Lys Gly Arg Phe Thr Ile Ser Lys Thr Ser Ser Ile Thr Val
65                  70                  75                  80

Thr Leu Gln Met Thr Ser Leu Thr Ala Ala Asp Thr Ala Thr Tyr Phe
                85                  90                  95

Cys Ala Arg Ser Cys Asp Val Asn Tyr Tyr Gly Phe Asp Pro Trp Gly
            100                 105                 110

Pro Gly Thr Leu Val Thr Ile Ser Ser
        115                 120

<210> SEQ ID NO 338
<211> LENGTH: 109
<212> TYPE: PRT
<213> ORGANISM: Artificial sequence
<220> FEATURE:
<223> OTHER INFORMATION: Synthetic peptide

<400> SEQUENCE: 338

Glu Leu Val Leu Thr Gln Thr Pro Ala Pro Val Ser Ala Ala Val Gly
1               5                   10                  15

Asp Thr Val Thr Ile Lys Cys Gln Ala Ser Gln Asn Lys Gly Thr Asn
            20                  25                  30

Leu Ala Trp Tyr Gln Gln Lys Pro Gly Gln Pro Pro Lys Leu Leu Ile
        35                  40                  45

Tyr Leu Ser Ser Thr Leu Ala Ser Gly Val Pro Pro Arg Phe Lys Gly
    50                  55                  60

Ser Arg Ser Gly Thr Glu Tyr Thr Leu Thr Ile Ser Asp Leu Glu Cys
65                  70                  75                  80

Ala Asp Ala Ala Thr Tyr Phe Cys Gln Ser Thr Tyr Tyr Gly Ser Asn
                85                  90                  95

Gly Leu Thr Phe Gly Gly Gly Thr Glu Val Glu Ile Lys
            100                 105

<210> SEQ ID NO 339
<211> LENGTH: 9
<212> TYPE: PRT
<213> ORGANISM: Artificial sequence
<220> FEATURE:
<223> OTHER INFORMATION: Synthetic peptide

<400> SEQUENCE: 339

Gly Phe Ser Phe Ser Ser Ser Glu Phe
1               5

<210> SEQ ID NO 340
<211> LENGTH: 9
<212> TYPE: PRT
<213> ORGANISM: Artificial sequence
<220> FEATURE:
<223> OTHER INFORMATION: Synthetic peptide

<400> SEQUENCE: 340

Ile Tyr Gly Gly Leu Ser Asp Asp Thr
1               5

<210> SEQ ID NO 341
<211> LENGTH: 13

```
<212> TYPE: PRT
<213> ORGANISM: Artificial sequence
<220> FEATURE:
<223> OTHER INFORMATION: Synthetic peptide

<400> SEQUENCE: 341

Ala Arg Ser Cys Asp Val Asn Tyr Tyr Gly Phe Asp Pro
1               5                   10

<210> SEQ ID NO 342
<211> LENGTH: 6
<212> TYPE: PRT
<213> ORGANISM: Artificial sequence
<220> FEATURE:
<223> OTHER INFORMATION: Synthetic peptide

<400> SEQUENCE: 342

Gln Asn Lys Gly Thr Asn
1               5

<210> SEQ ID NO 343
<211> LENGTH: 11
<212> TYPE: PRT
<213> ORGANISM: Artificial sequence
<220> FEATURE:
<223> OTHER INFORMATION: Synthetic peptide

<400> SEQUENCE: 343

Gln Ser Thr Tyr Tyr Gly Ser Asn Gly Leu Thr
1               5                   10

<210> SEQ ID NO 344
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 344
gagcagtcgt tggaggagtc cggggggagac ctggtcaagc ctggggcatc cctgacactc    60
acctgcaaag cctctggatt ctccttcagt agcagtgaat tcatgtgctg ggtccgccag   120
gctccaggga aagggctgga gtggatcgca tgcatttatg gtgggcttag tgacgacacc   180
tatttcgcga gctgggcgaa aggccgattc accatctcca aaacctcgtc gatcacggtg   240
actctgcaaa tgaccagtct gacagccgcg gacacggcca cctatttctg tgcgagatcc   300
tgtgatgtta attattatgg ttttgatccc tgggggccagg caccctggt caccatctct   360 tca                                                                 363

<210> SEQ ID NO 345
<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 345
gagctcgtgc tgacccagac accagccccc gtgtctgcag ctgtgggaga cacagtcacc    60
atcaagtgcc aggccagtca gaataagggt actaatttag cctggtatca gcagaaacca   120
gggcagcctc ccaagctcct gatctatctg tcatccactc tggcatctgg ggtcccaccg   180
cggttcaaag gcagtagatc tgggacagag tacactctca ccatcagcga cctggagtgt   240
gccgatgctg ccacttactt tgtcaatct acttattatg gtagtaatgg tctgactttc   300
```
ggcggaggga ccgaggtgga aatcaaa        327

<210> SEQ ID NO 346
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 346
ggattctcct tcagtagcag tgaattc        27

<210> SEQ ID NO 347
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 347
atttatggtg ggcttagtga cgacacc        27

<210> SEQ ID NO 348
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 348
gcgagatcct gtgatgttaa ttattatggt tttgatccc        39

<210> SEQ ID NO 349
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 349
cagaataagg gtactaat        18

<210> SEQ ID NO 350
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 350
caatctactt attatggtag taatggtctg act        33

<210> SEQ ID NO 351
<211> LENGTH: 121
<212> TYPE: PRT
<213> ORGANISM: Artificial sequence
<220> FEATURE:
<223> OTHER INFORMATION: Synthetic peptide

<400> SEQUENCE: 351

Glu Gln Ser Leu Glu Ser Gly Gly Gly Leu Val Gln Pro Glu Gly Ser
1               5                   10                  15

Leu Thr Leu Thr Cys Thr Ala Ser Gly Phe Ser Phe Ser Asn Ser Tyr
            20                  25                  30

```
Tyr Met Cys Trp Val Arg Gln Ala Pro Gly Lys Gly Leu Glu Trp Ile
            35                  40                  45

Gly Cys Ile Tyr Thr Gly Ser Ser Ser Gly Thr Tyr Tyr Ala Ser Trp
 50                  55                  60

Ala Glu Gly Arg Phe Thr Ile Ser Lys Thr Pro Ser Thr Thr Val Thr
 65                  70                  75                  80

Leu Gln Met Thr Ser Leu Thr Ala Ala Asp Thr Ala Thr Tyr Phe Cys
                 85                  90                  95

Ser Arg Lys Leu Thr Asn Phe Asn Gly Ala Tyr Leu Asp Leu Trp Gly
                100                 105                 110

Pro Gly Thr Leu Val Thr Val Ser Ser
            115                 120
```

<210> SEQ ID NO 352
<211> LENGTH: 108
<212> TYPE: PRT
<213> ORGANISM: Artificial sequence
<220> FEATURE:
<223> OTHER INFORMATION: Synthetic peptide

<400> SEQUENCE: 352

```
Glu Leu Val Leu Thr Gln Thr Pro Ala Ser Val Glu Ala Ala Val Gly
 1               5                  10                  15

Gly Thr Val Thr Ile Lys Cys Gln Ala Ser Gln Ser Ile Tyr Ser Tyr
                 20                  25                  30

Leu Ala Trp Tyr Gln Gln Lys Pro Gly Gln Pro Pro Lys Val Leu Ile
             35                  40                  45

Tyr Lys Ala Ser Thr Leu Ala Ser Gly Val Pro Ser Arg Phe Lys Gly
 50                  55                  60

Ser Gly Ser Gly Thr Glu Phe Thr Leu Thr Ile Ser Asp Leu Glu Cys
 65                  70                  75                  80

Ala Asp Ala Ala Thr Tyr Tyr Cys Gln Asn Asn Asn Gly Gly Ser Asp
                 85                  90                  95

Asn Thr Phe Gly Gly Gly Thr Glu Val Val Val Lys
                100                 105
```

<210> SEQ ID NO 353
<211> LENGTH: 9
<212> TYPE: PRT
<213> ORGANISM: Artificial sequence
<220> FEATURE:
<223> OTHER INFORMATION: Synthetic peptide

<400> SEQUENCE: 353

```
Gly Phe Ser Phe Ser Asn Ser Tyr Tyr
 1               5
```

<210> SEQ ID NO 354
<211> LENGTH: 9
<212> TYPE: PRT
<213> ORGANISM: Artificial sequence
<220> FEATURE:
<223> OTHER INFORMATION: Synthetic peptide

<400> SEQUENCE: 354

```
Ile Tyr Thr Gly Ser Ser Ser Gly Thr
 1               5
```

<210> SEQ ID NO 355
<211> LENGTH: 14
<212> TYPE: PRT

<213> ORGANISM: Artificial sequence
<220> FEATURE:
<223> OTHER INFORMATION: Synthetic peptide

<400> SEQUENCE: 355

Ser Arg Lys Leu Thr Asn Phe Asn Gly Ala Tyr Leu Asp Leu
1               5                   10

<210> SEQ ID NO 356
<211> LENGTH: 6
<212> TYPE: PRT
<213> ORGANISM: Artificial sequence
<220> FEATURE:
<223> OTHER INFORMATION: Synthetic peptide

<400> SEQUENCE: 356

Gln Ser Ile Tyr Ser Tyr
1               5

<210> SEQ ID NO 357
<211> LENGTH: 10
<212> TYPE: PRT
<213> ORGANISM: Artificial sequence
<220> FEATURE:
<223> OTHER INFORMATION: Synthetic peptide

<400> SEQUENCE: 357

Gln Asn Asn Asn Gly Gly Ser Asp Asn Thr
1               5                   10

<210> SEQ ID NO 358
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 358

```
gagcagtcgt tggagtccgg gggaggcctg gtccagcctg agggatccct gacactcacc      60
tgcacagctt ctggattctc cttcagtaat agttattata tgtgctgggt ccgccaggct     120
ccagggaagg ggctggagtg gatcggatgc atttatactg tagtagtag tggcacttac      180 tacgcgagct gggcggaagg ccgattcacc atctccaaaa ccccgtcgac cacggtgact     240
ctgcaaatga ccagtctgac agccgcggac acggccacct atttctgttc gagaaagctt     300
accaatttca tggtgctta tttagatttg tggggcccag gcaccctggt caccgtctct      360
tca                                                                   363
```

<210> SEQ ID NO 359
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 359

```
gagctcgtgc tgacccagac accagcctcc gtggaggcag ctgtgggagg cacagtcacc      60
atcaagtgcc aggccagtca gagcatttac agctacttag cctggtatca gcagaaacca     120
gggcagcctc ccaaggtcct gatctacaag gcttccactc tggcatctgg ggtcccatcg     180
cggttcaaag gcagtggatc tgggacagag ttcactctca ccatcagcga cctggagtgt     240
gccgatgctg ccacttacta ctgtcaaaat aataatggtg gtagtgataa tactttcggc     300
```
ggagggaccg aggtggtggt caaa                                          324

<210> SEQ ID NO 360
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 360
ggattctcct tcagtaatag ttattat                                        27

<210> SEQ ID NO 361
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 361
atttatactg gtagtagtag tggcact                                        27

<210> SEQ ID NO 362
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 362
tcgagaaagc ttaccaattt caatggtgct tatttagatt tg                       42

<210> SEQ ID NO 363
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 363
cagagcattt acagctac                                                  18

<210> SEQ ID NO 364
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 364
caaaataata atggtggtag tgataatact                                     30

<210> SEQ ID NO 365
<211> LENGTH: 117
<212> TYPE: PRT
<213> ORGANISM: Artificial sequence
<220> FEATURE:
<223> OTHER INFORMATION: Synthetic peptide

<400> SEQUENCE: 365

Glu Gln Ser Val Glu Glu Ser Gly Gly Arg Leu Val Ala Pro Gly Gly
1               5                   10                  15

Ser Leu Thr Leu Thr Cys Thr Val Ser Gly Phe Ser Leu Ser Ser Tyr
            20                  25                  30

Ala Met Ser Trp Val Arg Gln Ala Pro Gly Lys Gly Leu Glu Trp Ile 35                  40                  45

Gly Val Met Tyr Asn Ser Gly Ser Ala Tyr Tyr Ala Ser Trp Ala Lys
        50                  55                  60

Gly Arg Phe Thr Ile Ser Arg Thr Ser Thr Val Asp Leu Lys Val
65                  70                  75                  80

Thr Ser Leu Thr Thr Glu Asp Thr Ala Thr Tyr Phe Cys Gly Arg Gly
                85                  90                  95

Gly Ser Asn Ser Ala Trp Gly Asp Asp Leu Trp Gly Pro Gly Thr Leu
                100                 105                 110

Val Thr Val Ser Ser
        115

<210> SEQ ID NO 366
<211> LENGTH: 111
<212> TYPE: PRT
<213> ORGANISM: Artificial sequence
<220> FEATURE:
<223> OTHER INFORMATION: Synthetic peptide

<400> SEQUENCE: 366

Glu Leu Asp Met Thr Gln Thr Pro Ala Ser Val Ser Glu Pro Val Gly
1               5                   10                  15

Gly Thr Val Thr Ile Lys Cys Gln Ala Ser Gln Ser Ile Ser Ile Arg
            20                  25                  30

Tyr Phe Ser Trp Tyr Gln Gln Lys Pro Gly Gln Pro Pro Lys Leu Leu
        35                  40                  45

Ile Tyr Gly Ala Ser Thr Leu Ala Ser Gly Val Pro Ser Arg Phe Lys
    50                  55                  60

Gly Ser Gly Ser Gly Thr Asp Phe Thr Leu Thr Ile Ser Asp Leu Glu
65                  70                  75                  80

Cys Ala Asp Ala Ala Thr Tyr Tyr Cys Gln Asp Ser Asn Tyr Asn Ser
                85                  90                  95

Asn Tyr Phe Gly Ala Phe Gly Gly Thr Glu Val Val Val Lys
            100                 105                 110

<210> SEQ ID NO 367
<211> LENGTH: 8
<212> TYPE: PRT
<213> ORGANISM: Artificial sequence
<220> FEATURE:
<223> OTHER INFORMATION: Synthetic peptide

<400> SEQUENCE: 367

Gly Phe Ser Leu Ser Ser Tyr Ala
1               5

<210> SEQ ID NO 368
<211> LENGTH: 7
<212> TYPE: PRT
<213> ORGANISM: Artificial sequence
<220> FEATURE:
<223> OTHER INFORMATION: Synthetic peptide

<400> SEQUENCE: 368

Met Tyr Asn Ser Gly Ser Ala
1               5

<210> SEQ ID NO 369
<211> LENGTH: 13
<212> TYPE: PRT
<213> ORGANISM: Artificial sequence

```
<220> FEATURE:
<223> OTHER INFORMATION: Synthetic peptide

<400> SEQUENCE: 369

Gly Arg Gly Gly Ser Asn Ser Ala Trp Gly Asp Asp Leu
1               5                   10

<210> SEQ ID NO 370
<211> LENGTH: 7
<212> TYPE: PRT
<213> ORGANISM: Artificial sequence
<220> FEATURE:
<223> OTHER INFORMATION: Synthetic peptide

<400> SEQUENCE: 370

Gln Ser Ile Ser Ile Arg Tyr
1               5

<210> SEQ ID NO 371
<211> LENGTH: 12
<212> TYPE: PRT
<213> ORGANISM: Artificial sequence
<220> FEATURE:
<223> OTHER INFORMATION: Synthetic peptide

<400> SEQUENCE: 371

Gln Asp Ser Asn Tyr Asn Ser Asn Tyr Phe Gly Ala
1               5                   10

<210> SEQ ID NO 372
<211> LENGTH: 351
<212> TYPE: DNA
<213> ORGANISM: Artificial sequence
<220> FEATURE:
<223> OTHER INFORMATION: Synthetic oligonucleotide

<400> SEQUENCE: 372
gagcagtcgg tggaggagtc cgggggtcgc ctggtagcgc ctggaggatc cctgacactc      60
acctgcacag tctctggatt ctccctcagt agctatgcaa tgagctgggt ccgccaggct     120
ccagggaagg ggctagaatg gatcggagtc atgtataata gtggtagcgc atactacgcg     180
agctgggcga aggccgatt caccatctcc agaacctcga ccacggtgga tctgaaagtg     240
accagtctga caaccgagga cacggccacc tatttctgtg cagagggggg atccaatagt     300
gcctggggtg atgacttgtg gggcccaggc accctggtca ccgtctcctc a              351

<210> SEQ ID NO 373
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 373
gagctcgata tgacccagac accagcctcc gtgtctgaac tgtgggagg cacagtcacc       60 atcaagtgcc aggccagtca gagtattagt attaggtact tttcttggta tcagcagaaa    120
ccagggcagc ctcccaagct cctgatctat ggtgcatcca ctctggcatc tgggtccca     180 tcgcggttca aggcagtgg atctgggaca gacttcactc tcaccatcag cgacctggag    240
tgtgccgatg ctgccactta ctactgtcaa gatagtaatt ataatagtaa ttattttgga    300
gctttcggcg gagggaccga ggtggtggtc aaa                                  333
```

```
<210> SEQ ID NO 374
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 374
ggattctccc tcagtagcta tgca                                          24

<210> SEQ ID NO 375
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 375
atgtataata gtggtagcgc a                                             21

<210> SEQ ID NO 376
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 376
ggcagagggg gatccaatag tgcctggggt gatgacttg                          39

<210> SEQ ID NO 377
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 377
cagagtatta gtattaggta c                                             21

<210> SEQ ID NO 378
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 378
caagatagta attataatag taattatttt ggagct                             36

<210> SEQ ID NO 379
<211> LENGTH: 117
<212> TYPE: PRT
<213> ORGANISM: Artificial sequence
<220> FEATURE:
<223> OTHER INFORMATION: Synthetic peptide

<400> SEQUENCE: 379
```

Glu Gln Ser Leu Glu Ser Gly Gly Gly Leu Ile Thr Pro Gly Gly Thr
1               5                   10                  15

Leu Thr Leu Thr Cys Thr Ala Ser Gly Phe Thr Val Thr Arg Tyr Tyr
            20                  25                  30

Met Asn Trp Val Arg Gln Ala Pro Gly Lys Gly Leu Glu Trp Ile Gly
        35                  40                  45

Tyr Ile Tyr Ala Ser Ser Lys Thr Tyr Tyr Ala Asn Trp Ala Lys Gly

```
                50                  55                  60
Arg Phe Thr Ile Ser Lys Thr Ser Thr Val Asp Leu Lys Met Thr
 65                  70                  75                  80

Ser Leu Thr Ala Glu Asp Thr Gly Thr Tyr Phe Cys Ala Arg Gly Gly
                 85                  90                  95

Val Gly Asn Ser Gly Leu Asn Leu Asp Leu Trp Gly Pro Gly Thr Leu
            100                 105                 110

Val Thr Ile Ser Ser
            115

<210> SEQ ID NO 380
<211> LENGTH: 110
<212> TYPE: PRT
<213> ORGANISM: Artificial sequence
<220> FEATURE:
<223> OTHER INFORMATION: Synthetic peptide

<400> SEQUENCE: 380

Glu Leu Val Leu Thr Gln Thr Pro Ala Ser Val Ser Glu Pro Val Gly
 1               5                  10                  15

Gly Thr Val Thr Ile Lys Cys Gln Ala Ser Gln Ser Ile Gly Ser Trp
                20                  25                  30

Leu Ala Trp Tyr Gln Gln Lys Pro Gly Gln Pro Pro Lys Leu Leu Ile
            35                  40                  45

Tyr Gln Ala Ser Arg Leu Ala Ser Gly Val Ser Ser Arg Phe Gly Gly
        50                  55                  60

Ser Gly Ser Gly Thr Glu Phe Thr Leu Thr Ile Ser Asp Leu Glu Cys
 65                  70                  75                  80

Ala Asp Ala Ala Thr Tyr Tyr Cys Gln Gln Ala Glu Tyr Ser Gly Asp
                 85                  90                  95

Val Glu Asn Thr Phe Gly Gly Gly Thr Glu Val Val Val Lys
            100                 105                 110

<210> SEQ ID NO 381
<211> LENGTH: 8
<212> TYPE: PRT
<213> ORGANISM: Artificial sequence
<220> FEATURE:
<223> OTHER INFORMATION: Synthetic peptide

<400> SEQUENCE: 381

Gly Phe Thr Val Thr Arg Tyr Tyr
 1               5

<210> SEQ ID NO 382
<211> LENGTH: 7
<212> TYPE: PRT
<213> ORGANISM: Artificial sequence
<220> FEATURE:
<223> OTHER INFORMATION: Synthetic peptide

<400> SEQUENCE: 382

Ile Tyr Ala Ser Ser Lys Thr
 1               5

<210> SEQ ID NO 383
<211> LENGTH: 14
<212> TYPE: PRT
<213> ORGANISM: Artificial sequence
<220> FEATURE:
<223> OTHER INFORMATION: Synthetic peptide
```

<400> SEQUENCE: 383

Ala Arg Gly Gly Val Gly Asn Ser Gly Leu Asn Leu Asp Leu
1               5                   10

<210> SEQ ID NO 384
<211> LENGTH: 6
<212> TYPE: PRT
<213> ORGANISM: Artificial sequence
<220> FEATURE:
<223> OTHER INFORMATION: Synthetic peptide

<400> SEQUENCE: 384

Gln Ser Ile Gly Ser Trp
1               5

<210> SEQ ID NO 385
<211> LENGTH: 12
<212> TYPE: PRT
<213> ORGANISM: Artificial sequence
<220> FEATURE:
<223> OTHER INFORMATION: Synthetic peptide

<400> SEQUENCE: 385

Gln Gln Ala Glu Tyr Ser Gly Asp Val Glu Asn Thr
1               5                   10

<210> SEQ ID NO 386
<211> LENGTH: 351
<212> TYPE: DNA
<213> ORGANISM: Artificial sequence
<220> FEATURE:
<223> OTHER INFORMATION: Synthetic oligonucleotide

<400> SEQUENCE: 386
gagcagtcgt tggagtccgg aggaggcctg ataacgcctg gaggaaccct gacactcacc    60
tgcacagcct ctggattcac cgtcactagg tattatatga actgggtccg ccaggctcca   120
gggaaggggc tggaatggat cggatacatt tatgctagta gtaagacata ctacgcgaac   180
tgggcgaaag gccgattcac catctccaaa acctcgacca cggtggatct gaagatgacc   240
agtctgacag ccgaggacac gggcacctat ttctgtgcca gagggggtgt tggtaatagt   300
ggcttgaacc ttgacttgtg ggcccaggc accctggtca ccatctcttc a             351

<210> SEQ ID NO 387
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 387
gagctcgtgc tgacccagac accagcctcc gtgtctgaac tgtgggagg cacagtcacc     60 atcaagtgtc aggccagtca gagcattggc agttggttag cctggtatca gcagaaacca   120
gggcagcctc ccaagctcct gatctaccag gcatccagac tggcatctgg ggtctcatcg   180
cggttcggag gcagtggatc tgggacagaa ttcactctca ccatcagcga cctggagtgt   240
gccgatgctg ccacttacta ctgtcaacag gctgagtata gtggtgatgt tgagaatact   300
ttcggcggag ggaccgaggt ggtggtcaaa                                    330

<210> SEQ ID NO 388
<211> LENGTH: 24
<212> TYPE: DNA

<210> SEQ ID NO 388
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 388
ggattcaccg tcactaggta ttat                                              24

<210> SEQ ID NO 389
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 389
atttatgcta gtagtaagac a                                                 21

<210> SEQ ID NO 390
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 390
gccagagggg gtgttggtaa tagtggcttg aaccttgact tg                          42

<210> SEQ ID NO 391
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 391
cagagcattg gcagttgg                                                     18

<210> SEQ ID NO 392
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 392
caacaggctg agtatagtgg tgatgttgag aatact                                 36

<210> SEQ ID NO 393
<211> LENGTH: 121
<212> TYPE: PRT
<213> ORGANISM: Artificial sequence
<220> FEATURE:
<223> OTHER INFORMATION: Synthetic peptide

<400> SEQUENCE: 393

Glu Gln Ser Leu Glu Glu Ser Gly Gly Asp Leu Val Lys Pro Gly Ala
1               5                   10                  15

Ser Leu Thr Leu Ala Cys Thr Ala Ser Gly Phe Ser Phe Ser Asp Gly
            20                  25                  30

Tyr Tyr Met Cys Trp Val Arg Gln Ala Pro Gly Lys Gly Leu Glu Trp
        35                  40                  45

Ile Gly Cys Ile His Ser Ser Gly Ser Ile Tyr Tyr Ala Ser Trp
    50                  55                  60

Ala Lys Gly Arg Phe Thr Ile Ser Lys Thr Ser Ser Thr Met Val Thr

```
                65                  70                  75                  80
Leu Gln Met Ser Ser Leu Thr Ala Ala Asp Thr Ala Thr Tyr Phe Cys
                    85                  90                  95
Ala Arg Asp Ser Glu Ser Tyr Gly Tyr Asn Pro Cys Glu Leu Trp Gly
               100                 105                 110
Pro Gly Thr Leu Val Thr Ile Ser Ser
           115                 120

<210> SEQ ID NO 394
<211> LENGTH: 111
<212> TYPE: PRT
<213> ORGANISM: Artificial sequence
<220> FEATURE:
<223> OTHER INFORMATION: Synthetic peptide

<400> SEQUENCE: 394

Glu Leu Val Met Thr Gln Thr Pro Ala Ser Val Ser Glu Ala Val Gly
1               5                   10                  15
Gly Thr Val Thr Ile Lys Cys Gln Ala Ser Gln Thr Ile Ser Asn Tyr
            20                  25                  30
Leu Ala Trp Tyr Gln Gln Lys Pro Gly Gln Arg Pro Lys Leu Leu Ile
        35                  40                  45
Tyr Ala Ala Ser Ser Leu Ala Ser Gly Val Ser Ser Arg Phe Arg Gly
    50                  55                  60
Ser Arg Ser Gly Thr Glu Tyr Thr Leu Thr Ile Thr Asp Leu Glu Cys
65                  70                  75                  80
Asp Asp Ala Ala Thr Tyr Tyr Cys Gln Cys Thr Tyr Tyr Gly Thr Thr
                85                  90                  95
Tyr Ile Gly Gly Ala Phe Gly Gly Gly Thr Glu Val Glu Ile Lys
            100                 105                 110

<210> SEQ ID NO 395
<211> LENGTH: 9
<212> TYPE: PRT
<213> ORGANISM: Artificial sequence
<220> FEATURE:
<223> OTHER INFORMATION: Synthetic peptide

<400> SEQUENCE: 395

Gly Phe Ser Phe Ser Asp Gly Tyr Tyr
1               5

<210> SEQ ID NO 396
<211> LENGTH: 7
<212> TYPE: PRT
<213> ORGANISM: Artificial sequence
<220> FEATURE:
<223> OTHER INFORMATION: Synthetic peptide

<400> SEQUENCE: 396

Ile His Ser Ser Ser Gly Ser
1               5

<210> SEQ ID NO 397
<211> LENGTH: 14
<212> TYPE: PRT
<213> ORGANISM: Artificial sequence
<220> FEATURE:
<223> OTHER INFORMATION: Synthetic peptide

<400> SEQUENCE: 397

Ala Arg Asp Ser Glu Ser Tyr Gly Tyr Asn Pro Cys Glu Leu
```

<210> SEQ ID NO 398
<211> LENGTH: 6
<212> TYPE: PRT
<213> ORGANISM: Artificial sequence
<220> FEATURE:
<223> OTHER INFORMATION: Synthetic peptide

<400> SEQUENCE: 398

Gln Thr Ile Ser Asn Tyr
1               5

<210> SEQ ID NO 399
<211> LENGTH: 13
<212> TYPE: PRT
<213> ORGANISM: Artificial sequence
<220> FEATURE:
<223> OTHER INFORMATION: Synthetic peptide

<400> SEQUENCE: 399

Gln Cys Thr Tyr Tyr Gly Thr Thr Tyr Ile Gly Gly Ala
1               5                   10

<210> SEQ ID NO 400
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 400
gagcagtcgt tggaggagtc cggggggagac ctggtcaagc ctggggcatc cctgacactc        60
gcctgcacag cttctggatt ctccttcagt gacggctact atatgtgctg ggtccggcag       120
gctccaggga aggggctgga gtggatcgga tgcattcatt ctagtagtgg tagtatttat       180
tacgcgagct gggcgaaagg ccgattcacc atctccaaaa cctcgtcgac catggtgact       240
ctgcaaatga gcagtctgac agccgcggac acggccacct atttctgtgc gagagattcg       300
gagagttatg gttataatcc ttgtgagttg tggggcccag gcaccctggt caccatctct       360
tca                                                                     363

<210> SEQ ID NO 401
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 401
gagctcgtga tgacccagac accagcctcc gtgtctgaag ctgtgggagg cacagtcacc        60
atcaagtgcc aggccagtca gaccattagt aactacttag cctggtatca gcagaaacca       120
gggcagcgtc ccaagctcct gatctatgct gcatccagtc tggcatctgg ggtctcatcg       180
cggttcagag gcagtagatc tgggacagaa tacactctca ccatcaccga cctggagtgt       240
gacgatgctg ccacttacta ctgtcaatgt acttattatg gtaccactta tattgggggg       300
gctttcggcg gagggaccga ggtggaaatc aaa                                    333

<210> SEQ ID NO 402
<211> LENGTH: 27
<212> TYPE: DNA
<213> ORGANISM: Artificial sequence

```
<220> FEATURE:
<223> OTHER INFORMATION: Synthetic oligonucleotide

<400> SEQUENCE: 402
ggattctcct tcagtgacgg ctactat                                          27

<210> SEQ ID NO 403
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 403
attcattcta gtagtggtag t                                                21

<210> SEQ ID NO 404
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 404
gcgagagatt cggagagtta tggttataat ccttgtgagt tg                         42

<210> SEQ ID NO 405
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 405
cagaccatta gtaactac                                                    18

<210> SEQ ID NO 406
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 406
caatgtactt attatggtac cacttatatt gggggggct                             39

<210> SEQ ID NO 407
<211> LENGTH: 110
<212> TYPE: PRT
<213> ORGANISM: Artificial sequence
<220> FEATURE:
<223> OTHER INFORMATION: Synthetic peptide

<400> SEQUENCE: 407

Gln Ser Val Lys Glu Ser Gly Gly Arg Leu Val Thr Pro Gly Gly Ser
1               5                   10                  15

Leu Thr Leu Thr Cys Thr Val Ser Gly Phe Ser Leu Ser Asn Tyr Asn
            20                  25                  30

Ile Gln Trp Val Arg Gln Ala Pro Gly Lys Gly Leu Glu Trp Ile Gly
        35                  40                  45

Phe Ile Ser Pro Ala Gly Asn Gly Tyr Tyr Ala Ser Trp Ala Lys Gly
    50                  55                  60

Arg Phe Thr Ile Ser Lys Ala Ser Ser Thr Thr Val Glu Leu Lys Met
65                  70                  75                  80
```

```
Thr Ser Leu Thr Ala Ser Asp Thr Ala Thr Tyr Phe Cys Ala Arg His
            85                  90                  95

Trp Asp Leu Trp Gly Pro Gly Thr Leu Val Thr Ile Ser Ser
            100                 105                 110

<210> SEQ ID NO 408
<211> LENGTH: 109
<212> TYPE: PRT
<213> ORGANISM: Artificial sequence
<220> FEATURE:
<223> OTHER INFORMATION: Synthetic peptide

<400> SEQUENCE: 408

Glu Leu Val Leu Thr Gln Thr Ala Ser Ser Val Ser Ala Ala Val Gly
1               5                   10                  15

Gly Thr Val Thr Ile Ser Cys Gln Ser Ser Gln Ser Val Tyr Ser Asn
            20                  25                  30

Tyr Leu Ser Trp Phe Gln Gln Lys Pro Gly Gln Pro Pro Lys Glu Leu
        35                  40                  45

Val Tyr Trp Thr Ser Thr Leu Gln Ser Gly Val Pro Ser Arg Phe Ser
    50                  55                  60

Gly Ser Gly Ser Gly Thr Gln Phe Thr Leu Thr Ile Ser Asp Leu Glu
65              70                  75                  80

Cys Asp Asp Ala Ala Thr Tyr Tyr Cys Leu Gly Tyr Ser Gly Tyr Gly Trp
            85                  90                  95

Phe Tyr Ala Phe Gly Gly Gly Thr Glu Val Val Val Lys
            100                 105

<210> SEQ ID NO 409
<211> LENGTH: 8
<212> TYPE: PRT
<213> ORGANISM: Artificial sequence
<220> FEATURE:
<223> OTHER INFORMATION: Synthetic peptide

<400> SEQUENCE: 409

Gly Phe Ser Leu Ser Asn Tyr Asn
1               5

<210> SEQ ID NO 410
<211> LENGTH: 7
<212> TYPE: PRT
<213> ORGANISM: Artificial sequence
<220> FEATURE:
<223> OTHER INFORMATION: Synthetic peptide

<400> SEQUENCE: 410

Ile Ser Pro Ala Gly Asn Gly
1               5

<210> SEQ ID NO 411
<211> LENGTH: 6
<212> TYPE: PRT
<213> ORGANISM: Artificial sequence
<220> FEATURE:
<223> OTHER INFORMATION: Synthetic peptide

<400> SEQUENCE: 411

Ala Arg His Trp Asp Leu
1               5

<210> SEQ ID NO 412
```

<211> LENGTH: 7
<212> TYPE: PRT
<213> ORGANISM: Artificial sequence
<220> FEATURE:
<223> OTHER INFORMATION: Synthetic peptide

<400> SEQUENCE: 412

Gln Ser Val Tyr Ser Asn Tyr
1               5

<210> SEQ ID NO 413
<211> LENGTH: 10
<212> TYPE: PRT
<213> ORGANISM: Artificial sequence
<220> FEATURE:
<223> OTHER INFORMATION: Synthetic peptide

<400> SEQUENCE: 413

Leu Gly Gly Tyr Ser Gly Trp Phe Tyr Ala
1               5                   10

<210> SEQ ID NO 414
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 414
cagtcggtga aggagtccgg gggtcgcctg gtcacgcctg gaggatccct gacactcacc      60
tgcacagtct ctggattctc cctcagtaac tacaacatac aatgggtccg ccaggctcca     120
gggaaggggc tggaatggat cggcttcatt agtccagctg gtaacggata ctacgcgagc     180
tgggcgaaag gccgattcac catctccaaa gcctcgtcga ccacggtgga gctgaaaatg     240
accagtctga cggcttcaga cacggccacc tatttctgtg ccagacattg gacttgtgg      300 ggcccaggca ccctggtcac catctcctca                                       330

<210> SEQ ID NO 415
<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 415
gagctcgtgc tgacccagac tgcatcgtcc gtgtctgcag ctgtgggagg cacagtcacc      60
atcagttgcc agtccagtca gagtgtttat agtaactact atcctggttt cagcagaaa     120 ccaggacagc ctcccaagga actagtctat tggacatcca ctctgcaatc tggggtccca     180
tcgcggttca gcggcagtgg atctgggaca cagttcactc tcaccatcag cgacctggag     240
tgtgacgatg ctgccactta ttattgtcta ggcggttata gtggttggtt ttatgctttc     300
ggcggaggga ccgaggtggt ggtcaaa                                          327

<210> SEQ ID NO 416
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 416
ggattctccc tcagtaacta caac                                             24

<210> SEQ ID NO 417
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 417
attagtccag ctggtaacgg a        21

<210> SEQ ID NO 418
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 418
gccagacatt gggacttg        18

<210> SEQ ID NO 419
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 419
cagagtgttt atagtaacta c        21

<210> SEQ ID NO 420
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 420
ctaggcggtt atagtggttg gttttatgct        30

<210> SEQ ID NO 421
<211> LENGTH: 111
<212> TYPE: PRT
<213> ORGANISM: Artificial sequence
<220> FEATURE:
<223> OTHER INFORMATION: Synthetic peptide

<400> SEQUENCE: 421

Glu Gln Ser Leu Lys Glu Ser Gly Gly Arg Leu Val Thr Pro Gly Gly
1               5                   10                  15

Ser Leu Thr Leu Thr Cys Thr Ala Ser Gly Phe Asp Ile Asn Asn Tyr
            20                  25                  30

Asn Ile Gln Trp Val Arg Gln Ala Pro Gly Lys Gly Leu Glu Trp Ile
        35                  40                  45

Gly Phe Ile Ser Pro Ala Gly Asn Glu Tyr Ser Ala Thr Trp Ala Lys
    50                  55                  60

Gly Arg Phe Thr Ile Tyr Lys Thr Ser Ser Thr Thr Val Glu Leu Lys
65                  70                  75                  80

Met Thr Ser Leu Thr Ala Ser Asp Thr Ala Thr Tyr Phe Cys Ala Arg
                85                  90                  95

His Trp Asp Ser Trp Gly Pro Gly Thr Leu Val Thr Ile Ser Ser
            100                 105                 110

<210> SEQ ID NO 422
<211> LENGTH: 109
<212> TYPE: PRT
<213> ORGANISM: Artificial sequence
<220> FEATURE:
<223> OTHER INFORMATION: Synthetic peptide

<400> SEQUENCE: 422

Glu Leu Val Met Thr Gln Thr Glu Ser Pro Val Ser Ala Ala Val Gly
1               5                   10                  15

Gly Thr Val Thr Ile Ser Cys Gln Ser Gln Ser Val Tyr Ser Asn
                20                  25                  30

Arg Leu Ser Trp Phe Gln Gln Lys Pro Gly Gln Pro Pro Lys Glu Leu
            35                  40                  45

Val Tyr Trp Thr Ser Thr Leu Gln Ser Gly Val Pro Ser Arg Phe Ser
        50                  55                  60

Gly Ser Gly Ser Gly Thr Gln Phe Thr Leu Thr Ile Ser Asp Leu Glu
65                  70                  75                  80

Cys Asp Asp Ala Ala Thr Tyr Tyr Cys Leu Gly Gly Tyr Ser Gly Asn
                85                  90                  95

Ile Tyr Val Phe Gly Gly Gly Thr Glu Val Glu Ile Lys
            100                 105

<210> SEQ ID NO 423
<211> LENGTH: 8
<212> TYPE: PRT
<213> ORGANISM: Artificial sequence
<220> FEATURE:
<223> OTHER INFORMATION: Synthetic peptide

<400> SEQUENCE: 423

Gly Phe Asp Ile Asn Asn Tyr Asn
1               5

<210> SEQ ID NO 424
<211> LENGTH: 7
<212> TYPE: PRT
<213> ORGANISM: Artificial sequence
<220> FEATURE:
<223> OTHER INFORMATION: Synthetic peptide

<400> SEQUENCE: 424

Ile Ser Pro Ala Gly Asn Glu
1               5

<210> SEQ ID NO 425
<211> LENGTH: 6
<212> TYPE: PRT
<213> ORGANISM: Artificial sequence
<220> FEATURE:
<223> OTHER INFORMATION: Synthetic peptide

<400> SEQUENCE: 425

Ala Arg His Trp Asp Ser
1               5

<210> SEQ ID NO 426
<211> LENGTH: 7
<212> TYPE: PRT
<213> ORGANISM: Artificial sequence
<220> FEATURE:
<223> OTHER INFORMATION: Synthetic peptide

```
<400> SEQUENCE: 426

Gln Ser Val Tyr Ser Asn Arg
1               5

<210> SEQ ID NO 427
<211> LENGTH: 10
<212> TYPE: PRT
<213> ORGANISM: Artificial sequence
<220> FEATURE:
<223> OTHER INFORMATION: Synthetic peptide

<400> SEQUENCE: 427

Leu Gly Gly Tyr Ser Gly Asn Ile Tyr Val
1               5                   10

<210> SEQ ID NO 428
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 428
gagcagtcgt tgaaggagtc cggggggtcgc ctggtcacgc ctggaggatc cctgacactc    60
acctgcacag cctctggatt cgacatcaat aactacaaca tacaatgggt ccgccaggct   120
ccagggaagg gctggagtg gatcggattc attagtccag ctggtaacga atactcagcg   180
acctgggcga aaggccgatt caccatttac aaaacctcgt cgaccacggt ggagctgaaa   240
atgaccagtc tgacggcttc agacacggcc acctatttct gtgccagaca ttgggactcg   300
tggggcccag gcaccctggt caccatctcc tca                                333

<210> SEQ ID NO 429
<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 429
gagctcgtga tgacccagac tgaatcgccc gtgtctgcag ctgtgggagg cacagtcacc    60
atcagttgcc agtccagtca gagtgtttat agtaaccgct atcctggtt tcagcagaaa   120 ccagggcagc ctcccaagga actagtctat tggacatcca ctctgcaatc tggggtccca   180
tcgcggttca gcggcagtgg atctgggaca caattcactc tcaccatcag cgacctggag   240
tgtgacgatg ctgccactta ttattgtcta ggcggttata gtggcaatat ttatgttttc   300
ggcggaggga ccgaggtgga aatcaaa                                      327

<210> SEQ ID NO 430
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 430
ggattcgaca tcaataacta caac                                          24

<210> SEQ ID NO 431
<211> LENGTH: 21
<212> TYPE: DNA
<213> ORGANISM: Artificial sequence
```

```
<220> FEATURE:
<223> OTHER INFORMATION: Synthetic oligonucleotide

<400> SEQUENCE: 431
attagtccag ctggtaacga a                                              21

<210> SEQ ID NO 432
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 432
gccagacatt gggactcg                                                  18

<210> SEQ ID NO 433
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 433
cagagtgttt atagtaaccg c                                              21

<210> SEQ ID NO 434
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 434
ctaggcggtt atagtggcaa tatttatgtt                                     30

<210> SEQ ID NO 435
<211> LENGTH: 118
<212> TYPE: PRT
<213> ORGANISM: Artificial sequence
<220> FEATURE:
<223> OTHER INFORMATION: Synthetic peptide

<400> SEQUENCE: 435

Glu Gln Ser Val Glu Glu Ser Gly Gly Arg Leu Val Thr Pro Gly Thr
1               5                   10                  15

Pro Leu Thr Leu Thr Cys Thr Val Ser Gly Phe Ser Leu Ser Ser Phe
            20                  25                  30

His Met Cys Trp Val Arg Gln Ala Pro Gly Lys Gly Leu Glu Tyr Ile
        35                  40                  45

Gly Ile Ile Tyr Pro Gly Gly Ser Thr Gly Tyr Ala Asn Trp Ala Lys
    50                  55                  60

Gly Arg Phe Thr Val Ser Lys Ala Ser Asn Thr Val Asp Leu Lys Ile
65                  70                  75                  80

Ser Ser Pro Thr Thr Glu Asp Thr Ala Thr Tyr Phe Cys Ala Arg Val
                85                  90                  95

Asn Tyr Gly Asp Trp Ile Asn Gly Met Asp Leu Trp Gly Pro Gly Thr
            100                 105                 110

Leu Val Thr Ile Ser Ser
        115

<210> SEQ ID NO 436
```

```
<211> LENGTH: 110
<212> TYPE: PRT
<213> ORGANISM: Artificial sequence
<220> FEATURE:
<223> OTHER INFORMATION: Synthetic peptide

<400> SEQUENCE: 436

Glu Leu Asp Met Thr Gln Thr Pro Ala Ser Val Ser Glu Pro Val Gly
1               5                   10                  15

Gly Thr Val Thr Ile Lys Cys Gln Ala Ser Gln Ser Ile Gly Ser Asn
            20                  25                  30

Leu Ala Trp Tyr Gln Gln Lys Pro Gly Gln Arg Pro Lys Leu Leu Ile
        35                  40                  45

Tyr Lys Ala Ser Thr Leu Ala Ser Gly Val Pro Ser Arg Phe Lys Gly
    50                  55                  60

Ser Gly Ser Gly Thr Asp Phe Thr Leu Thr Ile Ser Asp Leu Glu Cys
65                  70                  75                  80

Ala Asp Ala Ala Ser Tyr Tyr Cys Gln Gln Ala Tyr Trp Ser Gly Asn
                85                  90                  95

Val Asp Asn Val Phe Gly Gly Gly Thr Glu Val Glu Ile Lys
                100                 105                 110

<210> SEQ ID NO 437
<211> LENGTH: 8
<212> TYPE: PRT
<213> ORGANISM: Artificial sequence
<220> FEATURE:
<223> OTHER INFORMATION: Synthetic peptide

<400> SEQUENCE: 437

Gly Phe Ser Leu Ser Ser Phe His
1               5

<210> SEQ ID NO 438
<211> LENGTH: 7
<212> TYPE: PRT
<213> ORGANISM: Artificial sequence
<220> FEATURE:
<223> OTHER INFORMATION: Synthetic peptide

<400> SEQUENCE: 438

Ile Tyr Pro Gly Gly Ser Thr
1               5

<210> SEQ ID NO 439
<211> LENGTH: 14
<212> TYPE: PRT
<213> ORGANISM: Artificial sequence
<220> FEATURE:
<223> OTHER INFORMATION: Synthetic peptide

<400> SEQUENCE: 439

Ala Arg Val Asn Tyr Gly Asp Trp Ile Asn Gly Met Asp Leu
1               5                   10

<210> SEQ ID NO 440
<211> LENGTH: 6
<212> TYPE: PRT
<213> ORGANISM: Artificial sequence
<220> FEATURE:
<223> OTHER INFORMATION: Synthetic peptide

<400> SEQUENCE: 440

Gln Ser Ile Gly Ser Asn
1               5
```

<210> SEQ ID NO 441
<211> LENGTH: 12
<212> TYPE: PRT
<213> ORGANISM: Artificial sequence
<220> FEATURE:
<223> OTHER INFORMATION: Synthetic peptide

<400> SEQUENCE: 441

Gln Gln Ala Tyr Trp Ser Gly Asn Val Asp Asn Val
1               5                   10

<210> SEQ ID NO 442
<211> LENGTH: 354
<212> TYPE: DNA
<213> ORGANISM: Artificial sequence
<220> FEATURE:
<223> OTHER INFORMATION: Synthetic oligonucleotide

<400> SEQUENCE: 442

```
gagcagtcgg tggaggagtc cgggggtcgc ctggtcacgc ctgggacacc cctgacactc      60
acctgcacag tctctggatt ctccctcagt agctttcaca tgtgctgggt ccgccaggct     120
ccagggaagg ggctggaata catcggaatc atttatcctg gtggtagcac aggctacgcg     180
aactgggcga aaggccgatt caccgtctcc aaggcctcga atacggtgga tctgaaaatc     240
agcagtccga caaccgagga cacggccacc tatttctgtg ccagagttaa ttatggtgat     300
tggatcaatg gtatggactt gtggggccca ggcacactgg tcaccatctc ctca           354
```

<210> SEQ ID NO 443
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 443

```
gagctcgata tgacccagac accagcctcc gtgtctgaac ctgtgggagg cacagtcacc      60
atcaagtgcc aggccagtca gagcattggt agtaatttag cctggtatca gcagaaacca     120
gggcaacgtc ccaagctcct aatctacaag gcttccactc tggcatctgg ggtcccatcg     180
cggttcaaag gcagtggatc tgggacagac ttcactctca ccatcagcga cctggagtgt     240
gccgatgctg ccagttacta ctgtcaacag gcttattgga gtggtaatgt tgataatgtt     300
ttcggcggag ggaccgaggt ggaaatcaaa                                       330
```

<210> SEQ ID NO 444
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 444

```
ggattctccc tcagtagctt tcac                                              24
```

<210> SEQ ID NO 445
<211> LENGTH: 21
<212> TYPE: DNA
<213> ORGANISM: Artificial sequence
<220> FEATURE:
<223> OTHER INFORMATION: Synthetic oligonucleotide -continued

<400> SEQUENCE: 445
atttatcctg gtggtagcac a                                         21

<210> SEQ ID NO 446
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 446
gccagagtta attatggtga ttggatcaat ggtatggact tg                  42

<210> SEQ ID NO 447
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 447
cagagcattg gtagtaat                                             18

<210> SEQ ID NO 448
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 448
caacaggctt attggagtgg taatgttgat aatgtt                         36

<210> SEQ ID NO 449
<211> LENGTH: 120
<212> TYPE: PRT
<213> ORGANISM: Artificial sequence
<220> FEATURE:
<223> OTHER INFORMATION: Synthetic peptide

<400> SEQUENCE: 449

Gln Ser Val Lys Glu Ser Gly Gly Asp Leu Val Lys Pro Gly Ala Ser
1               5                   10                  15

Leu Thr Leu Ala Cys Thr Ala Ser Gly Phe Ser Phe Ser Asp Gly Tyr
            20                  25                  30

Tyr Met Cys Trp Val Arg Gln Ala Pro Gly Lys Gly Leu Glu Trp Ile
        35                  40                  45

Gly Cys Ile His Ser Ser Gly Ser Ile Tyr Tyr Ala Ser Trp Ala
    50                  55                  60

Lys Gly Arg Phe Thr Ile Ser Lys Thr Ser Thr Met Val Thr Leu
65                  70                  75                  80

Gln Met Ser Ser Leu Thr Ala Ala Asp Thr Ala Thr Tyr Phe Cys Ala
                85                  90                  95

Arg Asp Ser Glu Ser Tyr Gly Tyr Asn Pro Cys Glu Leu Trp Gly Pro
            100                 105                 110

Gly Thr Leu Val Thr Ile Ser Ser
        115                 120

<210> SEQ ID NO 450
<211> LENGTH: 111
<212> TYPE: PRT
<213> ORGANISM: Artificial sequence

```
<220> FEATURE:
<223> OTHER INFORMATION: Synthetic peptide

<400> SEQUENCE: 450

Glu Leu Asp Leu Thr Gln Thr Pro Ala Ser Val Ser Glu Ala Val Gly
1               5                   10                  15

Gly Thr Val Thr Ile Lys Cys Gln Ala Ser Gln Thr Ile Ser Asn Tyr
            20                  25                  30

Leu Ala Trp Tyr Gln Gln Lys Pro Gly Gln Arg Pro Lys Leu Leu Ile
        35                  40                  45

Tyr Ala Ala Ser Ser Leu Ala Ser Gly Val Ser Ser Arg Phe Arg Gly
    50                  55                  60

Ser Arg Ser Gly Thr Glu Tyr Thr Leu Thr Ile Thr Asp Leu Glu Cys
65                  70                  75                  80

Asp Asp Ala Ala Thr Tyr Tyr Cys Gln Cys Thr Tyr Tyr Gly Thr Thr
                85                  90                  95

Tyr Val Gly Gly Ala Phe Gly Gly Thr Glu Leu Glu Ile Lys
            100                 105                 110

<210> SEQ ID NO 451
<211> LENGTH: 9
<212> TYPE: PRT
<213> ORGANISM: Artificial sequence
<220> FEATURE:
<223> OTHER INFORMATION: Synthetic peptide

<400> SEQUENCE: 451

Gly Phe Ser Phe Ser Asp Gly Tyr Tyr
1               5

<210> SEQ ID NO 452
<211> LENGTH: 8
<212> TYPE: PRT
<213> ORGANISM: Artificial sequence
<220> FEATURE:
<223> OTHER INFORMATION: Synthetic peptide

<400> SEQUENCE: 452

Ile His Ser Ser Ser Gly Ser Ile
1               5

<210> SEQ ID NO 453
<211> LENGTH: 13
<212> TYPE: PRT
<213> ORGANISM: Artificial sequence
<220> FEATURE:
<223> OTHER INFORMATION: Synthetic peptide

<400> SEQUENCE: 453

Arg Asp Ser Glu Ser Tyr Gly Tyr Asn Pro Cys Glu Leu
1               5                   10

<210> SEQ ID NO 454
<211> LENGTH: 6
<212> TYPE: PRT
<213> ORGANISM: Artificial sequence
<220> FEATURE:
<223> OTHER INFORMATION: Synthetic peptide

<400> SEQUENCE: 454

Gln Thr Ile Ser Asn Tyr
1               5
```

```
<210> SEQ ID NO 455
<211> LENGTH: 13
<212> TYPE: PRT
<213> ORGANISM: Artificial sequence
<220> FEATURE:
<223> OTHER INFORMATION: Synthetic peptide

<400> SEQUENCE: 455

Gln Cys Thr Tyr Tyr Gly Thr Thr Tyr Val Gly Gly Ala
1               5                   10

<210> SEQ ID NO 456
<211> LENGTH: 360
<212> TYPE: DNA
<213> ORGANISM: Artificial sequence
<220> FEATURE:
<223> OTHER INFORMATION: Synthetic oligonucleotide

<400> SEQUENCE: 456
cagtcggtga aggagtccgg gggagacctg gtcaagcctg ggcatccct gacactcgcc      60 tgcacagcct ctggattctc cttcagtgac ggctactata tgtgctgggt ccggcaggct     120
ccagggaagg ggctggagtg gatcggatgc attcattcta gtagtggtag catttattac     180
gcgagctggg cgaaaggccg attcaccatc tccaaaacct cgtcgaccat ggtgactctg     240
caaatgagca gtctgacagc cgcggacacg gccacctatt tctgtgcgag agattcggag     300
agttatggtt ataatccttg tgagttgtgg ggcccaggca ccctggtcac catctcttca     360

<210> SEQ ID NO 457
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 457
gagctcgatc tgacccagac accagcctcc gtgtctgaag ctgtgggagg cacagtcacc      60
atcaagtgcc aggccagtca gaccattagt aactacttag cctggtatca gcagaaacca     120
gggcagcgtc ccaagctcct gatctatgct gcatccagtc tggcatctgg ggtctcatcg     180
cggttcagag gcagtagatc tgggacagaa tacactctca ccatcaccga cctggagtgt     240
gacgatgctg ccacttacta ctgtcaatgt acttattatg gtaccactta tgttgggggg     300
gctttcggcg gagggaccga gctggaaatc aaa                                  333

<210> SEQ ID NO 458
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 458
ggattctcct tcagtgacgg ctactat                                          27

<210> SEQ ID NO 459
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 459
attcattcta gtagtggtag catt                                             24
```

<210> SEQ ID NO 460
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 460
agagattcgg agagttatgg ttataatcct tgtgagttg                     39

<210> SEQ ID NO 461
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 461
cagaccatta gtaactac                                            18

<210> SEQ ID NO 462
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 462
caatgtactt attatggtac cacttatgtt gggggggct                     39

<210> SEQ ID NO 463
<211> LENGTH: 120
<212> TYPE: PRT
<213> ORGANISM: Artificial sequence
<220> FEATURE:
<223> OTHER INFORMATION: Synthetic peptide

<400> SEQUENCE: 463

Ser Ser Ser Val Glu Glu Ser Gly Gly Arg Leu Val Thr Pro Gly Thr
1               5                   10                  15

Pro Leu Thr Leu Thr Cys Thr Val Ser Gly Phe Ser Leu Gly Ser Tyr
            20                  25                  30

Ala Met Gly Trp Val Arg Gln Gly Pro Gly Lys Gly Leu Glu Trp Ile
        35                  40                  45

Gly Ala Val Tyr Gly Thr Thr Gly Tyr Ile Tyr Phe Ala Thr Trp Ala
    50                  55                  60

Lys Gly Arg Phe Thr Ile Ser Lys Thr Ser Thr Val Asp Leu Lys
65                  70                  75                  80

Ile Thr Ser Pro Thr Thr Glu Asp Thr Ala Thr Tyr Phe Cys Ala Arg
                85                  90                  95

Gly Tyr Leu Thr Asp Ser Ile Ala Asn Gly Phe Gly Val Trp Gly Pro
            100                 105                 110

Gly Thr Leu Val Thr Val Ser Ser
        115                 120

<210> SEQ ID NO 464
<211> LENGTH: 111
<212> TYPE: PRT
<213> ORGANISM: Artificial sequence
<220> FEATURE:
<223> OTHER INFORMATION: Synthetic peptide

<400> SEQUENCE: 464

Glu Leu Asp Leu Thr Gln Thr Pro Ala Ser Val Ser Glu Pro Val Gly
1               5                   10                  15

Gly Thr Val Thr Ile Lys Cys Gln Ala Ser Gln Thr Ile Thr Asn Arg
            20                  25                  30

Tyr Leu Ala Trp Tyr Gln Gln Lys Pro Gly Gln Pro Pro Lys Leu Leu
        35                  40                  45

Ile Tyr Gln Ser Ser Lys Leu Ala Ser Gly Val Ser Ser Arg Phe Lys
50                  55                  60

Gly Ser Gly Ser Gly Thr Asp Phe Thr Leu Thr Ile Ser Asp Leu Glu
65                  70                  75                  80

Cys Ala Asp Ala Ala Thr Tyr Tyr Cys Gln Cys Thr Asp Tyr Gly Ser
                85                  90                  95

Thr Tyr Leu Gly Thr Phe Gly Gly Thr Glu Val Glu Ile Lys
            100                 105                 110

<210> SEQ ID NO 465
<211> LENGTH: 8
<212> TYPE: PRT
<213> ORGANISM: Artificial sequence
<220> FEATURE:
<223> OTHER INFORMATION: Synthetic peptide

<400> SEQUENCE: 465

Gly Phe Ser Leu Gly Ser Tyr Ala
1               5

<210> SEQ ID NO 466
<211> LENGTH: 8
<212> TYPE: PRT
<213> ORGANISM: Artificial sequence
<220> FEATURE:
<223> OTHER INFORMATION: Synthetic peptide

<400> SEQUENCE: 466

Val Tyr Gly Thr Thr Gly Tyr Ile
1               5

<210> SEQ ID NO 467
<211> LENGTH: 15
<212> TYPE: PRT
<213> ORGANISM: Artificial sequence
<220> FEATURE:
<223> OTHER INFORMATION: Synthetic peptide

<400> SEQUENCE: 467

Ala Arg Gly Tyr Leu Thr Asp Ser Ile Ala Asn Gly Phe Gly Val
1               5                   10                  15

<210> SEQ ID NO 468
<211> LENGTH: 7
<212> TYPE: PRT
<213> ORGANISM: Artificial sequence
<220> FEATURE:
<223> OTHER INFORMATION: Synthetic peptide

<400> SEQUENCE: 468

Gln Thr Ile Thr Asn Arg Tyr
1               5

<210> SEQ ID NO 469
<211> LENGTH: 12
<212> TYPE: PRT

```
<213> ORGANISM: Artificial sequence
<220> FEATURE:
<223> OTHER INFORMATION: Synthetic peptide

<400> SEQUENCE: 469

Gln Cys Thr Asp Tyr Gly Ser Thr Tyr Leu Gly Thr
1               5                   10

<210> SEQ ID NO 470
<211> LENGTH: 360
<212> TYPE: DNA
<213> ORGANISM: Artificial sequence
<220> FEATURE:
<223> OTHER INFORMATION: Synthetic oligonucleotide

<400> SEQUENCE: 470
agcagttcgg tggaggagtc cggggggtcgc ctggtcacgc ctgggacacc cctgacactc    60
acctgcacag tctctggatt ctccctcggt agctatgcaa tgggctgggt ccgccagggt   120
ccagggaagg ggctggaatg gatcggagcc gtatatggta ctactggtta tatatacttc   180
gcgacttggg caaaaggccg attcaccatc tccaaaacct cgaccacggt ggatctgaaa   240
atcaccagtc cgacaaccga ggacacggcc acctatttct gtgccagagg atatcttact   300
gatagtattg ctaacggctt tggcgtctgg ggcccaggca ccctggtcac cgtctcctca   360

<210> SEQ ID NO 471
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 471
gagctcgatc tgacccagac accagcctcc gtgtctgaac tgtgggagg cacagtcacc     60 atcaagtgcc aggccagtca gactattact aataggtact tagcctggta tcagcagaaa   120
ccagggcagc ctcccaagct cctgatctac cagtcatcca actggcatc tggggtctca   180 tcgcggttca aaggcagtgg atctgggaca gacttcactc tcaccatcag cgacctggag   240
tgtgccgatg ctgccactta ctactgtcaa tgtactgatt atggtagtac ttatttgggt   300
actttcggcg gagggaccga ggtggaaatc aaa                                333

<210> SEQ ID NO 472
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 472
ggattctccc tcggtagcta tgca                                            24

<210> SEQ ID NO 473
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 473
gtatatggta ctactggtta tata                                            24

<210> SEQ ID NO 474
```

```
<211> LENGTH: 45
<212> TYPE: DNA
<213> ORGANISM: Artificial sequence
<220> FEATURE:
<223> OTHER INFORMATION: Synthetic oligonucleotide

<400> SEQUENCE: 474
gccagaggat atcttactga tagtattgct aacggctttg gcgtc            45

<210> SEQ ID NO 475
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 475
cagactatta ctaataggta c                                      21

<210> SEQ ID NO 476
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 476
caatgtactg attatggtag tacttatttg ggtact                      36

<210> SEQ ID NO 477
<211> LENGTH: 121
<212> TYPE: PRT
<213> ORGANISM: Artificial sequence
<220> FEATURE:
<223> OTHER INFORMATION: Synthetic peptide

<400> SEQUENCE: 477
```

Glu Gln Ser Leu Glu Glu Ser Gly Gly Asp Leu Val Lys Pro Glu Gly
1               5                   10                  15

Ser Leu Thr Leu Thr Cys Thr Ala Ser Gly Phe Ser Phe Asn Ser Asn
            20                  25                  30

Tyr Trp Ile Cys Trp Val Arg Gln Thr Pro Gly Lys Gly Leu Glu Trp
        35                  40                  45

Ile Gly Cys Ile Tyr Ser Gly Ser Ser Gly Asp Thr Tyr Tyr Ala Ser
    50                  55                  60

Trp Ala Lys Gly Arg Phe Thr Ile Ser Lys Thr Ser Thr Thr Val
65                  70                  75                  80

Thr Leu Gln Met Thr Ser Leu Thr Ala Ala Asp Thr Ala Thr Tyr Phe
                85                  90                  95

Cys Ala Arg Gly Ala Asp Tyr Val Tyr Trp Ser Tyr Gly Leu Trp Gly
            100                 105                 110

Pro Gly Thr Leu Val Thr Ile Ser Ser
        115                 120

```
<210> SEQ ID NO 478
<211> LENGTH: 108
<212> TYPE: PRT
<213> ORGANISM: Artificial sequence
<220> FEATURE:
<223> OTHER INFORMATION: Synthetic peptide

<400> SEQUENCE: 478
```

Glu Leu Val Leu Thr Gln Thr Pro Ala Ser Val Ser Ala Ala Val Gly

```
            1               5                  10                 15
Gly Thr Leu Thr Ile Lys Cys Gln Ala Ser Glu Thr Ile Gly Thr Asn
                20                  25                 30
Leu Ala Trp Tyr Gln Gln Lys Pro Gly Gln Pro Pro Lys Leu Leu Ile
            35                  40                 45
Tyr Leu Ala Ser Tyr Leu Ala Ser Gly Val Ser Ser Arg Phe Lys Gly
        50                  55                 60
Ser Arg Ser Gly Thr Glu Phe Thr Leu Thr Ile Ser Asp Leu Asp Cys
65                  70                  75                 80
Asp Asp Ala Ala Thr Tyr Tyr Cys Gln Ser Thr His Phe Gly Asn Gly
                85                  90                 95
His Thr Phe Gly Gly Gly Thr Glu Val Val Val Lys
                100                 105
```

<210> SEQ ID NO 479
<211> LENGTH: 9
<212> TYPE: PRT
<213> ORGANISM: Artificial sequence
<220> FEATURE:
<223> OTHER INFORMATION: Synthetic peptide

<400> SEQUENCE: 479

```
Gly Phe Ser Phe Asn Ser Asn Tyr Trp
1               5
```

<210> SEQ ID NO 480
<211> LENGTH: 9
<212> TYPE: PRT
<213> ORGANISM: Artificial sequence
<220> FEATURE:
<223> OTHER INFORMATION: Synthetic peptide

<400> SEQUENCE: 480

```
Ile Tyr Ser Gly Ser Ser Gly Asp Thr
1               5
```

<210> SEQ ID NO 481
<211> LENGTH: 13
<212> TYPE: PRT
<213> ORGANISM: Artificial sequence
<220> FEATURE:
<223> OTHER INFORMATION: Synthetic peptide

<400> SEQUENCE: 481

```
Ala Arg Gly Ala Asp Tyr Val Tyr Trp Ser Tyr Gly Leu
1               5                  10
```

<210> SEQ ID NO 482
<211> LENGTH: 6
<212> TYPE: PRT
<213> ORGANISM: Artificial sequence
<220> FEATURE:
<223> OTHER INFORMATION: Synthetic peptide

<400> SEQUENCE: 482

```
Glu Thr Ile Gly Thr Asn
1               5
```

<210> SEQ ID NO 483
<211> LENGTH: 10
<212> TYPE: PRT
<213> ORGANISM: Artificial sequence
<220> FEATURE:
<223> OTHER INFORMATION: Synthetic peptide

<400> SEQUENCE: 483

Gln Ser Thr His Phe Gly Asn Gly His Thr
1               5                   10

<210> SEQ ID NO 484
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 484
gagcagtcgt tggaggagtc cggggggagac ctggtcaagc ctgagggatc cctgacactc    60
acctgcacag cctctggatt ctccttcaat agcaactact ggatatgctg ggtccgccag   120
actccaggga aggggctgga gtggatcgga tgcatttata gtggtagtag tggtgacact   180
tactacgcga gctgggcgaa aggccgattc accatctcca aaacctcgtc gaccacggtg   240
actctacaaa tgaccagtct gacagccgcg gacacggcca cctatttctg tgcgcggggg   300
gctgattatg tttattggag ttatggcttg tggggcccag gtaccctggt caccatctct   360
tca                                                                 363

<210> SEQ ID NO 485
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 485
gagctcgtgc tgacccagac accagcctcc gtgtctgcag ctgtgggagg cacactcacc    60
atcaagtgcc aggccagtga gaccattggc acgaatttgg cctggtatca gcagaaacca   120
gggcagcctc ccaagctcct catctatctg catcctatc tggcatctgg ggtctcatcg   180
cggttcaaag gcagtagatc tgggacagag ttcactctca ccatcagcga cctggactgt   240
gacgatgctg ccacttacta ctgtcaaagc actcattttg gtaatggtca tactttcggc   300
ggagggaccg aggtggtggt caaa                                          324

<210> SEQ ID NO 486
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 486
ggattctcct tcaatagcaa ctactgg                                        27

<210> SEQ ID NO 487
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 487
atttatagtg gtagtagtgg tgacact                                        27

<210> SEQ ID NO 488
<211> LENGTH: 39

```
<212> TYPE: DNA
<213> ORGANISM: Artificial sequence
<220> FEATURE:
<223> OTHER INFORMATION: Synthetic oligonucleotide

<400> SEQUENCE: 488
gcgcgggggg ctgattatgt ttattggagt tatggcttg                              39

<210> SEQ ID NO 489
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 489
gagaccattg gcacgaat                                                      18

<210> SEQ ID NO 490
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 490
caaagcactc attttggtaa tggtcatact                                         30

<210> SEQ ID NO 491
<211> LENGTH: 117
<212> TYPE: PRT
<213> ORGANISM: Artificial sequence
<220> FEATURE:
<223> OTHER INFORMATION: Synthetic peptide

<400> SEQUENCE: 491
```

Glu Gln Ser Val Glu Ser Gly Gly Gly Leu Ile Thr Pro Gly Gly Thr
1               5                   10                  15

Leu Thr Leu Thr Cys Thr Ala Ser Gly Phe Thr Val Thr Arg Tyr Tyr
            20                  25                  30

Met Asn Trp Val Arg Gln Ala Pro Gly Lys Gly Leu Glu Trp Ile Gly
        35                  40                  45

Tyr Ile Tyr Ala Ser Ser Lys Thr Tyr Tyr Ala Asn Trp Ala Lys Gly
    50                  55                  60

Arg Phe Thr Ile Ser Lys Thr Ser Thr Thr Val Asp Leu Lys Met Thr
65                  70                  75                  80

Ser Leu Thr Ala Glu Asp Thr Gly Thr Tyr Phe Cys Ala Arg Gly Gly
                85                  90                  95

Val Gly Asn Ser Gly Leu Asn Leu Asp Leu Trp Gly Pro Gly Thr Leu
            100                 105                 110

Val Thr Ile Ser Ser
        115

```
<210> SEQ ID NO 492
<211> LENGTH: 110
<212> TYPE: PRT
<213> ORGANISM: Artificial sequence
<220> FEATURE:
<223> OTHER INFORMATION: Synthetic peptide

<400> SEQUENCE: 492
```

Glu Leu Asp Met Thr Gln Thr Pro Ala Ser Val Ser Glu Pro Val Gly
1               5                   10                  15

Gly Thr Val Thr Ile Lys Cys Gln Ala Ser Gln Ser Ile Gly Ser Trp
            20                  25                  30

Leu Ala Trp Tyr Gln Gln Lys Pro Gly Gln Pro Pro Lys Leu Leu Ile
        35                  40                  45

Tyr Gln Ala Ser Arg Leu Ala Ser Gly Val Ser Arg Phe Gly Gly
50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Gln Ala Glu Tyr Ser Gly Asp
                85                  90                  95

Val Glu Asn Thr Phe Gly Gly Thr Glu Val Val Val Lys
            100                 105                 110

<210> SEQ ID NO 493
<211> LENGTH: 8
<212> TYPE: PRT
<213> ORGANISM: Artificial sequence
<220> FEATURE:
<223> OTHER INFORMATION: Synthetic peptide

<400> SEQUENCE: 493

Gly Phe Thr Val Thr Arg Tyr Tyr
1               5

<210> SEQ ID NO 494
<211> LENGTH: 7
<212> TYPE: PRT
<213> ORGANISM: Artificial sequence
<220> FEATURE:
<223> OTHER INFORMATION: Synthetic peptide

<400> SEQUENCE: 494

Ile Tyr Ala Ser Ser Lys Thr
1               5

<210> SEQ ID NO 495
<211> LENGTH: 14
<212> TYPE: PRT
<213> ORGANISM: Artificial sequence
<220> FEATURE:
<223> OTHER INFORMATION: Synthetic peptide

<400> SEQUENCE: 495

Ala Arg Gly Gly Val Gly Asn Ser Gly Leu Asn Leu Asp Leu
1               5                   10

<210> SEQ ID NO 496
<211> LENGTH: 6
<212> TYPE: PRT
<213> ORGANISM: Artificial sequence
<220> FEATURE:
<223> OTHER INFORMATION: Synthetic peptide

<400> SEQUENCE: 496

Gln Ser Ile Gly Ser Trp
1               5

<210> SEQ ID NO 497
<211> LENGTH: 12
<212> TYPE: PRT
<213> ORGANISM: Artificial sequence
<220> FEATURE:
<223> OTHER INFORMATION: Synthetic peptide

<400> SEQUENCE: 497

Gln Gln Ala Glu Tyr Ser Gly Asp Val Glu Asn Thr
1               5                   10

<210> SEQ ID NO 498
<211> LENGTH: 351
<212> TYPE: DNA
<213> ORGANISM: Artificial sequence
<220> FEATURE:
<223> OTHER INFORMATION: Synthetic oligonucleotide

<400> SEQUENCE: 498

```
gagcagtcgg tggagtccgg aggaggcctg ataacgcctg aggaaccct  gacactcacc    60
tgcacagcct ctggattcac cgtcactagg tattatatga actgggtccg ccaggctcca   120
gggaaggggc tggaatggat cgatacatt  tatgctagta gtaagacata ctacgcgaac   180
tgggcgaaag ccgattcac  catctccaaa acctcgacca cggtggatct gaagatgacc   240
agtctgacag ccgaggacac gggcaccat  ttctgtgcca gaggggggtgt tggtaatagt   300
ggcttgaacc ttgacttgtg gggcccaggc accctggtca ccatctcctc a            351
```

<210> SEQ ID NO 499
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 499

```
gagctcgata tgacccagac accagcctcc gtgtctgaac ctgtgggagg cacagtcacc    60
atcaagtgtc aggccagtca gagcattggc agttggttag cctggtatca gcagaaacca   120
gggcagcctc ccaagctcct gatctaccag gcatccagac tggcatctgg ggtctcatcg   180
cggttcggag gcagtggatc tgggacagaa ttcactctca ccatcagcga cctggagtgt   240
gccgatgctg ccacttacta ctgtcaacag gctgagtata tggtgatgt  tgagaatact   300
ttcggcggag ggaccgaggt ggtggtcaaa                                     330
```

<210> SEQ ID NO 500
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 500

```
ggattcaccg tcactaggta ttat                                            24
```

<210> SEQ ID NO 501
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 501

```
atttatgcta gtagtaagac a                                               21
```

<210> SEQ ID NO 502
<211> LENGTH: 42
<212> TYPE: DNA
<213> ORGANISM: Artificial sequence
<220> FEATURE:

<210> SEQ ID NO 503
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 502
gccagagggg gtgttggtaa tagtggcttg aaccttgact tg                      42

<210> SEQ ID NO 503
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 503
cagagcattg gcagttgg                                                 18

<210> SEQ ID NO 504
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 504
caacaggctg agtatagtgg tgatgttgag aatact                             36

<210> SEQ ID NO 505
<211> LENGTH: 119
<212> TYPE: PRT
<213> ORGANISM: Artificial sequence
<220> FEATURE:
<223> OTHER INFORMATION: Synthetic peptide

<400> SEQUENCE: 505

Glu Gln Ser Val Glu Glu Ser Gly Gly Asp Leu Val Lys Pro Gly Ala
1               5                   10                  15

Ser Leu Thr Leu Thr Cys Thr Ala Ser Gly Phe Ser Phe Thr Tyr Trp
            20                  25                  30

Ile Cys Trp Val Arg Gln Ala Pro Gly Lys Gly Leu Glu Trp Ile Ala
        35                  40                  45

Cys Ile Tyr Ala Gly Ser Gly Asp Thr Tyr Tyr Ala Ser Trp Ala
    50                  55                  60

Lys Gly Arg Phe Thr Ile Ser Lys Thr Ser Thr Thr Val Thr Leu
65                  70                  75                  80

Gln Met Thr Ser Leu Thr Ala Ala Asp Thr Ala Thr Tyr Phe Cys Ala
                85                  90                  95

Arg Ser Pro Asp Tyr Val Ala Trp Gly Tyr Asp Leu Trp Gly Pro Gly
            100                 105                 110

Thr Arg Val Thr Val Ser Ser
        115

<210> SEQ ID NO 506
<211> LENGTH: 110
<212> TYPE: PRT
<213> ORGANISM: Artificial sequence
<220> FEATURE:
<223> OTHER INFORMATION: Synthetic peptide

<400> SEQUENCE: 506

Glu Leu Val Leu Thr Gln Thr Pro Ala Ser Val Ser Ala Ala Val Gly
1               5                   10                  15

Gly Thr Val Thr Ile Asn Cys Gln Ala Ser Gln Ser Ile Gly Thr Asn
            20                  25                  30

```
Leu Val Trp Tyr Gln Gln Lys Pro Gly Gln Pro Pro Lys Leu Leu Phe
        35                  40                  45

Tyr Tyr Ala Ser Thr Leu Ala Ser Gly Val Pro Ser Arg Phe Arg Gly
    50                  55                  60

Ser Arg Ser Gly Thr Glu Tyr Thr Leu Thr Ile Ser Asp Leu Glu Cys
65                  70                  75                  80

Ala Asp Ala Ala Thr Tyr Tyr Cys Gln Cys Ile Tyr Tyr Gly Gly Asn
                85                  90                  95

Tyr Gly His Thr Phe Gly Gly Gly Thr Glu Val Val Val Lys
                100                 105                 110

<210> SEQ ID NO 507
<211> LENGTH: 9
<212> TYPE: PRT
<213> ORGANISM: Artificial sequence
<220> FEATURE:
<223> OTHER INFORMATION: Synthetic peptide

<400> SEQUENCE: 507

Ala Ser Gly Phe Ser Phe Thr Tyr Trp
1               5

<210> SEQ ID NO 508
<211> LENGTH: 9
<212> TYPE: PRT
<213> ORGANISM: Artificial sequence
<220> FEATURE:
<223> OTHER INFORMATION: Synthetic peptide

<400> SEQUENCE: 508

Ile Tyr Ala Gly Ser Ser Gly Asp Thr
1               5

<210> SEQ ID NO 509
<211> LENGTH: 13
<212> TYPE: PRT
<213> ORGANISM: Artificial sequence
<220> FEATURE:
<223> OTHER INFORMATION: Synthetic peptide

<400> SEQUENCE: 509

Ala Arg Ser Pro Asp Tyr Val Ala Trp Gly Tyr Asp Leu
1               5                   10

<210> SEQ ID NO 510
<211> LENGTH: 6
<212> TYPE: PRT
<213> ORGANISM: Artificial sequence
<220> FEATURE:
<223> OTHER INFORMATION: Synthetic peptide

<400> SEQUENCE: 510

Gln Ser Ile Gly Thr Asn
1               5

<210> SEQ ID NO 511
<211> LENGTH: 12
<212> TYPE: PRT
<213> ORGANISM: Artificial sequence
<220> FEATURE:
<223> OTHER INFORMATION: Synthetic peptide

<400> SEQUENCE: 511

Gln Cys Ile Tyr Tyr Gly Gly Asn Tyr Gly His Thr
```

<210> SEQ ID NO 512
<211> LENGTH: 357
<212> TYPE: DNA
<213> ORGANISM: Artificial sequence
<220> FEATURE:
<223> OTHER INFORMATION: Synthetic oligonucleotide

<400> SEQUENCE: 512
gagcagtcgg tggaggagtc cgggggagac ctggtcaagc ctggggcatc cctgacactc       60
acctgcacag cctctggatt ctccttcacc tactggatat gctgggtccg ccaggctcca      120
gggaaggggc tggagtggat cgcatgcatt tatgctggta gtagtggtga cacttactac      180
gcgagctggg cgaaaggccg attcaccatc tccaaaacct cgtcgaccac ggtgactctg      240
caaatgacca gtctgacagc cgcggacacg gccaccatt tctgtgcgag atccccgat       300
tatgttgctt ggggatatga cttgtggggc ccaggcaccc gggtcaccgt ctcttca        357

<210> SEQ ID NO 513
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 513
gagctcgtgc tgacccagac accagcctcc gtgtctgcgg ctgtgggagg cacagtcacc       60
atcaattgcc aggccagtca gagtattggt actaatttag tctggtatca gcagaaacca      120
gggcagcctc ccaagctcct cttctattat gcatccactc tggcatctgg ggtcccatcg      180
cggttcagag gcagtagatc tgggacagag tacactctca ccatcagcga cctggagtgt      240
gccgatgctg ccacttatta ttgtcaatgt atttattatg gtggtaatta tggtcatact      300
ttcggcggag ggaccgaggt ggtggtcaaa                                        330

<210> SEQ ID NO 514
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 514
gcctctggat tctccttcac ctactgg                                           27

<210> SEQ ID NO 515
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 515
atttatgctg gtagtagtgg tgacact                                           27

<210> SEQ ID NO 516
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 516

```
gcgagatccc ccgattatgt tgcttgggga tatgacttg                           39
```

<210> SEQ ID NO 517
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 517

```
cagagtattg gtactaat                                                  18
```

<210> SEQ ID NO 518
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 518

```
caatgtattt attatggtgg taattatggt catact                              36
```

<210> SEQ ID NO 519
<211> LENGTH: 116
<212> TYPE: PRT
<213> ORGANISM: Artificial sequence
<220> FEATURE:
<223> OTHER INFORMATION: Synthetic peptide

<400> SEQUENCE: 519

Glu Gln Ser Val Glu Ser Gly Gly Arg Leu Val Thr Pro Gly Thr
1               5                   10                  15

Pro Leu Thr Leu Thr Cys Thr Ala Ser Gly Phe Thr Ile Ser Asp Tyr
            20                  25                  30

His Met Cys Trp Val Arg Gln Ala Pro Gly Lys Gly Leu Glu Trp Ile
        35                  40                  45

Gly Leu Ile Arg Ala Ser His Ser Thr Ala Tyr Ala Ser Trp Ala Asn
    50                  55                  60

Gly Arg Phe Thr Ile Ser Arg Thr Ser Thr Thr Val Asp Leu Lys Ile
65                  70                  75                  80

Thr Ser Pro Thr Ser Glu Asp Thr Ala Thr Tyr Phe Cys Ala Arg Tyr
                85                  90                  95

Gly Gly Ser Gly Ile Gly Cys Asn Leu Trp Gly Pro Gly Thr Leu Val
            100                 105                 110

Thr Ile Ser Ser
        115

<210> SEQ ID NO 520
<211> LENGTH: 110
<212> TYPE: PRT
<213> ORGANISM: Artificial sequence
<220> FEATURE:
<223> OTHER INFORMATION: Synthetic peptide

<400> SEQUENCE: 520

Glu Leu Val Leu Thr Gln Thr Pro Ala Ser Val Ser Glu Pro Val Gly
1               5                   10                  15

Gly Thr Val Thr Ile Lys Cys Gln Ala Ser Gln Ser Ile Asp Ser Asn
            20                  25                  30

Leu Ala Trp Tyr Gln Gln Lys Pro Gly Gln Pro Pro Lys Gln Leu Ile
        35                  40                  45

```
Tyr Ala Val Ser Asn Leu Ala Ser Gly Val Pro Ser Arg Phe Lys Gly
             50                  55                  60

Ser Gly Ser Gly Thr Glu Phe Thr Leu Thr Ile Ser Asp Leu Glu Cys
 65                  70                  75                  80

Ala Asp Ala Ala Ser Tyr Tyr Cys Glu Cys Thr Tyr Tyr Gly Asn Ser
                 85                  90                  95

Tyr Val Gly Gly Phe Gly Gly Gly Thr Glu Val Glu Ile Lys
            100                 105                 110
```

<210> SEQ ID NO 521
<211> LENGTH: 8
<212> TYPE: PRT
<213> ORGANISM: Artificial sequence
<220> FEATURE:
<223> OTHER INFORMATION: Synthetic peptide

<400> SEQUENCE: 521

```
Gly Phe Thr Ile Ser Asp Tyr His
 1               5
```

<210> SEQ ID NO 522
<211> LENGTH: 7
<212> TYPE: PRT
<213> ORGANISM: Artificial sequence
<220> FEATURE:
<223> OTHER INFORMATION: Synthetic peptide

<400> SEQUENCE: 522

```
Ile Arg Ala Ser His Ser Thr
 1               5
```

<210> SEQ ID NO 523
<211> LENGTH: 12
<212> TYPE: PRT
<213> ORGANISM: Artificial sequence
<220> FEATURE:
<223> OTHER INFORMATION: Synthetic peptide

<400> SEQUENCE: 523

```
Ala Arg Tyr Gly Gly Ser Gly Ile Gly Cys Asn Leu
 1               5                  10
```

<210> SEQ ID NO 524
<211> LENGTH: 6
<212> TYPE: PRT
<213> ORGANISM: Artificial sequence
<220> FEATURE:
<223> OTHER INFORMATION: Synthetic peptide

<400> SEQUENCE: 524

```
Gln Ser Ile Asp Ser Asn
 1               5
```

<210> SEQ ID NO 525
<211> LENGTH: 12
<212> TYPE: PRT
<213> ORGANISM: Artificial sequence
<220> FEATURE:
<223> OTHER INFORMATION: Synthetic peptide

<400> SEQUENCE: 525

```
Glu Cys Thr Tyr Tyr Gly Asn Ser Tyr Val Gly Gly
 1               5                  10
```

```
<210> SEQ ID NO 526
<211> LENGTH: 348
<212> TYPE: DNA
<213> ORGANISM: Artificial sequence
<220> FEATURE:
<223> OTHER INFORMATION: Synthetic oligonucleotide

<400> SEQUENCE: 526
gagcagtcgg tggaggagtc cgggggtcgc ctggtcacgc ctgggacacc cctgacactc      60
acctgcacag cctctggatt caccatcagt gactaccaca tgtgctgggt ccgccaggct     120
ccagggaagg ggctggagtg gatcggactc attcgggcta gtcattccac agcctacgcg     180
agctgggcga atggccgatt caccatctcc agaacctcga ccacggtgga tctgaagatc     240
accagtccga caagtgagga cacggccacc tatttctgtg ccagatatgg tggtagtggt     300
attggttgta atttgtgggg cccaggcacc ctggtcacca tctcctca                  348

<210> SEQ ID NO 527
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 527
gagctcgtgc tgacccagac accagcctcc gtgtctgaac ctgtgggagg cacagtcacc      60
atcaagtgcc aggccagtca gagcattgat agtaatttag cctggtatca gcagaaacca     120
gggcagcctc ccaagcaact gatctatgct gtatccaatt tggcatctgg ggtcccatcg     180
cggttcaaag gcagtggatc tgggacagag ttcactctca ccatcagcga cctggagtgt     240
gccgatgccg ccagttatta ttgtgaatgt acttattatg gtaatagtta tgttggtggt     300
ttcggcggag ggaccgaggt ggaaatcaaa                                      330

<210> SEQ ID NO 528
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 528
ggattcacca tcagtgacta ccac                                             24

<210> SEQ ID NO 529
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 529
attcgggcta gtcattccac a                                                21

<210> SEQ ID NO 530
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 530
gccagatatg gtggtagtgg tattggttgt aatttg                                36
```

<210> SEQ ID NO 531
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 531
cagagcattg atagtaat                                                    18

<210> SEQ ID NO 532
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 532
gaatgtactt attatggtaa tagttatgtt ggtggt                                36

<210> SEQ ID NO 533
<211> LENGTH: 287
<212> TYPE: PRT
<213> ORGANISM: Homo sapiens

<400> SEQUENCE: 533

Met Ser Pro His Pro Thr Ala Leu Leu Gly Leu Val Leu Cys Leu Ala
1               5                   10                  15

Gln Thr Ile His Thr Gln Glu Glu Asp Leu Pro Arg Pro Ser Ile Ser
            20                  25                  30

Ala Glu Pro Gly Thr Val Ile Pro Leu Gly Ser His Val Thr Phe Val
        35                  40                  45

Cys Arg Gly Pro Val Gly Val Gln Thr Phe Arg Leu Glu Arg Glu Ser
    50                  55                  60

Arg Ser Thr Tyr Asn Asp Thr Glu Asp Val Ser Gln Ala Ser Pro Ser
65                  70                  75                  80

Glu Ser Glu Ala Arg Phe Arg Ile Asp Ser Val Ser Glu Gly Asn Ala
                85                  90                  95

Gly Pro Tyr Arg Cys Ile Tyr Tyr Lys Pro Pro Lys Trp Ser Glu Gln
            100                 105                 110

Ser Asp Tyr Leu Glu Leu Leu Val Lys Glu Thr Ser Gly Gly Pro Asp
        115                 120                 125

Ser Pro Asp Thr Glu Pro Gly Ser Ser Ala Gly Pro Thr Gln Arg Pro
    130                 135                 140

Ser Asp Asn Ser His Asn Glu His Ala Pro Ser Gln Gly Leu Lys
145                 150                 155                 160

Ala Glu His Leu Tyr Ile Leu Ile Gly Val Ser Val Val Phe Leu Phe
                165                 170                 175

Cys Leu Leu Leu Leu Val Leu Phe Cys Leu His Arg Gln Asn Gln Ile
            180                 185                 190

Lys Gln Gly Pro Pro Arg Ser Lys Asp Glu Glu Gln Lys Pro Gln Gln
        195                 200                 205

Arg Pro Asp Leu Ala Val Asp Val Leu Glu Arg Thr Ala Asp Lys Ala
    210                 215                 220

Thr Val Asn Gly Leu Pro Glu Lys Asp Arg Glu Thr Asp Thr Ser Ala
225                 230                 235                 240

Leu Ala Ala Gly Ser Ser Gln Glu Val Thr Tyr Ala Gln Leu Asp His
                245                 250                 255

-continued

```
Trp Ala Leu Thr Gln Arg Thr Ala Arg Ala Val Ser Pro Gln Ser Thr
            260                 265                 270

Lys Pro Met Ala Glu Ser Ile Thr Tyr Ala Ala Val Ala Arg His
        275                 280                 285

<210> SEQ ID NO 534
<211> LENGTH: 861
<212> TYPE: DNA
<213> ORGANISM: Homo sapiens

<400> SEQUENCE: 534
atgtctcccc accccaccgc cctcctgggc ctagtgctct gcctggccca gaccatccac      60
acgcaggagg aagatctgcc cagaccctcc atctcggctg agccaggcac cgtgatcccc     120
ctggggagcc atgtgacttt cgtgtgccgg ggcccggttg gggttcaaac attccgcctg     180
gagagggaga gtagatccac atacaatgat actgaagatg tgtctcaagc tagtccatct     240
gagtcagagg ccagattccg cattgactca gtaagtgaag aaatgccgg gccttatcgc      300 tgcatctatt ataagccccc taaatggtct gagcagagtg actacctgga gctgctggtg     360
aaagaaacct ctggaggccc ggactccccg gacacagagc ccggctcctc agctggaccc     420
acgcagaggc cgtcggacaa cagtcacaat gagcatgcac ctgcttccca aggcctgaaa     480
gctgagcatc tgtatattct catcggggtc tcagtggtct tcctcttctg tctcctcctc     540
ctggtcctct tctgcctcca tcgccagaat cagataaagc aggggccccc cagaagcaag     600
gacgaggagc agaagccaca gcagaggcct gacctggctg ttgatgttct agagaggaca     660
gcagacaagg ccacagtcaa tggacttcct gagaaggaca gagagacgga cacctcggcc     720
ctggctgcag ggagttccca ggaggtgacg tatgctcagc tggaccactg ggccctcaca     780
cagaggacag cccgggctgt gtccccacag tccacaaagc ccatggccga gtccatcacg     840
tatgcagccg ttgccagaca c                                              861

<210> SEQ ID NO 535
<211> LENGTH: 78
<212> TYPE: PRT
<213> ORGANISM: Artificial sequence
<220> FEATURE:
<223> OTHER INFORMATION: Synthetic peptide

<400> SEQUENCE: 535

Asp Ser Ile Ser Ala Glu Pro Gly Thr Val Ile Pro Leu Gly Ser His
1               5                   10                  15

Val Thr Phe Val Gly Val Gln Thr Phe Arg Glu Arg Glu Ser Arg Ser
            20                  25                  30

Thr Tyr Asn Asp Thr Glu Asp Val Ser Gln Ala Ser Pro Ser Glu Ile
        35                  40                  45

Asp Ser Val Ser Glu Gly Asn Ala Gly Pro Tyr Arg Ile Tyr Tyr Lys
    50                  55                  60

Pro Pro Lys Trp Ser Glu Gln Ser Asp Tyr Leu Glu Leu Leu
65                  70                  75
```

ANTI-LEUKOCYTE-ASSOCIATED IMMUNOGLOBULIN-LIKE RECEPTOR 1 (LAIR1) MONOCLONAL ANTIBODIES AND METHOD OF USE THEREOF TO TREAT CANCER

CROSS-REFERENCE TO RELATED APPLICATIONS

This application is a national phase application under 35 U.S.C. § 371 of International Application No. PCT/US2018/012040, filed Jan. 2, 2018, which claims priority to U.S. provisional patent applications 62/445,673, filed Jan. 12, 2017, and 62/441,551, filed Jan. 2, 2017, the disclosure of each of which is incorporated herein by reference.

FIELD OF THE DISCLOSURE

The present disclosure relates generally to the fields of medicine, oncology, and immunology. In particular, the disclosure relates to anti-LAIR1 antibodies and uses thereof in treatment of cancer, inflammation and autoimmune diseases.

BACKGROUND

Human leukocyte-associated immunoglobulin-like receptor 1 (LAIR1) is a type I transmembrane glycoprotein consisting of 287 amino acids that contains a single extracellular C2-type Ig-like domain followed by a stalk region connected to the single transmembrane domain and 2 cytoplasmic immunoreceptor tyrosine-based inhibitory motifs (ITIMs) that relay the inhibitory signal.

LAIR1 is structurally related to several other inhibitory Ig superfamily members, including LILRBs, localized to the leukocyte receptor complex (LRC) on human chromosome 19q13.4, suggesting that these molecules have evolved from a common ancestral gene. LAIR1 consists of 10 exons.

LAIR1 is expressed in T cells, B cells, natural killer (NK) cells, macrophages, and dendritic cells, as well as hematopoietic progenitors including human CD34+ cells. It has been demonstrated that LAIR1 is expressed on acute myeloid leukemia (AML) stem cells and differentiated AML and acute lymphocytic leukemia (ALL) cells where LAIR1 is essential for AML development by activating SHP-1/CAMK/CREB pathway.

Due to the immune inhibitory function and leukemia stem-ness function of LAIR1, there is a need for antibodies that modulate the activity of LAIR1, which will have utilities as immune checkpoint modulators and as therapeutics for cancers or autoimmune diseases.

BRIEF SUMMARY OF THE INVENTION

Thus, in one aspect, the present disclosure provides an isolated monoclonal antibody or an antigen-binding fragment thereof that binds specifically to LAIR1. In certain embodiments, the antibody or antigen-binding fragment, when bound to LAIR1, modulates the activity of LAIR1. In certain embodiments, the antibody or antigen-binding fragment, when bound to LAIR1, activates LAIR1. In certain embodiments, the antibody or antigen-binding fragment, when bound to LAIR1, suppresses activation of LAIR1. In certain embodiments, the antibody or antigen-binding fragment, when bound to LAIR1, specifically blocks binding of collagen Ito LAIR1.

In some embodiments, the monoclonal antibody or antigen-binding fragment thereof can specifically bind to the Ig domain of LAIR1 (amino acid residues 25-121). In some embodiments, the monoclonal antibody or antigen-binding fragment thereof can specifically bind to an epitope contained within the Ig domain of LAIR1. In some embodiments, the monoclonal antibody or antigen-binding fragment thereof can specifically bind to an epitope of LAIR1 contained within the amino acid residues 25-47, 53-81, 88-96 and/or 102-119. In some embodiments, the monoclonal antibody or antigen-binding fragment thereof can specifically bind to an epitope of LAIR1 contained within the amino acid residues 30-34, 45-47 and/or 88-89. In some embodiments, the monoclonal antibody or antigen-binding fragment thereof can specifically bind to an epitope of LAIR1 contained within the amino acid residues 37-41, 116-119, 98-105, 59-63 and/or 66-71. In some embodiments, the monoclonal antibody or antigen-binding fragment thereof can specifically bind to an epitope of LAIR1 comprising amino acid residues 30-34, 37-41, 45-47, 59-63, 66-71, 88-89, 98-105, 108-110 or 116-119. In some embodiments, the monoclonal antibody or antigen-binding fragment thereof can specifically bind to an epitope of LAIR1 comprising amino acid residues 35-36, 44, 53-56, 64-65, 73-81, 89-96, 106-107 or 111-115. In some embodiments, the monoclonal antibody or antigen-binding fragment thereof can specifically bind to an epitope of LAIR1 comprising amino acid residues 25, 35, 56, 65-68, 73, 75-77, 80, 89, 93, 106, 107 or 109. In some embodiments, the monoclonal antibody or an antigen-binding fragment thereof can specifically bind to an epitope of LAIR1 contained within amino acid residues 59-69 and/or 100-112. In some embodiments, the monoclonal antibody or an antigen-binding fragment thereof can specifically bind to an epitope of LAIR1 comprising amino acid residues 59, 61, 65, 67, 68, 69, 100, 102, 109, 111 or 112. In some embodiments, the monoclonal antibody or an antigen-binding fragment thereof can specifically bind to an epitope of LAIR1 comprising amino acid residues 59, 61 and 109. In some embodiments, the monoclonal antibody or an antigen-binding fragment thereof can specifically bind to an epitope of LAIR1comprising amino acid residues 61 or 62 of LAIR1. In some embodiments, the monoclonal antibody or an antigen-binding fragment thereof can specifically bind to an epitope of LAIR1comprising amino acid residues 68 or 69 of LAIR1. In some embodiments, the monoclonal antibody or an antigen-binding fragment thereof can specifically bind to an epitope of LAIR1comprising amino acid residues 61 or 62, 65 or 66, and 111 or 112 of LAIR1. In some embodiments, the monoclonal antibody or an antigen-binding fragment thereof can specifically bind to an epitope of LAIR1comprising amino acid residues 111 or 112 of LAIR1.

In certain embodiments, the isolated monoclonal antibody or an antigen-binding fragment thereof comprises (a) a heavy chain variable region comprising the following complementary determining regions (CDRs): a heavy chain CDR1 that is a CDR1 in SEQ ID NO: 1, 15, 29, 43, 57, 71, 85, 99, 113, 127, 141, 155, 169, 183, 197, 211, 225, 239, 253, 267, 281, 295, 309, 323, 337, 351, 365, 379, 393, 407, 421, 435, 449, 463, 477, 491, 505 or 519, a heavy chain CDR2 that is a CDR2 in SEQ ID NO: 1, 15, 29, 43, 57, 71, 85, 99, 113, 127, 141, 155, 169, 183, 197, 211, 225, 239, 253, 267, 281, 295, 309, 323, 337, 351, 365, 379, 393, 407, 421, 435, 449, 463, 477, 491, 505 or 519, and a heavy chain CDR3 that is a CDR3 in SEQ ID NO: 1, 15, 29, 43, 57, 71, 85, 99, 113, 127, 141, 155, 169, 183, 197, 211, 225, 239, 253, 267, 281, 295, 309, 323, 337, 351, 365, 379, 393, 407, 421, 435, 449, 463, 477, 491, 505 or 519; and (b) a light chain variable region comprising the following CDRs: a light chain CDR1 that is a CDR1 in SEQ ID NO: 2, 16, 30, 44, 58, 72, 86, 100, 114, 128, 142, 156, 170, 184, 198, 212, 226, 240, 254, 268, 282, 296, 310, 324, 338, 352, 366, 380, 394, 408, 422, 436, 450, 464, 478, 492, 506 or 520, a light chain CDR2 that is a CDR2 in SEQ ID NO: 2, 16, 30, 44, 58, 72, 86, 100, 114, 128, 142, 156, 170, 184, 198, 212, 226, 240, 254, 268, 282, 296, 310, 324, 338, 352, 366, 380, 394, 408, 422, 436, 450, 464, 478, 492, 506 or 520, and a light chain CDR3 that is a CDR3 in SEQ ID NO: 2, 16, 30, 44, 58, 72, 86, 100, 114, 128, 142, 156, 170, 184, 198, 212, 226, 240, 254, 268, 282, 296, 310, 324, 338, 352, 366, 380, 394, 408, 422, 436, 450, 464, 478, 492, 506 or 520.

In certain embodiments, the heavy chain variable region comprises: a CDR1 comprising SEQ ID NO: 3, 17, 31, 45, 59, 73, 87, 101, 115, 129, 143, 157, 171, 185, 199, 213, 227, 241, 255, 269, 283, 297, 311, 325, 339, 353, 367, 381, 395, 409, 423, 437, 451, 465, 479, 493, 507 or 521, a CDR2 comprising SEQ ID NO: 4, 18, 32, 46, 60, 74, 88, 102, 116, 130, 144, 158, 172, 186, 200, 214, 228, 242, 256, 270, 284, 298, 312, 326, 340, 354, 368, 382, 396, 410, 424, 438, 452, 466, 480, 494, 508 or 522, and a CDR3 comprising SEQ ID NO: 5, 19, 33, 47, 61, 75, 89, 103, 117, 131, 145, 159, 173, 187, 201, 215, 229, 243, 257, 271, 285, 299, 313, 327, 341, 355, 369, 383, 397, 411, 425, 439, 453, 467, 481, 495, 509 or 523.

In certain embodiments, the light chain variable region comprises: a CDR1 comprising SEQ ID NO: 6, 20, 34, 48, 62, 76, 90, 104, 118, 132, 146, 160, 174, 188, 202, 216, 230, 244, 258, 272, 286, 300, 314, 328, 342, 356, 370, 384, 398, 412, 426, 440, 454, 468, 482, 496, 510 or 524, a CDR2 comprising amino acid sequence DAS, RAS, LAS, KAS, YAS, GAS, GPS, LSS, QAS, AAS, WTS, QSS, or AVS, and a CDR3 comprising SEQ ID NO: 7, 21, 35, 49, 63, 77, 91, 105, 119, 133, 147, 161, 175, 189, 203, 217, 231, 245, 259, 273, 287, 301, 315, 329, 343, 357, 371, 385, 399, 413, 427, 441, 455, 469, 483, 497, 511 or 525.

In certain embodiments, the isolated monoclonal antibody or an antigen-binding fragment thereof comprises: (a) a heavy chain variable region having an amino acid sequence at least about 90% identical to SEQ ID NO: 1, 15, 29, 43, 57, 71, 85, 99, 113, 127, 141, 155, 169, 183, 197, 211, 225, 239, 253, 267, 281, 295, 309, 323, 337, 351, 365, 379, 393, 407, 421, 435, 449, 463, 477, 491, 505 or 519; and (b) a light chain variable region having an amino acid sequence at least about 90% identical to SEQ ID NO: 2, 16, 30, 44, 58, 72, 86, 100, 114, 128, 142, 156, 170, 184, 198, 212, 226, 240, 254, 268, 282, 296, 310, 324, 338, 352, 366, 380, 394, 408, 422, 436, 450, 464, 478, 492, 506 or 520. In certain embodiments, the heavy chain variable region has an amino acid sequence of SEQ ID NO: 1, 15, 29, 43, 57, 71, 85, 99, 113, 127, 141, 155, 169, 183, 197, 211, 225, 239, 253, 267, 281, 295, 309, 323, 337, 351, 365, 379, 393, 407, 421, 435, 449, 463, 477, 491, 505 or 519, and wherein the light chain variable region has an amino acid sequence of SEQ ID NO: 2, 16, 30, 44, 58, 72, 86, 100, 114, 128, 142, 156, 170, 184, 198, 212, 226, 240, 254, 268, 282, 296, 310, 324, 338, 352, 366, 380, 394, 408, 422, 436, 450, 464, 478, 492, 506 or 520.

In some embodiments, the isolated monoclonal antibody or an antigen binding fragment thereof competes for the same epitope with the isolated monoclonal antibody or an antigen-binding fragment thereof as provided herein.

In certain embodiments, the antibody is characterized by clone-paired heavy and light chain CDR sequences contained in the heavy chain and light chain variable region sequences listed in Table 1. In certain embodiments, each CDR is defined in accordance with Kabat definition, the Chothia definition, the combination of Kabat definition and Chothia definition, the AbM definition, or the contact definition of CDR. In certain embodiments, the antibody is characterized by clone-paired heavy and light chain variable region sequences listed in Table 1.

In certain embodiments, the antibody is characterized by clone-paired heavy chain and light chain variable region sequences having amino acid sequences at least about 70%, 80%, 90%, or 95% identity to the clone-paired sequences in Table 1.

In another aspect, the present disclosure provides an isolated monoclonal antibody or an antigen-binding fragment thereof, which competes for the same epitope with an antibody described herein. In certain embodiments, the antibody competes for the same epitope with an antibody having clone-paired heavy and light chain variable regions in Table 1.

In certain embodiments, the isolated monoclonal antibody described herein is a chimeric, humanized, or human antibody. In certain embodiments, isolated monoclonal antibody described herein is of the IgG1, IgG2, IgG3 or IgG4 type. In certain embodiments, the antigen-binding fragment described herein is a recombinant ScFv (single chain fragment variable) antibody, Fab fragment, F(ab')2 fragment, or Fv fragment.

In another aspect, there is provided a pharmaceutical composition comprising an isolated monoclonal antibody or an antigen-binding fragment thereof as provided herein, and at least one pharmaceutically acceptable carrier.

In another aspect, there is provided an isolated nucleic acid that encodes the isolated monoclonal antibody or an antigen-binding fragment thereof as provided herein.

In another aspect, there is provided a vector comprising the isolated nucleic acid as provided herein.

In another aspect, there is provided a host cell comprising the vector as provided herein. The host cell may be a mammalian cell. The host cell may be a CHO cell.

In another aspect, there is provided a hybridoma encoding or producing the isolated monoclonal antibody as provided herein.

In another aspect, there is provided a process of producing an antibody. The method may comprise culturing the host cell as provided herein under conditions suitable for expressing the antibody, and recovering the antibody.

In another aspect, there is provided a method of treating or ameliorating the effects of a cancer or an autoimmune disease in a subject. The method may comprise administering to the subject a therapeutically effective amount of the antibody or an antigen-binding fragment thereof as provided herein. In certain embodiments, the cancer is acute myeloid leukemia. In certain embodiments, the antibody or an antigen-binding fragment thereof is administered intravenously, intra-arterially, intra-tumorally or subcutaneously.

In yet another aspect, there is provided a method of detecting a cancer cell or cancer stem cell in a sample or subject. In certain embodiments, the method comprises contacting a subject or a sample from the subject with the antibody or an antigen-binding fragment thereof as provided herein, and detecting binding of said antibody to a cancer cell or cancer stem cell in said subject or sample. The sample can be a body fluid or biopsy. The sample can be blood, sputum, tears, saliva, mucous, serum, urine or feces. In certain embodiments, the detection comprises immunohistochemistry, ELISA, RIA or Western blot.

The use of the word "a" or "an" when used in conjunction with the term "comprising" in the claims and/or the specification may mean "one," but it is also consistent with the meaning of "one or more," "at least one," and "one or more than one."

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the disclosure will become apparent to those skilled in the art from this detailed description.

BRIEF DESCRIPTION OF FIGURES

The following drawings form part of the present specification and are included to further demonstrate certain aspects of the present disclosure. The disclosure may be better understood by reference to one or more of these drawings in combination with the detailed description of specific embodiments presented herein.

FIG. 45 shows the first set (Set 1) of binning groups determined. Five epitope bins were identified for 14 rabbit mAbs using the method described in FIGS. 41-44.

FIG. 46 shows the second set (Set 2) of binning groups determined. Two epitope bins were identified for 7 rabbit mAbs using the method described in FIGS. 41-44.

FIG. 47 shows the third set (Set 3) of binning groups determined. Two epitope bins were identified for 7 rabbit mAbs using the method described in FIGS. 41-44.

FIG. 48 shows the fourth set (Set 4) of binning groups determined. Two epitope bins were identified for 7 rabbit mAbs using the method described in Figure in FIGS. 41-44.

FIGS. 53A-E show the screening of anti-LAIR1 antagonist and agonist antibodies. FIG. 53A describes an initial screening method to identify antibodies binding to LAIR1. Here, potential anti-LAIR1 antibodies in the conditioned-medium of monoclonal antibody-producing rabbit plasma cells were pre-incubated on Protein A coated wells. The LAIR1 reporter cells (indicating functional binding of LAIR1, as described in Kang et al Nat Cell Biol 2015, 17(5):665-677) were then plated and their GFP+% were detected after 24 hours. The conditioned-medium that can induce GFP+% upregulation possibly contains LAIR1-binding monoclonal antibodies. FIG. 53B summarizes the data from using a method to identify antagonist anti-LAIR1 antibodies. Here, the LAIR1 ligand collagen I was coated on the surface of the wells, then soluble Abs were added, and the percentage of GFP+LAIR1 reporter cells were detected after 24 hours. An antagonist anti-LAIR1 antibody, as a soluble form, is capable of inhibiting collagen I-induced GFP+ signal (shown as GFP+%) in the reporter cells. FIG. 53C shows the data from using a method to further narrow down antagonist anti-LAIR1 antibodies. The LAIR1 ligand collagen I was coated on the surface of the wells, then soluble Abs and K562 cells (that express Fc receptors on cell surface) were added, and the percentage of GFP+ LAIR1 reporter cells were detected after 24 hours. An antagonist anti-LAIR1 antibody, as a soluble form, is capable of inhibiting collagen I-induced GFP+ signal (shown as GFP+%) in the reporter cells even in the presence of Fc receptor positive cells in the co-culture. FIG. 53D shows that two potential agonist antibodies (LA-94 and LA-192) and the N297A Fc mutant version of LA-94 (N297A94), and four potential antagonist antibodies (LA-235, LA-219, LA-252, LA-259) and N297A Fc mutant version of LA-235 (N297A235) were suggested using the LAIR1 reporter cell system following the methods in FIGS. 53A-C. All the GFP expression information was summarized in the table (lower panel). While an antagonist anti-LAIR1 antibody, as a soluble form, is capable of inhibiting collagen I-induced GFP+ signal in the reporter cells even in the presence of Fc receptor positive cells, an agonist anti-LAIR1 antibody, as a soluble form, can induce GFP+ signal in the reporter cells. FIG. 53E shows that the dose-dependent activity of the antagonist antibody anti-LAIR1 LA-235 to inhibit collagen-induced GFP+(%) of LAIR1 reporter cells. In contrast, the agonist Ab LA-94 shows an ability to enhance the collagen-induced GFP+(%) of LAIR1 reporter cells.

FIG. 54A shows that $1\times10^6$ luciferase stably expressing THP-1 cells were transplanted into NSG mice through tail vein injection at day 0, and after 30 minutes, anti-LAIR1 antibody was administrated through ophthalmic vein injection. Tumor development was monitored by BLI imaging. FIG. 54B shows the survival curve of mice from FIG. 54A. FIG. 54C shows that $5\times10^6$ GFP+MV4-11 cells were transplanted into NSG mice through tail vein injection at day 0, and after 30 minutes, 10 mg/kg anti-LAIR1 antibodies were administrated through ophthalmic vein injection. Tissues were harvested after 24 hours and homing of GFP+MV4-11 cells were detected through flow cytometry, expressed as a ratio of MV4-11 cells in liver (LVR), bone marrow (BM), and spleen (SP) to those in peripheral blood (PB) (expressed as LVR/PB, BM/PB, and SP/PB, respectively).

FIG. 54D shows that $1\times10^5$/well human endothelial cells were plated on the upper well of the 24 well transwell plate at day -7. $1\times10^5$ MV4-11 cells were added at day 0, and the cell number of MV4-11 cells in the lower well were counted using flow cytometry at day 1 (18 hours later).

FIG. 55A shows the schematic of human LAIR1 ectopically-expressed MLL-AF9 mouse model. FIG. 55B shows that GFP+ cells used for transplantation in A are human LAIR1 positive but do not express mouse LAIR1. FIG. 55C shows that human LAIR1 ectopically-expressed in mouse bone marrow cells up-regulated phosphorylated SHP1 (left), and increased the number of colony formation unit (CFU) (right). FIG. 55D shows that 100 µg anti-LAIR1 antibody per mouse was injected to mice that had been transplanted with the human LAIR1 ectopically-expressed cells, at days 5, 7, and 9 after transplantation. Periphery blood samples were collected at day 15, and the percentage of GFP+ cells were detected using flow cytometry.

In FIG. 57A, indicated concentrations of anti-CD3 antibody was coated on the surface of the wells of a 96-well flat-bottom plate, and $1\times10^5$ PBMC mixed with control or LA-192 anti-LAIR1 antibodies (final concentration 50 µg/ml) were incubated. The percentage of CD3+ T cells were detected by flow cytometry at day 5. In FIG. 57B, human T cells/GFP+THP-1 cells mixture was treated by indicated control or various anti-LAIR1 antibodies. Apoptosis of GFP+THP-1 cells was measured after 4 hr.

DETAILED DESCRIPTION OF THE DISCLOSURE

Figures 1A, 1B:
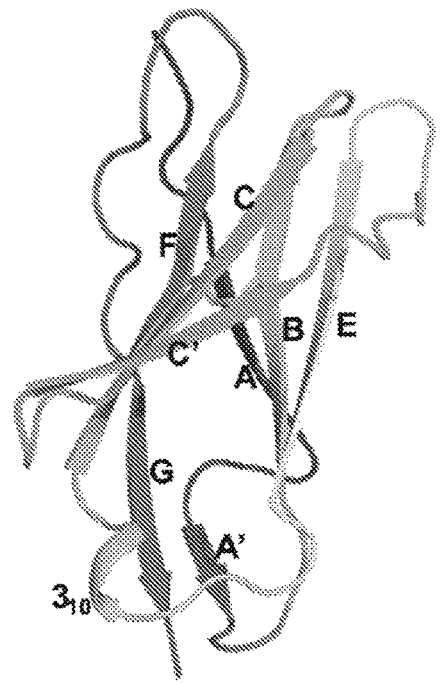
FIG. 1A is a ribbon drawing of the LAIR-1 ectodomain (or extracellular domain or ECD) structure in rainbow colors from N-terminus (blue) to C-terminus (red). The disulfide bond between beta-strands B and F, characteristic of Ig-like domains, is indicated in stick representation. (The figure is based on T. Harma C et al., "Crystal structure and collagen-binding site of immune inhibitory receptor LAIR-1: unexpected implications for collagen binding by platelet receptor GPVI" Blood (2010) 115(7):1364-73)
FIG. 1B shows specific amino acid residues in the sequence of LAIR1 Ig domain (amino acid residues 25-121; SEQ ID NO: 535) that serve the ligand binding functions (underlined residues are beta-strands).
Figure 2:
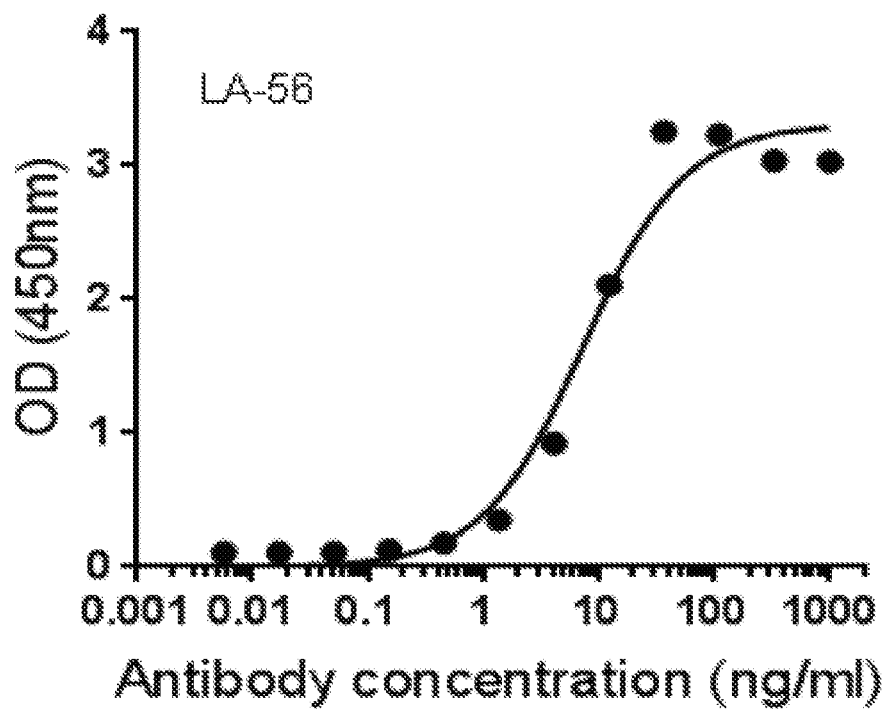
FIG. 2 shows the binding of mAb LA-56 to ECD of LAIR1 in ELISA.
Figure 3:
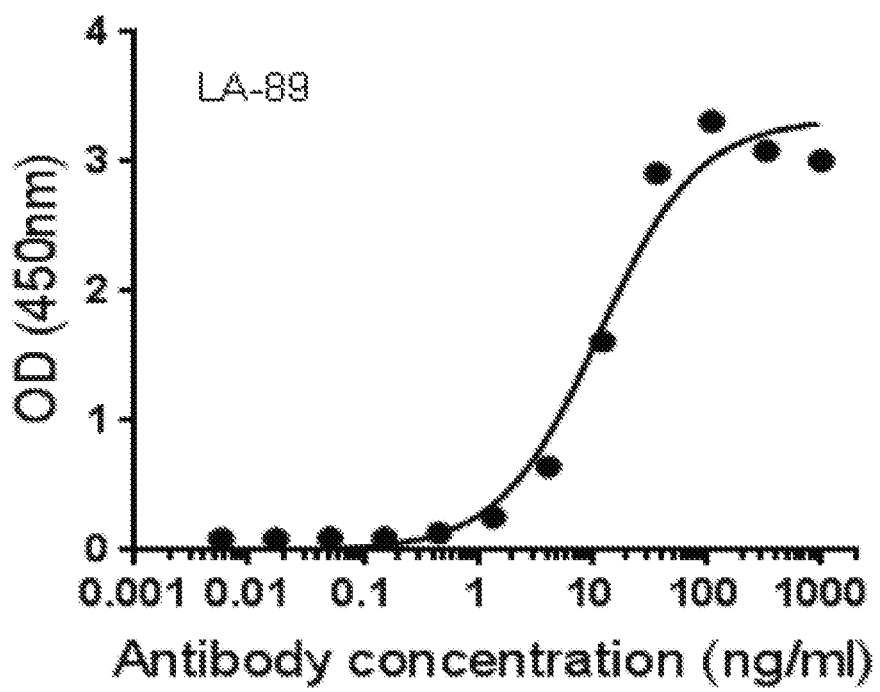
FIG. 3 shows the binding of mAb LA-89 to ECD of LAIR1 in ELISA.
Figure 4:
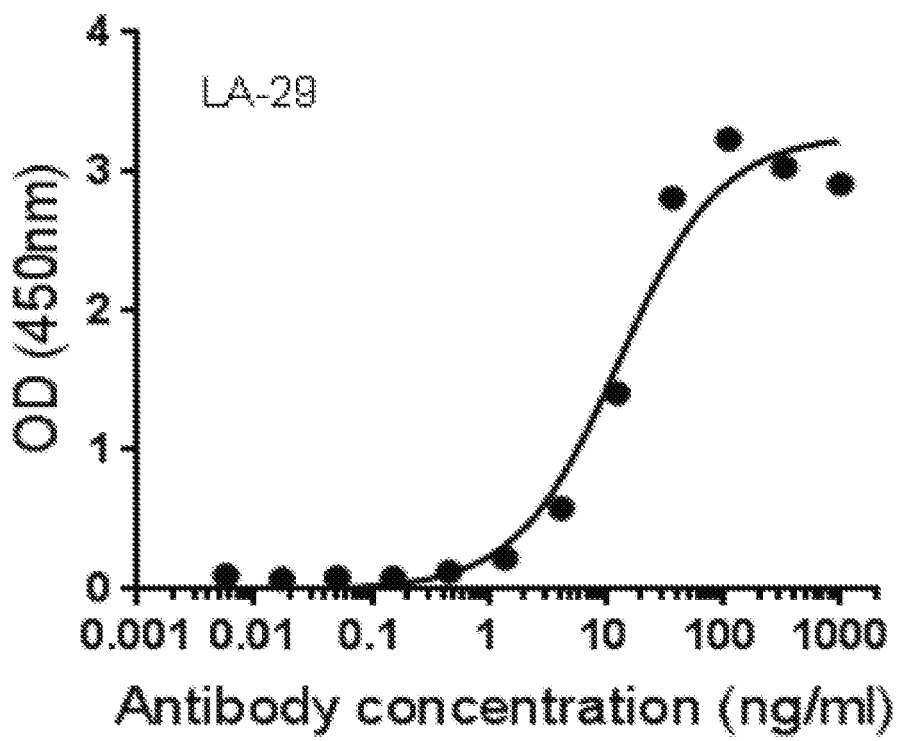
FIG. 4 shows the binding of mAb LA-29 to ECD of LAIR1 in ELISA.
Figure 5:
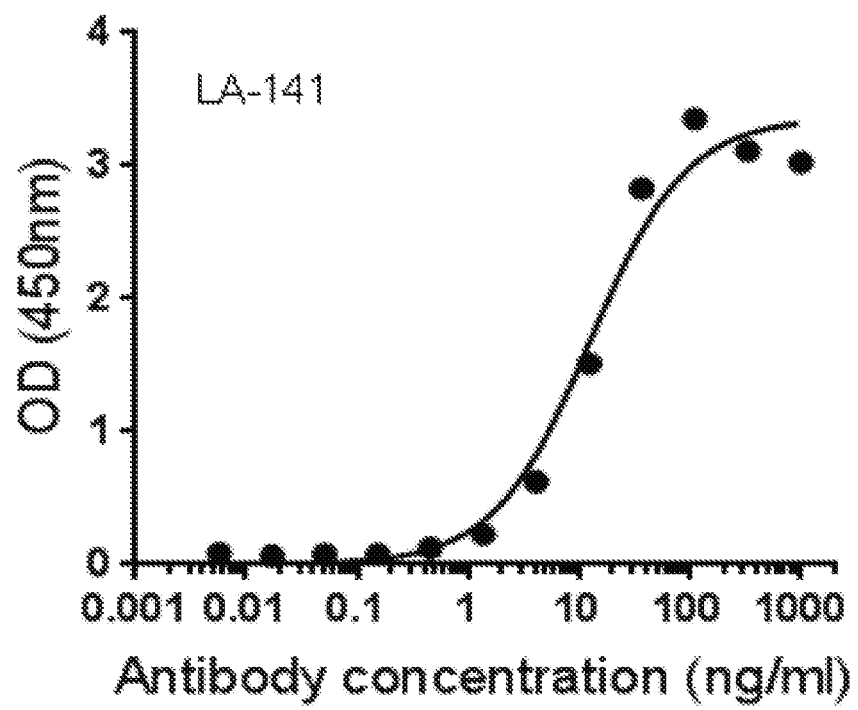
FIG. 5. shows the binding of mAb LA-141 to ECD of LAIR1 in ELISA.
Figure 6:
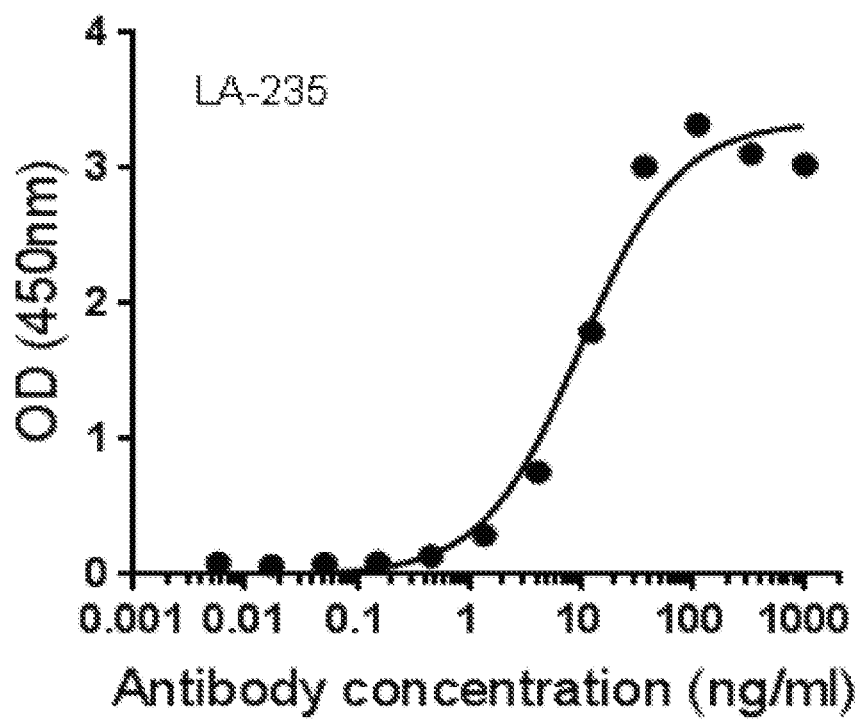
FIG. 6 shows the binding of mAb LA-235 to ECD of LAIR1 in ELISA.
Figure 7:
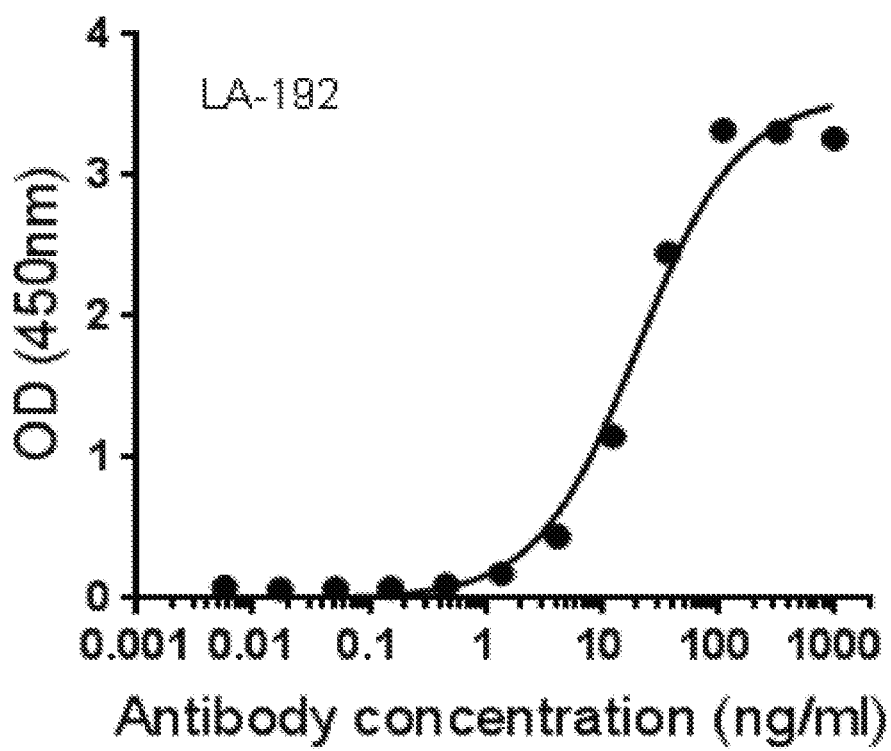
FIG. 7 shows the binding of mAb LA-192 to ECD of LAIR1 in ELISA.
Figure 8:
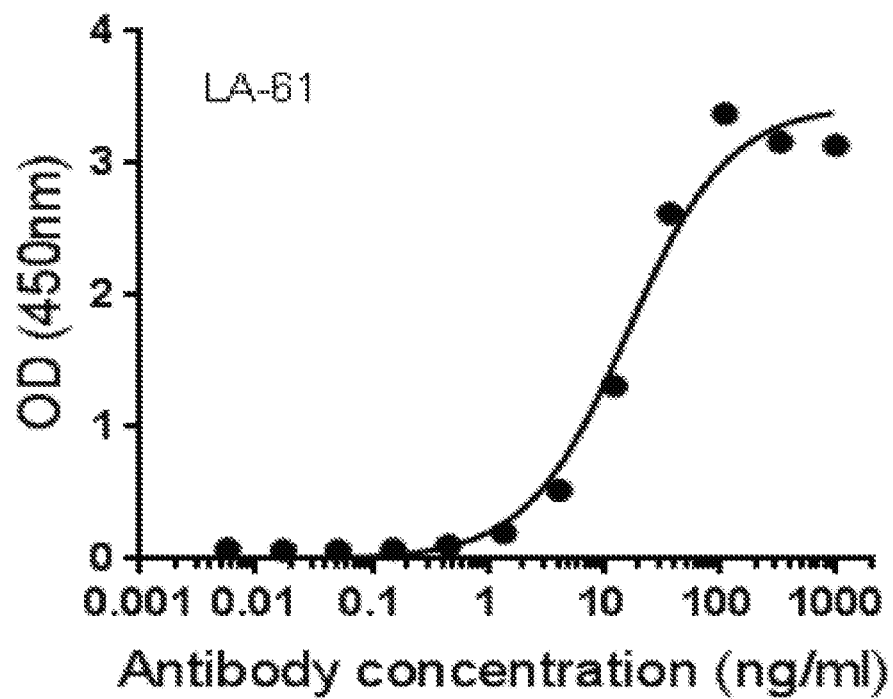
FIG. 8 shows the binding of mAb LA-61 to ECD of LAIR1 in ELISA.
Figure 9:
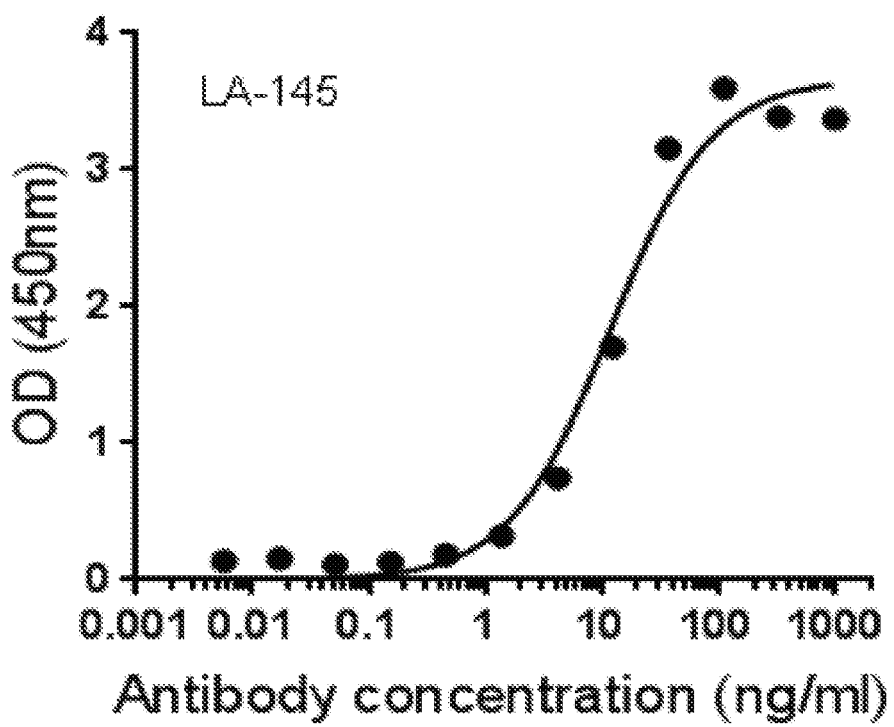
FIG. 9 shows the binding of mAb LA-145 to ECD of LAIR1 in ELISA.
Figure 10:
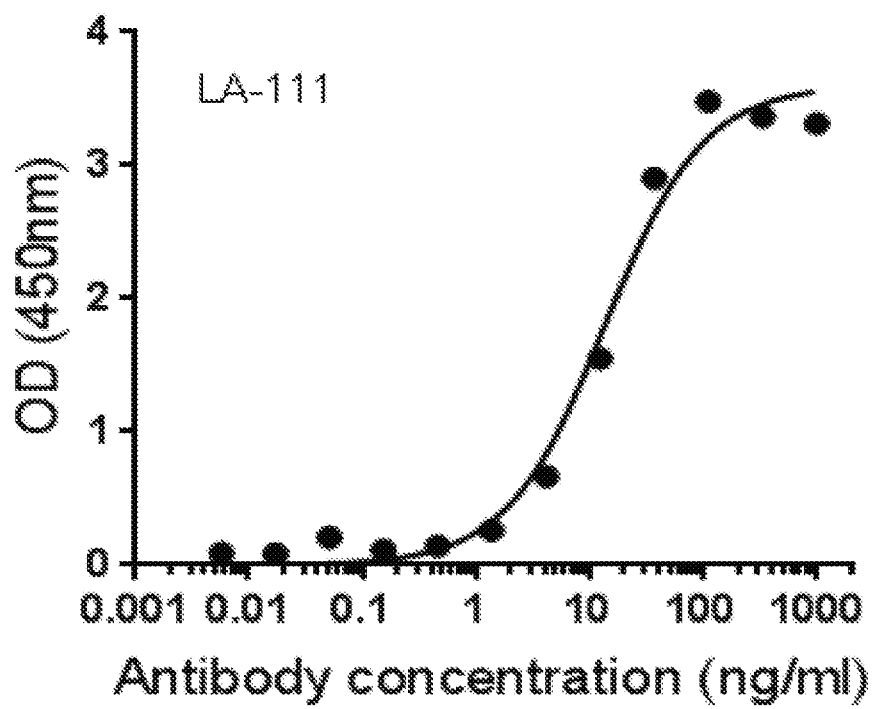
FIG. 10 shows the binding of mAb LA-111 to ECD of LAIR1 in ELISA.
Figure 11:
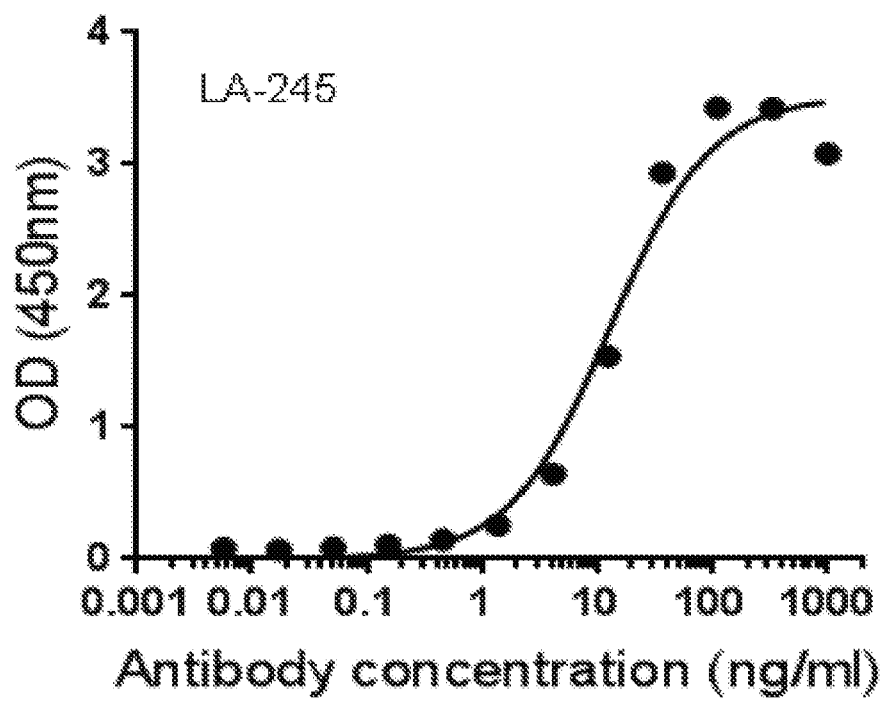
FIG. 11 shows the binding of mAb LA-245 to ECD of LAIR1 in ELISA.
Figure 12:
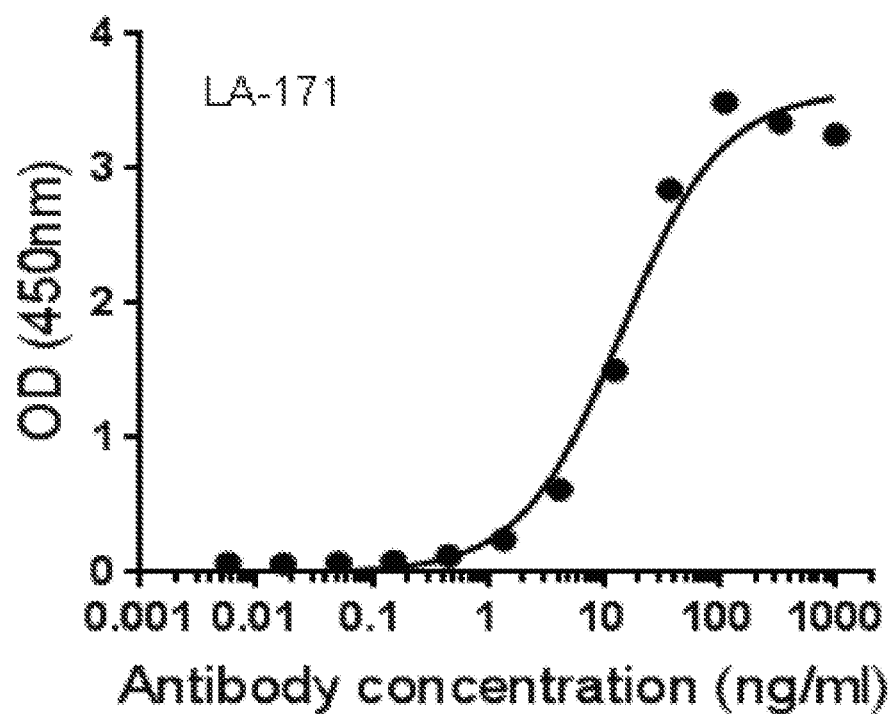
FIG. 12 shows the binding of mAb LA-171 to ECD of LAIR1 in ELISA.
Figure 13:
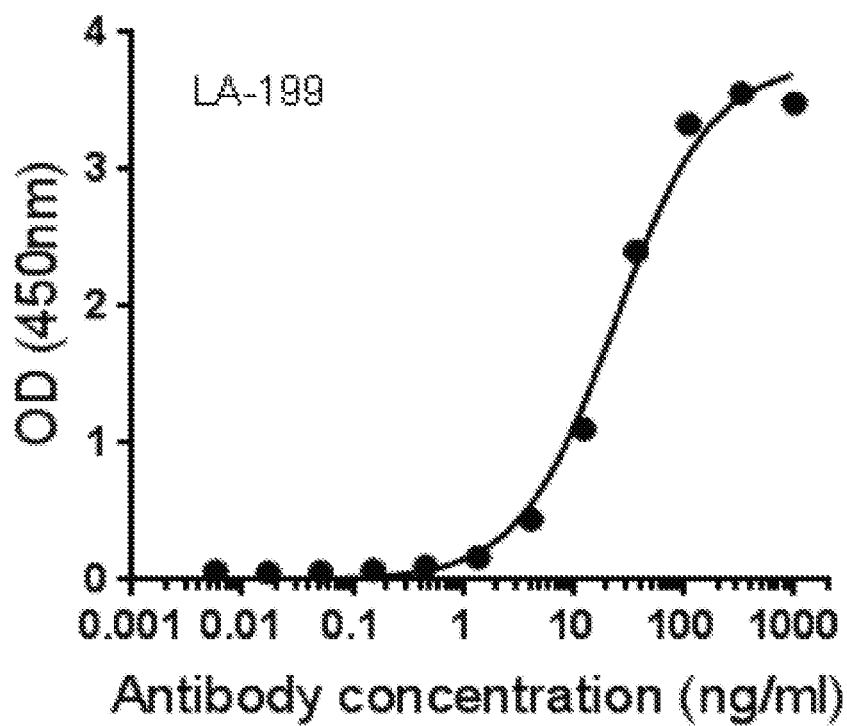
FIG. 13 shows the binding of mAb LA-199 to ECD of LAIR1 in ELISA.
Figure 14:
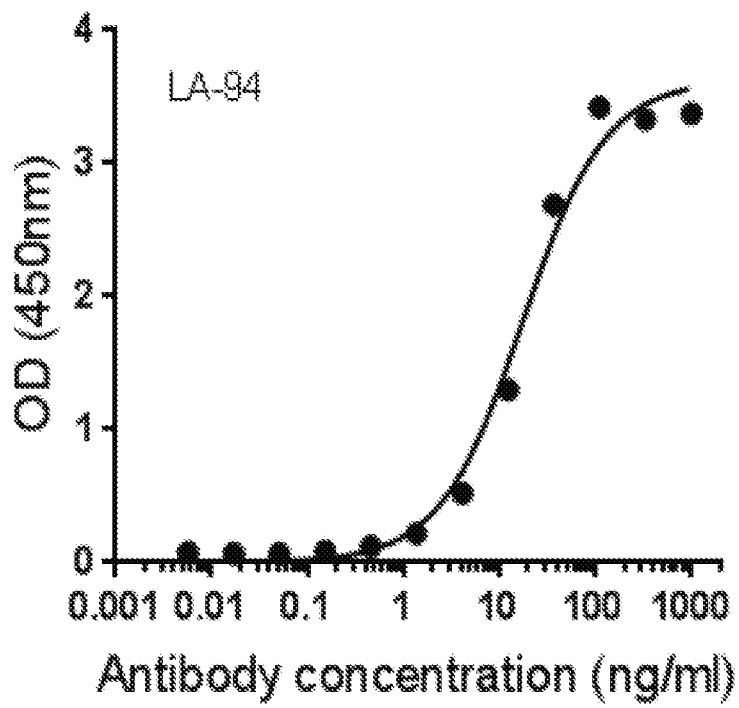
FIG. 14 shows the binding of mAb LA-94 to ECD of LAIR1 in ELISA.
Figure 15:
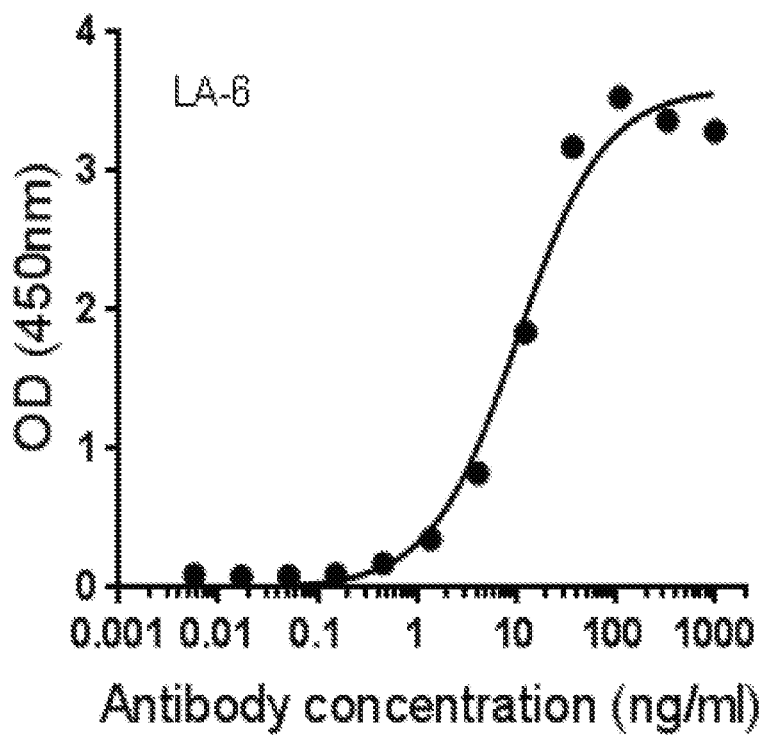
FIG. 15 shows the binding of mAb LA-6 to ECD of LAIR1 in ELISA.
Figure 16:
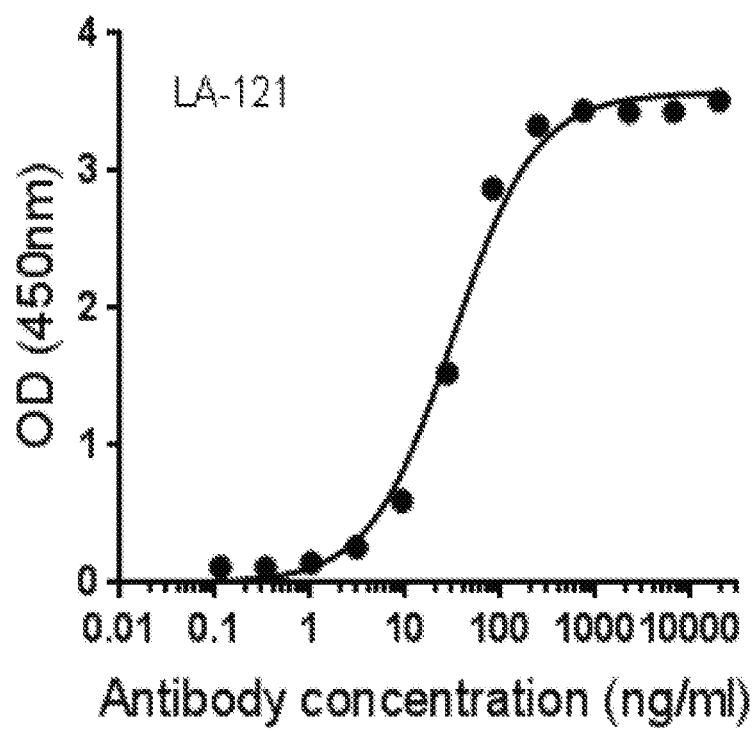
FIG. 16 shows the binding of mAb LA-121 to ECD of LAIR1 in ELISA.
Figure 17:
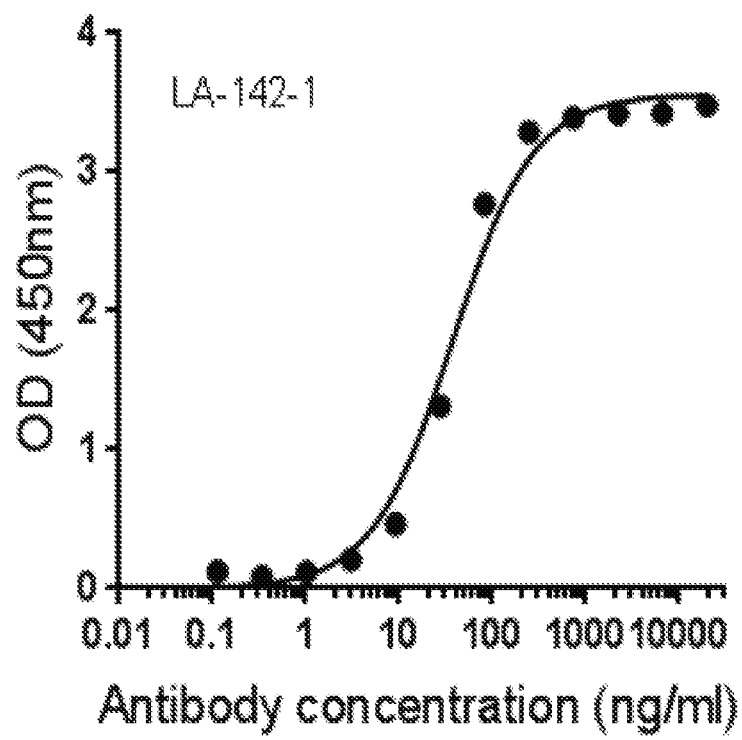
FIG. 17 shows the binding of mAb LA-142-1 to ECD of LAIR1 in ELISA.
Figure 18:
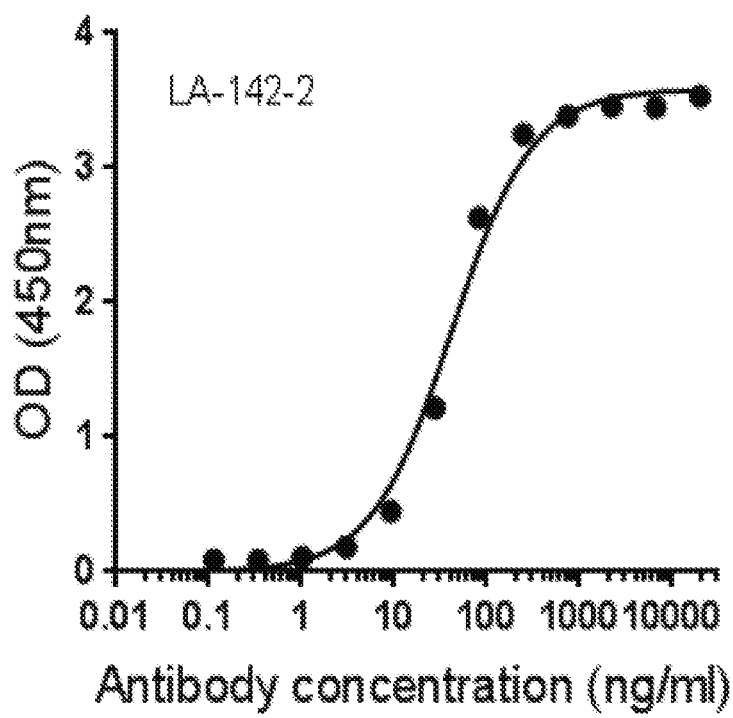
FIG. 18 shows the binding of mAb LA-142-2 to ECD of LAIR1 in ELISA.
Figure 19:
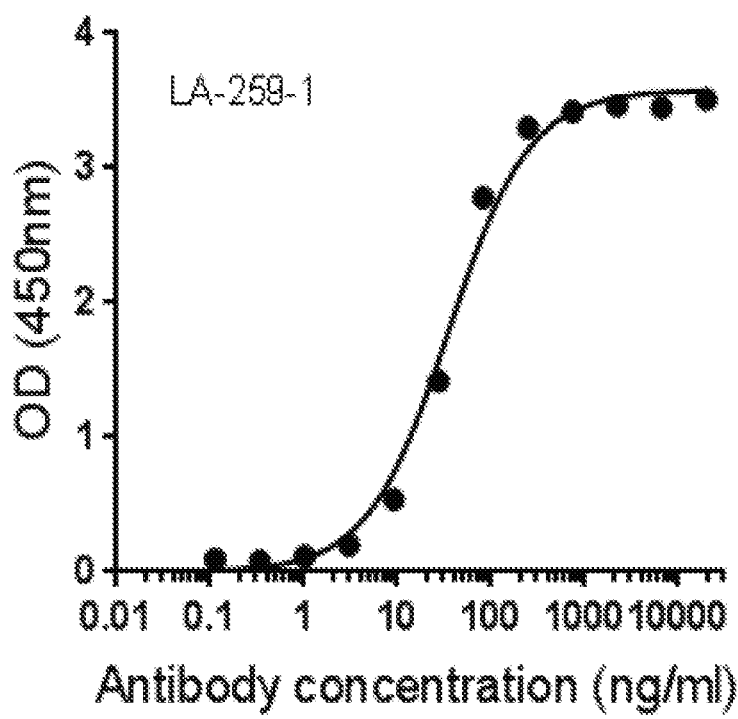
FIG. 19 shows the binding of mAb LA-259-1 to ECD of LAIR1 in ELISA.
Figure 20:
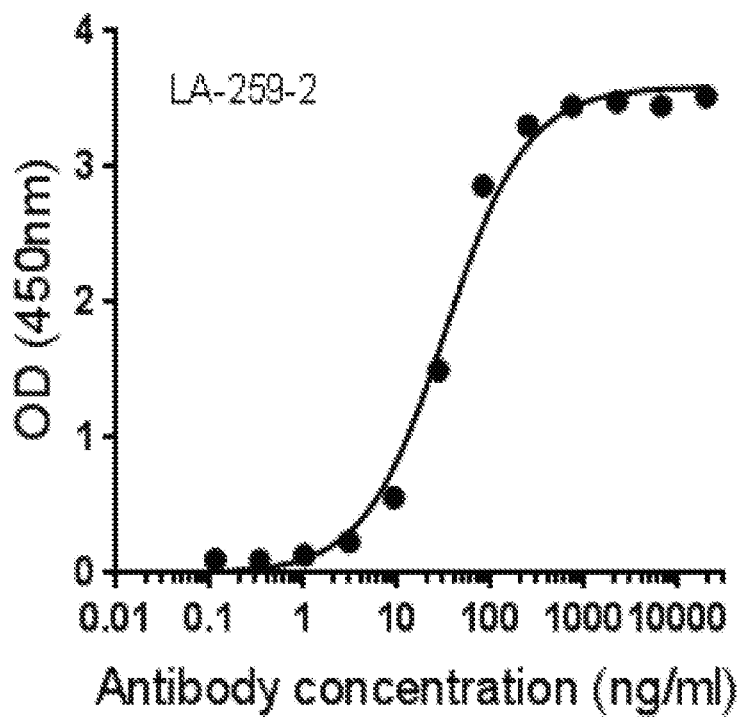
FIG. 20 shows the binding of mAb LA-259-2 to ECD of LAIR1 in ELISA.
Figure 21:
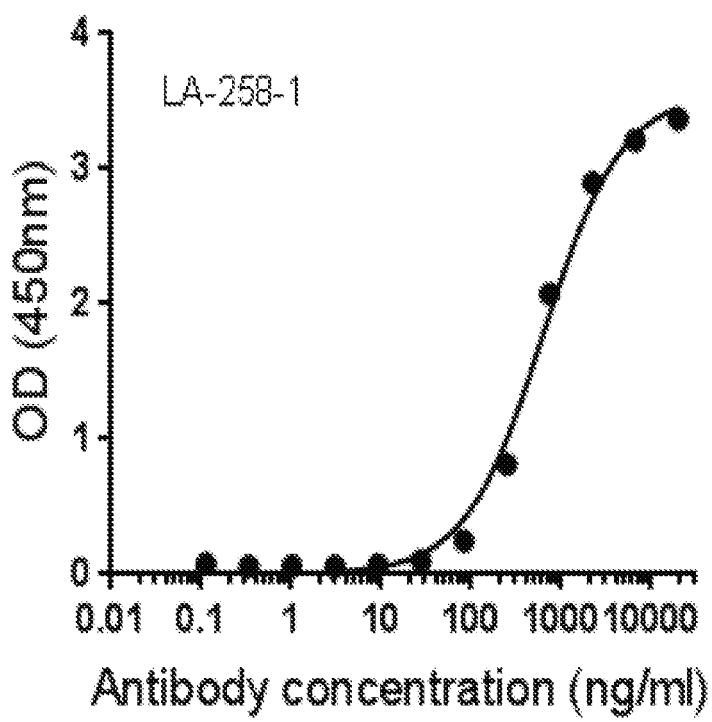
FIG. 21 shows the binding of mAb LA-258-1 to ECD of LAIR1 in ELISA.
Figure 22:
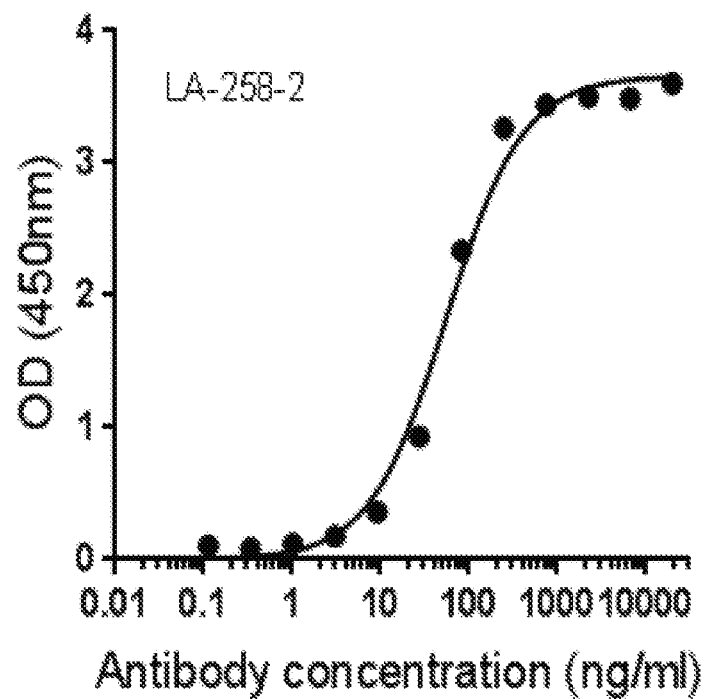
FIG. 22 shows the binding of mAb LA-258-2 to ECD of LAIR1 in ELISA.
Figure 23:
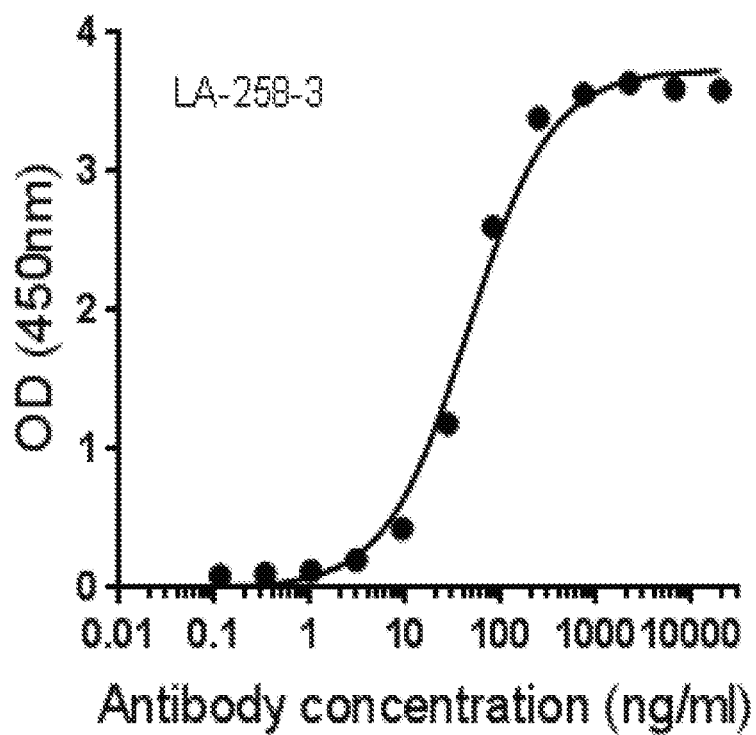
FIG. 23 shows the binding of mAb LA-258-3 to ECD of LAIR1 in ELISA.
Figure 24:
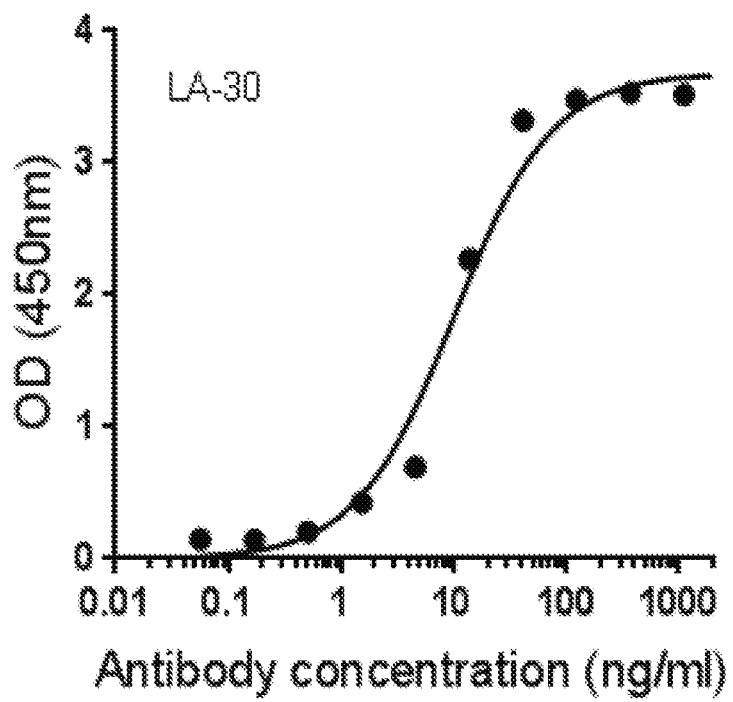
FIG. 24 shows the binding of mAb LA-30 to ECD of LAIR1 in ELISA.
Figure 25:
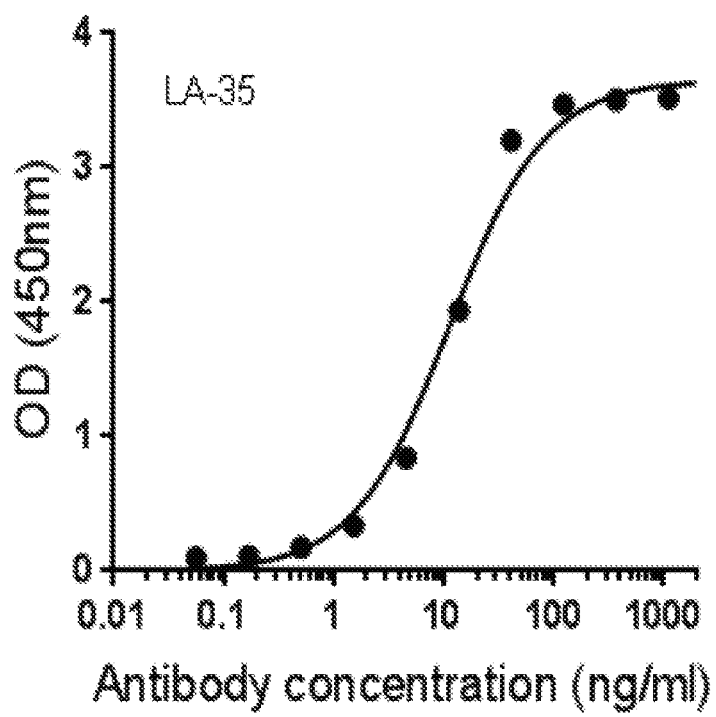
FIG. 25 shows the binding of mAb LA-35 to ECD of LAIR1 in ELISA.
Figure 26:
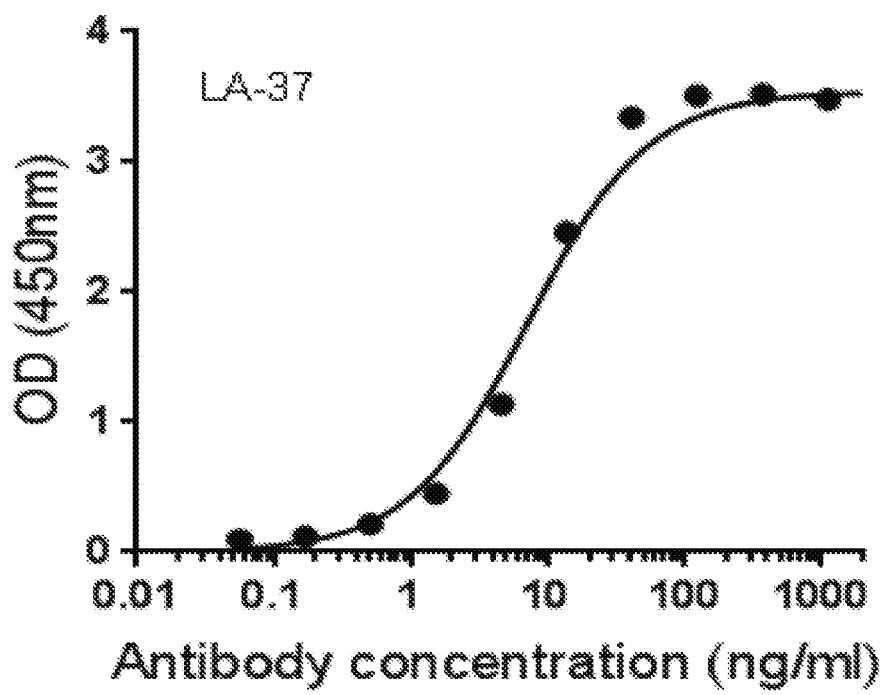
FIG. 26 shows the binding of mAb LA-37 to ECD of LAIR1 in ELISA.
Figure 27:
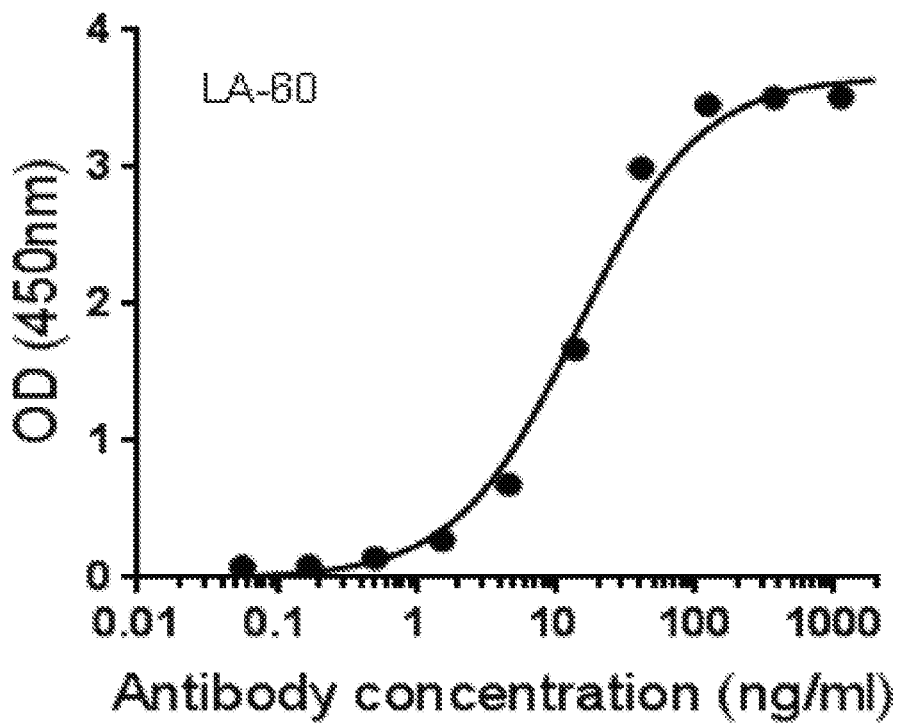
FIG. 27 shows the binding of mAb LA-60 to ECD of LAIR1 in ELISA.
Figure 28:
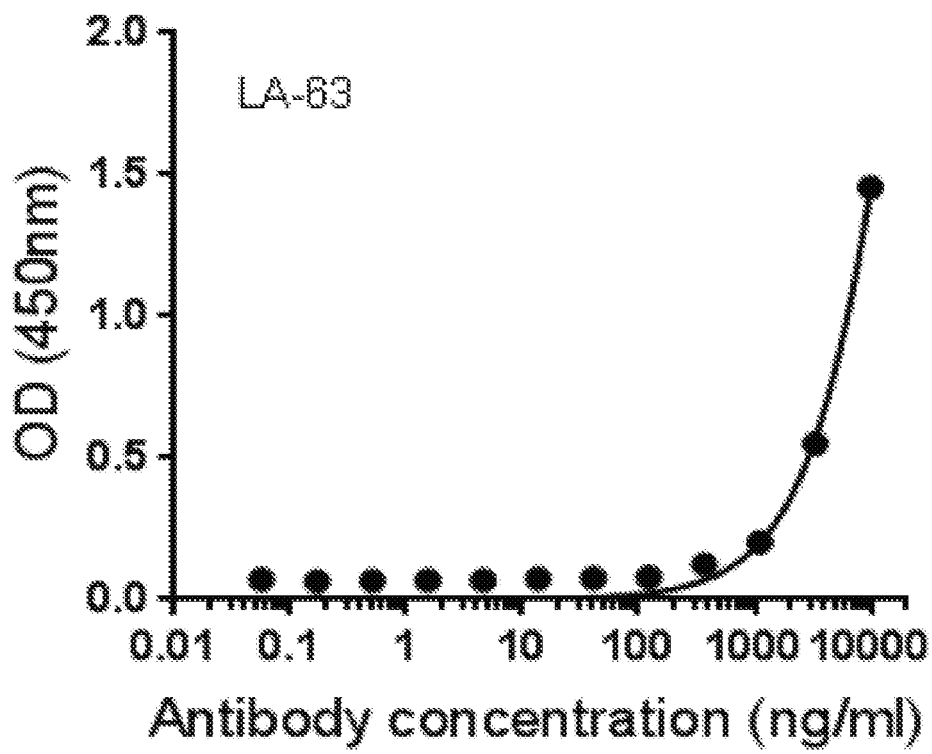
FIG. 28 shows the binding of mAb LA-63 to ECD of LAIR1 in ELISA.
Figure 29:
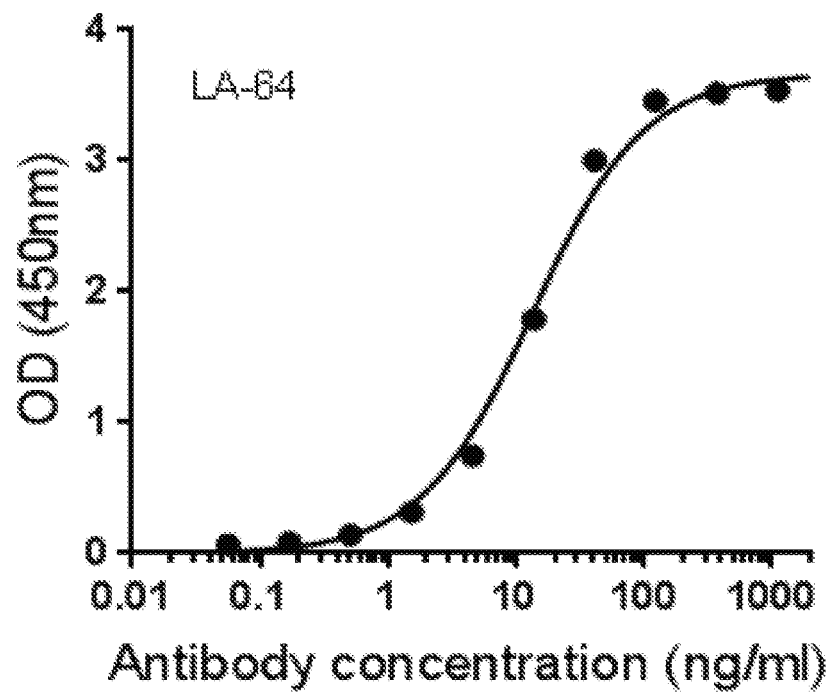
FIG. 29 shows the binding of mAb LA-64 to ECD of LAIR1 in ELISA.
Figure 30:
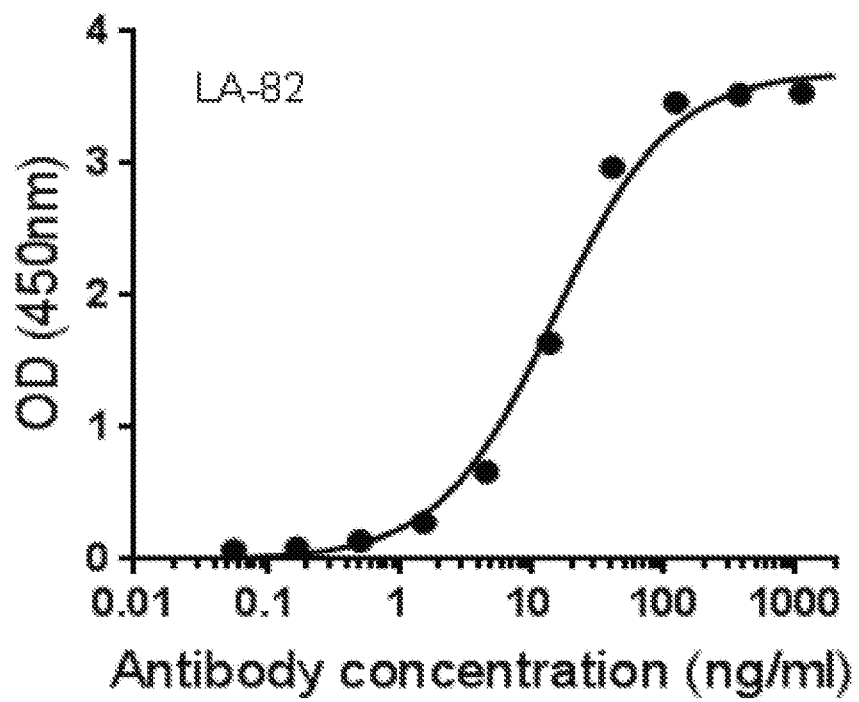
FIG. 30 shows the binding of mAb LA-82 to ECD of LAIR1 in ELISA.
Figure 31:
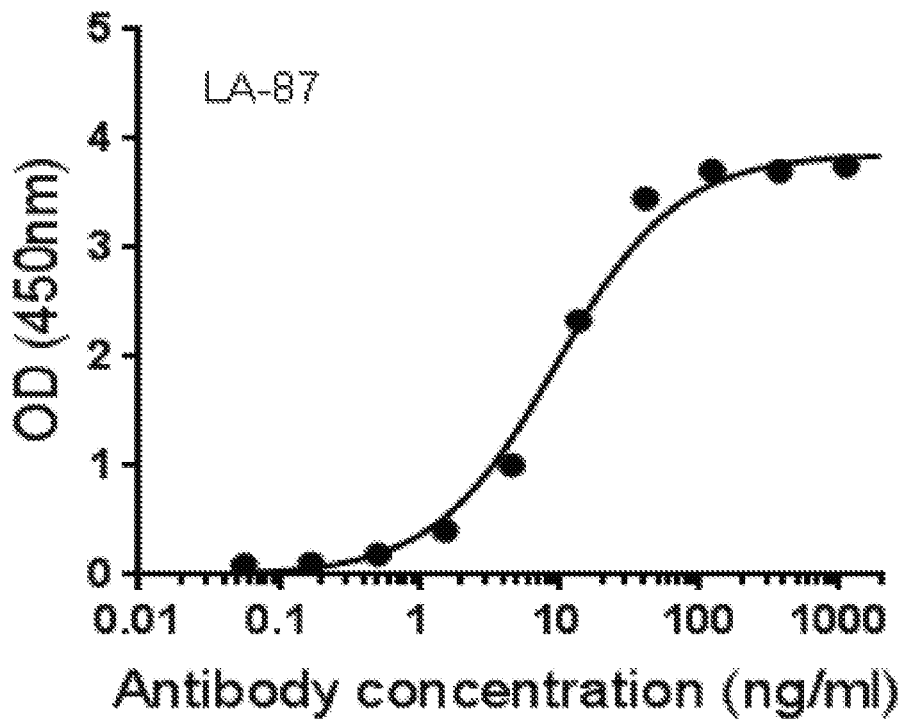
FIG. 31 shows the binding of mAb LA-87 to ECD of LAIR1 in ELISA.
Figure 32:
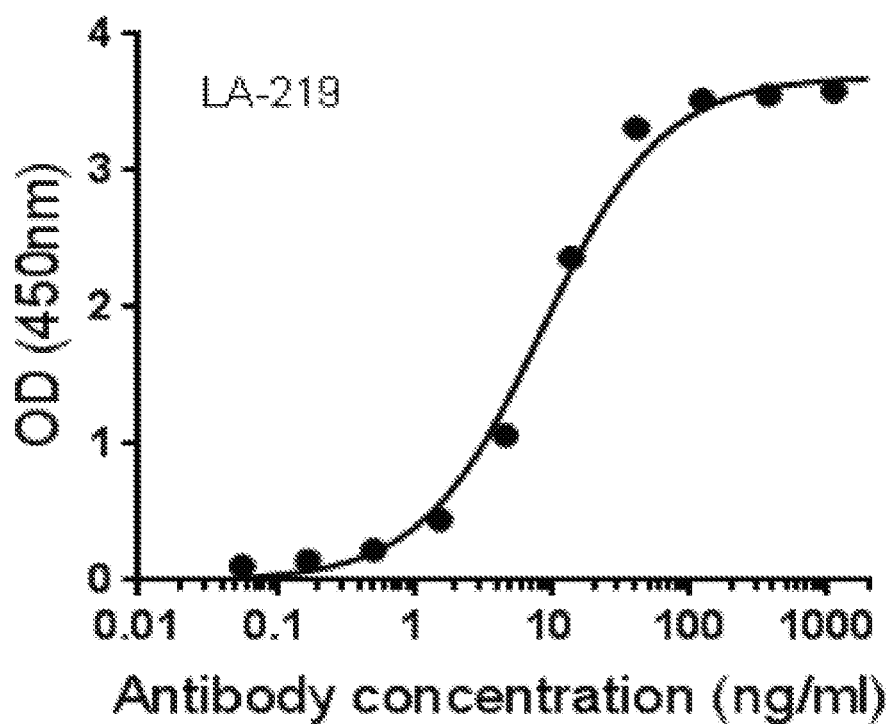
FIG. 32 shows the binding of mAb LA-219 to ECD of LAIR1 in ELISA.
Figure 33:
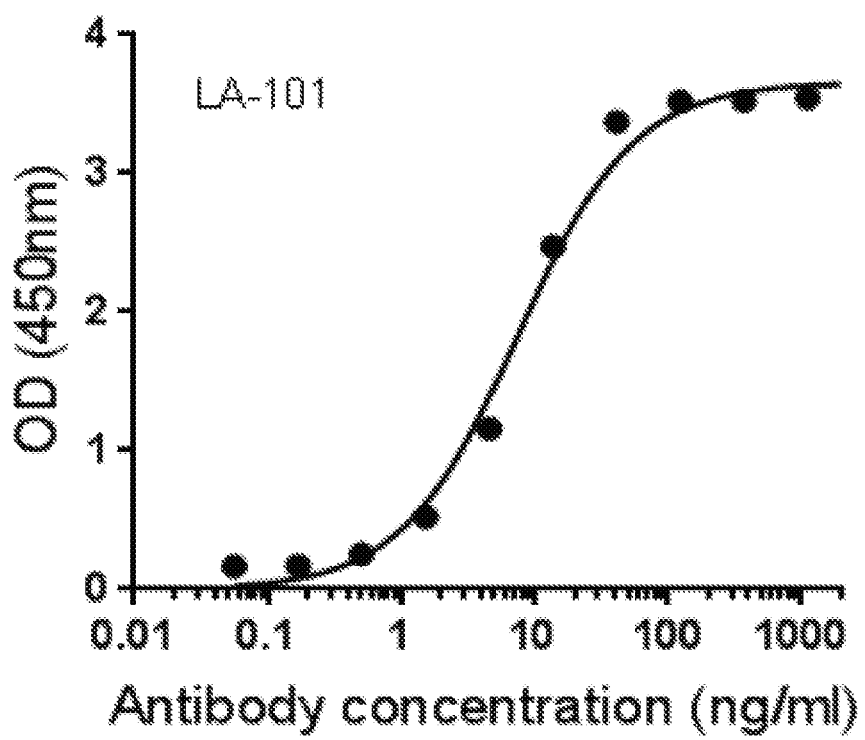
FIG. 33 shows the binding of mAb LA-101 to ECD of LAIR1 in ELISA.
Figure 34:
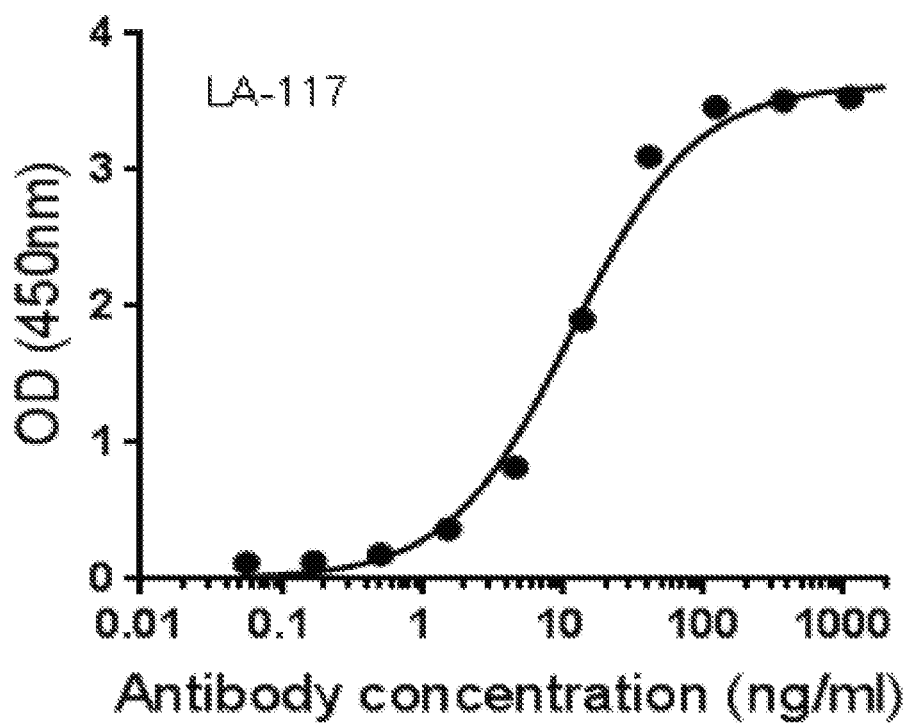
FIG. 34 shows the binding of mAb LA-117 to ECD of LAIR1 in ELISA.
Figure 35:
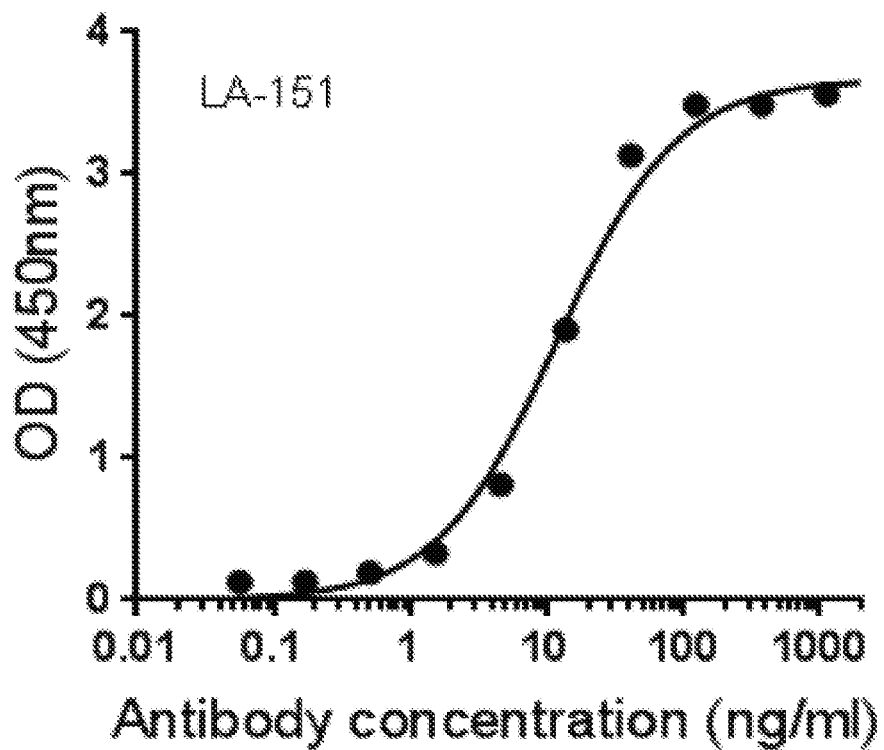
FIG. 35 shows the binding of mAb LA-151 to ECD of LAIR1 in ELISA.
Figure 36:
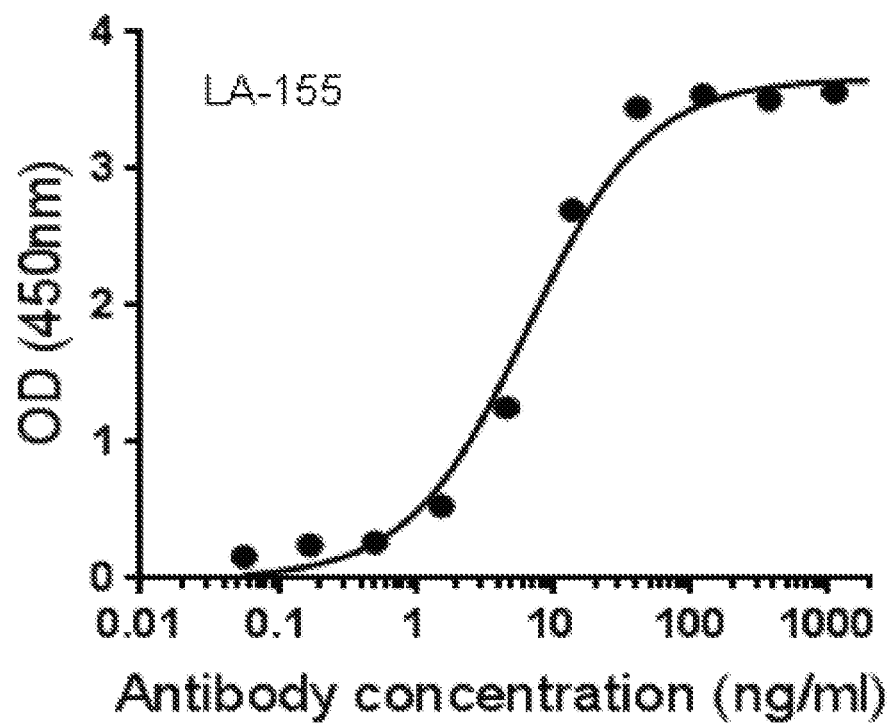
FIG. 36 shows the binding of mAb LA-155 to ECD of LAIR1 in ELISA.
Figure 37:
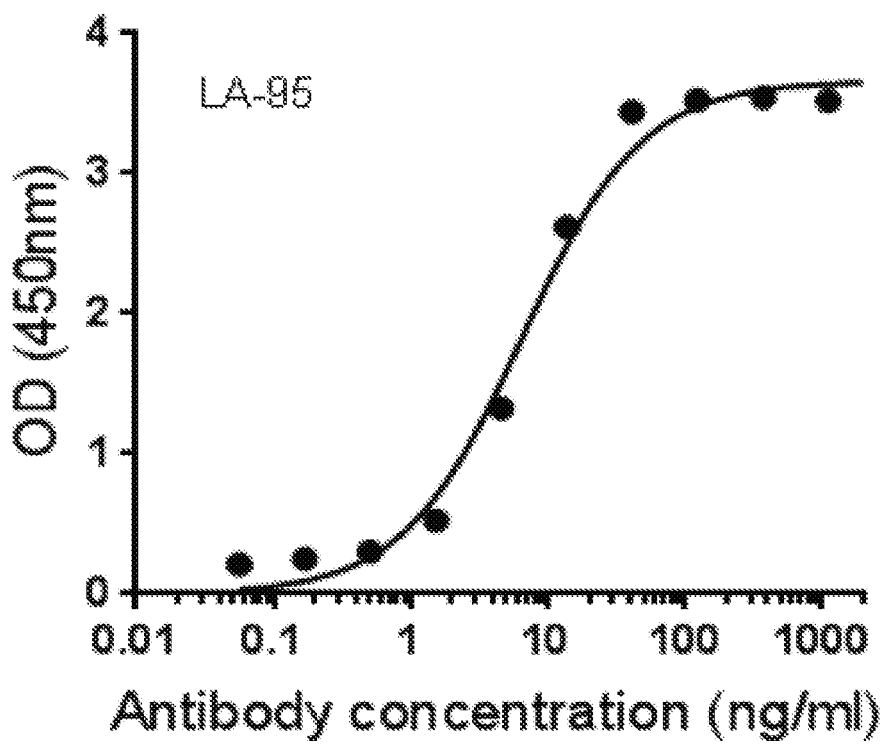
FIG. 37 shows the binding of mAb LA-95 to ECD of LAIR1 in ELISA.
Figure 38:
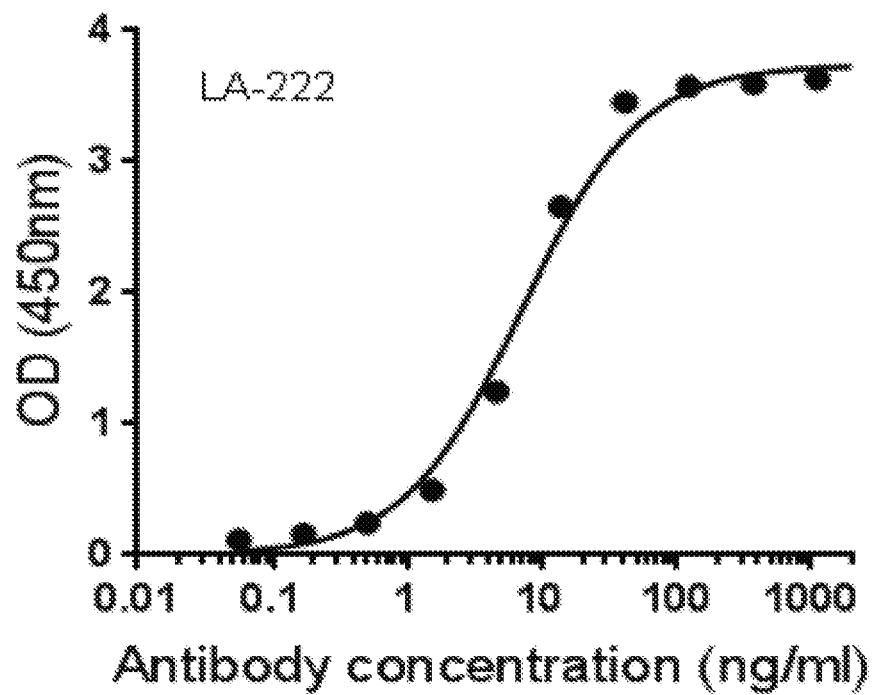
FIG. 38 shows the binding of mAb LA-222 to ECD of LAIR1 in ELISA.
Figure 39:
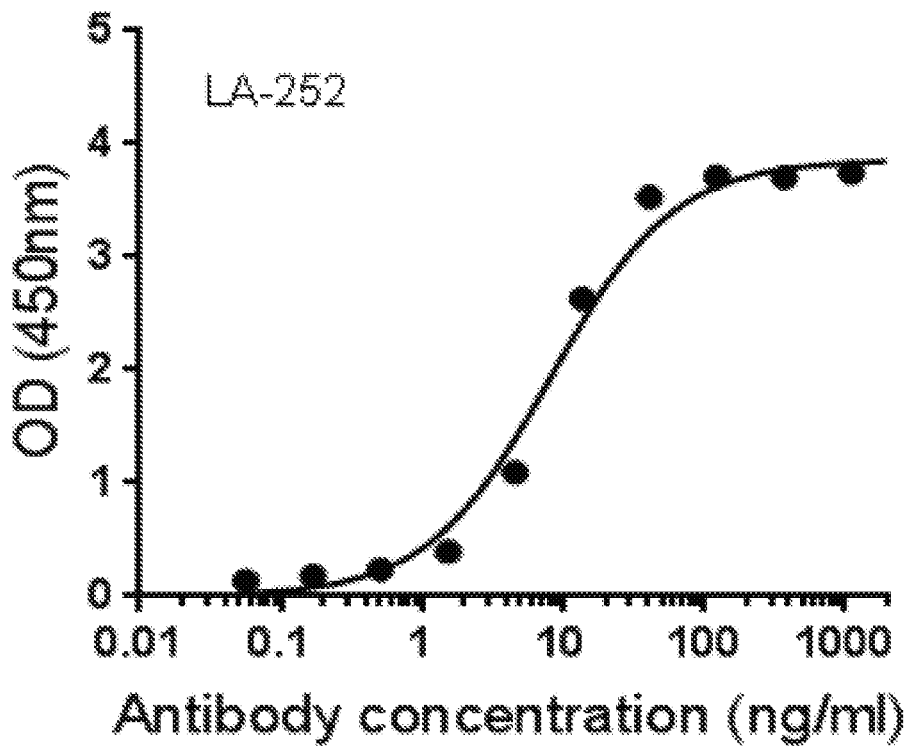
FIG. 39 shows the binding of mAb LA-252 to ECD of LAIR1 in ELISA.

The following description of the disclosure is merely intended to illustrate various embodiments of the disclosure. As such, the specific modifications discussed are not to be construed as limitations on the scope of the disclosure. It will be apparent to one skilled in the art that various equivalents, changes, and modifications may be made without departing from the scope of the disclosure, and it is understood that such equivalent embodiments are to be included herein. All references cited herein, including pub-

Definition

It is to be understood that both the foregoing general description and the following detailed description are exemplary and explanatory only and are not restrictive of the invention as claimed. In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise. Also, the use of the term "portion" can include part of a moiety or the entire moiety.

The term "about" as used herein when referring to a measurable value such as an amount, a temporal duration, and the like, is meant to encompass variations of up to ±10% from the specified value. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the disclosed subject matter. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

The term "antibody" refers to an intact immunoglobulin of any isotype, or a fragment thereof that can compete with the intact antibody for specific binding to the target antigen, and includes, for instance, chimeric, humanized, fully human, and bispecific antibodies. An "antibody" is a species of an antigen binding protein. An intact antibody will generally comprise at least two full-length heavy chains and two full-length light chains, but in some instances can include fewer chains such as antibodies naturally occurring in camelids which can comprise only heavy chains. Antibodies can be derived solely from a single source, or can be "chimeric," that is, different portions of the antibody can be derived from two different antibodies as described further below. The antigen binding proteins, antibodies, or binding fragments can be produced in hybridomas, by recombinant DNA techniques, or by enzymatic or chemical cleavage of intact antibodies. Unless otherwise indicated, the term "antibody" includes, in addition to antibodies comprising two full-length heavy chains and two full-length light chains, derivatives, variants, fragments, and muteins thereof, examples of which are described below. Furthermore, unless explicitly excluded, antibodies include monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), and fragments thereof, respectively. In some embodiments, the term also encompasses peptibodies.

Naturally occurring antibody structural units typically comprise a tetramer. Each such tetramer typically is composed of two identical pairs of polypeptide chains, each pair having one full-length "light" (in certain embodiments, about 25 kDa) and one full-length "heavy" chain (in certain embodiments, about 50-70 kDa). The amino-terminal portion of each chain typically includes a variable region of about 100 to 110 or more amino acids that typically is responsible for antigen recognition. The carboxy-terminal portion of each chain typically defines a constant region that can be responsible for effector function. Human light chains are typically classified as kappa and lambda light chains. Heavy chains are typically classified as mu, delta, gamma, alpha, or epsilon, and define the antibody's isotype as IgM, IgD, IgG, IgA, and IgE, respectively. IgG has several subclasses, including, but not limited to, IgG1, IgG2, IgG3, and IgG4. IgM has subclasses including, but not limited to, IgM1 and IgM2. IgA is similarly subdivided into subclasses including, but not limited to, IgA1 and IgA2. Within full-length light and heavy chains, typically, the variable and constant regions are joined by a "J" region of about 12 or more amino acids, with the heavy chain also including a "D" region of about 10 more amino acids. See, e.g., Fundamental Immunology, Ch. 7 (Paul, W., ed., 2nd ed. Raven Press, N.Y. (1989)) (incorporated by reference in its entirety for all purposes). The variable regions of each light/heavy chain pair typically form the antigen binding site.

The term "variable region" or "variable domain" refers to a portion of the light and/or heavy chains of an antibody, typically including approximately the amino-terminal 120 to 130 amino acids in the heavy chain and about 100 to 110 amino terminal amino acids in the light chain. In certain embodiments, variable regions of different antibodies differ extensively in amino acid sequence even among antibodies of the same species. The variable region of an antibody typically determines specificity of a particular antibody for its target.

The variable regions typically exhibit the same general structure of relatively conserved framework regions (FR) joined by three hyper variable regions, also called complementarity determining regions or CDRs. The CDRs from the two chains of each pair typically are aligned by the framework regions, which can enable binding to a specific epitope. From N-terminal to C-terminal, both light and heavy chain variable regions typically comprise the domains FR1, CDR1, FR2, CDR2, FR3, CDR3 and FR4. The assignment of amino acids to each domain is typically in accordance with the definitions of Kabat Sequences of Proteins of Immunological Interest (National Institutes of Health, Bethesda, Md. (1987 and 1991)), Chothia & Lesk, J. Mol. Biol., 196:901-917 (1987) or Chothia et al., Nature, 342: 878-883 (1989).

In certain embodiments, an antibody heavy chain binds to an antigen in the absence of an antibody light chain. In certain embodiments, an antibody light chain binds to an antigen in the absence of an antibody heavy chain. In certain embodiments, an antibody binding region binds to an antigen in the absence of an antibody light chain. In certain embodiments, an antibody binding region binds to an antigen in the absence of an antibody heavy chain. In certain embodiments, an individual variable region specifically binds to an antigen in the absence of other variable regions.

In certain embodiments, definitive delineation of a CDR and identification of residues comprising the binding site of an antibody is accomplished by solving the structure of the antibody and/or solving the structure of the antibody-ligand complex. In certain embodiments, that can be accomplished by any of a variety of techniques known to those skilled in the art, such as X-ray crystallography. In certain embodiments, various methods of analysis can be employed to identify or approximate the CDR regions. Examples of such methods include, but are not limited to, the Kabat definition, the Chothia definition, the AbM definition and the contact definition.

The Kabat definition is a standard for numbering the residues in an antibody and is typically used to identify CDR regions. See, e.g., Johnson & Wu, Nucleic Acids Res., 28: 214-8 (2000). The Chothia definition is similar to the Kabat definition, but the Chothia definition takes into account positions of certain structural loop regions. See, e.g., Chothia et al., J. Mol. Biol., 196: 901-17 (1986); Chothia et al., Nature, 342: 877-83 (1989). The AbM definition uses an integrated suite of computer programs produced by Oxford Molecular Group that model antibody structure. See, e.g., Martin et al., Proc Natl Acad Sci (USA), 86:9268-9272 (1989); "AbM™, A Computer Program for Modeling Variable Regions of Antibodies," Oxford, UK; Oxford Molecular, Ltd. The AbM definition models the tertiary structure of an antibody from primary sequence using a combination of knowledge databases and ab initio methods, such as those described by Samudrala et al., "Ab Initio Protein Structure Prediction Using a Combined Hierarchical Approach," in PROTEINS, Structure, Function and Genetics Suppl., 3:194-198 (1999). The contact definition is based on an analysis of the available complex crystal structures. See, e.g., MacCallum et al., J. Mol. Biol., 5:732-45 (1996).

By convention, the CDR regions in the heavy chain are typically referred to as H1, H2, and H3 and are numbered sequentially in the direction from the amino terminus to the carboxy terminus. The CDR regions in the light chain are typically referred to as L1, L2, and L3 and are numbered sequentially in the direction from the amino terminus to the carboxy terminus.

The term "light chain" includes a full-length light chain and fragments thereof having sufficient variable region sequence to confer binding specificity. A full-length light chain includes a variable region domain, VL, and a constant region domain, CL. The variable region domain of the light chain is at the amino-terminus of the polypeptide. Light chains include kappa chains and lambda chains.

The term "heavy chain" includes a full-length heavy chain and fragments thereof having sufficient variable region sequence to confer binding specificity. A full-length heavy chain includes a variable region domain, VH, and three constant region domains, CH1, CH2, and CH3. The VH domain is at the amino-terminus of the polypeptide, and the CH domains are at the carboxyl-terminus, with the CH3 being closest to the carboxy-terminus of the polypeptide. Heavy chains can be of any isotype, including IgG (including IgG1, IgG2, IgG3 and IgG4 subtypes), IgA (including IgA1 and IgA2 subtypes), IgM and IgE.

A bispecific or bifunctional antibody typically is an artificial hybrid antibody having two different heavy/light chain pairs and two different binding sites. Bispecific antibodies can be produced by a variety of methods including, but not limited to, fusion of hybridomas or linking of Fab' fragments. See, e.g., Songsivilai et al., Clin. Exp. Immunol., 79: 315-321 (1990); Kostelny et al., J. Immunol., 148:1547-1553 (1992).

The term "antigen" refers to a substance capable of inducing adaptive immune responses. Specifically, an antigen is a substance which serves as a target for the receptors of an adaptive immune response. Typically, an antigen is a molecule that binds to antigen-specific receptors but cannot induce an immune response in the body by itself. Antigens are usually proteins and polysaccharides, less frequently also lipids. Suitable antigens include without limitation parts of bacteria (coats, capsules, cell walls, flagella, fimbrai, and toxins), viruses, and other microorganisms. Antigens also include tumor antigens, e.g., antigens generated by mutations in tumors. As used herein, antigens also include immunogens and haptens.

The term "antigen-binding fragment" as used herein refers to a portion of a protein which is capable of binding specifically to an antigen. In certain embodiment, the antigen-binding fragment is derived from an antibody comprising one or more CDRs, or any other antibody fragment that binds to an antigen but does not comprise an intact native antibody structure. Examples of antigen-binding fragment include, without limitation, a diabody, a Fab, a Fab', a F(ab')$_2$, an Fv fragment, a disulfide stabilized Fv fragment (dsFv), a (dsFv)2, a bispecific dsFv (dsFv-dsFv'), a disulfide stabilized diabody (ds diabody), a single-chain antibody molecule (scFv), an scFv dimer (bivalent diabody), a multispecific antibody, a single domain antibody (sdAb), a camelid antibody or a nanobody, a domain antibody, and a bivalent domain antibody. In certain embodiments, an antigen-binding fragment is capable of binding to the same antigen to which the parent antibody binds. In certain embodiments, an antigen-binding fragment may comprise one or more CDRs from a particular human antibody grafted to a framework region from one or more different human antibodies.

A "Fab fragment" comprises one light chain and the CH1 and variable regions of one heavy chain. The heavy chain of a Fab molecule cannot form a disulfide bond with another heavy chain molecule.

A "Fab' fragment" comprises one light chain and a portion of one heavy chain that contains the VH domain and the CH1 domain and also the region between the CH1 and CH2 domains, such that an interchain disulfide bond can be formed between the two heavy chains of two Fab' fragments to form an F(ab')$_2$ molecule.

A "F(ab')$_2$ fragment" contains two light chains and two heavy chains that contain the VH and CH1 domains and also a portion of the constant region between the CH1 and CH2 domains, such that an interchain disulfide bond is formed between the two heavy chains. A F(ab')$_2$ fragment thus is composed of two Fab' fragments that are held together by a disulfide bond between the two heavy chains.

An "Fc" region comprises two heavy chain fragments comprising the CH1 and CH2 domains of an antibody. The two heavy chain fragments are held together by two or more disulfide bonds and by hydrophobic interactions of the CH3 domains.

The "Fv region" comprises the variable regions from both the heavy and light chains, but lacks the constant regions.

"Single-chain antibodies" are Fv molecules in which the heavy and light chain variable regions have been connected by a flexible linker to form a single polypeptide chain, which forms an antigen binding region. Single chain antibodies are discussed in detail in International Patent Application Publication No. WO 88/01649 and U.S. Pat. Nos. 4,946,778 and 5,260,203, the disclosures of which are incorporated by reference.

A "domain antibody" is an immunologically functional immunoglobulin fragment containing only the variable region of a heavy chain or the variable region of a light chain. In some instances, two or more VH regions are covalently joined with a peptide linker to create a bivalent domain antibody. The two VH regions of a bivalent domain antibody can target the same or different antigens.

A "bivalent antigen binding protein" or "bivalent antibody" comprises two antigen binding sites. In some instances, the two binding sites have the same antigen specificities. Bivalent antigen binding proteins and bivalent antibodies can be bispecific, see, infra. A bivalent antibody other than a "multispecific" or "multifunctional" antibody, in certain embodiments, typically is understood to have each of its binding sites identical.

A "multispecific antigen binding protein" or "multispecific antibody" is one that targets more than one antigen or epitope.

A "bispecific," "dual-specific" or "bifunctional" antigen binding protein or antibody is a hybrid antigen binding protein or antibody, respectively, having two different antigen binding sites. Bispecific antigen binding proteins and antibodies are a species of multispecific antigen binding protein antibody and can be produced by a variety of methods including, but not limited to, fusion of hybridomas or linking of Fab' fragments. See, e.g., Songsivilai and Lachmann, 1990, Clin. Exp. Immunol. 79:315-321; Kostelny et al., 1992, J. Immunol. 148:1547-1553. The two binding sites of a bispecific antigen binding protein or antibody will bind to two different epitopes, which can reside on the same or different protein targets.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity that reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative and exemplary embodiments for measuring binding affinity are described in the following.

An antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope. For example, the LAIR' specific antibodies of the present invention are specific to LAIR1. In some embodiments, the antibody that binds to LAIR1 has a dissociation constant ($K_d$) of ≤100 nM, ≤10 nM, nM, ≤0.1 nM, ≤0.01 nM, or ≤0.001 nM (e.g. $10^{-8}$M or less, e.g. from $10^{-8}$M to $10^{-13}$M, e.g., from $10^{-9}$M to $10^{-13}$ M). $K_d$ as used herein refers to the ratio of the dissociation rate to the association rate ($k_{off}/k_{on}$), may be determined using surface plasmon resonance methods for example using instrument such as Biacore.

The term "compete" when used in the context of antigen binding proteins (e.g., antibody or antigen-binding fragment thereof) that compete for the same epitope means competition between antigen binding proteins as determined by an assay in which the antigen binding protein (e.g., antibody or antigen-binding fragment thereof) being tested prevents or inhibits (e.g., reduces) specific binding of a reference antigen binding protein (e.g., a ligand, or a reference antibody) to a common antigen (e.g., LAIR1 or a fragment thereof). Numerous types of competitive binding assays can be used to determine if one antigen binding protein competes with another, for example: solid phase direct or indirect radioimmunoassay (RIA), solid phase direct or indirect enzyme immunoassay (EIA), sandwich competition assay (see, e.g., Stahli et al., 1983, Methods in Enzymology 9:242-253); solid phase direct biotin-avidin EIA (see, e.g., Kirkland et al., 1986, J. Immunol. 137:3614-3619) solid phase direct labeled assay, solid phase direct labeled sandwich assay (see, e.g., Harlow and Lane, 1988, Antibodies, A Laboratory Manual, Cold Spring Harbor Press); solid phase direct label RIA using 1-125 label (see, e.g., Morel et al., 1988, Molec. Immunol. 25:7-15); solid phase direct biotin-avidin EIA (see, e.g., Cheung, et al., 1990, Virology 176:546-552); and direct labeled RIA (Moldenhauer et al., 1990, Scand. J. Immunol. 32:77-82). Typically, such an assay involves the use of purified antigen bound to a solid surface or cells bearing either of these, an unlabelled test antigen binding protein and a labeled reference antigen binding protein. Competitive inhibition is measured by determining the amount of label bound to the solid surface or cells in the presence of the test antigen binding protein. Usually the test antigen binding protein is present in excess. Antigen binding proteins identified by competition assay (competing antigen binding proteins) include antigen binding proteins binding to the same epitope as the reference antigen binding proteins and antigen binding proteins binding to an adjacent epitope sufficiently proximal to the epitope bound by the reference antigen binding protein for steric hindrance to occur. Additional details regarding methods for determining competitive binding are provided in the examples herein. Usually, when a competing antigen binding protein is present in excess, it will inhibit (e.g., reduce) specific binding of a reference antigen binding protein to a common antigen by at least 40-45%, 45-50%, 50-55%, 55-60%, 60-65%, 65-70%, 70-75% or 75% or more. In some instances, binding is inhibited by at least 80-85%, 85-90%, 90-95%, 95-97%, or 97% or more.

The term "epitope" as used herein refers to the specific group of atoms or amino acids on an antigen to which an antibody binds. The epitope can be either linear epitope or a conformational epitope. A linear epitope is formed by a continuous sequence of amino acids from the antigen and interacts with an antibody based on their primary structure. A conformational epitope, on the other hand, is composed of discontinuous sections of the antigen's amino acid sequence and interacts with the antibody based on the 3D structure of the antigen. In general, an epitope is approximately five or six amino acid in length. Two antibodies may bind the same epitope within an antigen if they exhibit competitive binding for the antigen.

The term "host cell" means a cell that has been transformed, or is capable of being transformed, with a nucleic acid sequence and thereby expresses a gene of interest. The term includes the progeny of the parent cell, whether or not the progeny is identical in morphology or in genetic make-up to the original parent cell, so long as the gene of interest is present.

The term "identity" refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) are preferably addressed by a particular mathematical model or computer program (i.e., an "algorithm"). Methods that can be used to calculate the identity of the aligned nucleic acids or polypeptides include those described in Computational Molecular Biology, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al., 1988, SIAM J. Applied Math. 48:1073.

In calculating percent identity, the sequences being compared are typically aligned in a way that gives the largest match between the sequences. One example of a computer program that can be used to determine percent identity is the GCG program package, which includes GAP (Devereux et al., 1984, Nucl. Acid Res. 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span", as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see, Dayhoff et al., 1978, Atlas of Protein Sequence and Structure 5:345-352 for the PAM 250 comparison matrix; Henikoff et al., 1992, Proc. Natl. Acad. Sci. U.S.A. 89:10915-10919 for the BLOSUM 62 comparison matrix) is also used by the algorithm.

Examples of parameters that can be employed in determining percent identity for polypeptides or nucleotide sequences using the GAP program can be found in Needleman et al., 1970, J. Mol. Biol. 48:443-453.

Certain alignment schemes for aligning two amino acid sequences may result in matching of only a short region of the two sequences, and this small aligned region may have very high sequence identity even though there is no significant relationship between the two full-length sequences. Accordingly, the selected alignment method (GAP program) can be adjusted if so desired to result in an alignment that spans at least 50 or other number of contiguous amino acids of the target polypeptide.

As used herein, an "isolated" biological component (such as a nucleic acid, peptide or cell) has been substantially separated, produced apart from, or purified away from other biological components or cells of the organism in which the component naturally occurs, i.e., other chromosomal and extrachromosomal DNA and RNA, cells and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids.

The term "oligonucleotide" means a polynucleotide comprising 200 or fewer nucleotides. In some embodiments, oligonucleotides are 10 to 60 bases in length. In other embodiments, oligonucleotides are 12, 13, 14, 15, 16, 17, 18, 19, or 20 to 40 nucleotides in length. Oligonucleotides can be single stranded or double stranded, e.g., for use in the construction of a mutant gene. Oligonucleotides can be sense or antisense oligonucleotides. An oligonucleotide can include a label, including a radiolabel, a fluorescent label, a hapten or an antigenic label, for detection assays. Oligonucleotides can be used, for example, as PCR primers, cloning primers or hybridization probes.

The term "operably linked" refers to an arrangement of elements wherein the components so described are configured so as to perform their usual function. Thus, a given signal peptide that is operably linked to a polypeptide directs the secretion of the polypeptide from a cell. In the case of a promoter, a promoter that is operably linked to a coding sequence will direct the expression of the coding sequence. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

The term "polynucleotide" or "nucleic acid" includes both single-stranded and double-stranded nucleotide polymers. The nucleotides comprising the polynucleotide can be ribonucleotides or deoxyribonucleotides or a modified form of either type of nucleotide. Said modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoramidate.

The terms "polypeptide" or "protein" means a macromolecule having the amino acid sequence of a native protein, that is, a protein produced by a naturally-occurring and non-recombinant cell; or it is produced by a genetically-engineered or recombinant cell, and comprise molecules having the amino acid sequence of the native protein, or molecules having deletions from, additions to, and/or substitutions of one or more amino acids of the native sequence. The term also includes amino acid polymers in which one or more amino acids are chemical analogs of a corresponding naturally-occurring amino acid and polymers. The terms "polypeptide" and "protein" specifically encompass LAIR1 antigen binding proteins, antibodies, or sequences that have deletions from, additions to, and/or substitutions of one or more amino acid of antigen-binding protein. The term "polypeptide fragment" refers to a polypeptide that has an amino-terminal deletion, a carboxyl-terminal deletion, and/or an internal deletion as compared with the full-length native protein. Such fragments can also contain modified amino acids as compared with the native protein. In certain embodiments, fragments are about five to 500 amino acids long. For example, fragments can be at least 5, 6, 8, 10, 14, 20, 50, 70, 100, 110, 150, 200, 250, 300, 350, 400, or 450 amino acids long. Useful polypeptide fragments include immunologically functional fragments of antibodies, including binding domains. In the case of a LAIR1-binding antibody, useful fragments include but are not limited to a CDR region, a variable domain of a heavy and/or light chain, a portion of an antibody chain or just its variable region including two CDRs, and the like.

The pharmaceutically acceptable carriers useful in this invention are conventional. Remington's Pharmaceutical Sciences, by E. W. Martin, Mack Publishing Co., Easton, Pa., 15th Edition (1975), describes compositions and formulations suitable for pharmaceutical delivery of the fusion proteins herein disclosed. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

As used herein, the term "subject" refers to a human or any non-human animal (e.g., mouse, rat, rabbit, dog, cat, cattle, swine, sheep, horse or primate). A human includes pre and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

As used herein, an "effective amount" or "therapeutically effective amount" means the amount of agent that is sufficient to prevent, treat, reduce and/or ameliorate the symptoms and/or underlying causes of any disorder or disease, or the amount of an agent sufficient to produce a desired effect on a cell. In one embodiment, a "therapeutically effective amount" is an amount sufficient to reduce or eliminate a symptom of a disease. In another embodiment, a therapeutically effective amount is an amount sufficient to overcome the disease itself.

"Treating" or "treatment" of a condition as used herein includes preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition, or some combination thereof.

As used herein, a "vector" refers to a nucleic acid molecule as introduced into a host cell, thereby producing a transformed host cell. A vector may include nucleic acid sequences that permit it to replicate in the host cell, such as an origin of replication. A vector may also include one or more therapeutic genes and/or selectable marker genes and other genetic elements known in the art. A vector can transduce, transform or infect a cell, thereby causing the cell to express nucleic acids and/or proteins other than those native to the cell. A vector optionally includes materials to aid in achieving entry of the nucleic acid into the cell, such as a viral particle, liposome, protein coating or the like.

Anti-LAIR1 Antibodies

Leukocyte-associated immunoglobulin-like receptor 1 is a protein that in humans is encoded by the LAIR1 gene. LAIR1 has also been designated as CD305 (cluster of differentiation 305). LAIR1 is a type I transmembrane glycoprotein that contains one extracellular Ig-like domain and two intracellular ITIMs. Like the genes that encode LILRBs, lair1 is localized to the leukocyte receptor complex (LRC) on human chromosome 19q13.4. LAIR1 binds collagens, and its ITIMs recruit SHP-1 and SHP-2. LAIR1 is expressed in T cells, B cells, natural killer (NK) cells, macrophages, and dendritic cells, as well as hematopoietic progenitors including human $CD34^+$ cells. The inventors have found that LAIR1 is expressed on AML stem cells and differentiated AML and ALL cells and its inhibition blocks AML-SC activity and leukemia development In one aspect, the present disclosure provides a monoclonal antibody or antigen-binding fragment thereof that when binding to LAIR1, modulates the activity of LAIR1. The monoclonal antibodies described herein were prepared using standard methods, followed by screening, characterization and functional assessment. In certain embodiment, variable regions were sequenced and then subcloned into a human expression vector to produce the chimeric antibody genes, which were then expressed and purified. These chimeric antibodies were tested for antigen binding, signaling blocking, and in xenograft experiments.

A. General Methods

It will be understood that monoclonal antibodies binding to LAIR1 will have several applications. These include the production of diagnostic kits for use in detecting and diagnosing cancer, as well as for cancer therapies. In these contexts, one may link such antibodies to diagnostic or therapeutic agents, use them as capture agents or competitors in competitive assays, or use them individually without additional agents being attached thereto. The antibodies may be mutated or modified, as discussed further below. Methods for preparing and characterizing antibodies are well known in the art (see, e.g., Antibodies: A Laboratory Manual, Cold Spring Harbor Laboratory, 1988; U.S. Pat. No. 4,196,265).

The methods for generating monoclonal antibodies (MAbs) generally begin along the same lines as those for preparing polyclonal antibodies. The first step for both these methods is immunization of an appropriate host. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodimyde and bis-biazotized benzidine. As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

Following immunization, somatic cells with the potential for producing antibodies, specifically B lymphocytes (B cells), are selected for use in the MAb generating protocol. These cells may be obtained from biopsied spleens or lymph nodes, or from circulating blood. The antibody-producing B lymphocytes from the immunized animal are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas). Any one of a number of myeloma cells may be used, as are known to those of skill in the art (Goding, pp. 65-66, 1986; Campbell, pp. 75-83, 1984).

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986). Fusion procedures usually produce viable hybrids at low frequencies, about $1\times10^{-6}$ to $1\times10^{-8}$. However, this does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine. Ouabain is added if the B cell source is an Epstein Barr virus (EBV) transformed human B cell line, in order to eliminate EBV transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain is also used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like. The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

MAbs produced by either means may be further purified, if desired, using filtration, centrifugation and various chromatographic methods such as FPLC or affinity chromatography. Fragments of the monoclonal antibodies of the disclosure can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present disclosure can be synthesized using an automated peptide synthesizer.

It also is contemplated that a molecular cloning approach may be used to generate monoclonal antibodies. For this, RNA can be isolated from the hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately $10^4$ times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present disclosure include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

B. Antibodies of the Present Disclosure

1. Antibodies to LAIR1

Antibodies or antigen-binding fragments thereof according to the present disclosure may be defined, in the first instance, by their binding specificity, which in this case is for LAIR1. Those of skill in the art, by assessing the binding specificity/affinity of a given antibody using techniques well known to those of skill in the art, can determine whether such antibodies fall within the scope of the instant claims.

In one aspect, there are provided antibodies and antigen-binding fragments specifically bind to LAIR1. In some embodiments, when bound to LAIR1, such antibodies modulate the activation of LAIR1. In certain embodiments, the antibody or antigen-binding fragment, when bound to LAIR1, activates LAIR1. In certain embodiments, the antibody or antigen-binding fragment, when bound to LAIR1, suppresses activation of LAIR1. In certain embodiments, the antibody or antigen-binding fragment, when bound to LAIR1, can specifically interfere with, block or reduce the interaction between collagen I and LAIR1. In certain embodiments, the antibody or antigen-binding fragment provided herein is capable of inhibiting collagen-mediated activity of LAIR1. In certain embodiments, the antibody or antigen-binding fragment provided herein is capable of enhancing collagen-mediated activity of LAIR1. In certain embodiments, the antibodies or antigen-binding fragments provided herein specifically or selectively bind to human LAIR1 (SEQ ID NO: 533).

In certain embodiments, the monoclonal antibody or antigen-binding fragment thereof provided herein are capable of specifically binding to LAIR1 with a binding affinity about $10^{-6}$ M or less (e.g. $10^{-6}$ M, $10^{-8}$ M, $10^{-9}$ M, $10^{-19}$M, $10^{-11}$ M, $10^{-12}$ M, $10^{-13}$M) as measured by plasmon resonance binding assay. The binding affinity can be represented by $K_D$ value, which is calculated as the ratio of dissociation rate to association rate ($k_{off}/k_{on}$) when the binding between the antigen and the antigen-binding molecule reaches equilibrium. The antigen-binding affinity (e.g. $K_D$) can be appropriately determined using suitable methods known in the art, including, for example, plasmon resonance binding assay using instruments such as Biacore (see, for example, Murphy, M. et al, Current protocols in protein science, Chapter 19, unit 19.14, 2006).

In certain embodiments, the monoclonal antibody or antigen-binding fragment thereof provided herein are capable of binding to LAIR1 with $EC_{50}$ (i.e., 50% binding concentration) of 0.001 μg/ml-1 μg/ml (e.g. 0.001 μg/ml-0.5 μg/ml, 0.001 μg/ml-0.2 μg/ml, 0.001 μg/ml-0.1 μg/ml, 0.01 μg/ml-0.2 μg/ml, 0.01 μg/ml-0.1 μg/ml, 0.01 μg/ml-0.05 μg/ml, 0.01 μg/ml-0.03 μg/ml or 0.001 μg/ml-0.01 μg/ml,) as measured by ELISA, or $EC_{50}$ of 0.01 μg/ml-1 μg/ml (e.g. 0.01 μg/ml-0.5 μg/ml, 0.01 μg/ml-0.2 μg/ml, 0.05 μg/ml-1 μg/ml, 0.05 μg/ml-0.5 μg/ml or 0.05 μg/ml-0.2 μg/ml) as measured by FACS. Binding of the antibodies to LAIR1 can be measured by methods known in the art, for example, ELISA, FACS, surface plasmon resonance, GST pull down, epitope-tag, immunoprecipitation, Far-Western, fluorescence resonance energy transfer, time resolved fluorescence immunoassays (TR-FIA), radioimmunoassays (RIA), enzyme immunoassays, latex agglutination, Western blot, and immunohistochemistry or other binding assays. In an illustrative example, the test antibody (i.e., first antibody) is allowed to bind to immobilized LAIR1 or cells expressing LAIR1, after washing away the unbound antibody, and a labeled secondary antibody is introduced which can bind to and thus allow the detection of the bound first antibody. The detection can be conducted with a microplate reader when immobilized LAIR1 is used, or by using FACS analysis when the cells expressing LAIR1 are used.

In some embodiments, the antibody or antigen-binding fragment has an $IC_{50}$ for blocking the binding of collagen to LAIR1 of less than 1 μM, 1000 nM to 100 nM, 100 nM to 10 nM, 10 nM to 1 nM, 1000 pM to 500 pM, 500 pM to 200 pM, less than 200 pM, 200 pM to 150 pM, 200 pM to 100 pM, 100 pM to 10 pM, 10 pM to 1 pM.

In some embodiments, the antibodies or antigen-binding fragments provided herein having clone-paired CDRs from the heavy and light chains variable region sequences as illustrated in Table 1. Such antibodies may be produced by the clones discussed below in the Examples section using methods described herein. In certain embodiments, each CDR is defined in accordance with Kabat definition, the Chothia definition, the combination of Kabat definition and Chothia definition, the AbM definition, or the contact definition of CDR. In certain embodiments, the antibody or antigen-binding fragment is characterized by clone-paired heavy and light chain CDR sequences from Tables 2 and.

In certain embodiments, the antibodies may be defined by their variable sequence, which include additional "framework" regions. The antibody is characterized by clone-paired heavy chain and light chain amino acid sequences from Table 1. Furthermore, the antibodies sequences may vary from these sequences, particularly in regions outside the CDRs. For example, the amino acids may vary from those set out above by a given percentage, e.g., 80%, 85%, 90%, 91%, 92%, 93%, 94%, 95%, 96%, 97%, 98% or 99% homology, or the amino acids may vary from those set out above by permitting conservative substitutions (discussed below). Each of the foregoing apply to the amino acid sequences of Table 1. In another embodiment, the antibody derivatives of the present disclosure comprise VL and VH domains having up to 0, 1, 2, 3, 4, 5, 6, 7, 8, 9, 10 or more conservative or non-conservative amino acid substitutions, while still exhibiting the desired binding and functional properties.

While the antibodies of the present disclosure were generated as IgG's, it may be useful to modify the constant regions to alter their function. The constant regions of the antibodies typically mediate the binding of the antibody to host tissues or factors, including various cells of the immune system (e.g., effector cells) and the first component (C1q) of the classical complement system. Thus, the term "antibody" includes intact immunoglobulins of types IgA, IgG, IgE, IgD, IgM (as well as subtypes thereof), wherein the light chains of the immunoglobulin may be of types kappa or lambda. Within light and heavy chains, the variable and constant regions are joined by a 35 "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989).

The present disclosure further comprises nucleic acids which hybridize to nucleic acids encoding the antibodies disclosed herein. In general, the nucleic acids hybridize under moderate or high stringency conditions to nucleic acids that encode antibodies disclosed herein and also encode antibodies that maintain the ability to specifically bind to an LAIR1. A first nucleic acid molecule is "hybridizable" to a second nucleic acid molecule when a single stranded form of the first nucleic acid molecule can anneal to the second nucleic acid molecule under the appropriate conditions of temperature and solution ionic strength (see Sambrook et al., supra). The conditions of temperature and ionic strength determine the "stringency" of the hybridization. Typical moderate stringency hybridization conditions are 40% formamide, with 5× or 6×SSC and 0.1% SDS at 42° C. High stringency hybridization conditions are 50% formamide, 5× or 6×SSC (0.15M NaCl and 0.015M Na-citrate) at 42° C. or, optionally, at a higher temperature (e.g., 57° C., 59° C., 60° C., 62° C., 63° C., 65° C. or 68° C.). Hybridization requires that the two nucleic acids contain complementary sequences, although, depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the higher the stringency under which the nucleic acids may hybridize. For hybrids of greater than 100 nucleotides in length, equations for calculating the melting temperature have been derived (see Sambrook et al., supra). For hybridization with shorter nucleic acids, e.g., oligonucleotides, the position of mismatches becomes more important, and the length of the oligonucleotide determines its specificity (see Sambrook et al., supra).

2. Exemplary Epitopes

In another aspect, the present disclosure provides epitopes to which anti-LAIR1 antibodies bind.

In some embodiments, epitopes that are bound by the antibodies described herein are useful. In certain embodiments, an epitope provided herein can be utilized to isolate antibodies or antigen binding proteins that bind to LAIR1. In certain embodiments, an epitope provided herein can be utilized to generate antibodies or antigen binding proteins which bind to LAIR1. In certain embodiments, an epitope or a sequence comprising an epitope provided herein can be utilized as an immunogen to generate antibodies or antigen binding proteins that bind to LAIR1. In certain embodiments, an epitope described herein or a sequence comprising an epitope described herein can be utilized to interfere with biological activity of LAIR1.

In some embodiments, antibodies or antigen-binding fragments thereof that bind to any of the epitopes are particularly useful. In some embodiments, an epitope provided herein, when bound by an antibody, modulates the biological activity of LAIR1. In some embodiments, an epitope provided herein, when bound by an antibody, activates LAIR1. In some embodiments, an epitope provided herein, when bound by an antibody, suppress the activation of LAIR1. In some embodiments, an epitope provided herein, when bound by an antibody, modulates the interaction between collagen and LAIR1.

In some embodiments, the domain(s)/region(s) containing residues that are in contact with or are buried by an antibody can be identified by mutating specific residues in LAIR1 and determining whether the antibody can bind the mutated LAIR1 protein. By making a number of individual mutations, residues that play a direct role in binding or that are in sufficiently close proximity to the antibody such that a mutation can affect binding between the antibody and antigen can be identified. From knowledge of these amino acids, the domain(s) or region(s) of the antigen that contain residues in contact with the antigen binding protein or covered by the antibody can be elucidated. Such a domain can include the binding epitope of an antigen binding protein.

In some embodiments, the monoclonal antibody or antigen-binding fragment thereof can specifically bind to the Ig domain of LAIR1 (amino acid residues 25-121). In some embodiments, the monoclonal antibody or antigen-binding fragment thereof can specifically bind to an epitope contained within the Ig domain of LAIR1. In some embodiments, the monoclonal antibody or antigen-binding fragment thereof can specifically bind to an epitope of LAIR1 contained within the amino acid residues 25-47, 53-81, 88-96 and/or 102-119. In some embodiments, the monoclonal antibody or antigen-binding fragment thereof can specifically bind to an epitope of LAIR1 contained within the amino acid residues 30-34, 45-47 and/or 88-89. In some embodiments, the monoclonal antibody or antigen-binding fragment thereof can specifically bind to an epitope of LAIR1 contained within the amino acid residues 37-41, 116-119, 98-105, 59-63 and/or 66-71. In some embodiments, the monoclonal antibody or antigen-binding fragment thereof can specifically bind to an epitope of LAIR1 comprising amino acid residues 30-34, 37-41, 45-47, 59-63, 66-71, 88-89, 98-105, 108-110 or 116-119. In some embodiments, the monoclonal antibody or antigen-binding fragment thereof can specifically bind to an epitope of LAIR1 comprising amino acid residues 35-36, 44, 53-56, 64-65, 73-81, 89-96, 106-107 or 111-115. In some embodiments, the monoclonal antibody or antigen-binding fragment thereof can specifically bind to an epitope of LAIR1 comprising amino acid residues 25, 35, 56, 65-68, 73, 75-77, 80, 89, 93, 106, 107 or 109. In some embodiments, the monoclonal antibody or an antigen-binding fragment thereof can specifically bind to an epitope of LAIR1 contained within amino acid residues 59-69 and/or 100-112. In some embodiments, the monoclonal antibody or an antigen-binding fragment thereof can specifically bind to an epitope of LAIR1 comprising amino acid residues 59, 61, 65, 67, 68, 69, 100, 102, 109, 111 or 112. In some embodiments, the monoclonal antibody or an antigen-binding fragment thereof can specifically bind to an epitope of LAIR1 comprising amino acid residues 59, 61 and 109. In some embodiments, the monoclonal antibody or an antigen-binding fragment thereof can specifically bind to an epitope of LAIR1 comprising amino acid residues 61 or 62 of LAIR1. In some embodiments, the monoclonal antibody or an antigen-binding fragment thereof can specifically bind to an epitope of LAIR1 comprising amino acid residues 68 or 69 of LAIR1. In some embodiments, the monoclonal antibody or an antigen-binding fragment thereof can specifically bind to an epitope of LAIR1 comprising amino acid residues 61 or 62, 65 or 66, and 111 or 112 of LAIR1. In some embodiments, the monoclonal antibody or an antigen-binding fragment thereof can specifically bind to an epitope of LAIR1 comprising amino acid residues 111 or 112 of LAIR1.

3. Competing Antigen Binding Proteins

In another aspect, the present disclosure provides antigen-binding proteins that compete with one of the exemplified antibodies or antigen-binding fragment binding to the epitope described herein for specific binding to LAIR1. Such antigen binding proteins can also bind to the same epitope as one of the herein exemplified antibodies or the antigen-binding fragment, or an overlapping epitope. Antigen-binding proteins that compete with or bind to the same epitope as the exemplified antibodies are expected to show similar functional properties. The exemplified antibodies include those described above, including those with the heavy and light chain variable regions and CDRs listed in Tables 1-5.

C. Engineering of Antibody Sequences

In various embodiments, one may choose to engineer sequences of the identified antibodies for a variety of reasons, such as improved expression, improved crossreactivity or diminished off-target binding. The following is a general discussion of relevant techniques for antibody engineering.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers. Assay of binding and neutralization may be performed using antibodies collected from hybridoma supernatants and purified by FPLC, using Protein G columns. Recombinant full length IgG antibodies may be generated by subcloning heavy and light chain Fv DNAs from the cloning vector into an IgG plasmid vector, transfected into HEK293 cells or CHO cells, and antibodies collected and purified from the HEK293 or CHO cell supernatant.

The rapid availability of antibody produced in the same host cell and cell culture process as the final cGMP manufacturing process has the potential to reduce the duration of process development programs.

Antibody molecules will comprise fragments (such as F(ab'), F(ab)$_2$) that are produced, for example, by the proteolytic cleavage of the mAbs, or single-chain immunoglobulins producible, for example, via recombinant means. Such antibody derivatives are monovalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

1. Antigen Binding Modifications

In related embodiments, the antibody is a derivative of the disclosed antibodies, e.g., an antibody comprising the CDR sequences identical to those in the disclosed antibodies (e.g., a chimeric, or CDR-grafted antibody). Alternatively, one may wish to make modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, nonaromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present disclosure also contemplates isotype modification. By modifying the Fc region to have a different isotype, different functionalities can be achieved. For example, changing to IgG$_1$ can increase antibody dependent cell cytotoxicity, switching to class A can improve tissue distribution, and switching to class M can improve valency.

Modified antibodies may be made by any technique known to those of skill in the art, including expression through standard molecular biological techniques, or the chemical synthesis of polypeptides. Methods for recombinant expression are addressed elsewhere in this document.

2. Fc Region Modifications

The antibodies disclosed herein can also be engineered to include modifications within the Fc region, typically to alter one or more functional properties of the antibody, such as serum half-life, complement fixation, Fc receptor binding, and/or effector function (e.g., antigen-dependent cellular cytotoxicity). Furthermore, the antibodies disclosed herein can be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat. The antibodies disclosed herein also include antibodies with modified (or blocked) Fc regions to provide altered effector functions. See, e.g., U.S. Pat. No. 5,624,821; WO2003/086310; WO2005/120571; WO2006/0057702. Such modification can be used to enhance or suppress various reactions of the immune system, with possible beneficial effects in diagnosis and therapy. Alterations of the Fc region include amino acid changes (substitutions, deletions and insertions), glycosylation or deglycosylation (deglycosylation may also be referred to as aglycosylaton), and adding multiple Fc. Changes to the Fc can also alter the half-life of antibodies in therapeutic antibodies, enabling less frequent dosing and thus increased convenience and decreased use of material. This mutation has been reported to abolish the heterogeneity of inter-heavy chain disulfide bridges in the hinge region.

In one embodiment, the hinge region of CH1 is modified such that the number of cysteine residues in the hinge region is increased or decreased. This approach is described further in U.S. Pat. No. 5,677,425. The number of cysteine residues in the hinge region of CH1 is altered, for example, to facilitate assembly of the light and heavy chains or to increase or decrease the stability of the antibody. In another embodiment, the antibody is modified to increase its biological half-life. Various approaches are possible. For example, one or more of the following mutations can be introduced: T252L, T254S, T256F, as described in U.S. Pat. No. 6,277,375. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022. In yet other embodiments, the Fc region is altered by replacing at least one amino acid residue with a different amino acid residue to alter the effector function(s) of the antibodies. For example, one or more amino acids selected from amino acid residues 234, 235, 236, 237, 297, 318, 320 and 322 can be replaced with a different amino acid residue such that the antibody has an altered affinity for an effector ligand but retains the antigen binding ability of the parent antibody. The effector ligand to which affinity is altered can be, for example, an Fc receptor or the C1 component of complement. This approach is described in further detail in U.S. Pat. Nos. 5,624,821 and 5,648,260.

In another example, one or more amino acid residues within amino acid positions 231 and 239 are altered to thereby alter the ability of the antibody to fix complement. This approach is described further in PCT Publication WO 94/29351. In yet another example, the Fc region is modified to increase or decrease the ability of the antibodies to mediate antibody dependent cellular cytotoxicity (ADCC) and/or to increase or decrease the affinity of the antibodies for an Fcγ receptor by modifying one or more amino acids at the following positions: 238, 239, 243, 248, 249, 252, 254, 255, 256, 258, 264, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072. Moreover, the binding sites on human IgG1 for FcγR1, FcγRII, FcγRIII and FcRn have been mapped and variants with improved binding have been described. Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A.

In one embodiment, the Fc region is modified to decrease the ability of the antibodies to mediate effector function and/or to increase anti-inflammatory properties by modifying residues 243 and 264. In one embodiment, the Fc region of the antibody is modified by changing the residues at positions 243 and 264 to alanine. In one embodiment, the Fc region is modified to decrease the ability of the antibody to mediate effector function and/or to increase anti-inflammatory properties by modifying residues 243, 264, 267 and 328. In still another embodiment, the antibody comprises a particular glycosylation pattern. For example, an aglycosylated antibody can be made (i.e., the antibody lacks glycosylation). The glycosylation pattern of an antibody may be altered to, for example, increase the affinity or avidity of the antibody for an antigen. Such modifications can be accomplished by, for example, altering one or more of the glycosylation sites within the antibody sequence. For example, one or more amino acid substitutions can be made that result removal of one or more of the variable region framework glycosylation sites to thereby eliminate glycosylation at that site. Such a glycosylation may increase the affinity or avidity of the antibody for antigen. See, e.g., U.S. Pat. Nos. 5,714,350 and 6,350,861.

An antibody may also be made in which the glycosylation pattern includes hypofucosylated or afucosylated glycans, such as a hypofucosylated antibodies or afucosylated antibodies have reduced amounts of fucosyl residues on the glycan. The antibodies may also include glycans having an increased amount of bisecting GlcNac structures. Such altered glycosylation patterns have been demonstrated to increase the ADCC ability of antibodies. Such modifications can be accomplished by, for example, expressing the antibodies in a host cell in which the glycosylation pathway was been genetically engineered to produce glycoproteins with particular glycosylation patterns. These cells have been described in the art and can be used as host cells in which to express recombinant antibodies of the invention to thereby produce an antibody with altered glycosylation. For example, the cell lines Ms704, Ms705, and Ms709 lack the fucosyltransferase gene, FUT8 (α (1,6)-fucosyltransferase), such that antibodies expressed in the Ms704, Ms705, and Ms709 cell lines lack fucose on their carbohydrates. The Ms704, Ms705, and Ms709 FUT8−/− cell lines were created by the targeted disruption of the FUT8 gene in CHO/DG44 cells using two replacement vectors (see U.S. Patent Publication No. 20040110704. As another example, EP 1 176 195 describes a cell line with a functionally disrupted FUT8 gene, which encodes a fucosyl transferase, such that antibodies expressed in such a cell line exhibit hypofucosylation by reducing or eliminating the α-1,6 bond-related enzyme. EP 1 176 195 also describes cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 describes a variant CHO cell line, Lec13 cells, with reduced ability to attach fucose to Asn (297)-linked carbohydrates, also resulting in hypofucosylation of antibodies expressed in that host cell. Antibodies with a modified glycosylation profile can also be produced in chicken eggs, as described in PCT Publication WO 06/089231. Alternatively, antibodies with a modified glycosylation profile can be produced in plant cells, such as Lemna (U.S. Pat. No. 7,632,983). Methods for production of antibodies in a plant system are disclosed in the U.S. Pat. Nos. 6,998,267 and 7,388,081. PCT Publication WO 99/54342 describes cell lines engineered to express glycoprotein-modifying glycosyl transferases (e.g., β(1,4)-N-acetylglucosaminyltransferase III (GnTIII)) such that antibodies expressed in the engineered cell lines exhibit increased bisecting GlcNac structures which results in increased ADCC activity of the antibodies.

Alternatively, the fucose residues of the antibodies can be cleaved off using a fucosidase enzyme; e.g., the fucosidase α-L-fucosidase removes fucosyl residues from antibodies. Antibodies disclosed herein further include those produced in lower eukaryote host cells, in particular fungal host cells such as yeast and filamentous fungi have been genetically engineered to produce glycoproteins that have mammalian- or human-like glycosylation patterns. A particular advantage of these genetically modified host cells over currently used mammalian cell lines is the ability to control the glycosylation profile of glycoproteins that are produced in the cells such that compositions of glycoproteins can be produced wherein a particular N-glycan structure predominates (see, e.g., U.S. Pat. Nos. 7,029,872 and 7,449,308). These genetically modified host cells have been used to produce antibodies that have predominantly particular N-glycan structures.

In addition, since fungi such as yeast or filamentous fungi lack the ability to produce fucosylated glycoproteins, antibodies produced in such cells will lack fucose unless the cells are further modified to include the enzymatic pathway for producing fucosylated glycoproteins (See for example, PCT Publication WO2008112092). In particular embodiments, the antibodies disclosed herein further include those produced in lower eukaryotic host cells and which comprise fucosylated and nonfucosylated hybrid and complex N-glycans, including bisected and multiantennary species, including but not limited to N-glycans such as GlcNAc(1-4)Man3GlcNAc2; Gal(1-4)GlcNAc(1-4)Man3GlcNAc2; NANA(1-4)Gal(1-4)GlcNAc(1-4)Man3GlcNAc2. In particular embodiments, the antibody compositions provided herein may comprise antibodies having at least one hybrid N-glycan selected from the group consisting of GlcNAcMan5GlcNAc2; GalGlcNAcMan5GlcNAc2; and NANAGalGlcNAcMan5GlcNAc2. In particular aspects, the hybrid N-glycan is the predominant N-glycan species in the composition. In further aspects, the hybrid N-glycan is a particular N-glycan species that comprises about 30%, 40%, 50%, 60%, 70%, 80%, 90%, 95%, 97%, 98%, 99%, or 100% of the hybrid N-glycans in the composition.

In particular embodiments, the antibody compositions provided herein comprise antibodies having at least one complex N-glycan selected from the group consisting of GlcNAcMan3GlcNAc2; GalGlcNAcMan3GlcNAc2; NANAGalGlcNAcMan3GlcNAc2; GlcNAc2Man3GlcNAc2; GalGlcNAc2Man3GlcNAc2; Gal2GlcNAc2Man3GlcNAc2; NANAGal2GlcNAc2Man3GlcNAc2; and NANA2Gal2GlcNAc2Man3GlcNAc2. In particular aspects, the complex N-glycan is the predominant N-glycan species in the composition. In further aspects, the complex N-glycan is a particular N-glycan species that comprises about 30%, 40%, 50%, 60%, 70%, 80%, 90%, 95%, 97%, 98%, 99%, or 100% of the complex N-glycans in the composition. In particular embodiments, the N-glycan is fusosylated. In general, the fucose is in an α1,3-linkage with the GlcNAc at the reducing end of the N-glycan, an α1,6-linkage with the GlcNAc at the reducing end of the N-glycan, an α1,2-linkage with the Gal at the non-reducing end of the N-glycan, an α1,3-linkage with the GlcNac at the non-reducing end of the N-glycan, or an α1,4-linkage with a GlcNAc at the non-reducing end of the N-glycan.

Therefore, in particular aspects of the above the glycoprotein compositions, the glycoform is in an α1,3-linkage or α1,6-linkage fucose to produce a glycoform selected from the group consisting of Man5GlcNAc2(Fuc), GlcNAcMan5GlcNAc2(Fuc), Man3GlcNAc2(Fuc), GlcNAcMan3GlcNAc2(Fuc), GlcNAc2Man3GlcNAc2 (Fuc), GalGlcNAc2Man3GlcNAc2(Fuc), Gal2GlcNAc2Man3GlcNAc2(Fuc), NANAGal2GlcNAc2Man3GlcNAc2(Fuc), and NANA2Gal2GlcNAc2Man3GlcNAc2 (Fuc); in an α1,3-linkage or α1,4-linkage fucose to produce a glycoform selected from the group consisting of GlcNAc(Fuc)Man5GlcNAc2, GlcNAc(Fuc)Man3GlcNAc2, GlcNAc2(Fuc1-2)Man3GlcNAc2, GalGlcNAc2(Fuc1-2)Man3GlcNAc2, Gal2GlcNAc2(Fuc1-2)Man3GlcNAc2, NANAGal2GlcNAc2(Fuc1-2)Man3GlcNAc 2, and NANA2Gal2GlcNAc2(Fuc1-2)Man3GlcNAc2; or in an α1,2-linkage fucose to produce a glycoform selected from the group consisting of Gal(Fuc)GlcNAc2Man3GlcNAc2, Gal2(Fuc1-2)GlcNAc2Man3GlcNAc2, NANAGal2(Fuc1-2)GlcNAc2Man3GlcNAc2, and NANA2Gal2(Fuc1-2)GlcNAc2Man3GlcNAc2.

In further aspects, the antibodies comprise high mannose N-glycans, including but not limited to, Man8GlcNAc2, Man7GlcNAc2, Man6GlcNAc2, Man5GlcNAc2, Man4GlcNAc2, or N-glycans that consist of the Man3GlcNAc2 N-glycan structure. In further aspects of the above, the complex N-glycans further include fucosylated and non-fucosylated bisected and multiantennary species.

As used herein, the terms "N-glycan" and "glycoform" are used interchangeably and refer to an N-linked oligosaccharide, for example, one that is attached by an asparagine-Nacetylglucosamine linkage to an asparagine residue of a polypeptide. N-linked glycoproteins contain an N-acetylglucosamine residue linked to the amide nitrogen of an asparagine residue in the protein.

D. Single Chain Antibodies

A Single Chain Variable Fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alaine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5 \times 10^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the $V_H$ C terminus and an abundance of arginines and prolines at other positions as the only common features of the selected tethers.

The recombinant antibodies of the present disclosure may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stabilizing and coagulating agent. However, it is contemplated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

E. Purification

In certain embodiments, the antibodies of the present disclosure may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present disclosure, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens may be used to simultaneously purify and select appropriate antibodies. Such methods often utilize the selection agent bound to a support, such as a column, filter or bead. The antibodies is bound to a support, contaminants removed (e.g.e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

F. Antibody Composition

The present disclosure also provides compositions comprising anti-LAIR1 antibodies and/or antigens for generating the same.

1. Pharmaceutical Composition

The pharmaceutical compositions provided herein comprise a prophylactically or therapeutically effective amount of an antibody or a fragment thereof, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical agents are described in "Remington's Pharmaceutical Sciences." Such compositions will contain a prophylactically or therapeutically effective amount of the antibody or fragment thereof, preferably in purified form, together with a suitable amount of carrier so as to provide the form for proper administration to the patient. The formulation should suit the mode of administration, which can be oral, intravenous, intraarterial, intrabuccal, intranasal, nebulized, bronchial inhalation, or delivered by mechanical ventilation.

Antibodies of the present disclosure, as described herein, can be formulated for parenteral administration, e.g., formulated for injection via the intradermal, intravenous, intramuscular, subcutaneous, intra-tumoral or even intraperitoneal routes. The antibodies could alternatively be administered by a topical route directly to the mucosa, for example by nasal drops, inhalation, or by nebulizer. Pharmaceutically acceptable salts, include the acid salts and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Passive transfer of antibodies, known as artificially acquired passive immunity, generally will involve the use of intravenous injections. The forms of antibody can be human or animal blood plasma or serum, as pooled human immunoglobulin for intravenous (IVIG) or intramuscular (IG) use, as high-titer human IVIG or IG from immunized or from donors recovering from disease, and as monoclonal antibodies (MAbs). Such immunity generally lasts for only a short period of time, and there is also a potential risk for hypersensitivity reactions, and serum sickness, especially from gamma globulin of non-human origin. However, passive immunity provides immediate protection. The antibodies will be formulated in a carrier suitable for injection, i.e., sterile and syringeable.

Generally, the ingredients of compositions of the disclosure are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

2. Antibody Conjugates

Antibodies of the present disclosure may be linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radionuclides, antiviral agents, chelating agents, cytokines, growth factors, and oligo- or polynucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, photoaffinity molecules, colored particles or ligands, such as biotin.

Antibody conjugates are generally preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies of the present disclosure may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the disclosure may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as $SNCl_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated in the present disclosure are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and are described, for example, in U.S. Pat. Nos. 3,817,837, 3,850, 752, 3,939,350, 3,996,345, 4,277,437, 4,275,149 and 4,366, 241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

G. Methods of Use

The present disclosure further provides methods of using the monoclonal antibody or antigen-binding fragment thereof provided herein.

1. Treatment of Cancer

Cancers.

While hyperproliferative diseases can be associated with any disease which causes a cell to begin to reproduce uncontrollably, the prototypical example is cancer. One of the key elements of cancer is that the cell's normal apoptotic cycle is interrupted and thus agents that interrupt the growth of the cells are important as therapeutic agents for treating these diseases. Here, a potential requirement is the presence of LAIR1 on the surface of the cancer cell, and in particular on the surface of cancer stem cells, or on the surface of immune cells who are inhibited by such presence of LAIR1.

Cancer cells that may be treated according to the present disclosure include but are not limited to cells from the bladder, blood, bone, bone marrow, brain, breast, colon, esophagus, gastrointestine, gum, head, kidney, liver, lung, nasopharynx, neck, ovary, prostate, skin, stomach, pancreas, testis, tongue, cervix, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma;

papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; Leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; Mullerian mixed tumor; nephroblastoma; hepatoblastoma; carcinosarcoma; mesenchymoma, malignant; Brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In certain aspects, the tumor may comprise an osteosarcoma, angiosarcoma, rhabdosarcoma, leiomyosarcoma, Ewing sarcoma, glioblastoma, neuroblastoma, or leukemia.

2. Acute Myeloid Leukemia

Acute myeloid leukemia (AML), also known as acute myelogenous leukemia or acute nonlymphocytic leukemia (ANLL), is a cancer of the myeloid line of blood cells, characterized by the rapid growth of abnormal white blood cells that accumulate in the bone marrow and interfere with the production of normal blood cells. AML is the most common acute leukemia affecting adults, and its incidence increases with age. Although AML is a relatively rare disease, accounting for approximately 1.2% of cancer deaths in the United States, its incidence is expected to increase as the population ages.

The symptoms of AML are caused by replacement of normal bone marrow with leukemic cells, which causes a drop in red blood cells, platelets, and normal white blood cells. These symptoms include fatigue, shortness of breath, easy bruising and bleeding, and increased risk of infection. Several risk factors and chromosomal abnormalities have been identified, but the specific cause is not clear. As an acute leukemia, AML progresses rapidly and is typically fatal within weeks or months if left untreated.

AML has several subtypes; treatment and prognosis varies among subtypes. Five-year survival varies from 15-70%, and relapse rate varies from 33-78%, depending on subtype. AML is treated initially with chemotherapy aimed at inducing a remission; patients may go on to receive additional chemotherapy or a hematopoietic stem cell transplant. Recent research into the genetics of AML has resulted in the availability of tests that can predict which drug or drugs may work best for a particular patient, as well as how long that patient is likely to survive.

Most signs and symptoms of AML are caused by the replacement of normal blood cells with leukemic cells. A lack of normal white blood cell production makes the patient susceptible to infections; while the leukemic cells themselves are derived from white blood cell precursors, they have no infection-fighting capacity. A drop in red blood cell count (anemia) can cause fatigue, paleness, and shortness of breath. A lack of platelets can lead to easy bruising or bleeding with minor trauma.

The early signs of AML are often vague and nonspecific, and may be similar to those of influenza or other common illnesses. Some generalized symptoms include fever, fatigue, weight loss or loss of appetite, shortness of breath, anemia, easy bruising or bleeding, petechiae (flat, pin-head sized spots under the skin caused by bleeding), bone and joint pain, and persistent or frequent infections.

Enlargement of the spleen may occur in AML, but it is typically mild and asymptomatic. Lymph node swelling is rare in AML, in contrast to acute lymphoblastic leukemia. The skin is involved about 10% of the time in the form of leukemia cutis. Rarely, Sweet's syndrome, a paraneoplastic inflammation of the skin, can occur with AML.

Some patients with AML may experience swelling of the gums because of infiltration of leukemic cells into the gum tissue. Rarely, the first sign of leukemia may be the development of a solid leukemic mass or tumor outside of the bone marrow, called a chloroma. Occasionally, a person may show no symptoms, and the leukemia may be discovered incidentally during a routine blood test.

A number of risk factors for developing AML have been identified, including: other blood disorders, chemical exposures, ionizing radiation, and genetics.

"Preleukemic" blood disorders, such as myelodysplastic syndrome or myeloproliferative disease, can evolve into AML; the exact risk depends on the type of MDS/MPS. Exposure to anticancer chemotherapy, in particular alkylating agents, can increase the risk of subsequently developing AML. The risk is highest about three to five years after chemotherapy. Other chemotherapy agents, specifically epipodophyllotoxins and anthracyclines, have also been associated with treatment-related leukemia. These treatment-related leukemias are often associated with specific chromosomal abnormalities in the leukemic cells. Occupational chemical exposure to benzene and other aromatic organic solvents is controversial as a cause of AML. Benzene and many of its derivatives are known to be carcinogenic in vitro. While some studies have suggested a link between occupational exposure to benzene and increased risk of AML, others have suggested the attributable risk, if any, is slight. High amounts of ionizing radiation exposure can increase the risk of AML. A hereditary risk for AML appears to exist. Multiple cases of AML developing in a family at a rate higher than predicted by chance alone have been reported. Several congenital conditions may increase the risk of leukemia; the most common is probably Down syndrome, which is associated with a 10- to 18-fold increase in the risk of AML.

The first clue to a diagnosis of AML is typically an abnormal result on a complete blood count. While an excess of abnormal white blood cells (leukocytosis) is a common finding, and leukemic blasts are sometimes seen, AML can also present with isolated decreases in platelets, red blood cells, or even with a low white blood cell count (leukopenia). While a presumptive diagnosis of AML can be made via examination of the peripheral blood smear when there are circulating leukemic blasts, a definitive diagnosis usually requires an adequate bone marrow aspiration and biopsy.

Marrow or blood is examined via light microscopy, as well as flow cytometry, to diagnose the presence of leukemia, to differentiate AML from other types of leukemia (e.g., acute lymphoblastic leukemia—ALL), and to classify the subtype of disease (see below). A sample of marrow or blood is typically also tested for chromosomal abnormalities by routine cytogenetics or fluorescent in situ hybridization. Genetic studies may also be performed to look for specific mutations in genes such as FLT3, nucleophosmin, and KIT, which may influence the outcome of the disease.

Cytochemical stains on blood and bone marrow smears are helpful in the distinction of AML from ALL, and in subclassification of AML. The combination of a myeloperoxidase or Sudan black stain and a nonspecific esterase stain will provide the desired information in most cases. The myeloperoxidase or Sudan black reactions are most useful in establishing the identity of AML and distinguishing it from ALL. The nonspecific esterase stain is used to identify a monocytic component in AMLs and to distinguish a poorly differentiated monoblastic leukemia from ALL.

The diagnosis and classification of AML can be challenging, and should be performed by a qualified hematopathologist or hematologist. In straightforward cases, the presence of certain morphologic features (such as Auer rods) or specific flow cytometry results can distinguish AML from other leukemias; however, in the absence of such features, diagnosis may be more difficult.

According to the widely used WHO criteria, the diagnosis of AML is established by demonstrating involvement of more than 20% of the blood and/or bone marrow by leukemic myeloblasts. The French-American-British (FAB) classification is a bit more stringent, requiring a blast percentage of at least 30% in bone marrow (BM) or peripheral blood (PB) for the diagnosis of AML. AML must be carefully differentiated from "preleukemic" conditions such as myelodysplastic or myeloproliferative syndromes, which are treated differently.

Because acute promyelocytic leukemia (APL) has the highest curability and requires a unique form of treatment, it is important to quickly establish or exclude the diagnosis of this subtype of leukemia. Fluorescent in situ hybridization performed on blood or bone marrow is often used for this purpose, as it readily identifies the chromosomal translocation [t(15;17)(q22;q12);] that characterizes APL. There is also a need to molecularly detect the presence of PML/RARA fusion protein, which is an oncogenic product of that translocation.

First-line treatment of AML consists primarily of chemotherapy, and is divided into two phases: induction and post-remission (or consolidation) therapy. The goal of induction therapy is to achieve a complete remission by reducing the number of leukemic cells to an undetectable level; the goal of consolidation therapy is to eliminate any residual undetectable disease and achieve a cure. Hematopoietic stem cell transplantation is usually considered if induction chemotherapy fails or after a patient relapses, although transplantation is also sometimes used as front-line therapy for patients with high-risk disease.

All FAB subtypes except M3 are usually given induction chemotherapy with cytarabine (ara-C) and an anthracycline (most often daunorubicin). This induction chemotherapy regimen is known as "7+3" (or "3+7"), because the cytarabine is given as a continuous IV infusion for seven consecutive days while the anthracycline is given for three consecutive days as an IV push. Up to 70% of patients will achieve a remission with this protocol. Other alternative induction regimens, including high-dose cytarabine alone, FLAG-like regimens or investigational agents, may also be used. Because of the toxic effects of therapy, including myelosuppression and an increased risk of infection, induction chemotherapy may not be offered to the very elderly, and the options may include less intense chemotherapy or palliative care.

The M3 subtype of AML, also known as acute promyelocytic leukemia (APL), is almost universally treated with the drug all-trans-retinoic acid (ATRA) in addition to induction chemotherapy, usually an anthracycline. Care must be taken to prevent disseminated intravascular coagulation (DIC), complicating the treatment of APL when the promyelocytes release the contents of their granules into the peripheral circulation. APL is eminently curable, with well-documented treatment protocols.

The goal of the induction phase is to reach a complete remission. Complete remission does not mean the disease has been cured; rather, it signifies no disease can be detected with available diagnostic methods. Complete remission is obtained in about 50%-75% of newly diagnosed adults, although this may vary based on the prognostic factors described above. The length of remission depends on the prognostic features of the original leukemia. In general, all remissions will fail without additional consolidation therapy.

Even after complete remission is achieved, leukemic cells likely remain in numbers too small to be detected with current diagnostic techniques. If no further post-remission or consolidation therapy is given, almost all patients will eventually relapse. Therefore, more therapy is necessary to eliminate non-detectable disease and prevent relapse—that is, to achieve a cure.

The specific type of post-remission therapy is individualized based on a patient's prognostic factors (see above) and general health. For good-prognosis leukemias (i.e., inv(16), t(8;21), and t(15;17)), patients will typically undergo an additional three to five courses of intensive chemotherapy, known as consolidation chemotherapy. For patients at high risk of relapse (e.g., those with high-risk cytogenetics, underlying MDS, or therapy-related AML), allogeneic stem cell transplantation is usually recommended if the patient is able to tolerate a transplant and has a suitable donor. The best post-remission therapy for intermediate-risk AML (normal cytogenetics or cytogenetic changes not falling into good-risk or high-risk groups) is less clear and depends on the specific situation, including the age and overall health of the patient, the patient's personal values, and whether a suitable stem cell donor is available.

For patients who are not eligible for a stem cell transplant, immunotherapy with a combination of histamine dihydrochloride (Ceplene®; histamine dihydrochloride) and interleukin 2 (Proleukin®; aldesleukin) after the completion of consolidation has been shown to reduce the absolute relapse risk by 14%, translating to a 50% increase in the likelihood of maintained remission.

For patients with relapsed AML, the only proven potentially curative therapy is a hematopoietic stem cell transplant, if one has not already been performed. In 2000, the monoclonal antibody-linked cytotoxic agent gemtuzumab ozogamicin (Mylotarg®; gemtuzumab ozogamicin) was approved in the United States for patients aged more than 60 years with relapsed AML who are not candidates for high-dose chemotherapy. This drug was voluntarily withdrawn from the market by its manufacturer, Pfizer in 2010 and later relaunched by Pfizer in 2017 with modified prescribing information (PI). Since treatment options for relapsed AML are so limited, palliative care may be offered.

Patients with relapsed AML who are not candidates for stem cell transplantation, or who have relapsed after a stem cell transplant, may be offered treatment in a clinical trial, as conventional treatment options are limited. Agents under investigation include cytotoxic drugs such as clofarabine, as well as targeted therapies, such as farnesyl transferase inhibitors, decitabine, and inhibitors of MDR1 (multidrug-resistance protein). For relapsed acute promyelocytic leukemia (APL), arsenic trioxide has been tested in trials and approved by the U.S. FDA. Like ATRA, arsenic trioxide does not work with other subtypes of AML.

While acute myeloid leukemia is a curable disease, the chance of cure for a specific patient depends on a number of prognostic factors. The single most important prognostic factor in AML is cytogenetics, or the chromosomal structure of the leukemic cell. Certain cytogenetic abnormalities are associated with very good outcomes (for example, the (15:17) translocation in acute promyelocytic leukemia). About half of AML patients have "normal" cytogenetics; they fall into an intermediate risk group. A number of other cytogenetic abnormalities are known to associate with a poor prognosis and a high risk of relapse after treatment.

AML which arises from a pre-existing myelodysplastic syndrome (MDS) or myeloproliferative disease (so-called secondary AML) has a worse prognosis, as does treatment-related AML arising after chemotherapy for another previous malignancy. Both of these entities are associated with a high rate of unfavorable cytogenetic abnormalities.

In some studies, age >60 years and elevated lactate dehydrogenase level were also associated with poorer outcomes. As with most forms of cancer, performance status (i.e., the general physical condition and activity level of the patient) plays a major role in prognosis as well.

FLT3 internal tandem duplications (ITDs) have been shown to confer a poorer prognosis in AML. Treating these patients with more aggressive therapy, such as stem-cell transplantation in first remission, has not been shown to enhance long-term survival. ITDs of FLT3 may be associated with leukostasis. In 2017 Novartis received the US Food and Drug Administration (FDA) approval of Rydapt® (midostaurin, formerly PKC412) for the treatment of acute myeloid leukemia (AML) in newly diagnosed patients who are FMS-like tyrosine kinase 3 mutation-positive (FLT3+), as detected by an FDA-approved test, in combination with chemotherapy.

Researchers are investigating the clinical significance of c-KIT mutations in AML. These are prevalent, and clinically relevant because of the availability of tyrosine kinase inhibitors, such as imatinib and sunitinib that can block the activity of c-KIT pharmacologically. Other genes being investigated as prognostic factors or therapeutic targets include CEBPA, BAALC, ERG, and NPMJ.

3. Acute Lymphoblastic Leukemia (ALL)

Acute lymphoblastic leukemia (ALL) or acute lymphoid leukemia is an acute form of leukemia, or cancer of the white blood cells, characterized by the overproduction of cancerous, immature white blood cells—known as lymphoblasts. In persons with ALL, lymphoblasts are overproduced in the bone marrow and continuously multiply, causing damage and death by inhibiting the production of normal cells—such as red and white blood cells and platelets—in the bone marrow and by infiltrating to other organs. ALL is most common in childhood with a peak incidence at 2-5 years of age, and another peak in old age.

The symptoms of ALL are indicative of a reduced production of functional blood cells, because the leukemia wastes the resources of the bone marrow, which are normally used to produce new, functioning blood cells. These symptoms can include fever, increased risk of infection (especially bacterial infections like pneumonia, due to neutropenia; symptoms of such an infection include shortness of breath, chest pain, cough, vomiting, changes in bowel or bladder habits), increased tendency to bleed (due to thrombocytopenia) and signs indicative of anemia including pallor, tachycardia (high heart rate), fatigue and headache.

About 6,000 cases are reported in the U.S. every year; statistics from other countries are difficult to come by, although it is known to be more common in the United States, Italy and Costa Rica. Cure is a realistic goal and is achieved in over 80% of affected children, although only 20-40% of adults can be cured. "Acute" refers to the relatively short time course of the disease to differentiate it from chronic lymphocytic leukemia, which has a potential time course of many years.

The symptoms are not specific to ALL, but worsen to the point that medical help is sought. They result from the lack of normal and healthy blood cells because they are crowded out by malignant and immature leukocytes (white blood cells). Therefore, people with ALL experience symptoms from malfunctioning of their erythrocytes (red blood cells), leukocytes, and platelets. Laboratory tests that might show abnormalities include blood count tests, renal function tests, electrolyte tests, and liver enzyme tests.

The signs and symptoms of ALL are variable but follow from bone marrow replacement and/or organ infiltration, and include generalized weakness and fatigue, anemia, dizziness, frequent or unexplained fever and infection, weight loss and/or loss of appetite, excessive and unexplained bruising, bone pain, joint pain (caused by the spread of "blast" cells to the surface of the bone or into the joint from the marrow cavity), breathlessness, enlarged lymph nodes, liver and/or spleen, pitting edema (swelling) in the lower limbs and/or abdomen, and petechiae, which are tiny red spots or lines in the skin due to low platelet levels.

In general, cancer is caused by damage to DNA that leads to uncontrolled cellular growth and spreads throughout the body, either by increasing chemical signals that cause growth or by interrupting chemical signals that control growth. Damage can be caused through the formation of fusion genes, as well as the dysregulation of a proto-oncogene via juxtaposition of it to the promoter of another gene, e.g., the T-cell receptor gene. This damage may be caused by environmental factors such as chemicals, drugs or radiation, and occurs naturally during mitosis or other normal processes (although cells have numerous mechanisms of DNA repair that help to reduce this).

ALL is associated with exposure to radiation and chemicals in animals and humans. High level radiation exposure is a known risk factor for developing leukemia, as found by studies of survivors of atom bomb exposure in Hiroshima and Nagasaki. In animals, exposure to benzene and other chemicals can cause leukemia. Epidemiological studies have associated leukemia with workplace exposure to chemicals, but these studies are not as conclusive. Some evidence suggests that secondary leukemia can develop in individuals treated for other cancers with radiation and chemotherapy as a result of that treatment.

Diagnosing ALL begins with a medical history, physical examination, complete blood count, and blood smears. Because the symptoms are so general, many other diseases with similar symptoms must be excluded. Typically, the higher the white blood cell count the worse the prognosis. Blast cells are seen on blood smear in the majority of cases (blast cells are precursors (stem cells) to all immune cell lines). A bone marrow biopsy is conclusive proof of ALL. A lumbar puncture (also known as a spinal tap) will indicate if the spinal column and brain have been invaded.

Pathological examination, cytogenetics (in particular the presence of Philadelphia chromosome), and immunophenotyping establish whether myeloblastic (neutrophils, eosinophils, or basophils) or lymphoblastic (B lymphocytes or T lymphocytes) cells are the problem. RNA testing can establish how aggressive the disease is; different mutations have been associated with shorter or longer survival. Immunohistochemical testing may reveal TdT or CALLA antigens on the surface of leukemic cells. TdT is a protein expressed early in the development of pre-T and pre-B cells, whereas CALLA is an antigen found in 80% of ALL cases and also in the "blast crisis" of CML. Medical imaging (such as ultrasound or CT scanning) can find invasion of other organs commonly the lung, liver, spleen, lymph nodes, brain, kidneys, and reproductive organs.

The earlier acute lymphocytic leukemia is detected, the more effective the treatment. The aim is to induce a lasting remission, defined as the absence of detectable cancer cells in the body (usually less than 5% blast cells in the bone marrow). Treatment for acute leukemia can include chemotherapy, steroids, radiation therapy, intensive combined treatments (including bone marrow or stem cell transplants), and growth factors.

Chemotherapy is the initial treatment of choice. Most ALL patients will receive a combination of different treatments. There are no surgical options, due to the body-wide distribution of the malignant cells. In general, cytotoxic chemotherapy for ALL combines multiple antileukemic drugs in various combinations. Chemotherapy for ALL consists of three phases: remission induction, intensification, and maintenance therapy.

As the chemotherapy regimens can be intensive and protracted (often about 2 years in case of the GMALL UKALL, HyperCVAD or CALGB protocols; for ALL about 3 years, 2 months for males on COG protocols; 2 years, 2 months for females—longer for males, as testicles are a potential reservoir), many patients have an intravenous catheter inserted into a large vein (termed a central venous catheter or a Hickman line), or a Portacath, a cone-shaped port with a silicone nose that is surgically planted under the skin, usually near the collar bone, and the most effective product available, due to low infection risks and the long-term viability of a portacath.

Radiation therapy (or radiotherapy) is used on painful bony areas, in high disease burdens, or as part of the preparations for a bone marrow transplant (total body irradiation). Radiation in the form of whole-brain radiation is also used for central nervous system prophylaxis, to prevent recurrence of leukemia in the brain. Whole-brain prophylaxis radiation used to be a common method in treatment of children's ALL. Recent studies showed that CNS chemotherapy provided results as favorable but with less developmental side-effects. As a result, the use of whole-brain radiation has been more limited. Most specialists in adult leukemia have abandoned the use of radiation therapy for CNS prophylaxis, instead using intrathecal chemotherapy.

For some subtypes of relapsed ALL, aiming at biological targets such as the proteasome, in combination with chemotherapy, has given promising results in clinical trials. Selection of biological targets on the basis of their combinatorial effects on the leukemic lymphoblasts can lead to clinical trials for improvement in the effects of ALL treatment. In ongoing clinical trials, a CD19-CD3 bi-specific monoclonal murine antibody—Blinatumomab, is showing great promise.

Chimeric antigen receptors (CARs) have been developed as a promising therapy for ALL. This technology uses a single chain variable fragment (scFv) designed to recognize the cell surface marker CD19 as a method of treating ALL. CD19 is a molecule found on all B-cells and can be used as a means of distinguishing the potentially malignant B-cell population in the patient. In this therapy, mice are immunized with the CD19 antigen and produce anti-CD19 antibodies. Hybridomas developed from the mouse spleen cells fused to a myeloma cell line can be developed as a source for the cDNA encoding the CD19 specific antibody. The cDNA is sequenced and the sequence encoding the variable heavy and variable light chains of these antibodies are cloned together using a small peptide linker. This resulting sequence encodes the scFv. This can be cloned into a transgene encoding what will become the endodomain of the CAR. There are varying arrangements of subunits used as the endodomain but they generally consist of the hinge region that attaches to the scFv, a transmembrane region, the intracellular region of a costimulatory molecule such as CD28, and the intracellular domain of CD3-zeta containing ITAM repeats. Other sequences frequently included are: 4-1bb and OX40. The final transgene sequence, containing the scFv and endodomain sequences is then inserted into immune effector cells that are obtained from the patient and expanded in vitro. In previous trials these have been a type of T-cell capable of cytotoxicity. Inserting the DNA into the effector cell can be accomplished by several methods. Most commonly, this is done using a lentivirus which encodes the transgene. Pseudotyped, self-inactivating lentiviruses have been shown to be an effective method for the stable insertion of a desired transgene into the target cell genomic DNA. Other methods include electroporation and transfection but these are limited in their efficacy as transgene expression will diminish over time. The gene-modified effector cells are then transplanted back into the patient. Typically this process is done in conjunction with a conditioning regiment such as cyclophosphamide which has been shown to potentiate the effects of infused T-cells. This effect has been attributed to the creation of an immunologic space niche. The process as a whole results in an effector cell, typically a T-cell that can recognize a tumor cell antigen in a major histocompatibility complex independent manner and initiate a cytotoxic response 4. Chronic Lymphoblastic Leukemia (CLL)

B-cell chronic lymphocytic leukemia (B-CLL), also known as chronic lymphoid leukemia (CLL), is the most common type of leukemia (a type of cancer of the white blood cells) in adults. CLL affects B cell lymphocytes, which originate in the bone marrow, develop in the lymph nodes, and normally fight infection by producing antibodies. In CLL, B cells grow out of control and accumulate in the bone marrow and blood, where they crowd out healthy blood cells. CLL is a stage of small lymphocytic lymphoma (SLL), a type of B-cell lymphoma, which presents primarily in the lymph nodes. CLL and SLL are considered the same underlying disease, just with different appearances. CLL is a disease of adults. Most (>75%) people newly diagnosed with CLL are over the age of 50, and the majority are men. However, in rare cases, it can occur in teenagers and occasionally in children. Some of these may relate to an inherited predisposition.

Most people are diagnosed without symptoms as the result of a routine blood test that returns a high white blood cell count, but, as it advances, CLL results in swollen lymph nodes, spleen, and liver, and eventually anemia and infections. Early CLL is not treated, and late CLL is treated with chemotherapy and monoclonal antibodies.

DNA analysis has distinguished two major types of CLL, with different survival times. CLL that is positive for the marker ZAP-70 has an average survival of 8 years, while CLL negative for ZAP-70 has an average survival of more than 25 years. Many patients, especially older ones, with slowly progressing disease can be reassured and may not need any treatment in their lifetimes.

Most people are diagnosed without symptoms as the result of a routine blood test that returns a high white blood cell count. Less commonly, CLL may present with enlarged lymph nodes without a high white blood cell count or no evidence of the disease in the blood. This is referred to as small lymphocytic lymphoma. In some individuals the disease comes to light only after the neoplastic cells overwhelm the bone marrow resulting in anemia producing tiredness or weakness.

CLL is usually first suspected by the presence of lymphocytosis, an increase in a type of white blood cell, on a complete blood count (CBC) test. This frequently is an incidental finding on a routine physician visit. Most often the lymphocyte count is greater than 4000 cells per microliter (A) of blood, but can be much higher. The presence of a lymphocytosis in an elderly individual should raise strong suspicion for CLL, and a confirmatory diagnostic test, in particular flow cytometry, should be performed unless clinically unnecessary.

The diagnosis of CLL is based on the demonstration of an abnormal population of B lymphocytes in the blood, bone marrow, or tissues that display an unusual but characteristic pattern of molecules on the cell surface. This atypical molecular pattern includes the coexpression of cells surface markers cluster of differentiation 5 (CD5) and cluster of differentiation 23 (CD23). In addition, all the CLL cells within one individual are clonal, that is, genetically identical. In practice, this is inferred by the detection of only one of the mutually exclusive antibody light chains, kappa or lambda, on the entire population of the abnormal B cells. Normal B lymphocytes consist of a stew of different antibody-producing cells, resulting in a mixture of both kappa and lambda expressing cells. The lack of the normal distribution of kappa and lambda producing B cells is one basis for demonstrating clonality, the key element for establishing a diagnosis of any B cell malignancy (B cell non-Hodgkin lymphoma).

The combination of the microscopic examination of the peripheral blood and analysis of the lymphocytes by flow cytometry to confirm clonality and marker molecule expression is needed to establish the diagnosis of CLL. Both are easily accomplished on a small amount of blood. A flow cytometer is an instrument that can examine the expression of molecules on individual cells in fluids. This requires the use of specific antibodies to marker molecules with fluorescent tags recognized by the instrument. In CLL, the lymphocytes are genetically clonal, of the B cell lineage (expressing marker molecules cluster of differentiation 19 (CD19) and CD20), and characteristically express the marker molecules CD5 and CD23. These B cells resemble normal lymphocytes under the microscope, although slightly smaller, and are fragile when smeared onto a glass slide, giving rise to many broken cells, which are called "smudge" or "smear" cells.

The Matutes's CLL score allows the identification of a homogeneous subgroup of classical CLL, that differs from atypical/mixed CLL for the five markers' expression (CD5, CD23, FMC7, CD22 and immunoglobulin light chain) Matutes's CLL scoring system is very helpful for the differential diagnosis between classical CLL and the other B cell chronic lymphoproliferative disorders, but not for the immunological distinction between mixed/atypical CLL and mantle cell lymphoma (MCL malignant B cells). Discrimination between CLL and MCL can be improved by adding non-routine markers such as CD54 and CD200. Among routine markers, the most discriminating feature is the CD20/CD23 mean fluorescence intensity ratio. In contrast, FMC7 expression can surprisingly be misleading for borderline cases.

Staging, determining the extent of the disease, is done with the Rai staging system or the Binet classification (see details) and is based primarily on the presence of a low platelet or red cell count. Early stage disease does not need to be treated.

CLL treatment focuses on controlling the disease and its symptoms rather than on an outright cure. CLL is treated by chemotherapy, radiation therapy, biological therapy, or bone marrow transplantation. Symptoms are sometimes treated surgically (splenectomy removal of enlarged spleen) or by radiation therapy ("de-bulking" swollen lymph nodes).

Initial CLL treatments vary depending on the exact diagnosis and the progression of the disease, and even with the preference and experience of the health care practitioner.

Dozens of agents are used for CLL therapy. An initial treatment regimen that contains fludarabine, cyclophosphamide, and rituximab (known as FCR) has demonstrated higher overall response rates and complete response rates.

A study carried out by the researchers at the University of Pennsylvania used genetically modified T cells to attack cells that expressed the CD19 protein to fight the disease. In 2013, the researchers announced that 26 of 59 patients had achieved complete remission and that the original patient had remained tumor-free.

Leukemia is rarely associated with pregnancy, affecting only about 1 in 10,000 pregnant women. Treatment for chronic lymphocytic leukemias can often be postponed until after the end of the pregnancy. If treatment is necessary, then giving chemotherapy during the second or third trimesters is less likely to result in pregnancy loss or birth defects than treatment during the first trimester.

While generally considered incurable, CLL progresses slowly in most cases. Many people with CLL lead normal and active lives for many years—in some cases for decades. Because of its slow onset, early-stage CLL is, in general, not treated since it is believed that early CLL intervention does not improve survival time or quality of life. Instead, the condition is monitored over time to detect any change in the disease pattern.

The decision to start CLL treatment is taken when the patient's clinical symptoms or blood counts indicate that the disease has progressed to a point where it may affect the patient's quality of life. Clinical "staging systems" such as the Rai 4-stage system and the Binet classification can help to determine when and how to treat the patient. Determining when to start treatment and by what means is often difficult; studies have shown there is no survival advantage to treating the disease too early. The National Cancer Institute Working Group has issued guidelines for treatment, with specific markers that should be met before it is initiated.

Combination chemotherapy regimens are effective in both newly diagnosed and relapsed CLL. Combinations of fludarabine with alkylating agents (cyclophosphamide) produce higher response rates and a longer progression-free survival than single agents:

FC (fludarabine with cyclophosphamide)
FR (fludarabine with rituximab)
FCR (fludarabine, cyclophosphamide, and rituximab)
CHOP (cyclophosphamide, doxorubicin, vincristine and prednisolone)

Although the purine analogue fludarabine was shown to give superior response rates to chlorambucil as primary therapy, there is no evidence early use of fludarabine improves overall survival, and some clinicians prefer to reserve fludarabine for relapsed disease.

Chemoimmunotherapy with FCR has shown to improve response rates, progression-free survival and overall survival in a large randomized trial in CLL patients selected for good physical fitness. This has been the first clinical trial demonstrating that the choice of a first line therapy can improve the overall survival of patients with CLL. Alkylating agents approved for CLL include bendamustine and cyclophosphamide.

Targeted therapy attacks cancer cells at a specific target, with the aim of not harming normal cells. Monoclonal antibodies, such as alemtuzumab (directed against CD52), and rituximab and ofatumumab (directed against CD20), are used in CLL. Tyrosine kinase inhibitor therapy can also be used in CLL. In February 2014, the FDA granted ibrutinib approval to treat chronic lymphocytic leukemia. Ibrutinib is a Bruton's tyrosine kinase (BTK) inhibitor. In July 2014, the FDA and EMA granted idelalisib approval to treat different types of leukemia. Idelalisib is a PI3K inhibitor that targets the PI3Kδ pathway. It is taken orally.

Autologous stem cell transplantation, using the recipient's own cells, is not curative. Younger individuals, if at high risk for dying from CLL, may consider allogeneic hematopoietic stem cell transplantation (HSCT). Myeloablative (bone marrow killing) forms of allogeneic stem cell transplantation, a high-risk treatment using blood cells from a healthy donor, may be curative, but treatment-related toxicity is significant. An intermediate level, called reduced-intensity conditioning allogeneic stem cell transplantation, may be better tolerated by older or frail patients.

"Refractory" CLL is a disease that no longer responds favorably to treatment. In this case, more aggressive therapies, including lenalidomide, flavopiridol, and bone marrow (stem cell) transplantation, are considered. The monoclonal antibody, alemtuzumab (directed against CD52), may be used in patients with refractory, bone marrow-based disease.

Complications include Richter's syndrome, hypogammaglobulinemia leading to recurrent infection, warm autoimmune hemolytic anemia in 10-15% of patients, transformation to high grade lymphoma. Chronic lymphocytic leukemia may transform into Richter's syndrome, the development of fast-growing diffuse large B cell lymphoma, prolymphocytic leukemia, Hodgkin's lymphoma, or acute leukemia in a patient who has chronic lymphocytic leukemia. Its incidence is estimated to be around 5 percent in patients with CLL.

Gastrointestinal (GI) involvement can rarely occur with chronic lymphocytic leukemia. Some of the reported manifestations include intussusception, small intestinal bacterial contamination, colitis and others. Usually, GI complications with CLL occur after Richter transformation. There have been two case reports to date of GI involvement in chronic lymphocytic leukemia without Richter's transformation.

5. Non-Small Cell Lung Cancer

Non-small-cell lung carcinoma (NSCLC) is any type of epithelial lung cancer other than small cell lung carcinoma (SCLC). As a class, NSCLCs are relatively insensitive to chemotherapy, compared to small cell carcinoma. When possible, they are primarily treated by surgical resection with curative intent, although chemotherapy is increasingly being used both pre-operatively (neoadjuvant chemotherapy) and post-operatively (adjuvant chemotherapy).

The most common types of NSCLC are squamous cell carcinoma, large cell carcinoma, and adenocarcinoma, but there are several other types that occur less frequently, and all types can occur in unusual histologic variants and as mixed cell-type combinations. Sometimes the phrase "non-small-cell lung cancer" ("not otherwise specified", or NOS) is used generically, usually when a more specific diagnosis cannot be made. This is most often the case when a pathologist examines a small amount of malignant cells or tissue in a cytology or biopsy specimen.

Lung cancer in never-smokers is almost universally NSCLC, with a sizeable majority being adenocarcinoma. On relatively rare occasions, malignant lung tumors are found to contain components of both SCLC and NSCLC. In these cases, the tumors should be classified as combined small cell lung carcinoma (c-SCLC), and are (usually) treated like "pure" SCLC.

Adenocarcinoma of the lung is currently the most common type of lung cancer in "never smokers" (lifelong non-smokers). Adenocarcinomas account for approximately 40% of lung cancers. Historically, adenocarcinoma was more often seen peripherally in the lungs than small cell lung cancer and squamous cell lung cancer, both of which tended to be more often centrally located. Interestingly, however, recent studies suggest that the "ratio of centrally-to-peripherally occurring" lesions may be converging toward unity for both adenocarcinoma and squamous cell carcinoma.

Squamous cell carcinoma (SCC) of the lung is more common in men than in women. It is closely correlated with a history of tobacco smoking, more so than most other types of lung cancer. According to the Nurses' Health Study, the relative risk of SCC is approximately 5.5, both among those with a previous duration of smoking of 1 to 20 years, and those with 20 to 30 years, compared to never-smokers. The relative risk increases to approximately 16 with a previous smoking duration of 30 to 40 years, and approximately 22 with more than 40 years.

Large cell lung carcinoma (LCLC) is a heterogeneous group of undifferentiated malignant neoplasms originating from transformed epithelial cells in the lung. LCLC's have typically comprised around 10% of all NSCLC in the past, although newer diagnostic techniques seem to be reducing the incidence of diagnosis of "classic" LCLC in favor of more poorly differentiated squamous cell carcinomas and adenocarcinomas. LCLC is, in effect, a "diagnosis of exclusion", in that the tumor cells lack light microscopic characteristics that would classify the neoplasm as a small-cell carcinoma, squamous-cell carcinoma, adenocarcinoma, or other more specific histologic type of lung cancer. LCLC is differentiated from small cell lung carcinoma (SCLC) primarily by the larger size of the anaplastic cells, a higher cytoplasmic-to-nuclear size ratio, and a lack of "salt-and-pepper" chromatin.

More than one kind of treatment is often used, depending on the stage of the cancer, the individual's overall health, age, response to chemotherapy, and other factors such as the likely side effects of the treatment. NSCLCs are usually not very sensitive to chemotherapy and/or radiation, so surgery is the treatment of choice if diagnosed at an early stage, often with adjuvant (ancillary) chemotherapy involving cisplatin. Other treatment choices are chemotherapy, radiation therapy (radiotherapy), and targeted therapy.

New methods of giving radiation treatment allow doctors to be more accurate in treating lung cancers. This means less radiation affects nearby healthy tissues. New methods include Cyberknife and stereotactic radiosurgery (SRS). Other treatments are radiofrequency ablationand chemoembolization.

A wide variety of chemotherapies are used in advanced (metastatic) NSCLC. Some patients with particular mutations in the EGFR gene respond to EGFR tyrosine kinase inhibitors such as gefitinib. About 7% of NSCLC have EML4-ALK translocations; these may benefit from ALK inhibitors which are in clinical trials. Crizotinib gained FDA approval in August 2011.

6. Gastric Cancer

Stomach cancer or gastric cancer is cancer developing from the lining of the stomach. Early symptoms may include heartburn, upper abdominal pain, nausea and loss of appetite. Later signs and symptoms may include weight loss, yellow skin, vomiting, difficulty swallowing, and blood in the stool among others. The cancer may spread from the stomach to other parts of the body, particularly the liver, lungs, bones, lining of the abdomen and lymph nodes. The prognosis of stomach cancer is generally poor, due to the fact the tumor has often metastasized by the time of discovery and the fact that most people with the condition are elderly (median age is between 70 and 75 years) at presentation. The 5-year survival rate for stomach cancer is reported to be less than 10%.

The most common cause is infection by the bacteria *Helicobacter pylori*, which accounts for more than 60% of cases. Certain types of *H. pylori* have greater risks than others. Other common causes include eating pickled vegetables and smoking. About 10% of cases run in families and between 1% and 3% of cases are due to genetic syndromes inherited from a person's parents such as hereditary diffuse gastric cancer. Most cases of stomach cancers are gastric carcinomas. This type can be divided into a number of subtypes. Lymphomas and mesenchymal tumors may also develop within the stomach. Most of the time, stomach cancer develops through a number of stages over a number of years. Diagnosis is usually by biopsy done during endoscopy. This is then followed by medical imaging to determine if the disease has spread to other parts of the body. Japan and South Korea, two countries that have high rates of disease, screen for stomach cancer.

A Mediterranean diet lowers the risk of cancer as does the stopping of smoking. There is tentative evidence that treating *H. pylori* decreases the future risk. If cancer is treated early, many cases can be cured. Treatments may include some combination of surgery, chemotherapy, radiation therapy, and targeted therapy. If treated late, palliative care may be advised. Outcomes are often poor with a less than 10% 5-year survival rate globally. This is largely because most people with the condition present with advanced disease. In the United States 5-year survival is 28% while in South Korea it is over 65% partly due to screening efforts.

Globally stomach cancer is the fifth leading cause of cancer and the third leading cause of death from cancer making up 7% of cases and 9% of deaths. In 2012 it occurred in 950,000 people and caused 723,000 deaths. Before the 1930s in much of the world, including the United States and the United Kingdom, it was the most common cause of death from cancer. Rates of death have been decreasing in many areas of the world since then. This is believed to be due to the eating of less salted and pickled foods as a result of the development of refrigeration as a method of keeping food fresh. Stomach cancer occurs most commonly in East Asia and Eastern Europe and it occurs twice as often in males as in females.

Stomach cancer is often either asymptomatic (producing no noticeable symptoms) or it may cause only nonspecific symptoms (symptoms that are specific not only to stomach cancer, but also to other related or unrelated disorders) in its early stages. By the time symptoms occur, the cancer has often reached an advanced stage (see below) and may have also metastasized (spread to other, perhaps distant, parts of the body), which is one of the main reasons for its relatively poor prognosis. Early cancers may be associated with indigestion or a burning sensation (heartburn). However, less than 1 in every 50 people referred for endoscopy due to indigestion has cancer. Abdominal discomfort and loss of appetite, especially for meat, can occur.

Gastric cancers that have enlarged and invaded normal tissue can cause weakness, fatigue, bloating of the stomach after meals, abdominal pain in the upper abdomen, nausea and occasional vomiting, diarrhea or constipation. Further enlargement may cause weight loss or bleeding with vomiting blood or having blood in the stool, the latter apparent as black discolouration (melena) and sometimes leading to anemia. Dysphagia suggests a tumour in the cardia or extension of the gastric tumor into the esophagus.

Gastric cancer is a multifactorial disease. *Helicobacter pylori* infection is an essential risk factor in 65-80% of gastric cancers, but in only 2% of such infections. The mechanism by which *H. pylori* induces stomach cancer potentially involves chronic inflammation, or the action of *H. pylori* virulence factors such as CagA. Smoking increases the risk of developing gastric cancer significantly, from 40% increased risk for current smokers to 82% increase for heavy smokers. Gastric cancers due to smoking mostly occur in the upper part of the stomach near the esophagus. Some studies show increased risk with alcohol consumption as well.

Dietary factors are not proven causes, but some foods including smoked foods, salt and salt-rich foods, red meat, processed meat, pickled vegetables, and bracken are associated with a higher risk of stomach cancer. Nitrates and nitrites in cured meats can be converted by certain bacteria, including *H. pylori*, into compounds that have been found to cause stomach cancer in animals. On the other hand, fresh fruit and vegetable intake, citrus fruit intake, and antioxidant intake are associated with a lower risk of stomach cancer. A Mediterranean diet is also associated with lower rates of stomach cancer as does regular aspirin use.

There is a correlation between iodine deficiency and gastric cancer. Gastric cancer shows a male predominance in its incidence as up to two males are affected for every female. Estrogen may protect women against the development of this cancer form. Approximately 10% of cases show a genetic component.

People may possess certain risk factors, such as those that are physical or genetic, that can alter their susceptibility for gastric cancer. Obesity is one such physical risk factor that has been found to increase the risk of gastric adenocarcinoma by contributing to the development of gastroesophageal reflux disease (GERD). The exact mechanism by which obesity causes GERD is not completely known. Studies hypothesize that increased dietary fat leading to increased pressure on the stomach and the lower esophageal sphincter, due to excess adipose tissue, could play a role, yet no statistically significant data has been collected. However, the risk of gastric cardia adenocarcinoma, with GERD present, has been found to increase more than 2 times for an obese person. A genetic risk factor for gastric cancer is a genetic defect of the CDH1 gene known as hereditary diffuse gastric cancer (HDGC). The CDH1 gene, which codes for E-cadherin, lies on the 16th chromosome. When the gene experiences a particular mutation, gastric cancer develops through a mechanism that is not fully understood. This mutation is considered autosomal dominant meaning that half of a carrier's children will likely experience the same mutation. Diagnosis of hereditary diffuse gastric cancer usually takes place when at least two cases involving a family member, such as a parent or grandparent, are diagnosed, with at least one diagnosed before the age of 50. The diagnosis can also be made if there are at least three cases in the family, in which case age is not considered.

The International Cancer Genome Consortium is leading efforts to identify genomic changes involved in stomach cancer. A very small percentage of diffuse-type gastric cancers (see Histopathology below) arise from an inherited abnormal CDH1 gene. Genetic testing and treatment options are available for families at risk.

Other factors associated with increased risk are AIDS, diabetes, pernicious anemia, chronic atrophic gastritis, Menetrier's disease (hyperplastic, hypersecretory gastropathy), and intestinal metaplasia.

To find the cause of symptoms, the doctor asks about the patient's medical history, does a physical exam, and may order laboratory studies. Gastroscopic exam is the diagnostic method of choice. This involves insertion of a fibre optic camera into the stomach to visualize it. Upper GI series (may be called barium roentgenogram). Computed tomography or CT scanning of the abdomen may reveal gastric cancer, but is more useful to determine invasion into adjacent tissues, or the presence of spread to local lymph nodes. Wall thickening of more than 1 cm that is focal, eccentric and enhancing favours malignancy.

Abnormal tissue seen in a gastroscope examination will be biopsied by the surgeon or gastroenterologist. This tissue is then sent to a pathologist for histological examination under a microscope to check for the presence of cancerous cells. A biopsy, with subsequent histological analysis, is the only sure way to confirm the presence of cancer cells.

Various gastroscopic modalities have been developed to increase yield of detected mucosa with a dye that accentuates the cell structure and can identify areas of dysplasia. Endocytoscopy involves ultra-high magnification to visualise cellular structure to better determine areas of dysplasia. Other gastroscopic modalities such as optical coherence tomography are also being tested investigationally for similar applications.

A number of cutaneous conditions are associated with gastric cancer. A condition of darkened hyperplasia of the skin, frequently of the axilla and groin, known as acanthosis *nigricans*, is associated with intra-abdominal cancers such as gastric cancer. Other cutaneous manifestations of gastric cancer include tripe palms (a similar darkening hyperplasia of the skin of the palms) and the Leser-Trelat sign, which is the rapid development of skin lesions known as seborrheic keratoses. Various blood tests may be performed including a complete blood count (CBC) to check for anaemia, and a fecal occult blood test to check for blood in the stool.

Getting rid of *H. pylori* in those who are infected decreases the risk of stomach cancer, at least in those who are Asian. Low doses of vitamins, especially from a healthy diet, decrease the risk of stomach cancer. A previous review of supplementation did not find supporting evidence and possibly worse outcomes.

Cancer of the stomach is difficult to cure unless it is found at an early stage (before it has begun to spread). Unfortunately, because early stomach cancer causes few symptoms, the disease is usually advanced when the diagnosis is made. Treatment for stomach cancer may include surgery, chemotherapy, and/or radiation therapy. New treatment approaches such as biological therapy and improved ways of using current methods are being studied in clinical trials.

Surgery remains the only curative therapy for stomach cancer. Of the different surgical techniques, endoscopic mucosal resection (EMR) is a treatment for early gastric cancer (tumor only involves the mucosa) that has been pioneered in Japan, but is also available in the United States at some centers. In this procedure, the tumor, together with the inner lining of stomach (mucosa), is removed from the wall of the stomach using an electrical wire loop through the endoscope. The advantage is that it is a much smaller operation than removing the stomach. Endoscopic submucosal dissection (ESD) is a similar technique pioneered in Japan, used to resect a large area of mucosa in one piece. If the pathologic examination of the resected specimen shows incomplete resection or deep invasion by tumor, the patient would need a formal stomach resection.

Those with metastatic disease at the time of presentation may receive palliative surgery and while it remains controversial, due to the possibility of complications from the surgery itself and the fact that it may delay chemotherapy the data so far is mostly positive, with improved survival rates being seen in those treated with this approach.

The use of chemotherapy to treat stomach cancer has no firmly established standard of care. Unfortunately, stomach cancer has not been particularly sensitive to these drugs, and chemotherapy, if used, has usually served to palliatively reduce the size of the tumor, relieve symptoms of the disease and increase survival time. Some drugs used in stomach cancer treatment have included: 5-FU (fluorouracil) or its analog capecitabine, BCNU (carmustine), methyl-CCNU (semustine) and doxorubicin (Adriamycin), as well as mitomycin C, and more recently cisplatin and taxotere, often using drugs in various combinations. The relative benefits of these different drugs, alone and in combination, are unclear. Clinical researchers have explored the benefits of giving chemotherapy before surgery to shrink the tumor, or as adjuvant therapy after surgery to destroy remaining cancer cells. Recently, a targeted treatment called trastuzumab has become available for use with chemotherapy for the treatment of those overexpressing the HER2 gene in their tumor cells.

Radiation therapy (also called radiotherapy) may also be used to treat stomach cancer, often as an adjuvant to chemotherapy and/or surgery.

7. Administration of Antibodies

In some embodiments, the present disclosure provides methods of treating a LAIR1 associated condition in a subject, comprising administering to the subject a therapeutically effective amount of the monoclonal antibody or antigen-binding fragment thereof provided herein. In certain embodiments, the present disclosure provides methods of preventing, detecting, or diagnosing LAIR1 associated condition, comprising contacting the monoclonal antibody or the antigen-binding fragments thereof provided herein with a biological sample obtained from a subject suspect of or having or at risk of having the LAIR1 associated condition and determining the level of LAIR1 antibody or the antigen-binding fragments thereof that binds to LAIR1 in the biological sample.

The therapeutically effective amount (when used alone or in combination with other agents such as chemotherapeutic agents) of an antibody or antigen-binding fragment thereof provided herein will depend on various factors known in the art, such as for example type of disease to be treated, the type of antibody, body weight, age, past medical history, present medications, state of health of the subject, immune condition and potential for cross-reaction, allergies, sensitivities and adverse side-effects, as well as the administration route and the type, the severity and development of the disease and the discretion of the attending physician or veterinarian. In certain embodiments, the monoclonal antibody or antigen-binding fragment thereof provided herein may be administered at a therapeutically effective dosage of about 0.001 mg/kg to about 100 mg/kg one or more times per day (e.g., about 0.001 mg/kg, about 0.3 mg/kg, about 0.5 mg/kg, about 1 mg/kg, about 3 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg one or more times per day). In certain embodiments, the monoclonal antibody or antigen-binding fragment thereof is administered at a dosage of about 50 mg/kg or less, and in certain embodiments the dosage is 20 mg/kg or less, 10 mg/kg or less, 3 mg/kg or less, 1 mg/kg or less, 0.3 mg/kg or less, 0.1 mg/kg or less, or 0.01 mg/kg or less, or 0.001 mg/kg or less. In certain embodiments, the administration dosage may change over the course of treatment. For example, in certain embodiments the initial administration dosage may be higher than the subsequent administration dosages. In certain embodiments, the administration dosage may vary over the course of treatment depending on the reaction of the subject.

Dosage regimens may be adjusted to provide the optimum desired response (e.g., a therapeutic response). In certain embodiments, the monoclonal antibody or antigen-binding fragment thereof provided herein is administered to the subject at one time or over a series of treatments. In certain embodiments, the monoclonal antibody or antigen-binding fragment thereof provided herein is administered to the subject by one or more separate administrations, or by continuous infusion depending on the type and severity of the disease. Guidance can be found in for example, U.S. Pat. Nos. 4,657,760; 5,206,344; 5,225,212.

The monoclonal antibody and antigen-binding fragments provided herein may be administered by any route known in the art, such as for example parenteral (e.g., subcutaneous, intraperitoneal, intravenous, including intravenous infusion, intramuscular, or intradermal injection) or non-parenteral (e.g., oral, intranasal, intraocular, sublingual, rectal, or topical) routes.

In certain embodiments, the monoclonal antibody and antigen-binding fragments thereof provided herein may be administered in a controlled-release manner. A controlled-release parenteral preparations can be made as implants, oily injections or particulate systems (e.g. microspheres, microparticles, microcapsules, nanocapsules, nanospheres, and nanoparticles) (see Banga, A. J., Therapeutic Peptides and Proteins: Formulation, Processing, and Delivery Systems, Technomic Publishing Company, Inc., Lancaster, Pa., (1995); Kreuter, J., Colloidal Drug Delivery Systems, J. Kreuter, ed., Marcel Dekker, Inc., New York, N.Y., pp. 219-342 (1994); Tice & Tabibi, Treatise on Controlled Drug Delivery, A. Kydonieus, ed., Marcel Dekker, Inc. New York, N.Y., pp. 315-339, (1992)). In certain embodiments, the monoclonal antibody and antigen-binding fragments thereof disclosed herein may be administered in degradable or nondegradable polymeric matrices (see Langer, *Accounts Chem. Res.* 26:537-542, 1993).

Conditions associated with LAIR1 can be immune related diseases or disorders, infections, and cancers. In certain embodiments, the condition is solid tumors, hematological disorders, infectious diseases, autoimmune diseases or fibrotic diseases. In certain embodiments, the solid tumors include, for example, non-small cell lung cancer (squamous/nonsquamous), small cell lung cancer, renal cell cancer, colorectal cancer, colon cancer, ovarian cancer, breast cancer (including basal breast carcinoma, ductal carcinoma and lobular breast carcinoma), pancreatic cancer, gastric carcinoma, bladder cancer, esophageal cancer, mesothelioma, melanoma, head and neck cancer, thyroid cancer, sarcoma, prostate cancer, glioblastoma, cervical cancer, thymic carcinoma, melanoma, myelomas, mycoses fungoids, merkel cell cancer, hepatocellular carcinoma (HCC), fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, lymphoid malignancy, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, hepatoma, bile duct carcinoma, choriocarcinoma, Wilms' tumor, cervical cancer, testicular tumor, seminoma. In certain embodiments, the hematologic disorders include, for example, classical Hodgkin lymphoma (CHL), primary mediastinal large B-cell lymphoma, T-cell/histiocyte-rich B-cell lymphoma, acute lymphocytic leukemia (ALL), acute myelocytic leukemia, acute myelogenous leukemia and myeloblastic, promyelocytic, myelomonocytic, monocytic leukemia and erythroleukemia, chronic myelocytic (granulocytic) leukemia, chronic myelogenous leukemia, chronic lymphocytic leukemia, polycythemia vera, mast cell derived tumors, EBV-positive and -negative PTLD, and diffuse large B-cell lymphoma (DLBCL), plasmablastic lymphoma, extranodal NK/T-cell lymphoma, nasopharyngeal carcinoma, and HHV8-associated primary effusion lymphoma, non-Hodgkin's lymphoma, multiple myeloma, Waldenstrom's macroglobulinemia, heavy chain disease, myelodysplastic syndrome, hairy cell leukemia and myelodysplasia, neoplasm of the central nervous system (CNS), such as primary CNS lymphoma, spinal axis tumor, brain stem glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma. In certain embodiments, the cancer is acute myeloid leukemia (AML).

In some embodiments, the monoclonal antibody or antigen-binding fragment thereof provided herein can be administered alone or in combination with one or more additional therapeutic agents or means. For example, the monoclonal antibody or antigen-binding fragments thereof provided herein may be administered in combination with a second therapy, such as radiation therapy, chemotherapy, targeted therapies, gene therapy, immunotherapy, hormonal therapy, angiogenesis inhibition, palliative care, surgery for the treatment of cancer (e.g., tumorectomy), one or more anti-emetics or other treatments for complications arising from chemotherapy, or a second therapeutic agent for use in the treatment of cancer or any medical disorder mediated by LAIR1, for example, another antibody, therapeutic polynucleotide, chemotherapeutic agent(s), anti-angiogenic agent, cytokines, other cytotoxic agent(s), growth inhibitory agent(s). In certain of these embodiments, the monoclonal antibody or antigen-binding fragment thereof provided herein may be administered simultaneously with the one or more additional therapeutic agents, and in certain of these embodiments the monoclonal antibody or antigen-binding fragment thereof and the additional therapeutic agent(s) may be administered as part of the same pharmaceutical composition. However, an antibody or antigen-binding fragment thereof administered "in combination" with another therapeutic agent does not have to be administered simultaneously with or in the same composition as the agent. An antibody or antigen-binding fragment thereof administered prior to or after another agent is considered to be administered "in combination" with that agent as the phrase is used herein, even if the antibody or antigen-binding fragment and second agent are administered via different routes. Where possible, additional therapeutic agents administered in combination with the monoclonal antibody or antigen-binding fragments thereof provided herein are administered according to the schedule listed in the product information sheet of the additional therapeutic agent, or according to the Physicians' Desk Reference 2003 (Physicians' Desk Reference, 57th Ed; Medical Economics Company; ISBN: 1563634457; 57th edition (November 2002)) or protocols well known in the art.

H. Combination Therapies

It may also be desirable to provide combination treatments using antibodies of the present disclosure in conjunction with additional anti-cancer therapies. These therapies would be provided in a combined amount effective to achieve a reduction in one or more disease parameter. This process may involve contacting the cells/subjects with the both agents/therapies at the same time, e.g., using a single composition or pharmacological formulation that includes both agents, or by contacting the cell/subject with two distinct compositions or formulations, at the same time, wherein one composition includes the antibody and the other includes the other agent.

Alternatively, the antibody may precede or follow the other treatment by intervals ranging from minutes to weeks. One would generally ensure that a significant period of time did not expire between the time of each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 12 hours. In some situations, it may be desirable to extend the time period for treatment significantly; however, where several 10 days (2, 3, 4, 5, 6 or 7) to several weeks (1, 2, 3, 4, 5, 6, 7 or 8) lapse between the respective administrations.

It also is conceivable that more than one administration of either the antibody or the other therapy will be desired. Various combinations may be employed, where the antibody is "A," and the other therapy is "B," as exemplified below:

| A/B/A | B/A/B | B/B/A | A/A/B | B/A/A | A/B/B |
|-------|-------|-------|-------|-------|-------|
| B/B/B/A | B/B/A/B | A/A/B/B | A/B/A/B | A/B/B/A | B/B/A/A |
| B/A/B/A | B/A/A/B | B/B/B/A | A/A/A/B | B/A/A/A | A/B/A/A |
| A/A/B/A | A/B/B/B | B/A/B/B | B/B/A/B | | |

Other combinations are contemplated. To kill cells, inhibit cell growth, inhibit metastasis, inhibit angiogenesis or otherwise reverse or reduce the malignant phenotype of tumor cells, using the methods and compositions of the present invention, one may contact a target cell or site with an antibody and at least one other therapy. These therapies would be provided in a combined amount effective to kill or inhibit proliferation of cancer cells. This process may involve contacting the cells/site/subject with the agents/therapies at the same time.

Particular agents contemplated for combination therapy with antibodies of the present disclosure include chemotherapy and hematopoietic stem cell transplantation. Chemotherapy may include cytarabine (ara-C) and an anthracycline (most often daunorubicin), high-dose cytarabine alone, all-trans-retinoic acid (ATRA) in addition to induction chemotherapy, usually an anthracycline, histamine dihydrochloride (Ceplene®; histamine dihydrochloride) and interleukin 2 (Proleukin®; aldesleukin) after the completion of consolidation therapy, gemtuzumab ozogamicin (Mylotarg®; gemtuzumab ozogamicin) for patients aged more than 60 years with relapsed AML who are not candidates for high-dose chemotherapy, clofarabine, as well as targeted therapies, such as kinase inhibitors, farnesyl transferase inhibitors, decitabine, and inhibitors of MDR1 (multidrug-resistance protein), or arsenic trioxide or relapsed acute promyelocytic leukemia (APL).

In certain embodiments, the agents for combination therapy are selected from the groups consisting of an anthracycline topoisomerase inhibitor, a daunorubicin, a nucleoside metabolic inhibitor, a cytarabine, a combination of daunorubicin and cytarabine, a daunorubicin and cytarabine liposome for injection, Vyxeos, an all-trans-retinoic acid (ATRA), an arsenic, an arsenic trioxide, a histamine dihydrochloride, Ceplene® (histamine dihydrochloride), an interleukin-2, Proleukin® (aldesleukin), a gemtuzumab ozogamicin, Mylotarg® (gemtuzumab ozogamicin), a clofarabine, a farnesyl transferase inhibitor, a decitabine, an IDH1 inhibitor, an IDH2 inhibitor, an enasidenib, Idhifa, an IDO inhibitor, an epacadostat, a platinum complex derivative, oxaliplatin, a kinase inhibitor, a tyrosine kinase inhibitor, a PI3 kinase inhibitor, a BTK inhibitor, ibrutinib, a PD-1 antibody, a PD-L1 antibody, a CTLA-4 antibody, a LAG3 antibody, an ICOS antibody, a TIGIT antibody, a TIM3 antibody, an antibody binding to a tumor antigen, an antibody binding to a T-cell surface marker, an antibody binding to a myeloid cell or NK cell surface marker, an alkylating agent, a nitrosourea agent, an antimetabolite, an antitumor antibiotic, an alkaloid derived from a plant, a topoisomerase inhibitor, a hormone therapy medicine, a hormone antagonist, an aromatase inhibitor, and a P-glycoprotein inhibitor.

I. Treatment of Immune Disorders

In another aspect, the present disclosure provides methods of using the antibodies or the antigen-binding fragment thereof as disclosed herein to treat immune disorders, including without limitation, inflammation, autoimmune diseases and transplant rejections.

1. Inflammation and Autoimmune Diseases

An autoimmune disease, as used herein, refers to a condition arising from an abnormal immune response to a normal body part. There are more than 80 illnesses caused by autoimmune diseases. Nearly any body part can be involved. Autoimmune diseases have a wide variety of different effects, including damage to or destruction of tissues, altered organ growth and altered organ function. About 24 million (7%) people in the United States are affected by an autoimmune disease.

Some common diseases that are considered as an autoimmune disease or inflammation in nature include rheumatoid arthritis, systemic lupus erythematosus, alopecia areata, ankylosing spondylitis, antiphospholipid syndrome, autoimmune Addison's disease, autoimmune hemolytic anemia, autoimmune hepatitis, autoimmune inner ear disease, autoimmune lymphoproliferative syndrome (ALPS), autoimmune thrombocytopenic purpura (ATP), Behcet's disease, bullous pemphigoid, cardiomyopathy, celiac disease, celiac sprue-dermatitis, chronic fatigue immune deficiency syndrome (CFIDS), chronic inflammatory demyelinating polyneuropathy, cicatricial pemphigoid, cold agglutinin disease, Crest syndrome, Crohn's disease, Dego's disease, dermatomyositis, dermatomyositis juvenile, discoid lupus, essential mixed cryoglobulinemia, fibromyalgia-fibromyositis, grave's disease, Guillain-Barre, Hashimoto's thyroiditis, idiopathic pulmonary fibrosis, idiopathic thrombocytopenia purpura (ITP), IgA nephropathy, inflammatory bowel disease, insulin dependent diabetes (or Type I diabetes), juvenile arthritis, Meniere's disease, mixed connective tissue disease, multiple sclerosis, myasthenia gravis, pemphigus vulgaris, pernicious anemia, polyarteritis nodosa, polychondritis, polyglancular syndromes, polymyalgia rheumatic, polymyositis and dermatomyositis, primary biliary cirrhosis, psoriasis, Raymond's phenomenon, Reiter's syndrome, rheumatic fever, rheumatoid arthritis, sarcoidosis, scleroderma, Sjogren's syndrome, stiff-man syndrome, systemic lupus erythematosus, Takayasu arteritis, temporal arteritis/giant cell arteritis, ulcerative colitis, uveitis, vitiligo, and Wegener's granulomatosis.

Rheumatoid arthritis is a long-term autoimmune disease that primarily affects joints, typically resulting in warm, swollen and painful joints. Other symptoms include low red blood cell count, inflammation around the lungs and the heart, fever and low energy. While the cause of rheumatoid arthritis is not clear, it is believed to involve a combination of genetic and environment factors. The underlying mechanism involves the body's immune system mistakenly attacking the joints, resulting in inflammation and thickening of the joint capsule and also affecting the underlying bone and cartilage.

Systemic lupus erythematosus, also known as lupus, is an disease in which the body's immune system mistakenly attacks healthy tissues in many parts of the body. Common symptoms include panful and swollen joints, fever, chest pain, hair loss, mouth ulcers, swollen lymph nodes, feeling tired, and a red rash most commonly on the face. While the cause of lupus is still unknown, it may involve both genetic and environmental factors. The mechanism of lupus involves an immune response by autoantibodies against a person's own tissues, which are most commonly anti-nuclear antibodies that result in inflammation.

Type 1 diabetes is a form of diabetes mellitus in which not enough insulin is produced, which results in high blood sugar levels in the body. The symptoms of type 1 diabetes include frequent urination, increased thirst, increased hunger, weight loss, blurry vision, feeling tired and poor healing. While the cause of type 1 diabetes is unknown, the underlying mechanism involves an autoimmune destruction of the insulin-producing beta cells in the pancreas.

Multiple sclerosis is an autoimmune disease in which the insulating covers of nerve cells in the brain and spinal cord are damaged by a person's own immune system. The damage disrupts the ability of the nervous system to communicate, causing a range of symptoms including double vision, blindness in one eye, muscle weakness, trouble with sensation, or trouble with coordination. While the cause is not clear, the underlying mechanism of multiple sclerosis is thought to be destruction by the immune system. Proposed cause include genetic and environment factors.

While autoimmune diseases are pervasive, their cause is generally unclear. The human adaptive immune system, including both T cells and B cells, is capable of being reactive with self-antigens. But these self-reactive T cells and B cells are usually either killed prior to becoming active within the immune system, placed into a state of anergy, or removed from their role within the immune system by regulatory cells. When any one of these mechanisms fail, some self-reactive cells may become functional within the immune system and cause autoimmune diseases.

2. Transplant Rejection

Transplant rejection occurs when grafted tissue is rejected by the recipient's immune system, which destroys the grafted tissue. The underlying mechanism of rejection involves a combination of an adaptive immune response via cellular immunity which is mediated by killer T cells and humoral immunity mediated by activated B cells. Some components of innate immune response, such as phagocytes and soluble immune protein, may also be involved.

Acute transplant rejection may be treated with immunosuppressive therapy. Immunosuppressive drugs include corticosteroids, such as prednisolone and hydrocortisone, calcineurin inhibitors and mTOR inhibitors. Antibody specific to select immune components can also be used in immunosuppressive therapy.

J. Immunodetection Methods

In still further embodiments, the present disclosure concerns immunodetection methods for binding, purifying, removing, quantifying and otherwise generally detecting LAIR-related cancers. While such methods can be applied in a traditional sense, another use will be in quality control and monitoring of vaccine and other virus stocks, where antibodies according to the present disclosure can be used to assess the amount or integrity (i.e., long term stability) of H1 antigens in viruses. Alternatively, the methods may be used to screen various antibodies for appropriate/desired reactivity profiles.

Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of LAIR1 also is provided. The steps of various useful immunodetection methods have been described in the scientific literature, such as, e.g., Doolittle and Ben-Zeev (1999), Gulbis and Galand (1993), De Jager et al. (1993), and Nakamura et al. (1987). In general, the immunobinding methods include obtaining a sample suspected of containing LAIR1-related cancers, and contacting the sample with a first antibody in accordance with the present disclosure, as the case may be, under conditions effective to allow the formation of immunocomplexes.

These methods include methods for detecting or purifying LAIR1 or LAIR1-related cancer cells from a sample. The antibody will preferably be linked to a solid support, such as in the form of a column matrix, and the sample suspected of containing the LAIR1-related cancer cells will be applied to the immobilized antibody. The unwanted components will be washed from the column, leaving the LAIR1-expressing cells immunocomplexed to the immobilized antibody, which is then collected by removing the organism or antigen from the column.

The immunobinding methods also include methods for detecting and quantifying the amount of LAIR1-related cancer cells or related components in a sample and the detection and quantification of any immune complexes formed during the binding process. Here, one would obtain a sample suspected of containing LAIR1-related cancer cells, and contact the sample with an antibody that binds LAIR1 or components thereof, followed by detecting and quantifying the amount of immune complexes formed under the specific conditions. In terms of antigen detection, the biological sample analyzed may be any sample that is suspected of containing LAIR1-related cancers, such as a tissue section or specimen, a homogenized tissue extract, a biological fluid, including blood and serum, or a secretion, such as feces or urine.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to LAIR1. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

1. ELISAs

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the disclosure are immobilized onto a selected surface exhibiting protein affinity, such as a well in a polystyrene microtiter plate. Then, a test composition suspected of containing the LAIR1-related cancer cells is added to the wells. After binding and washing to remove non-specifically bound immune complexes, the bound antigen may be detected. Detection may be achieved by the addition of another anti-LAIR1 antibody that is linked to a detectable label. This type of ELISA is a simple "sandwich ELISA." Detection may also be achieved by the addition of a second anti-LAIR1 antibody, followed by the addition of a third antibody that has binding affinity for the second antibody, with the third antibody being linked to a detectable label.

In another exemplary ELISA, the samples suspected of containing the LAIR1-related cancer cells are immobilized onto the well surface and then contacted with the anti-LAIR1 antibodies of the disclosure. After binding and washing to remove non-specifically bound immune complexes, the bound anti-LAIR1 antibodies are detected. Where the initial anti-LAIR1 antibodies are linked to a detectable label, the immune complexes may be detected directly. Again, the immune complexes may be detected using a second antibody that has binding affinity for the first anti-LAIR1 antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

2. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus Western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF, but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

3. Immunohistochemistry

The antibodies of the present disclosure may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

4. Immunodetection Kits

In still further embodiments, the present disclosure concerns immunodetection kits for use with the immunodetection methods described above. As the antibodies may be used to detect LAIR1-related cancer cells, the antibodies may be included in the kit. The immunodetection kits will thus comprise, in suitable container means, a first antibody that binds to an LAIR1, and optionally an immunodetection reagent.

In certain embodiments, the antibody may be pre-bound to a solid support, such as a column matrix and/or well of a microtitre plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present disclosure.

The kits may further comprise a suitably aliquoted composition of LAIR1, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present disclosure will also typically include a means for containing the antibody, antigen, and any other reagent containers in close confinement for commercial sale. Such containers may include injection or blow-molded plastic containers into which the desired vials are retained.

K. Examples

The following examples are included to demonstrate preferred embodiments. It should be appreciated by those of skill in the art that the techniques disclosed in the examples that follow represent techniques discovered by the inventors to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

This example illustrates LAIR1 monoclonal antibodies (mAbs) binding to human LAIR1 extracellular domain (ECD).

The inventors have generated a group of monoclonal antibodies using human LAIR1 ECD as antigen. Details of the monoclonal antibodies sequences are listed in Tables 1-5.

TABLE 1

Variable region of the anti-LAIR1 antibodies, amino acid sequences
(See Table 6 below for SEQ ID NOs)

| mAbs | VH | VL |
|---|---|---|
| LA-56 | SSSVEESGGRLVTPGTPLTLTCTVSGFSLSAYWVGWVRQAPGKGLEYIGFVDVDIYYASWARGRFTISKTSSTTVDLILTSPTMEDTATYFCVRMSYNAMDLWGPGTLVTISS | ELDLTQTASSVSAAVGDTVTINCQSSESVYKDNFLSWYQQKPGQPPKLLIYRASTLASGVPSRFKGSGSGSQFTLTISDVVCDDAATYYCSGYRNSHDGLPFGGGTEVEIK |
| LA-89 | QSVKESGGRLVTPGTPLTLTCTVSGFSLSSNAISWVRQAPGKGLEWIGYIYGDGRTFYASWAKGRFTISKTSTTVDLKMTSLTSEDTATYFCIKSLHLWGPGTLVTISS | ELDMTQTASPVSAAVGGTVTINCQSSQSVYNKNQLFWYQQKPGQPPKLLIYDASTLASGVPSRYKGSGSGTQFTLTISGVQCDDAATYYCLGEYTGNIYTFGEGTEVVVK |
| LA-29 | SSSVEESGGGLVQPEGSLTLTCTASGFSFSSRYYMCWVRQAPGKGLEWIACIYNGDGSRYYASWAKGRFTISKTSSTTVTLQMTSLTAADTATYFCVRDRHTAFVDYGDDNLWGPGTLVTVSS | ELDLTQTPASVSEPVGGTVTIKCQASQSIYSNLAWYQQKPGQPPKLLIYRASTLASGVPSRFKGSGAGTEFTLTISDLECADAATYYCQCTYDGISYVPSSFGGGTEVVVK |
| LA-141 | QSLEESGGRLVKPDESLTLTCTVSGFSLSSNAMSWVRQAPGKGLEWIGYIYGDGRTFYANWAKGRITISRTSTTVDLKMTSLRTEDTATYFCVKSLILWGPGTLVTISS | ELDMTQTSPVSAAVGGTVTINCQSSHSVYNANQLYWYQQKPGQPPKLLIYDASTLASGVPSRFKGSGSGTQFLTLISGVQCDDAATYYCLGEYSGNIYVFGEGTEVEIN |
| LA-235 | SSSVEESEGRLVTPGTPLTLTCTVSGFSLSSYTMGWVRQAPGEGLEWIGTTSNDGSTYYASWAKGRFTISKTSSTTVDLMMTSLTTEDTATYFCVRGTNIRSLWGPGTLVTISS | ELVMTQTPASVEAAVGGTVTIKCQASQSIGSNLAWYQQKPGQPPKLLIYLASALASGVSSRFKGSGSGSDFTLTISDLECADAATYYCQCTYGSSNNNNYGDPFGGGTEVEIK |
| LA-192 | EQSLEESGGRLVTPGTPLTLTCTASGFSLSSYYMTWVRQAPGKGLEWIGYMHTGGGVVYASWATGRFTISRTSTTVDLKITSPTTEDTATYFCARSHAGYSTINRLDLWGVGTLVTISS | ELDLTQTPSSVSAAVGGTVTISCQSSPSVYTNNLSWFQQKPGQPPKLLIYDASKLESGVPSRFRGSGSGTQFTLTISDVQCDDAATYYCAGAYLSDSDTTFGGGTELEIK |
| LA-61 | GEQLMEESGGRLVTPGTPLTLTCTASGFDVNAYHMGWVRQAPGKGLEWIGYIYSGGTIFYANWAKGRFTLSRTSTTVDLKITSPTTEDTATYFCARGGYDNYNILYDLWGPGTLVTISS | ELDMTQTPASVSEPVGGTVTIKCQASQSISVYLAWYQQKPGQPPKLLIYDASTLTSGVPSRFKGSGSGTEFTLTISDLECADAAAYYCQSYDGTPTAAFGGGTEVVVK |
| LA-145 | SSSVEESGGRLVTPGTPLTLTCTVSGFSLSSYVMGWVRQAPGKGLEWIGTISIRSNTYYASWAKGRFTISKTSTTVDLKITSPITEDTATYFCARGAGNVYYSDYYFSLWGPGTLVTISS | ELVMTQPPASVSAAVGGTVTINCQASQNIYSNLAWYQQRPGQPPKLLIYKASTLASGVPSRFKGSGSGTDYTLTITDLECADAATYYCQTYYNMMDDGAAFGGGTEVEIK |
| LA-111 | EQSVEESGGGLVAPGGSLTLTCTVSGFSLSNYHMGWVRQAPGKGLEWIGYIYTHGTTFYASWAKGRFTISKTSTTVDLKMTRLTTGDTATYFCARGGYADYNILYNLWGPGTLVTISS | ELVLTQTPASVEAAVGGTVTINCQASQSISSYLAWYQQKPGQPPKLLIYDASDLASGVPSRFKGSRSGTEFTFTISDLECADAATYYCQTYDSSTTAAFGGGTEVEIK |
| LA-245 | QSLQESRGRLVTPGTPLTLTCTASGFSLSSYHMGWVRQAPGKGLEWIGYIHTNRNTWYANWAKGRFTISKTSSTTVNLRMTSPTTEDTATYFCARGSYGDYNFLFDVWGPGTLVTVSS | ELVMTQTPASVSEPVGGTVTINCQASEDISIYLAWYQQKPGQPPKLLIYDASTLESGVPSRFSGSGSRTQFTLTISDLECADAATYYCQQYSTTDTNNLFGGGTEVEIK |
| LA-171 | EQSVEESGGRLVTPGGSLTLTCTVSGFSLSSYNMGWVRQAPGKGLEYIGWISLGGNTYYASWVNGRFTISKTSTTVELKISSPTTEDTATYFCARGAGSLYYGDYYFTLWGPGTLVTISS | ELVLTQTPSSVSAAVGGTVTIKCQASQSIYSNLAWYQQKPGQPPKLLIYKASNLASGVPSRFKGSGSGTEYTLTISDLECADAATYYCQNYYGINDYGAAFGGGTEVVVK |
| LA-199 | EQSVEESGGRLVTPGTPLTLTCTASGFSLSSYAMIWVRQAPGEGLEWIGDIYAGGGATYYASWAKGRFTISKTSTTVDLKITSPTTEDTATYFCARAYGSGYDLWGPGTLVTVSS | ELDLTQTPASVEVAVGGTVTIKCQASQSISSYLSWYQQKPGQPPKLLIYYASTMASGVPSRFSGSGSGTQFTLTISDLECADAATYYCQQGDSRSNVDNIFGGGTEVVVK |
| LA-94 | EQSLEESEGRLVTPGTPLTLTCTASGFSLSGYHMSWVRQAPGKGLEYIGYISERGTSYYANWAKGRFTVSKSSSSTVVLSIISPTAEDTATYFCARYGGGDSAFILWGPGTLVTISS | ELVMTQTPASVSGPVGGTVTIKCQASHNIDNSLAWYQQKPGQPPKLLIYKASTLASGVSSRFKGSGSGTEYTLTISDLECADAATYYCQGTIGLNSGCAFGGGTEVEIK |
| LA-6 | GEQSVEESGGDLVKPEGSLTLTCTASGFSFSSGYYMCWVRQAPGKGLEWIGCIHSSSGNIYYASWAKGRFTISKTSSTTVDLQLTSLTAADTATYFCARDSEVYGWNPNDLWGPGTLVTVSS | ELDMTQTPASVSEPVGGTVTIKCQASQSISSYLAWYQQKPGQRPKLLIYGASNLASGVSSRFKGSRSGTQFTLTITDLECDDAATYYCQCSYYGNSYVGGAFGGGTEVVVK |
| LA-121 | EQSVEESGGRLVTPGTPLTLTCTASGFSLYKYNIQWVRQAPGKGLEYIGASTYAGYTYYASWAIGRVTISRTSTTVDLKMTSPTTEDTATYFCARHIDGDYSGYALWGPGTLVTISS | ELDLTQTPASVSAAVGGTVTIKCQASQSIDTWFGWYQQKPGQSPKLLIYGASKLASGVPPRFKGSGSGTEFTLTISDLECADAATYYCQNTYYGVRYLGGAFGGGTEVEIK |

TABLE 1-continued

Variable region of the anti-LAIR1 antibodies, amino acid sequences
(See Table 6 below for SEQ ID NOs)

| mAbs | VH | VL |
|---|---|---|
| LA-142-1 | AAVKESGGRLVTPGTPLTLTCTASGFSLYKYNIQWV RQAPGKGLEYIGASTYAGYTYYASWAKGRVTISRTS TTVDLKMTSPTTEDTATYFCARHIDGDYSGYALWG PGTLVTVSS | ELVLTQTPASVSAAVGGTVTIKCQASQSIGTWF AWYQQKPGQSPKLLIYGPSKLASGVPPRFKGS GSGTEFTLTISDLECADAATYYCQSTYFGVDYL GGTFGGGTEVEIK |
| LA-142-2 | AAVKESGGRLVTPGTPLTLTCTASGFSLYKYNIQWV RQAPGKGLEYIGASTYAGYTYYASWAKGRVTISRTS TTVDLKMTSPTTEDTATYFCARHIDGDYSGYALWG PGTLVTVSS | ELVLTQTPASVSAAVGGTVTIKCQASQSIGTWF AWYQQKPGQSPKLLIYGASNLASGVSSRFKGI RSGTEYTLTISDLECADAATYYCQCSDVGNTYG AAFGGGTEVEIN |
| LA-259-1 | QSVKESGGRLVTPGTPLTLTCTASGFSLYKYNIQWV RQAPGKGLEYIGASTYAGYTYYASWAKGRVTISRTS TTVDLKMTSPTTEDTATYFCARHIDGDYSGYALWG PGTLVTISS | ELVLTQTPASVSAAVGGTVTIKCQASQSIGTWF AWYQQKPGQSPKLLIYGPSKLASGVPPRFKGS GSGTEFTLTISDLECADAATYYCQSTYFGVDYL GGTFGGGTEVVVK |
| LA-259-2 | QSVKESGGRLVTPGTPLTLTCTASGFSLYKYNIQWV RQAPGKGLEYIGASTYAGYTYYASWAKGRVTISRTS TTVDLKMTSPTTEDTATYFCARHIDGDYSGYALWG PGTLVTISS | ELVMTQTPASVSAAVGGTVTIKCQASQSIGTW FAWYQQKPGQSPKLLIYGPSKLASGVPPRFKG SGSGTEFTLTISDLECDDAATYYCQSNGGSISN GWGSFGGGTEVVVK |
| LA-258-1 | QSVKESGGDLVKPEGSLTLTCKASGFSFSNSYYMC WVRQAPGKGLEWIACIYTGSTSGTYYASWVNGRF TISKTPSTTVTLQMTSLTVADTATYFCSRKLTNFNG AYLDLWGPGTLVTISS | ELVLTQTPASVEAAVGGTVTINCQASQSISNLL AWYQQKPGQRPKLLIYRASTLASGVSSRFKGS GSGTEYTLTISGVQCDDAATYYCQQGYTSNNV DNAFGGGTEVEIK |
| LA-258-2 | QSVKESGGDLVKPEGSLTLTCKASGFSFSNSYYMC WVRQAPGKGLEWIACIYTGSTSGTYYASWVNGRF TISKTPSTTVTLQMTSLTVADTATYFCSRKLTNFNG AYLDLWGPGTLVTISS | ELVMTQTPSSVEAAVGGTVTIKCQASQSIYSYL AWYQQKPGQPPKVLIYKASTLASGVPSRFKGS GSGTDFTLTISDLECADAATYYCQANNGGSDN NFGGGTEVEIK |
| LA-258-3 | QSVKESGGDLVKPEGSLTLTCKASGFSFSNSYYMC WVRQAPGKGLEWIACIYTGSTSGTYYASWVNGRF TISKTPSTTVTLQMTSLTVADTATYFCSRKLTNFNG AYLDLWGPGTLVTISS | ELVLTQTPASVEAAVGGTVTINCQASQSISNLL AWYQQKPGQPPKVLIYKASTLASGVPSRFKGS GSGTDFTLTISDLECADAATYYCQANNGGSDN NFGGGTEVVVKA |
| LA-30 | EQSVESGGGLVQPEGSLTLTCKASGFDFSRNAICW VRQAWYGPEWIACYSFSSSATYYASWAKSRFTISK TSSTTVTLQMTSLTAADTATYFCARVDIYGGSRYW GMWGPGTLVTISS | ELVMTQTPASVEAAVGGTVTIKCQASQNIGG DLAWYQQKPGQPPKLLIYRASTLESGVPSRFSG SGSGTEFTLTISDLECADAATYYCQDTDIGSGAF GGGTELEIK |
| LA-35 | EQSVKESGGRLVTPGTPLTLTCTVSGIDLSYYSMGW FRQAPGKGLEWIGVISSSDSTYYANWAKGRFTISKT STTVDLKIAGPTTEDTATYFCARVLANSYNAFNLW GPGSLVTISS | ELDLTQTPASVSEPVGGTVTIKCQASQSVGSRL AWYQQKPGQPPKLLIYKASTLASGVPSRFKGS GSGTQFTLTMSDLECADAATYYCQCTNISSAYL GAFGGGTEVEIK |
| LA-37 | EQSLEESGGDLVKPGASLTLTCKASGFSFSSSEFMC WVRQAPGKGLEWIACIYGGLSDDTYFASWAKGRF TISKTSSITVTLQMTSLTAADTATYFCARSCDVNYYG FDPWGPGTLVTISS | ELVLTQTPAPVSAAVGDTVTIKCQASQNKGTN LAWYQQKPGQPPKLLIYLSSTLASGVPPRFKGS RSGTEYTLTISDLECADAATYFCQSTYYGSNGLT FGGGTEVEIK |
| LA-60 | EQSLESGGGLVQPEGSLTLTCTASGFSFSNSYYMC WVRQAPGKGLEWIGCIYTGSSSGTYYASWAEGRF TISKTPSTTVTLQMTSLTAADTATYFCSRKLTNFNG AYLDLWGPGTLVTVSS | ELVLTQTPASVEAAVGGTVTIKCQASQSIYSYLA WYQQKPGQPPKVLIYKASTLASGVPSRFKGSG SGTEFTLTISDLECADAATYYCQNNNGGSDNT FGGGTEVVVK |
| LA-63 | EQSVEESGGRLVAPGGSLTLTCTVSGFSLSSYAMS WVRQAPGKGLEWIGVMYNSGSAYYASWAKGRFT ISRTSTTVDLKVTSLTTEDTATYFCGRGGSNSAWGD DLWGPGTLVTVSS | ELDMTQTPASVSEPVGGTVTIKCQASQSISIRY FSWYQQKPGQPPKLLIYGASTLASGVPSRFKGS GSGTDFTLTISDLECADAATYYCQDSNYNSNYF GAFGGGTEVVVK |
| LA-64 | EQSLESGGGLITPGGTLTLTCTASGFTVTRYYMNW VRQAPGKGLEWIGYIYASSKTYYANWAKGRFTISKT STTVDLKMTSLTAEDTGTYFCARGGVGNSGLNLDL WGPGTLVTISS | ELVLTQTPASVSEPVGGTVTIKCQASQSIGSWL AWYQQKPGQPPKLLIYGASRLASGVSSRFGGS GSGTEFTLTISDLECADAATYYCQQAEYSGDVE NTFGGGTEVVVK |
| LA-82 | EQSLEESGGDLVKPGASLTLACTASGFSFSDGYYMC WVRQAPGKGLEWIGCIHSSSGSIYYASWAKGRFTI SKTSSTMVTLQMSSLTAADTATYFCARDSESYGYN PCELWGPGTLVTISS | ELVMTQTPASVEAAVGGTVTIKCQASQTISNYL AWYQQKPGQRPKLLIYAASSLASGVSSRFRGS RSGTEYTLTITDLECDDAATYYCQCTYYGTTYIG GAFGGGTEVEIK |
| LA-87 | QSVKESGGRLVTPGGSLTLTCTVSGFSLSNYNIQWV RQAPGKGLEWIGFISPAGNGYYASWAKGRFTISKA SSTTVELKMTSLTASDTATYFCARHWDLWGPGTLV TISS | ELVLTQTASSVSAAVGGTVTISCQSSQSVYSNY LSWFQQKPGQPPKELVYWTSTLQSGVPSRFS GSGSGTQFTLTISDLECDDAATYYCLGGYSGW FYAFGGGTEVVVK |

TABLE 1-continued

Variable region of the anti-LAIR1 antibodies, amino acid sequences
(See Table 6 below for SEQ ID NOs)

| mAbs | VH | VL |
|---|---|---|
| LA-95 | EQSLKESGGRLVTPGGSLTLTCTASGFDINNYNIQW VRQAPGKGLEWIGFISPAGNEYSATWAKGRFTIYK TSSTTVELKMTSLTASDTATYFCARHWDSWGPGTL VTISS | ELVMTQTESPVSAAVGGTVTISCQSSQSVYSN RLSWFQQKPGQPPKELVYWTSTLQSGVPSRFS GSGSGTQFTLTISDLECDDAATYYCLGGYSGNI YVFGGGTEVEIK |
| LA-101 | EQSVEESGGRLVTPGTPLTLTCTVSGFSLSSFHMCW VRQAPGKGLEYIGIIYPGGSTGYANWAKGRFTVSK ASNTVDLKISSPTTEDTATYFCARVNYGDWINGMD LWGPGTLVTISS | ELDMTQTPASVSEPVGGTVTIKCQASQSIGSN LAWYQQKPGQRPKLLIYKASTLASGVPSRFKGS GSGTDFTLTISDLECADAASYYCQQAYWSGNV DNVFGGGTEVEIK |
| LA-117 | QSVKESGGDLVKPGASLTLACTASGFSFSDGYYMC WVRQAPGKGLEWIGCIHSSSGSIYYASWAKGRFTI SKTSSTMVTLQMSSLTAADTATYFCARDSESYGYN PCELWGPGTLVTISS | ELDLTQTPASVSEAVGGTVTIKCQASQTISNYL AWYQQKPGQRPKLLIYAASSLASGVSSRFRGS RSGTEYTLTITDLECDDAATYYCQCTYYGTTYV GGAFGGGTELEIK |
| LA-151 | SSSVEESGGRLVTPGTPLTLTCTVSGFSLGSYAMG WVRQGPGKGLEWIGAVYGTTGYIYFATWAKGRFT ISKTSSTVDLKITSPTTEDTATYFCARGYLTDSIANGF GVWGPGTLVTVSS | ELDLTQTPASVSEPVGGTVTIKCQASQTITNRY LAWYQQKPGQPPKLLIYQSSKLASGVSSRFKGS GSGTDFTLTISDLECADAATYYCQCTDYGSTYL GTFGGGTEVEIK |
| LA-155 | EQSLEESGGDLVKPEGSLTLTCTASGFSFNSNYWIC WVRQTPGKGLEWIGClYSGSSGDTYYASWAKGRF TISKTSSTTVTLQMTSLTAADTATYFCARGADYVYW SYGLWGPGTLVTISS | ELVLTQTPASVSAAVGGTLTIKCQASETIGTNLA WYQQKPGQPPKLLIYLASYLASGVSSRFKGSRS GTEFTLTISDLDCDDAATYYCQSTHFGNGHTF GGGTEVVVK |
| LA-219 | EQSVESGGGLITPGGTLTLTCTASGFTVTRYYMNW VRQAPGKGLEWIGYIYASSKTYYANWAKGRFTISKT STTVDLKMTSLTAEDTGTYFCARGGVGNSGLNLDL WGPGTLVTISS | ELDMTQTPASVSEPVGGTVTIKCQASQSIGSW LAWYQQKPGQPPKLLIYQASRLASGVSSRFGG SGSGTEFTLTISDLECADAATYYCQQAEYSGDV ENTFGGGTEVVVK |
| LA-222 | EQSVEESGGDLVKPGASLTLTCTASGFSFTYWICW VRQAPGKGLEWIACIYAGSSGDTYYASWAKGRFTI SKTSSTTVTLQMTSLTAADTATYFCARSPDYVAWG YDLWGPGTRVTVSS | ELVLTQTPASVSAAVGGTVTINCQASQSIGTNL VWYQQKPGQPPKLLFYYASTLASGVPSRFRGS RSGTEYTLTISDLECADAATYYCQCIYYGGNYG HTFGGGTEVVVK |
| LA-252 | EQSVEESGGRLVTPGTPLTLTCTASGFTISDYHMC WVRQAPGKGLEWIGLIRASHSTAYASWANGRFTIS RTSTTVDLKITSPTSEDTATYFCARYGGSIGCNLW GPGTLVTISS | ELVLTQTPASVSEPVGGTVTIKCQASQSIDSNL AWYQQKPGQPPKQLIYAVSNLASGVPSRFKGS GSGTEFTLTISDLECADAASYYCECTYYGNSYV GGFGGGTEVEIK |

TABLE 2

Heavy chain CDR sequences, amino acids (See Table 6 below for SEQ ID NOs)

| mAbs | HCDR1 | HCDR2 | HCDR3 |
|---|---|---|---|
| LA-56 | GFSLSAYW | VDVDIYY | RMSYNAMDL |
| LA-89 | GFSLSSNA | IYGDGRT | IKSLHL |
| LA-29 | GFSFSSRYY | IYNGDGS | VRDRHTAFVDYGDDNL |
| LA-141 | GFSLSSNA | IYGDGRT | VKSLIL |
| LA-235 | GFSLSSYT | TSNDGST | VRGTNIRSL |
| LA-192 | GFSLSSYY | MHTGGGV | ARSHAGYSTINRLDL |
| LA-61 | GFDVNAYH | IYSGGTI | ARGGYDNYNILYDL |
| LA-145 | GFSLSSYV | ISIRSNT | ARGAGNVYYSDYYFSL |
| LA-111 | GFSLSNYH | IYTHGTT | ARGGYADYNILYNL |
| LA-245 | GFSLSSYH | IHTNRNT | ARGSYGDYNFLFDV |
| LA-171 | GFSLSSYN | ISLGGNT | ARGAGSLYYGDYYFTL |
| LA-199 | GFSLSSYA | IYAGGGAT | ARAYGSGYDL |
| LA-94 | GFSLSGYH | ISERGTS | ARYGGGDSAFIL |
| LA-6 | GFSFSSGYY | IHSSSGN | ARDSEVYGWNPNDL |
| LA-121 | GFSLYKYN | STYAGYT | ARHIDGDYSGYAL |
| LA-142-1 | GFSLYKYN | STYAGYT | ARHIDGDYSGYAL |
| LA-142-2 | GFSLYKYN | STYAGYT | ARHIDGDYSGYAL |
| LA-259-1 | GFSLYKYN | STYAGYT | ARHIDGDYSGYAL |
| LA-259-2 | GFSLYKYN | STYAGYT | ARHIDGDYSGYAL |
| LA-258-1 | GFSFSNSYY | IYTGSTSGT | SRKLTNFNGAYLDL |
| LA-258-2 | GFSFSNSYY | IYTGSTSGT | SRKLTNFNGAYLDL |
| LA-258-3 | GFSFSNSYY | IYTGSTSGT | SRKLTNFNGAYLDL |
| LA-30 | GFDFSRNA | YSFSSSA | ARVDIYGGSRYWGM |
| LA-35 | GIDLSYYS | ISSSDST | ARVLANSYNAFNL |
| LA-37 | GFSFSSSEF | IYGGLSDDT | ARSCDVNYYGFDP |

TABLE 2-continued

Heavy chain CDR sequences, amino acids (See Table 6 below for SEQ ID NOs)

| mAbs | HCDR1 | HCDR2 | HCDR3 |
| --- | --- | --- | --- |
| LA-60 | GFSFSNSYY | IYTGSSSGT | SRKLTNFNGAYLDL |
| LA-63 | GFSLSSYA | MYNSGSA | GRGGSNSAWGDDL |
| LA-64 | GFTVTRYY | IYASSKT | ARGGVGNSGLNLDL |
| LA-82 | GFSFSDGYY | IHSSSGS | ARDSESYGYNPCEL |
| LA-87 | GFSLSNYN | ISPAGNG | ARHWDL |
| LA-95 | GFDINNYN | ISPAGNE | ARHWDS |
| LA-101 | GFSLSSFH | IYPGGST | ARVNYGDWINGMDL |

TABLE 2-continued

Heavy chain CDR sequences, amino acids (See Table 6 below for SEQ ID NOs)

| mAbs | HCDR1 | HCDR2 | HCDR3 |
| --- | --- | --- | --- |
| LA-117 | GFSFSDGYY | IHSSSGSI | RDSESYGYNPCEL |
| LA-151 | GFSLGSYA | VYGTTGYI | ARGYLTDSIANGFGV |
| LA-155 | GFSFNSYW | IYSGSSGDT | ARGADVYWSYGL |
| LA-219 | GFTVTRYY | IYASSKT | ARGGVGNSGLNLDL |
| LA-222 | ASGFSFTYW | IYAGSSGDT | ARSPDYVAWGYDL |
| LA-252 | GFTISDYH | IRASHST | ARYGGSGIGCNL |

TABLE 3

Heavy chain CDRs, nucleic acid sequences (See Table 6 below for SEQ ID NOs)

| mAbs | HCDR1 | HCDR2 | HCDR3 |
| --- | --- | --- | --- |
| LA-56 | ggattctccctcagtgcctactgg | gttgatgtcgatatatactac | agaatgtcttacaatgcaatggacctc |
| LA-89 | ggattctccctcagtagcaatgca | atttatggtgatggtcgtaca | atcaaatcactgcacttg |
| LA-29 | ggattctccttcagtagcagatactac | atttataatggtgatggcagc | gtgagagatcgccatactgcttttgttgattatggtgatgataacttg |
| LA-141 | ggattctccctcagtagcaatgca | atttatggtgatggtcgcaca | gtcaaatcacttatcttg |
| LA-235 | ggattctccctcagtagctacacc | actagtaatgatggtagtaca | gtcagaggtacgaatattagaagcttg |
| LA-192 | ggattctccctcagtagctactac | atgcatacgggtggtggcgta | gccagaagtcatgctggttatagtactataaatcggttggatctc |
| LA-61 | ggattcgacgtcaatgcctaccac | atttatagcggtggtaccata | gccagagggggttatgataattacaacattctatatgacttg |
| LA-145 | ggattctccctcagtagctatgta | attagtattcgaagtaataca | gccagaggtgctggtaatgtttattatagcgactactactttccttg |
| LA-111 | ggattctccctcagtaactaccac | atttatactcatggtaccaca | gccagagggggttatgctgattataatattttatataatttg |
| LA-245 | ggattctccctcagtagctaccac | attcatactaatcgtaataca | gctagaggctcttatggtgattataatttttcttttgacgtg |
| LA-171 | ggattctccctcagtagctacaac | attagtcttggtggtaacaca | gccagaggggctggtagtctttattatggggattactactttccttg |
| LA-199 | ggattctccctcagtagctatgca | atttatgctggtggtggtgccaca | gccagagcatatggtagtggttatgacttg |
| LA-94 | ggattctccctcagtggctatcat | attagtgagcgtggtaccctca | gccagatatggtggtggtgattcggcttttatcttg |
| LA-6 | ggattctccttcagtagcggctactac | atccatagtagtagtggtaat | gcgagggattcggaagtttatggttggaatcctaacgacttg |
| LA-121 | ggattctccctctataagtacaac | agtacttatgctggttacaca | gccagacatattgatggtgattatagtggataccccttg |
| LA-142-1 | ggattctccctctataagtacaat | agtacttatgctggttacaca | gccagacatattgatggtgattatagtggataccccttg |
| LA-142-2 | ggattctccctctataagtacaat | agtacttatgctggttacaca | gccagacatattgatggtgattatagtggataccccttg |
| LA-259-1 | ggattctccctctataagtacaat | agtacttatgctggttacaca | gccagacatattgatggtgattatagtggataccccttg |
| LA-259-2 | ggattctccctctataagtacaat | agtacttatgctggttacaca | gccagacatattgatggtgattatagtggataccccttg |

TABLE 3-continued

Heavy chain CDRs, nucleic acid sequences
(See Table 6 below for SEQ ID NOs)

| mAbs | HCDR1 | HCDR2 | HCDR3 |
|---|---|---|---|
| LA-258-1 | ggattctccttcagtaatagttattac | atttatactggtagtactagtggcact | tcgagaaagcttaccaatttcaatggtgcttatttagatttg |
| LA-258-2 | ggattctccttcagtaatagttattac | atttatactggtagtactagtggcact | tcgagaaagcttaccaatttcaatggtgcttatttagatttg |
| LA-258-3 | ggattctccttcagtaatagttattac | atttatactggtagtactagtggcact | tcgagaaagcttaccaatttcaatggtgcttatttagatttg |
| LA-30 | ggattcgacttcagtagaaatgca | tatagttttagtagtagtgcc | gcgagagttgatatttatggtggtagccgttatggggcatg |
| LA-35 | ggaatcgacctcagttactattca | attagtagtagtgatagcaca | gccagggtattggctaatagttataatgcctttaacttg |
| LA-37 | ggattctccttcagtagcagtgaattc | atttatggtgggcttagtgacgacacc | gcgagatcctgtgatgttaattattatggttttgatccc |
| LA-60 | ggattctccttcagtaatagttattat | atttatactggtagtagtagtggcact | tcgagaaagcttaccaatttcaatggtgcttatttagatttg |
| LA-63 | ggattctccctcagtagctatgca | atgtataatagtggtagcgca | ggcagaggggatccaatagtgcctggggtgatgacttg |
| LA-64 | ggattcaccgtcactaggtattat | atttatgctagtagtaagaca | gccagagggggtgttggtaatagtggcttgaaccttgacttg |
| LA-82 | ggattctccttcagtgacggctactat | attcattctagtagtggtagt | gcgagagattcggagagttatggttataatcctgtgagttg |
| LA-87 | ggattctccctcagtaactacaac | attagtccagctggtaacgga | gccagacattgggacttg |
| LA-95 | ggattcgacatcaataactacaac | attagtccagctggtaacgaa | gccagacattgggactcg |
| LA-101 | ggattctccctcagtagctttcac | atttatcctggtggtagcaca | gccagagttaattatggtgattggatcaatggtatggacttg |
| LA-117 | ggattctccttcagtgacggctactat | attcattctagtagtggtagcatt | agagattcggagagttatggttataatccttgtgagttg |
| LA-151 | ggattctccctcggtagctatgca | gtatatggtactactggttatata | gccagaggatatcttactgatagtattgctaacggctttggcgtc |
| LA-155 | ggattctccttcaatagcaactactgg | atttatagtggtagtagtggtgacact | gcgcgggggctgattatgtttattggagttatggcttg |
| LA-219 | ggattcaccgtcactaggtattat | atttatgctagtagtaagaca | gccagagggggtgttggtaatagtggcttgaaccttgacttg |
| LA-222 | gcctctggattctccttcacctactgg | atttatgctggtagtagtggtgacact | gcgagatcccccgattatgttgcttggggatatgacttg |
| LA-252 | ggattcaccatcagtgactaccac | attcgggctagtcattccaca | gccagatatggtggtagtggtattggttgtaatttg |

TABLE 4

Light chain CDRs, amino acid sequences (See Table 6 below for SEQ ID NOs)

| mAbs | LCDR1 | LCDR2 | LCDR3 |
|---|---|---|---|
| LA-56 | QSVYNKNQ | DAS | LGEYTGNIYT |
| LA-89 | QSIYSN | RAS | QCTYDGISYVPSS |
| LA-29 | HSVYNANQ | DAS | LGEYSGNIYV |
| LA-141 | QSIGSN | LAS | QCTYGSSNNNYGDP |
| LA-235 | PSVYTNN | DAS | AGAYLSDSDTT |
| LA-192 | QSISVY | DAS | QSYDGTPTAA |
| LA-61 | QSVYNNNY | DAS | AGFVSRSTDGAA |
| LA-145 | QNIYSN | KAS | QTYYNMMDDGAA |
| LA-111 | QSISSY | DAS | QTYDSSTTAA |
| LA-245 | EDISIY | DAS | QQYSTTDTNNL |

TABLE 4-continued

Light chain CDRs, amino acid sequences (See Table 6 below for SEQ ID NOs)

| mAbs | LCDR1 | LCDR2 | LCDR3 |
|---|---|---|---|
| LA-171 | QSIYSN | KAS | QNYYGINDYGAA |
| LA-199 | QSISSY | YAS | QQGDSRSNVDNI |
| LA-94 | HNIDNS | KAS | QGTIGLNSGCA |
| LA-6 | QSISSY | GAS | QCSYYGNSYVGGA |
| LA-121 | QSIDTW | GAS | QNTYYGVRYLGGA |
| LA-142-1 | QSIGTW | GPS | QSTYFGVDYLGGT |
| LA-142-2 | QSIGTW | GAS | QCSDVGNTYGAA |
| LA-259-1 | QSIGTW | GPS | QSTYFGVDYLGGT |
| LA-259-2 | QSIGTW | GPS | QSNGGSISNGWGS |
| LA-258-1 | QSISNL | RAS | QQGYTSNNVDNA |
| LA-258-2 | QSIYSY | KAS | QANNGGSDNN |
| LA-258-3 | QSISNL | KAS | QANNGGSDNN |
| LA-30 | QNIGGD | RAS | QDTDIGSGA |
| LA-35 | QSVGSR | KAS | QCTNISSAYLGA |
| LA-37 | QNKGTN | LSS | QSTYYGSNGLT |
| LA-60 | QSIYSY | KAS | QNNNGGSDNT |
| LA-63 | QSISIRY | GAS | QDSNYNSNYFGA |
| LA-64 | QSIGSW | QAS | QQAEYSGDVENT |
| LA-82 | QTISNY | AAS | QCTYYGTTYIGGA |
| LA-87 | QSVYSNY | WTS | LGGYSGWFYA |
| LA-95 | QSVYSNR | WTS | LGGYSGNIYV |
| LA-101 | QSIGSN | KAS | QQAYWSGNVDNV |
| LA-117 | QTISNY | AAS | QCTYYGTTYVGGA |
| LA-151 | QTITNRY | QSS | QCTDYGSTYLGT |
| LA-155 | ETIGTN | LAS | QSTHFGNGHT |
| LA-219 | QSIGSW | QAS | QQAEYSGDVENT |
| LA-222 | QSIGTN | YAS | QCIYYGGNYGHT |
| LA-252 | QSIDSN | AVS | ECTYYGNSYVGG |

TABLE 5

Light chain CDRs, nucleic acid sequences (See Table 6 below for SEQ ID NOs)

| mAbs | LCDR1 | LCDR2 | LCDR3 |
|---|---|---|---|
| LA-56 | caaagtgtttataataagaaccaa | gatgcatcc | ctaggagaatatactggtaatatatatact |
| LA-89 | cagagcatttacagcaat | agggcatcc | caatgtacttatgatggtattagttatgtccccagttct |
| LA-29 | cacagtgtttataatgccaaccaa | gatgcatcc | ctaggagaatatagtggtaatatctatgtt |
| LA-141 | cagagcattggtagtaat | ctggcatct | caatgcacttatggtagtagtaataataataattatggtgatcct |
| LA-235 | ccgagtgtttatactaacaac | gatgcatcc | gcaggcgcttacctcagtgatagtgatactact |
| LA-192 | cagagtattagtgtctac | gatgcatcc | caaagttatgatggtactcctactgcggct |
| LA-61 | cagagtgtttataataacaactac | gatgcatcc | gcaggatttgtgagtagaagtactgatggtgctgct |
| LA-145 | cagaacatttacagtaat | aaggcatcg | caaacctattataatatgatggatgatggtgctgct |
| LA-111 | cagagtattagtagttac | gatgcatcc | cagacttatgatagtagtactacagcggct |
| LA-245 | gaggatattagtatctac | gatgcatcc | caacaatatagtactacagatactaataatctt |
| LA-171 | cagagcatttacagcaat | aaggcatcc | caaaactactatggtattaatgattatggtgctgct |
| LA-199 | cagagcattagtagttat | tatgcatcc | caacagggtgatagtaggagtaatgttgataatatt |
| LA-94 | cacaacattgataatagt | aaggcatcc | caaggcactattggtcttaatagtgggtgtgct |
| LA-6 | cagagcattagtagctac | ggtgcatcc | caatgtagttattatggtaatagttatgttggggggct |
| LA-121 | cagagcattgatacttgg | ggtgcatcc | caaaacacttattatggtgttcgttatcttggaggtgct |
| LA-142-1 | cagagcattggtacttgg | ggtccatcc | caaagcacttatttcggtgttgattatcttggaggtact |
| LA-142-2 | cagagcattggtacttgg | ggtgcatcc | caatgttctgatgttggtaatacttatggcgctgct |
| LA-259-1 | cagagcattggtacttgg | ggtccatcc | caaagcacttatttcggtgttgattatcttggaggtact |
| LA-259-2 | cagagcattggtacttgg | ggtccatcc | caaagcaatggtggtagtattagtaatggttggggtagt |

TABLE 5-continued

Light chain CDRs, nucleic acid sequences (See Table 6 below for SEQ ID NOs)

| mAbs | LCDR1 | LCDR2 | LCDR3 |
|---|---|---|---|
| LA-258-1 | cagagcattagcaacctc | agggcatcc | caacagggttatactagtaataatgtcgataatgct |
| LA-258-2 | cagagcatttacagctac | aaggcttcc | caagctaataatggtggtagtgataataat |
| LA-258-3 | cagagcattagcaacctc | aaggcttcc | caagctaataatggtggtagtgataataat |
| LA-30 | cagaacattggtggcgac | agggcatcc | caagatactgatattggtagtggtgct |
| LA-35 | cagagcgttggtagtagg | aaggcatcc | caatgtactaatattagtagtgcttatctaggggct |
| LA-37 | cagaataagggtactaat | ctgtcatcc | caatctacttattatggtagtaatggtctgact |
| LA-60 | cagagcatttacagctac | aaggcttcc | caaaataataatggtggtagtgataatact |
| LA-63 | cagagtattagtattaggtac | ggtgcatcc | caagatagtaattataatagtaattattttggagct |
| LA-64 | cagagcattggcagttgg | caggcatcc | caacaggctgagtatagtggtgatgttgagaatact |
| LA-82 | cagaccattagtaactac | gctgcatcc | caatgtacttattatggtaccacttatattggggggct |
| LA-87 | cagagtgtttatagtaactac | tggacatcc | ctaggcggttatagtggttggttttatgct |
| LA-95 | cagagtgtttatagtaaccgc | tggacatcc | ctaggcggttatagtggcaatatttatgtt |
| LA-101 | cagagcattggtagtaat | aaggcttcc | caacaggcttattggagtggtaatgttgataatgtt |
| LA-117 | cagaccattagtaactac | gctgcatcc | caatgtacttattatggtaccacttatgttggggggct |
| LA-151 | cagactattactaataggtac | cagtcatcc | caatgtactgattatggtagtacttatttgggtact |
| LA-155 | gagaccattggcacgaat | ctggcatcc | caaagcactcattttggtaatggtcatact |
| LA-219 | cagagcattggcagttgg | caggcatcc | caacaggctgagtatagtggtgatgttgagaatact |
| LA-222 | cagagtattggtactaat | tatgcatcc | caatgtatttattatggtggtaattatggtcatact |
| LA-252 | cagagcattgatagtaat | gctgtatcc | gaatgtacttattatggtaatagttatgttggtggt |

TABLE 6

SEQ ID NOS of the anti-LAIR1 antibodies sequences

| | VH/VL SEQ ID NOS | | HCDR1/HCDR2/HCDR3 SEQ ID NOS | | LCDR1/LCDR3 SEQ ID NOS | |
|---|---|---|---|---|---|---|
| mAbs | Amino acids | Nucleic acids | Amino acids | Nucleic acids | Amino acids | Nucleic acids |
| LA-56 | 1/2 | 8/9 | 3/4/5 | 10/11/12 | 6/7 | 13/14 |
| LA-89 | 15/16 | 22/23 | 17/18/19 | 24/25/26 | 20/21 | 27/28 |
| LA-29 | 29/30 | 36/37 | 31/32/33 | 38/39/40 | 34/35 | V41/42 |
| LA-141 | 43/44 | 50/51 | 45/46/47 | 52/53/54 | 48/49 | 55/56 |
| LA-235 | 57/58 | 64/65 | 59/60/61 | 66/67/68 | 62/63 | 69/70 |
| LA-192 | 71/72 | 78/79 | 73/74/75 | 80/81/82 | 76/77 | 83/84 |
| LA-61 | 85/86 | 92/93 | 87/88/89 | 94/95/96 | 90/91 | 97/98 |
| LA-145 | 99/100 | 106/107 | 101/102/103 | 108/109/120 | 104/105 | 111/112 |
| LA-111 | 113/114 | 120/121 | 115/116/117 | 122/123/124 | 118/119 | 125/126 |
| LA-245 | 127/128 | 134/135 | 129/130/131 | 136/137/138 | 132/133 | 139/140 |
| LA-171 | 141/142 | 148/149 | 143/144/145 | 150/151/152 | 146/147 | 153/154 |
| LA-199 | 155/156 | 162/163 | 157/158/159 | 164/165/166 | 160/161 | 167/168 |
| LA-94 | 169/170 | 176/177 | 171/172/173 | 178/179/180 | 174/175 | 181/182 |
| LA-6 | 183/184 | 190/191 | 185/186/187 | 192/193/194 | 188/189 | 195/196 |
| LA-121 | 197/198 | 204/205 | 199/200/201 | 206/207/208 | 202/203 | 209/210 |
| LA-142-1 | 211/212 | 218/219 | 213/214/215 | 220/221/222 | 216/217 | 223/224 |
| LA-142-2 | 225/226 | 232/233 | 227/228/229 | 234/235/236 | 230/231 | 237/238 |
| LA-259-1 | 239/240 | 246/247 | 241/242/243 | 248/249/250 | 244/245 | 251/252 |
| LA-259-2 | 253/254 | 260/261 | 255/256/257 | 262/263/264 | 258/259 | 265/266 |
| LA-258-1 | 267/268 | 274/275 | 269/270/271 | 276/277/278 | 272/273 | 279/280 |
| LA-258-2 | 281/282 | 288/289 | 283/284/285 | 290/291/292 | 286/287 | 293/294 |
| LA-258-3 | 295/296 | 302/303 | 297/298/299 | 304/305/306 | 300/301 | 307/308 |
| LA-30 | 309/310 | 316/317 | 311/312/313 | 318/319/320 | 314/315 | 321/322 |

TABLE 6-continued

SEQ ID NOS of the anti-LAIR1 antibodies sequences

| mAbs | VH/VL SEQ ID NOS Amino acids | VH/VL SEQ ID NOS Nucleic acids | HCDR1/HCDR2/HCDR3 SEQ ID NO Amino acids | HCDR1/HCDR2/HCDR3 SEQ ID NO Nucleic acids | LCDR1/LCDR3 SEQ ID NOS Amino acids | LCDR1/LCDR3 SEQ ID NOS Nucleic acids |
|---|---|---|---|---|---|---|
| LA-35 | 323/324 | 330/331 | 325/326/327 | 332/333/334 | 328/329 | 335/336 |
| LA-37 | 337/338 | 344/345 | 339/340/341 | 346/347/348 | 342/343 | 349/350 |
| LA-60 | 351/352 | 358/359 | 353/354/355 | 360/361/362 | 356/357 | 363/364 |
| LA-63 | 365/366 | 372/373 | 367/368/369 | 374/375/376 | 370/371 | 377/378 |
| LA-64 | 379/380 | 386/387 | 381/382/383 | 388/389/390 | 384/385 | 391/392 |
| LA-82 | 393/394 | 400/401 | 395/396/397 | 402/403/404 | 398/399 | 405/406 |
| LA-87 | 407/408 | 414/415 | 409/410/411 | 416/417/418 | 412/413 | 419/420 |
| LA-95 | 421/422 | 428/429 | 423/424/425 | 430/431/432 | 426/427 | 433/434 |
| LA-101 | 435/436 | 442/443 | 437/438/439 | 444/445/446 | 440/441 | 447/448 |
| LA-117 | 449/450 | 456/457 | 451/452/453 | 458/459/460 | 454/455 | 461/462 |
| LA-151 | 463/464 | 470/471 | 465/466/467 | 472/473/474 | 468/469 | 475/476 |
| LA-155 | 477/478 | 484/485 | 479/480/481 | 486/487/488 | 482/483 | 489/490 |
| LA-219 | 491/492 | 498/499 | 493/494/495 | 500/501/502 | 496/497 | 503/504 |
| LA-222 | 505/506 | 512/513 | 507/508/509 | 514/515/516 | 510/511 | 517/518 |
| LA-252 | 519/520 | 526/527 | 521/522/523 | 528/529/530 | 524/525 | 531/532 |

The inventors then used a concentration titration (0-10 µg/ml) by ELISA to determine the LAIR1 monoclonal antibody (mAbs) binding to human LAIR1 ECD. The results of the ELISA assay are demonstrated in FIGS. 2-39 and Table 7. For FIGS. 2-39, X axis indicates the antibody concentrations and Y-axis is binding signals, measured as OD (450 nm). To perform the ELISA assay, LAIR1 ECD recombinant protein was coated on high absorption 96-well plates. Serial diluted (3-fold) LAIR1 mAb was added to the coated/blocked plates and detected using goat anti-rabbit F(ab')2 conjugated HRP as secondary antibody. All assays were repeated 3 times and the titration curves were fitted using 4-parameter fitting curve using the GraphPad software for $EC_{50}$ estimation.

TABLE 7

$EC_{50}$ of anti-LAIR1 antibodies binding to human LAIR1, as assayed by ELISA

| mAbs | $EC_{50}$ (ELISA, nM) |
|---|---|
| LA-56 | 0.05 |
| LA-89 | 0.08 |
| LA-29 | 0.02 |
| LA-141 | 0.05 |
| LA-235 | 0.03 |
| LA-192 | 0.04 |
| LA-61 | 0.05 |
| LA-145 | 0.08 |
| LA-111 | 0.09 |
| LA-245 | 0.09 |
| LA-171 | 0.09 |
| LA-199 | 0.16 |
| LA-94 | 0.12 |
| LA-6 | 0.07 |
| LA-121 | 0.21 |
| LA-142-1 | 0.25 |
| LA-142-2 | 0.28 |
| LA-259-1 | 0.23 |
| LA-259-2 | 0.22 |
| LA-258-1 | 4.21 |
| LA-258-2 | 0.37 |
| LA-258-3 | 0.30 |
| LA-30 | 0.07 |
| LA-35 | 0.08 |
| LA-37 | 0.05 |
| LA-60 | 0.10 |
| LA-63 | 234.22 |
| LA-64 | 0.09 |
| LA-82 | 0.10 |

TABLE 7-continued $EC_{50}$ of anti-LAIR1 antibodies binding to human LAIR1, as assayed by ELISA

| mAbs | $EC_{50}$ (ELISA, nM) |
|---|---|
| LA-87 | 0.06 |
| LA-95 | 0.04 |
| LA-101 | 0.05 |
| LA-117 | 0.08 |
| LA-151 | 0.08 |
| LA-155 | 0.04 |
| LA-219 | 0.06 |
| LA-222 | 0.05 |
| LA-252 | 0.05 |

For the purposes of this application, ELISA values may be determined as follows: LAIR1 extracellular domain (ECD) protein (with 6 HIS tag at the C-terminus) was produced recombinantly in HEK293 cells and was coated onto a high binding 96-well clear plate (Corning-Costar, Fisher Scientific) at 1 µg/ml concentration (100 µl/well) and incubated at 4° C. overnight. Plates were rinsed and then blocked with 200 µl/well of 5% non-fat milk in PBS for 2 hour at 37° C.

Serial dilutions of the LAIR1 monoclonal antibodies (IgGs or scFvs fragments), starting from 10 mg/ml and 3-fold titration down for 12 steps, were added to the 96-well plate for binding by incubating 45 minutes at 37° C. with a cover on the assay plate. Then the plates were washed with PBS containing Tween 20 (0.05% concentration) for 3 times and PBS one time. Secondary antibody of anti-human or anti-rabbit, or other species IgG specific antibodies with HRP conjugate (Jackson ImmunoResearch) was added for incubation at room temperature for 1 hour per manufacturer's suggested dilution. Detection was conducted by adding HRP substrate, TMB (ThermoFisher) for 10 minutes, and stopped by adding 50 µl/well of 2N $H_2SO_4$. The plates were read for absorbance at 450 nm using a plate reader (SpectraMax M4, Molecular Devices). Data were collected and graphed using a 4-parameter fitting curve with GrapPad Prism 7 software for $EC_{50}$ calculation.

Example 2

This example illustrates the effects of LAIR1 antibody on collagen I binding to LAIR1 ECD.

Collagen I has been proposed as a ligand of LAIR1 (Lebbink, R. J., de Ruiter, T., Adelmeijer, J. et al. 2006. Collagens are functional, high affinity ligands for the inhibitory immune receptor LAIR-1. J. Exp. Med. 203:1419.).

After characterized the binding of the group of LAIR1 antibodies to LAIR1 ECD, the inventors then assessed the effects of the LAIR1 antibodies on collagen I binding to LAIR1 ECD. To perform the assay, collagen I was coated onto a high binding 96-well clear plate (Corning-Costar, Fisher Scientific) at 2 µg/ml concentration (100 µl/well) and incubated at 4° C. overnight. LAIR1 extracellular domain (ECD) protein containing a 6×HIS tag at the C-terminus (at 10 µg/ml) was pre-incubated for 30-60 minutes with LAIR1 monoclonal antibodies (at 10 µg/ml). The LAIR1-his/LAIR1 antibody mixture was then added to the collagen I coated plates following a brief wash with PBS, pH 7.4.

The binding of LAIR1 to collagen I was identified using the ability of HRP conjugated anti-HIS tag antibody to bind to the HIS tagged LAIR1 that had bound the collagen 1 on the plate. This binding was demonstrated using TMB substrate and the plates were read at 450 nm using a plate reader.

Figure 40:
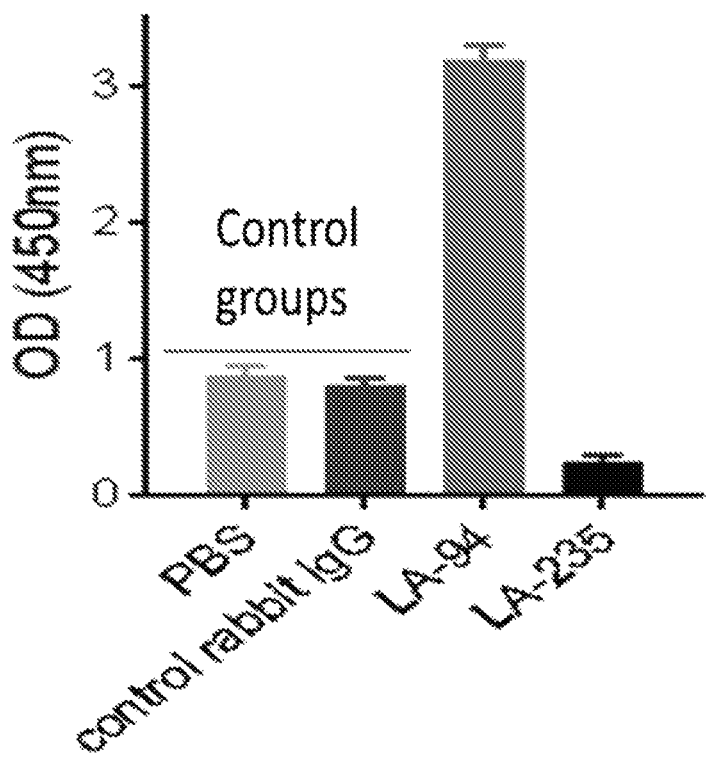
FIG. 40 shows the effects of anti-LAIR1 antibody on collagen I binding to LAIR1 ECD by a competition ELISA. Coating collagen I on a high absorption 96-well plate at 2 µg/ml, 100 µl/well at 4° C. overnight. Pre-incubate LAIR1-ECD with 6×his tag at 10 µg/ml with anti-LAIR1 antibodies (10 µg/ml) for 30-60 minutes. Add LAIR1-his/anti-LAIR1 mAb mixture to the collagen coated 96-well plates. Detection of LAIR1 binding by HRP conjugated anti-his tag antibody using TMB substrate and reading at 450 nm used a plate reader. The assay was repeated for 3 times.

As shown in FIG. 40, the control rabbit IgG or PBS did not inhibit the binding of LAIR1 to the collagen 1 coated plates. Pre-incubation with LAIR1 monoclonal antibody LA-94 enhanced the binding of LAIR1 to the collagen and pre-incubation with LAIR1 monoclonal antibody LA-235 inhibited the binding of LAIR1 to the collagen plate.

Example 3

Figure 41:
FIG. 41 illustrates the Octet RED96 System.

This example illustrates the BLI analysis of 38 anti-LAIR1 rabbit mAbs using classic sandwich epitope binning assay format performed in Octet RED96 (FIG. 41).

Figure 42:
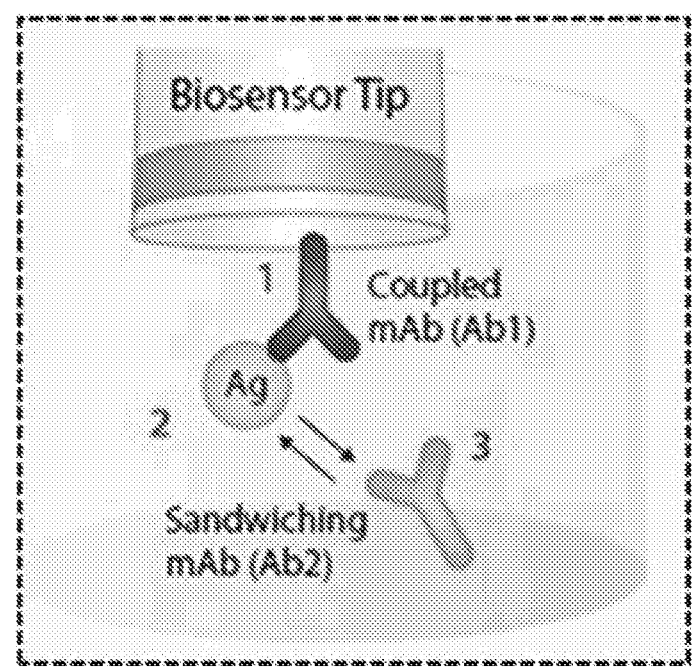
FIG. 42 illustrates the Classic Sandwich assay.
Figure 43:
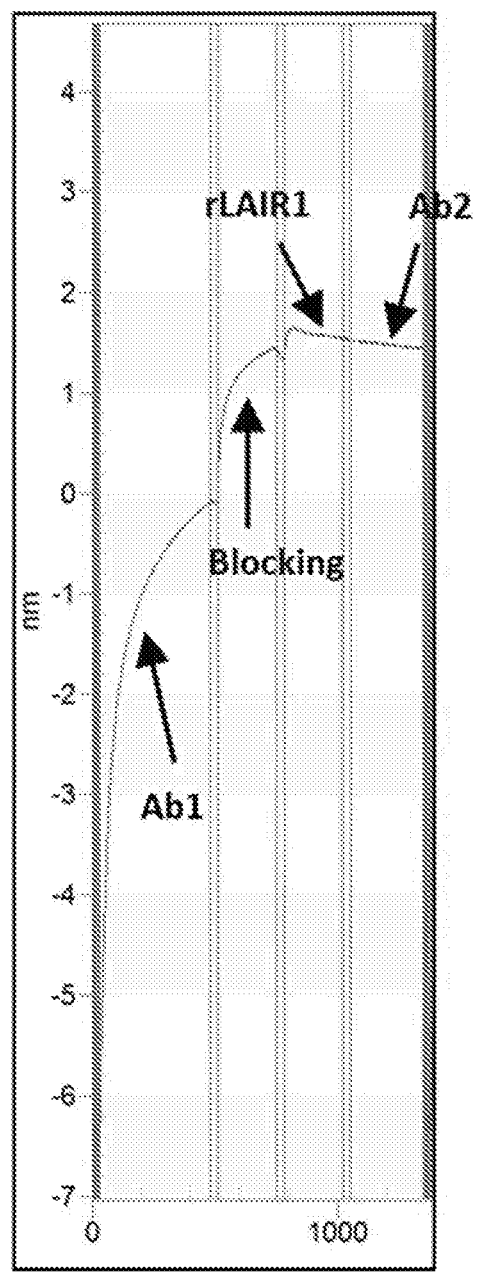
FIG. 43 graphically illustrates when the antibodies fall within the same epitope bin "+".
Figure 44:
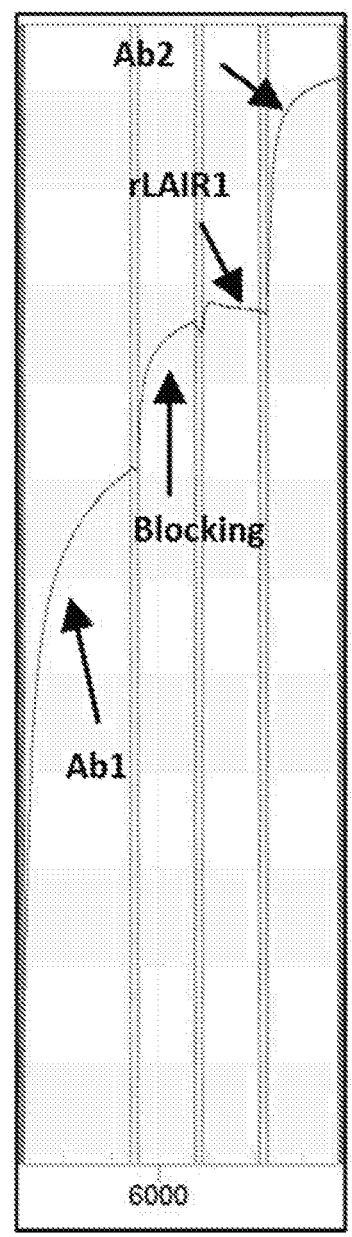
FIG. 44 graphically illustrates when the antibodies fall within different epitope bins "−".

The procedures used for epitope binning of LAIR1 mAbs are shown in FIG. 42. First antibodies (40 µg/mL) were loaded onto protein A sensors for Octet 8-channel Red96 and the sensors were blocked with a control rabbit antibody (200 µg/ml), followed by soaking the sensors in kinetics buffer for 10 sec. The sensors were then exposed to recombinant LAIR1 (25 µg/mL) for 4 min. Finally, the sensors were exposed to the competitor/second antibodies (40 µg/mL) for 4 min to check for the binding. Collected kinetic data was processed using ForteBio's data analysis software 7.0, and the antibody pairs were assessed for competitive binding. Detection of any additional binding on the sensor chip by the second antibody indicates an unoccupied epitope (non-competitor "−"), while no mding of the second antibody on the chip indicates blocked epitope (competitor "+").

As illustrated in FIG. 45, the first set (Set 1) of binning group determined five epitope bins for 14 rabbit mAbs.

As illustrated in FIG. 46, the second set (Set 2) of binning group determined two epitope bins for 7 rabbit mAbs.

As illustrated in FIG. 47, the third set (Set 3) of binning groups determined two epitope bins for 7 rabbit mAbs.

As illustrated in FIG. 48 the fourth set (Set 4) of binning groups determined two epitope bins for 7 rabbit mAbs.

Example 4

This example illustrates the kinetic binding sensorgrams for selected LAIR1 antibodies determined using the Octet.

To perform the assay, antibody (30 µg/mL) was loaded to the proteins A sensor for 4 min, followed by a short buffering to establish baseline in kinetics buffer. The loaded sensors were then exposed to a series of recombinant LAIR1 concentrations (0.1-200 nM) for kinetic binding detection. Background subtraction was used to correct the sensor drifting. All experiments were performed with shaking at 1,000 rpm. Background wavelength shifts were measured from reference sensors that were loaded only with antibody. ForteBio's data analysis software was used to fit the data to a 1:1 binding model to extract an association rate and dissociation rate. The KD was calculated using the ratio koff/koff using ForteBio's data analysis software 7.0.

Figure 49:
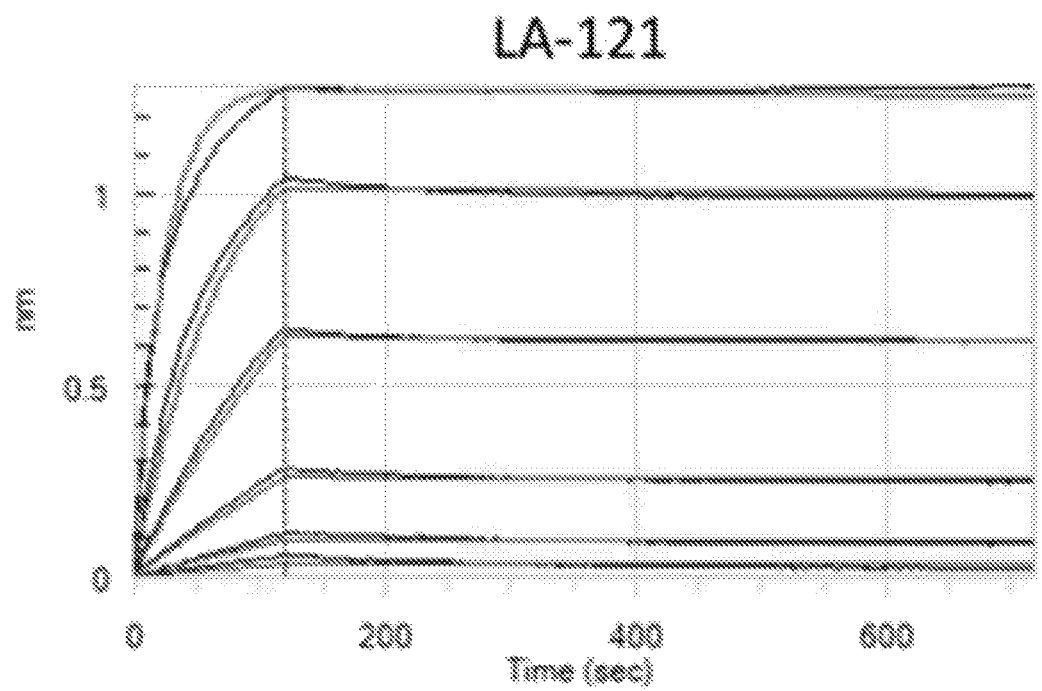
FIG. 49 shows the kinetic binding sensorgram for mAb LA-121 using Octet.

Kinetic binding sensorgram for mAb LA-121 using Octet is shown in FIG. 49.

Figure 50:
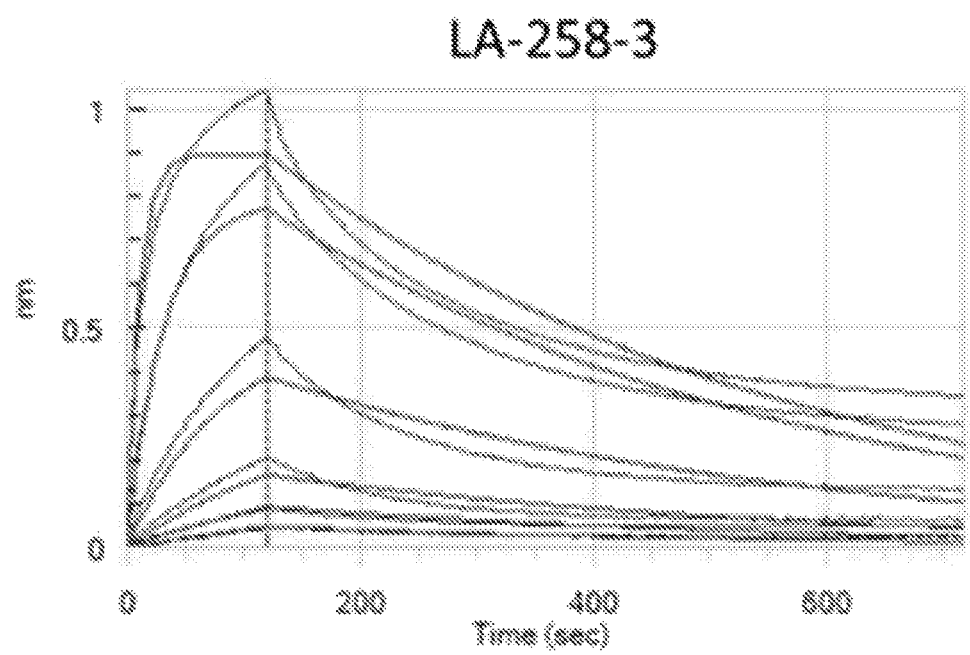
FIG. 50 shows the kinetic binding sensorgram for mAb LA-258-3 using Octet.

Kinetic binding sensorgram for mAb LA-258-3 using Octet is shown in FIG. 50.

Figure 51:
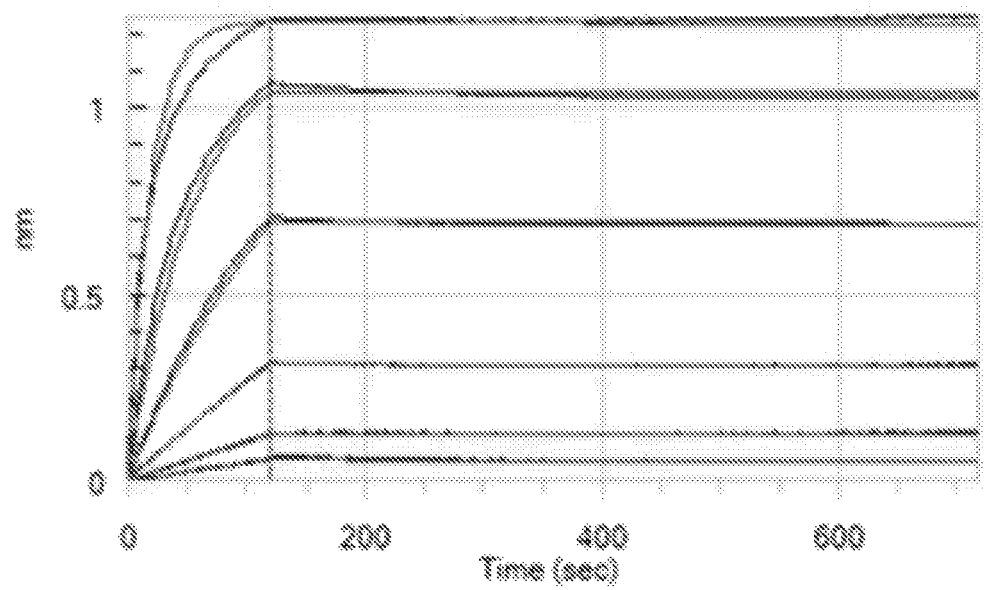
FIG. 51 shows the kinetic binding sensorgram for mAb LA-258-2 using Octet.

Kinetic binding sensorgram for mAb LA-258-2 using Octet is shown in FIG. 51.

Figure 52:
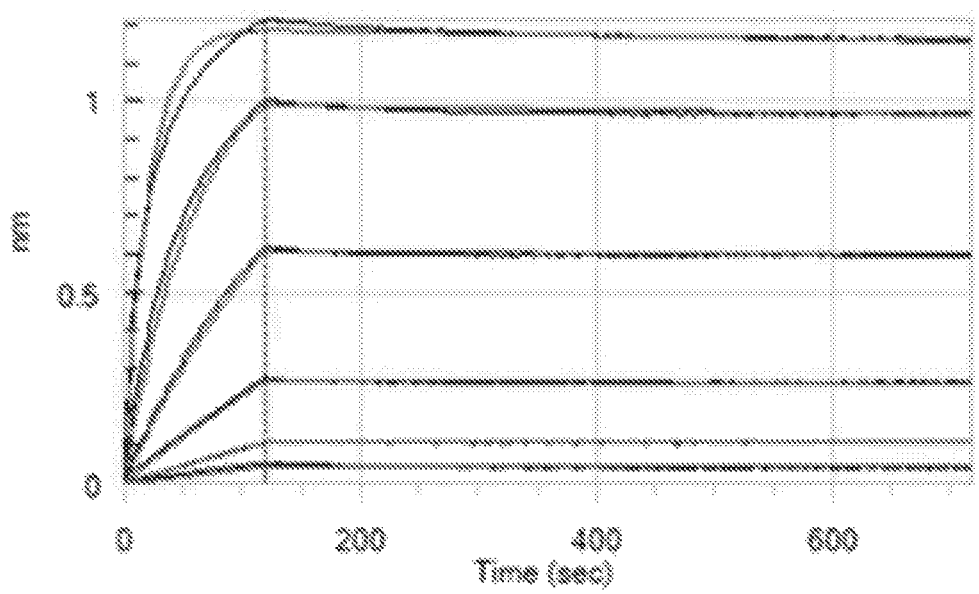
FIG. 52 shows the kinetic binding sensorgram for mAb LA-259-2 using Octet.

Kinetic binding sensorgram for mAb LA-259-2 using Octet is shown in FIG. 52.

The results of the kinetic binding assay for the anti-LAIR1 antibodies are shown in Table 8.

TABLE 8

Kinetic binding constants for anti-LAIR1 antibodies determined using Octet biosensor chip

| mAbs | $K_D$ (M) | Kon (1/Ms) | Kdis (1/s) | $R^2$ |
|---|---|---|---|---|
| LA-121 | 1.27E−10 | 1.90E+05 | 2.41E−05 | 0.9986 |
| LA-258-3 | 5.58E−09 | 3.97E+05 | 2.22E−03 | 0.9771 |
| LA-258-2 | 3.37E−11 | 2.38E+05 | 8.02E−06 | 0.9988 |
| LA-259-2 | 1.96E−10 | 2.16E+05 | 4.23E−05 | 0.9991 |

Example 5

This example illustrates the screening of anti-LAIR1 agonist and antagonist antibodies.

Figure 53A:
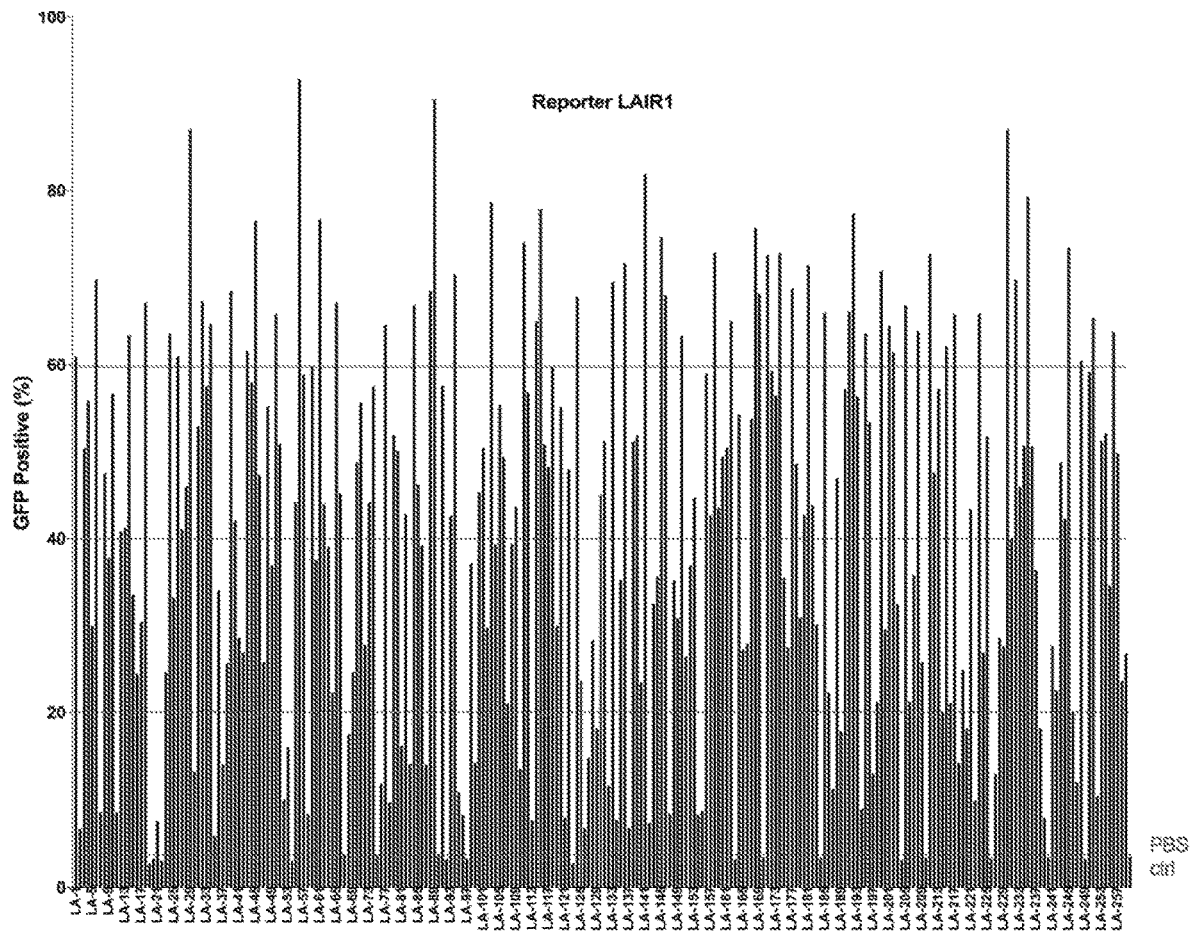

Anti-LAIR1 antibodies in the conditioned-medium of the monoclonal antibody producing rabbit plasma cells was incubated on Protein A coated wells. The percentages of GFP+LAIR1 reporter cells (indicating functional binding of LAIR1, as described in Kang et al Nat Cell Biol 2015, 17(5):665-677) were detected after 24 hours (FIG. 53A).

LAIR1 ligand collagen I was coated on the surface of the wells, then soluble Abs were added, and the percentage of GFP+LAIR1 reporter cells were detected after 24 hours (FIG. 53B).

LAIR1 ligand collagen I was coated on the surface of the wells, then soluble Abs and Fc receptor positive cell line K562 were added, and the percentage of GFP+LAIR1 reporter cells were detected after 24 hours (FIG. 53C).

Figure 53D:
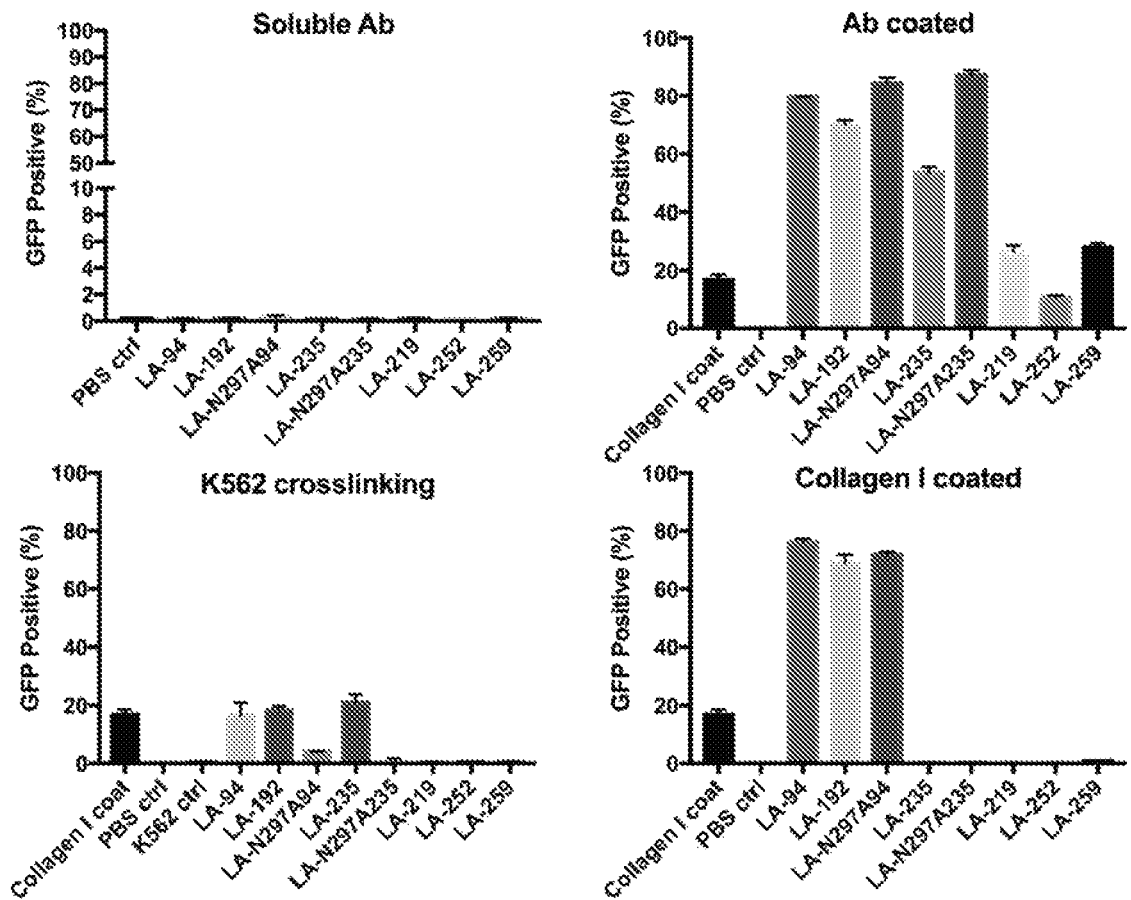

Two potential agonist antibodies (LA-94 and LA-192) and the N297A Fc mutant version of LA-94 (N297A94), four potential antagonist antibodies (LA-235, LA-219, LA-252, LA-259) and the N297A Fc mutant version for LA-235 (N297A235) were confirmed using the reporter cell system (FIG. 53D). All the GFP expression information was summarized in the table (lower panel of FIG. 53D).

Figure 53E:
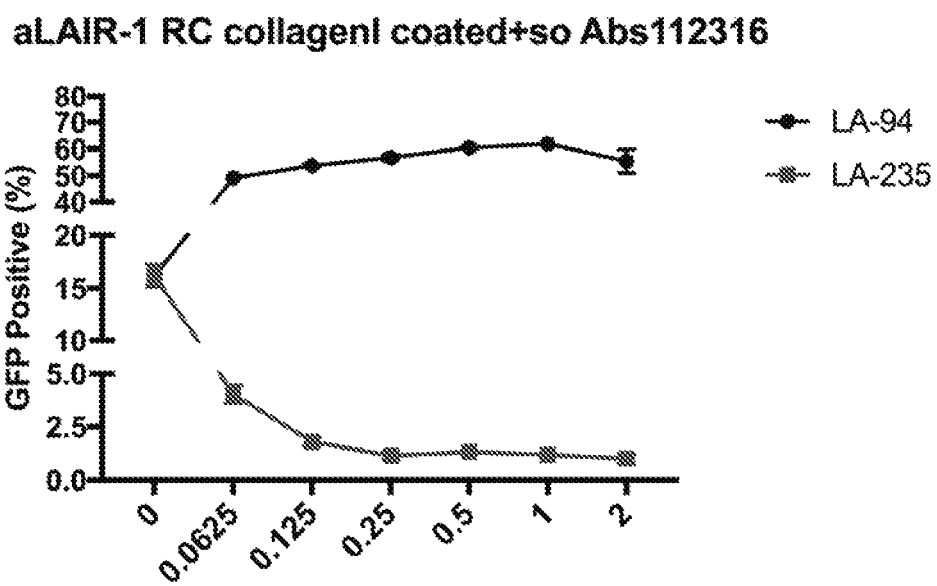

The antagonist anti-LAIR1 LA-235 demonstrated a dose-dependent activity to block collagen-induced upregulation of the LAIR1 reporter cells (FIG. 53E). In contrast, the agonist Ab LA-94 showed an ability to enhance the collagen-induced upregulation of the LAIR1 reporter cells.

Example 6

Figure 54A:
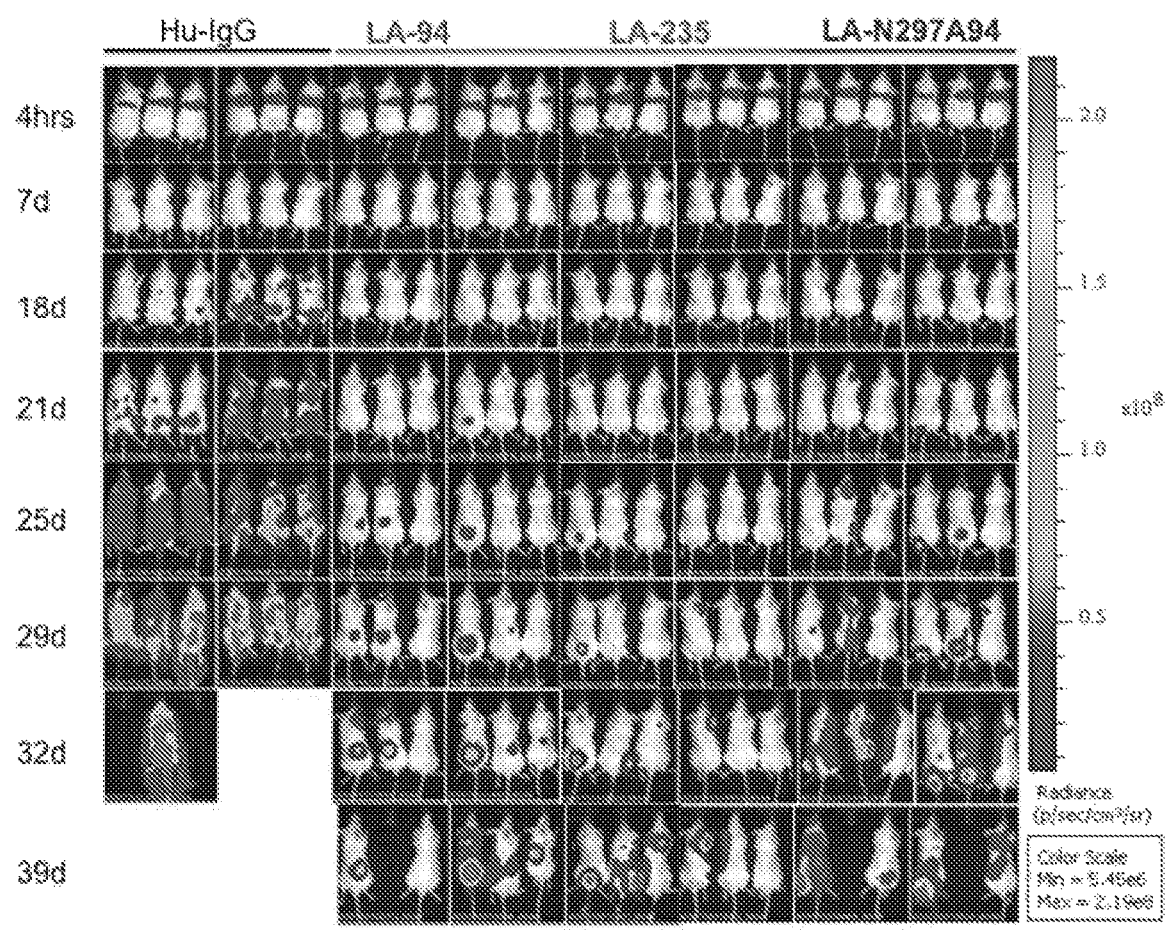
FIGS. 54A-D show that anti-LAIR1 antibody blocks leukemia development in an NSG xenograft model.

This example illustrates that anti-LAIR1 antibody blocks leukemia development in the NSG xenograft model $1 \times 10^6$ luciferase stably expressing THP-1 cells were transplanted into NSG mice through tail vein injection at day 0, and after 30 minutes, anti-LAIR1 antibody was administrated through Ophthalmic vein injection. Tumor development was monitored by BLI imaging (FIG. 54A).

Figure 54B:
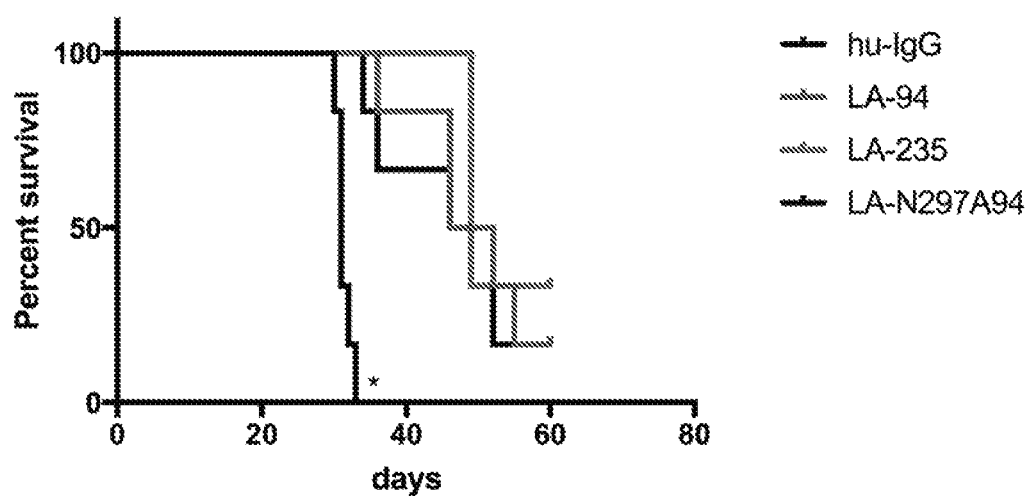

As shown in FIG. 54B, anti-LAIR1 antibodies LA-94, LA-235, and N297A mutant version of LA-94 significantly extended the lifespan of the mice.

Figure 54C:
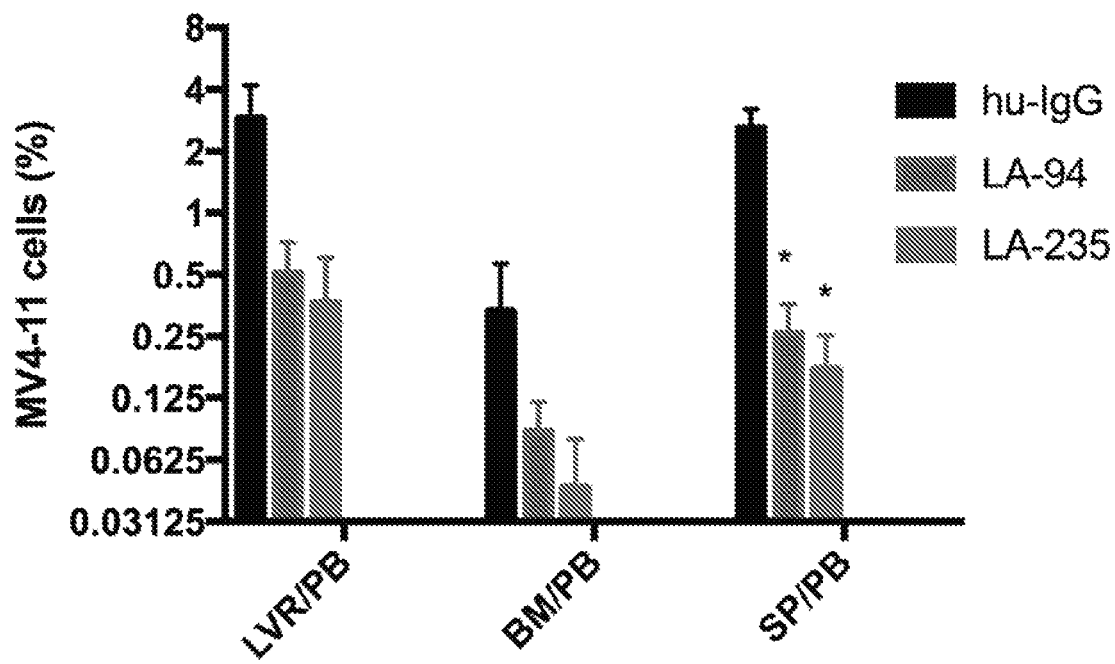

$5 \times 10^6$ GFP+MV4-11 cells were transplanted into NSG mice through tail vein injection at day 0, and after 30 minutes, 10 mg/kg anti-LAIR1 antibody were treated through Ophthalmic vein injection. Organs were harvested after 24 hours and GFP+MV4-11 cells were detected through flow cytometry. As shown in FIG. 54C, anti-LAIR1 antibody LA-94 and LA-235 significantly decreased the number of GFP+MV4-11 in the mice.

Figure 54D:
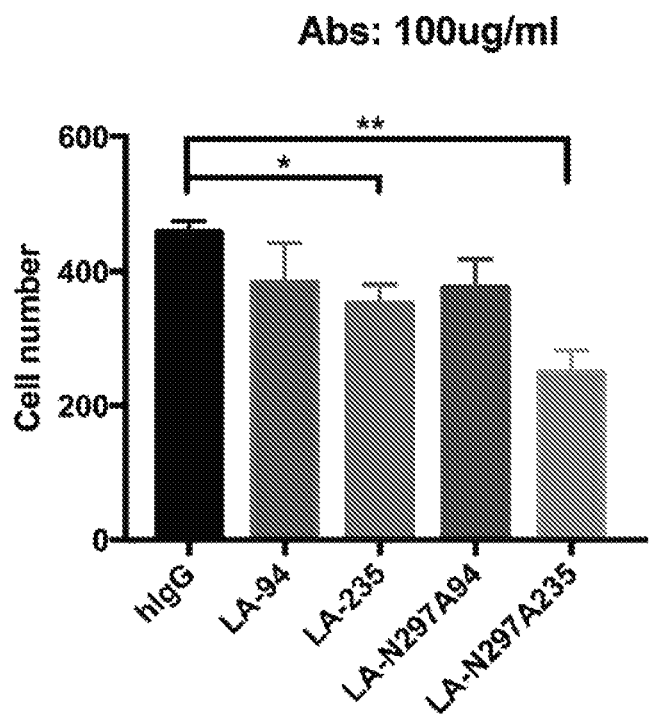

$1 \times 10^5$ /well human endothelia cells were plated on the upper room of the 24 well transwell plate on day −7. $1 \times 10^5$ MV4-11 cells were added on day 0, and the cell number of MV4-11 cells in lower room were counted using flow cytometry on day 1 (18 hours later). As shown in FIG. 54D, anti-LAIR1 antagonist antibody LA-235 and N297A235 significantly decreased the migration of MV4-11 cells.

Example 7

This example illustrates that anti-LAIR1 antibody blocks leukemia development in human LAIR1 expressed MLL-AF9 mouse model.

Figure 55A:
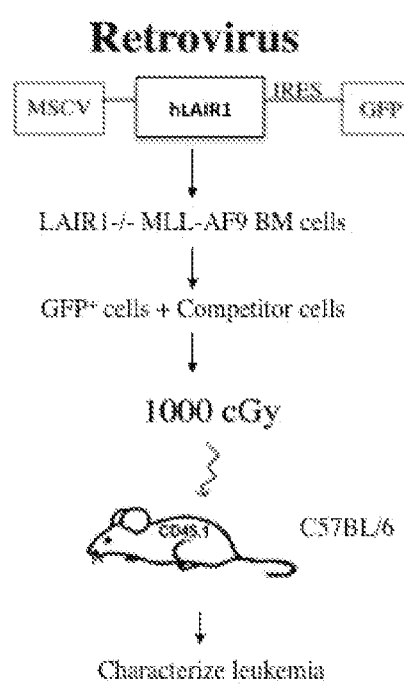
FIGS. 55A-D show that anti-LAIR1 antibody blocks leukemia development in human LAIR1 ectopically-expressed MLL-AF9 mouse model.

FIG. 55A shows the schematic of human LAIR1 expressed MLL-AF9 mouse model.

Figure 55B:
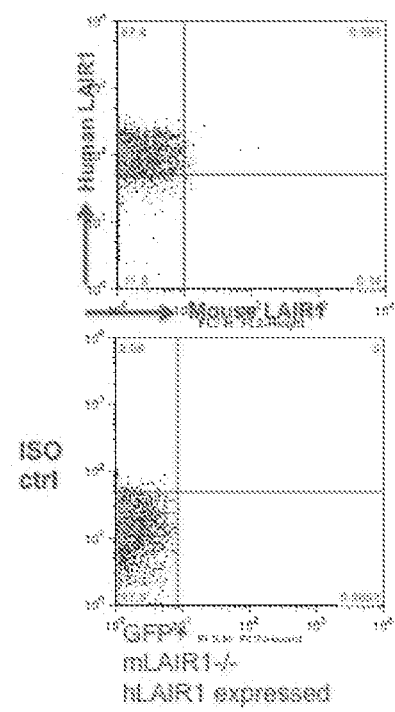

As shown in FIG. 55B, GFP+ cells used for transplantation in A are close to 100% human LAIR1 positive but do not express mouse LAIR1.

Figure 55C:
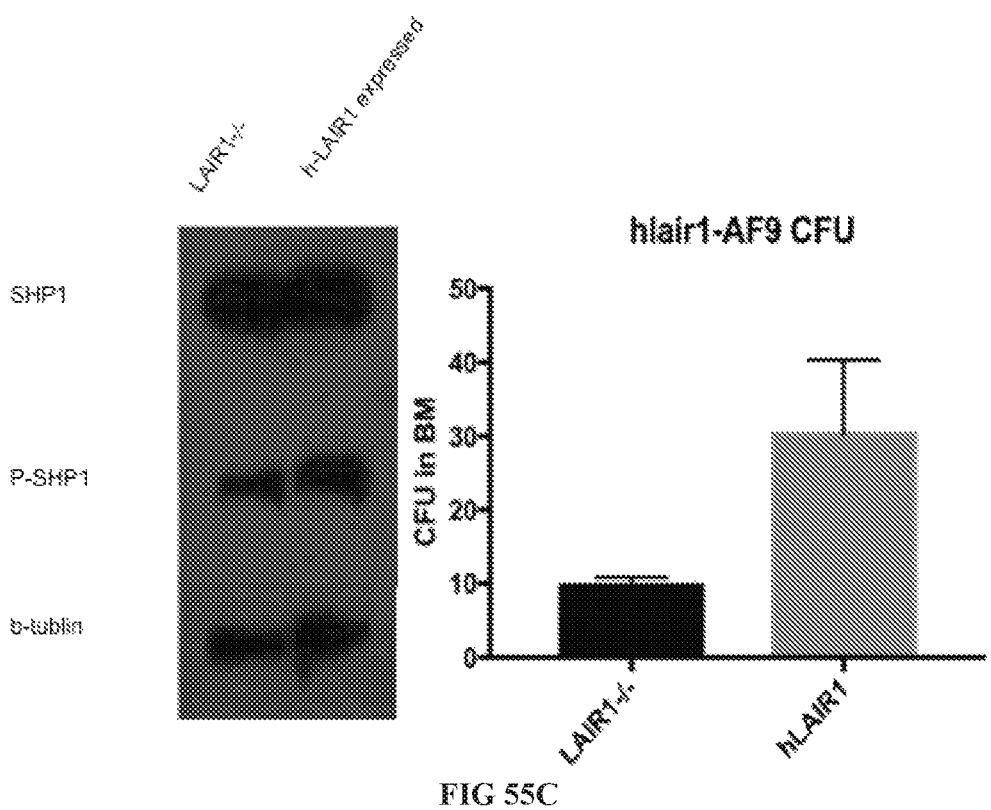

As shown in FIG. 55C, human LAIR1 expressed in mouse bone marrow cells up-regulated phosphorylated SHP1 (left), and increased the number of colony formation unit (CFU) (right).

Figure 55D:
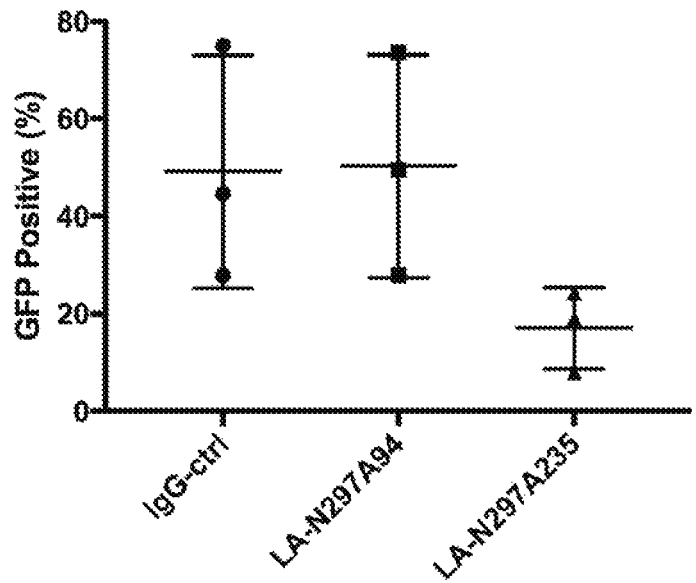

As shown in FIG. 55D, 100 μg anti-LAIR1 antibody per mouse was injected to the human LAIR1 expressed mouse model at days 5, 7, and 9 after transplantation. Periphery blood samples were collected at day 15, and the percentage of GFP+ cells were detected using flow cytometry.

Example 8

This example illustrates that anti-LAIR1 antibody demonstrates Fc-dependent ability to enhance phagocytosis of human macrophages. CFSE-stained THP-1 cells were incubated with control or anti-LAIR1 antibodies for 15 min on ice followed by PBS washing.

Figure 56:
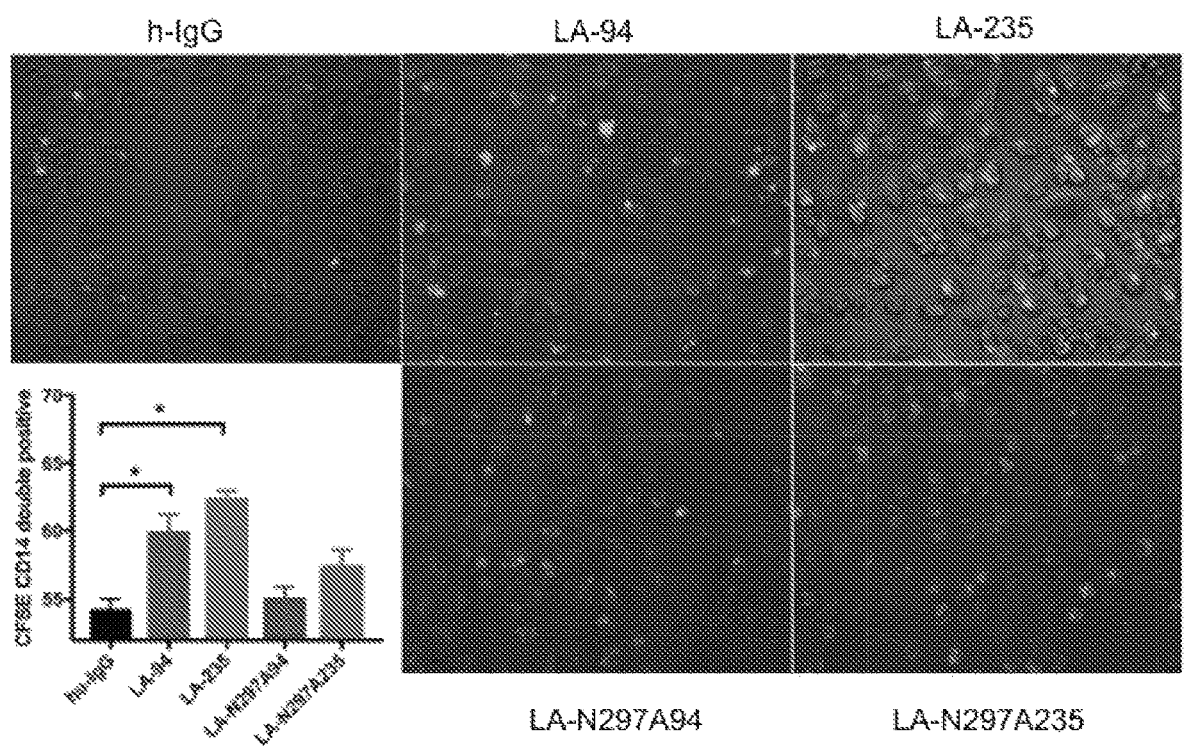
FIG. 56 shows that anti-LAIR1 demonstrates Fc-dependent ability to enhance phagocytosis of human macrophages. CFSE-stained THP-1 cells, which express LAIR1 on its surface, were incubated with control or anti-LAIR1 antibodies for 15 min on ice followed by PBS washing. The cells were then incubated with human PBMC-derived macrophages for 30 min. Phagocytosis of THP-1 cells by human macrophages was measured.

The cells were then incubated with human PBMC-derived macrophages for 30 min. Phagocytosis of THP-1 cells by human macrophages was measured. As shown in FIG. 56, anti-LAIR1 antibody LA-94 and LA-235 significantly increased the phagocytosis of THP-1 cells while N297A modification of the antibody substantially abolished the antibodies' ability to enhance phagocytosis, indicating that the antibodies' ability to enhance phagocytosis is Fc-dependent.

Example 9

Figure 57A:
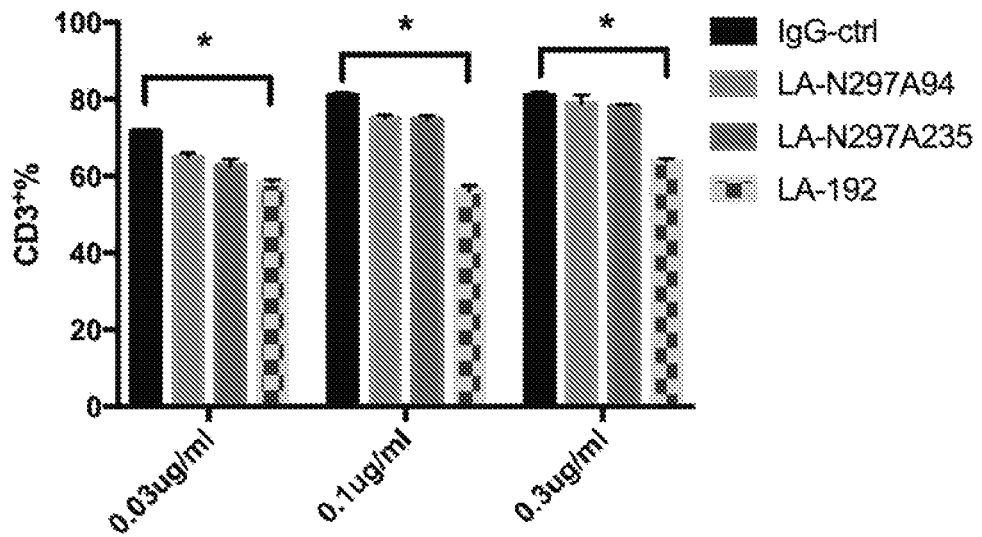
FIGS. 57A-B show that anti-LAIR1 agonist antibody inhibits T cell activity.

This example illustrates that anti-LAIR1 agonist antibody inhibits T cell activity Indicated concentrations of anti-CD3 antibody was coated on the surface of the wells of a 96-well flat-bottom plate, and then $1 \times 10^5$ PBMC mixed with control or anti-LAIR1 antibodies (final concentration 50 μg/ml) were incubated. The percentage of CD3+ T cells were detected by flow cytometry on day 5. As shown in FIG. 57A, anti-LAIR1 agonist antibody LA-192 significantly decreased the percentage of T cells in PBMC.

Figure 57B:
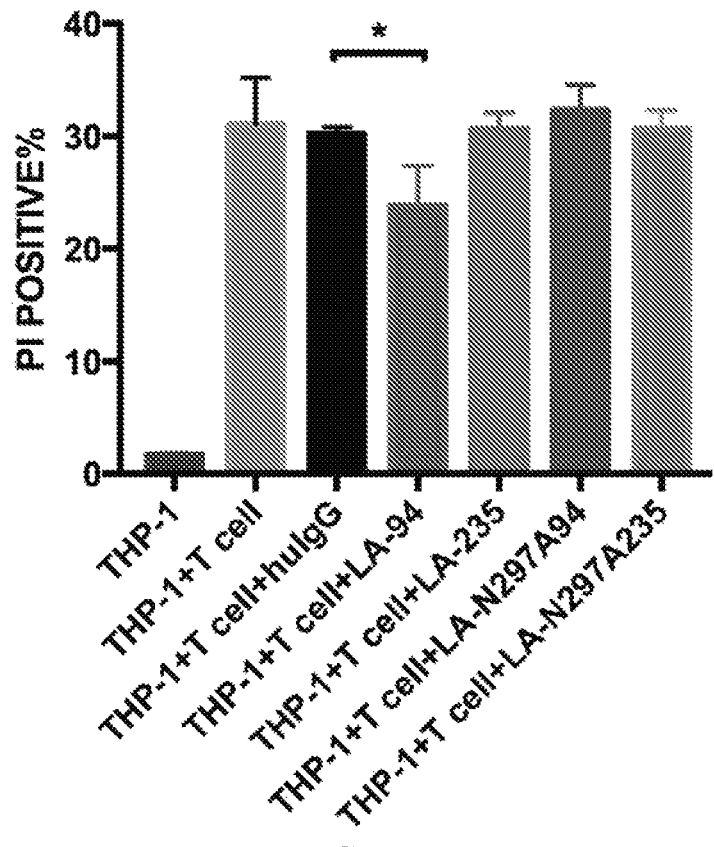

Human T cells/GFP+THP-1 cells mixture was treated by indicated control or anti-LAIR1 antibodies. Apoptosis of GFP+THP-1 cells was measured after 4 hr. As shown in FIG. 57B, anti-LAIR1 agonist antibody LA-94 significantly decreased apoptosis of THP-1 cells induced by T cells, implicating its inhibitory effect on T cell activity.

What is claimed:

1. An isolated monoclonal antibody or an antigen-binding fragment thereof comprising
 (a) a heavy chain variable region comprising the following complementary determining regions (CDRs):
  a heavy chain CDR1 that is a CDR1 in SEQ ID NO: 1, 15, 29, 43, 57, 71, 85, 99, 113, 127, 141, 155, 169, 183, 197, 211, 225, 239, 253, 267, 281, 295, 309, 323, 337, 351, 365, 379, 393, 407, 421, 435, 449, 463, 477, 491, 505 or 519, a heavy chain CDR2 that is a CDR2 in SEQ ID NO: 1, 15, 29, 43, 57, 71, 85, 99, 113, 127, 141, 155, 169, 183, 197, 211, 225, 239, 253, 267, 281, 295, 309, 323, 337, 351, 365, 379, 393, 407, 421, 435, 449, 463, 477, 491, 505 or 519, and a heavy chain CDR3 that is a CDR3 in SEQ ID NO: 1, 15, 29, 43, 57, 71, 85, 99, 113, 127, 141, 155, 169, 183, 197, 211, 225, 239, 253, 267, 281, 295, 309, 323, 337, 351, 365, 379, 393, 407, 421, 435, 449, 463, 477, 491, 505 or 519; and (b) a light chain variable region comprising the following CDRs:

a light chain CDR1 that is a CDR1 in SEQ ID NO: 2, 16, 30, 44, 58, 72, 86, 100, 114, 128, 142, 156, 170, 184, 198, 212, 226, 240, 254, 268, 282, 296, 310, 324, 338, 352, 366, 380, 394, 408, 422, 436, 450, 464, 478, 492, 506 or 520, a light chain CDR2 that is a CDR2 in SEQ ID NO: 2, 16, 30, 44, 58, 72, 86, 100, 114, 128, 142, 156, 170, 184, 198, 212, 226, 240, 254, 268, 282, 296, 310, 324, 338, 352, 366, 380, 394, 408, 422, 436, 450, 464, 478, 492, 506 or 520, and a light chain CDR3 that is a CDR3 in SEQ ID NO: 2, 16, 30, 44, 58, 72, 86, 100, 114, 128, 142, 156, 170, 184, 198, 212, 226, 240, 254, 268, 282, 296, 310, 324, 338, 352, 366, 380, 394, 408, 422, 436, 450, 464, 478, 492, 506 or 520.

2. The isolated monoclonal antibody or an antigen-binding fragment thereof of claim 1, wherein the heavy chain variable region comprises: a CDR1 comprising SEQ ID NO: 3, 17, 31, 45, 59, 73, 87, 101, 115, 129, 143, 157, 171, 185, 199, 213, 227, 241, 255, 269, 283, 297, 311, 325, 339, 353, 367, 381, 395, 409, 423, 437, 451, 465, 479, 493, 507 or 521, a CDR2 comprising SEQ ID NO: 4, 18, 32, 46, 60, 74, 88, 102, 116, 130, 144, 158, 172, 186, 200, 214, 228, 242, 256, 270, 284, 298, 312, 326, 340, 354, 368, 382, 396, 410, 424, 438, 452, 466, 480, 494, 508 or 522, and a CDR3 comprising SEQ ID NO: 5, 19, 33, 47, 61, 75, 89, 103, 117, 131, 145, 159, 173, 187, 201, 215, 229, 243, 257, 271, 285, 299, 313, 327, 341, 355, 369, 383, 397, 411, 425, 439, 453, 467, 481, 495, 509 or 523.

3. The isolated monoclonal antibody or an antigen-binding fragment thereof of claim 1, wherein the light chain variable region comprises: a CDR1 comprising SEQ ID NO: 6, 20, 34, 48, 62, 76, 90, 104, 118, 132, 146, 160, 174, 188, 202, 216, 230, 244, 258, 272, 286, 300, 314, 328, 342, 356, 370, 384, 398, 412, 426, 440, 454, 468, 482, 496, 510 or 524, a CDR2 comprising amino acid sequence DAS, RAS, LAS, KAS, YAS, GAS, GPS, LSS, QAS, AAS, WTS, QSS, or AVS, and a CDR3 comprising SEQ ID NO: 7, 21, 35, 49, 63, 77, 91, 105, 119, 133, 147, 161, 175, 189, 203, 217, 231, 245, 259, 273, 287, 301, 315, 329, 343, 357, 371, 385, 399, 413, 427, 441, 455, 469, 483, 497, 511 or 525.

4. The isolated monoclonal antibody or an antigen-binding fragment thereof according to claim 1 that is an F(ab)'2, an Fab, an Fv, or a single-chain Fv fragment.

5. The isolated monoclonal antibody or an antigen-binding fragment thereof according to claim 1, wherein the isolated monoclonal antibody is a murine, a rabbit, a chimeric, a humanized, or a human antibody.

6. A pharmaceutical composition comprising an isolated monoclonal antibody or an antigen-binding fragment thereof according to claim 1, and at least one pharmaceutically acceptable carrier.

7. A hybridoma or engineered cell encoding or producing the isolated monoclonal antibody or antigen-binding fragment thereof according to claim 1.

8. A method of treating or ameliorating the effect of a cancer in a subject in need thereof, the method comprising administering to said subject a therapeutically effective amount of the antibody or an antigen binding fragment thereof according to claim 1.

9. An isolated monoclonal antibody or an antigen-binding fragment thereof comprising:

(a) a heavy chain variable region having an amino acid sequence at least about 90% identical to SEQ ID NO: 1, 15, 29, 43, 57, 71, 85, 99, 113, 127, 141, 155, 169, 183, 197, 211, 225, 239, 253, 267, 281, 295, 309, 323, 337, 351, 365, 379, 393, 407, 421, 435, 449, 463, 477, 491, 505 or 519; and (b) a light chain variable region having an amino acid sequence at least about 90% identical to SEQ ID NO: 2, 16, 30, 44, 58, 72, 86, 100, 114, 128, 142, 156, 170, 184, 198, 212, 226, 240, 254, 268, 282, 296, 310, 324, 338, 352, 366, 380, 394, 408, 422, 436, 450, 464, 478, 492, 506 or 520.

10. The isolated monoclonal antibody or an antigen-binding fragment thereof of claim 9, wherein the heavy chain variable region has an amino acid sequence of SEQ ID NO: 1, 15, 29, 43, 57, 71, 85, 99, 113, 127, 141, 155, 169, 183, 197, 211, 225, 239, 253, 267, 281, 295, 309, 323, 337, 351, 365, 379, 393, 407, 421, 435, 449, 463, 477, 491, 505 or 519, and wherein the light chain variable region has an amino acid sequence of SEQ ID NO: 2, 16, 30, 44, 58, 72, 86, 100, 114, 128, 142, 156, 170, 184, 198, 212, 226, 240, 254, 268, 282, 296, 310, 324, 338, 352, 366, 380, 394, 408, 422, 436, 450, 464, 478, 492, 506 or 520.

* * * * *